US011820801B2

(12) United States Patent
Kim et al.

(10) Patent No.: US 11,820,801 B2
(45) Date of Patent: Nov. 21, 2023

(54) FUSION PROTEIN, AND PHARMACEUTICAL COMPOSITION FOR PREVENTING OR TREATING CANCER, CONTAINING SAME

(71) Applicant: GOOD T CELLS, INC., Seoul (KR)

(72) Inventors: Jung Ho Kim, Seoul (KR); Beom Seok Kim, Seoul (KR)

(73) Assignee: Good T Cells, Inc., Seoul (KR)

( * ) Notice: Subject to any disclaimer, the term of this patent is extended or adjusted under 35 U.S.C. 154(b) by 0 days.

(21) Appl. No.: 17/050,816

(22) PCT Filed: Apr. 26, 2019

(86) PCT No.: PCT/KR2019/005096
§ 371 (c)(1),
(2) Date: Oct. 26, 2020

(87) PCT Pub. No.: WO2019/209078
PCT Pub. Date: Oct. 31, 2019

(65) Prior Publication Data

US 2021/0130422 A1 May 6, 2021

(30) Foreign Application Priority Data

Apr. 26, 2018 (KR) ........................ 10-2018-0048343

(51) Int. Cl.
*A61K 38/17* (2006.01)
*C07K 14/47* (2006.01)
*A61P 35/00* (2006.01)
*A61K 38/00* (2006.01)

(52) U.S. Cl.
CPC .............. *C07K 14/47* (2013.01); *A61K 38/00* (2013.01); *A61P 35/00* (2018.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,116,964 | A | 5/1992 | Capon et al. | |
| 5,624,821 | A | 4/1997 | Winter et al. | |
| 6,086,875 | A | 7/2000 | Blumberg et al. | |
| 2005/0192211 | A1 | 9/2005 | Gillies et al. | |
| 2008/0300188 | A1 | 12/2008 | Yang et al. | |
| 2010/0196370 | A1 * | 8/2010 | Yu | A61P 43/00 435/69.6 |
| 2013/0142795 | A1 | 6/2013 | Bai et al. | |
| 2015/0239964 | A1 | 8/2015 | Lee | |
| 2016/0355557 | A1 | 12/2016 | Hong et al. | |
| 2021/0347849 | A1 | 11/2021 | Kim | |

FOREIGN PATENT DOCUMENTS

| | | |
|---|---|---|
| WO | 1996/032478 | 10/1996 |
| WO | 1997/034631 | 9/1997 |

OTHER PUBLICATIONS

Czajkowsky et al. (EMBO Mol. Med. 4: 1015-1028, 2021).*
Jazayeri et al. Biodrugs 22(1): 11-26, 2008.*
Yi et al. Exp. Cell Res. 317: 504-512, 2011.*
Johansson, M. el al. "The soluble form of the tumor suppressor Lrig1 potently inhibits in vivo glioma growth irrespective of EGF receptor status" Neum-Oncology (2013) vol. 15(9), pp. 200-121.
Chang, L. et al. "Restoration of LRIG 1 suppresses bladder cancer cell growth by directly targeting EGFR activity" Journal of Experimental & Clinical Cancer Research (2013) vol. 32(101), pp. 1-9.
Goebl, Nancy A. et al. "Neonatal Fc Receptor Mediates Internalization of Fc in Transfected Human Endothelial Cells" Molecular Biology of the Cell (2008) vol. 19, pp. 5490-5505.
Junghans, R.P. et al. "The protection receptor for IgG catabolism is the B2-microglobulin-containing neonatal intestinal transport receptor" Proc. Natl. Acad. Sci. (1996) vol. 93, pp. 5512-5516.
Osborn, Blaire L. et al. "Albutropin: a growth hormone—albumin fusion with improved pharmacokinetics and pharmacodynamics in rats and monkeys" European Journal of Pharmacology 456 (2002), pp. 149-158.
S. Goldoni et al., "A soluble ectodomain of LRIG1 inhibits cancer cell growth by attenuating basal and ligand-dependent EGFR activity," Oncogene, 26, 368-81 (2007).
M. Johansson et al., "The soluble form of the tumor suppressor Lrig1 potently inhibits in vivo glioma growth irrespective of EGF receptor status," Neuro-Oncology, 15(9), 1200-11 (2013).
M. Lindzen et al., "A recombinant decoy comprising EGFR and ErbB-4 inhibits tumor growth and metastasis," Oncogene, 31, 3505-15 (2012).
T. Rath et al., "Fc-fusion proteins and FcRn: structural insights for longer-lasting and more effective therapeutics," Crit. Revs. in Biotechnology, 35(2), 235-54 (2013).
Y. Xu et al., "LRIG1 Extracellular Domain: Structure and Function Analysis," J. Mol. Biol., 427, 1934-48 (2015).

(Continued)

*Primary Examiner* — Christine J Saoud
(74) *Attorney, Agent, or Firm* — McDonnell Boehnen Hulbert & Berghoff LLP

(57) ABSTRACT

The present invention relates to a fusion protein comprising an extracellular domain of leucine-rich and immunoglobulin-like domains-1 (Lrig-1) protein and an immunoglobulin Fc region. The fusion protein provided in the present invention can interact with a ligand for Lrig-1 protein, which is present on effector T cells, to inhibit the interaction between the effector T cells and regulatory T cells (Treg cells) having the Lrig-1 protein on their surface, so that activity of the regulatory T cells is inhibited and activity of the effector T cells is maintained or elevated, thereby effectively inhibiting growth of cancer cells, in particular, solid cancer cells.

17 Claims, 10 Drawing Sheets

Specification includes a Sequence Listing.

(56) References Cited

OTHER PUBLICATIONS

Korean Intellectual Property Office, acting as International Searching Authority for the World Intellectual Property Office, International Search Report and Written Opinion, International Patent Application No. PCT/KR2019/005096, dated Aug. 9, 2019, published with publication of application on Oct. 31, 2019.
T. Rath et al., "Fc-fusion proteins and FcRn: structural insights for longer-lasting and more effective therapeutics," Crit. Rev. Biotechnol., 35(2), 235-54 (2015).
M. Johansson et al., "The soluble form of the tumor suppressor Lrig1 potently inhibits in vivo growth irrespective of EGF receptor status," Neuro-Oncology, 15(9), 1200-11 (2013).

* cited by examiner

| No. | Chain | Start | End | Contiguous epitope positions | Number of Residue | Score |
|---|---|---|---|---|---|---|
| 1 | A | 9 | 56 | GDSLDCGGRGLAALPGDLPSSTRSLNLSYNKLSEIDPAGFEDLPNLQE | 48 | 0.86 |
| 2 | A | 399 | 455 | SDSFLCDCQLKWLPPWLIGRMLQAFVTATCAHPESLKGQSIFSVPPESFVCDDFLKA | 57 | 0.853 |
| 3 | A | 60 | 66 | NNNELTA | 7 | 0.614 |
| 4 | A | 376 | 393 | NAIRSVQFDAFVKMKNLK | 18 | 0.596 |
| 5 | A | 85 | 89 | NKIRS | 5 | 0.561 |
| 6 | A | 232 | 237 | VEVNSG | 6 | 0.541 |
| 7 | A | 256 | 261 | ARIHRK | 6 | 0.539 |
| 8 | A | 109 | 117 | NNITEVRNT | 9 | 0.52 |
| 9 | A | 183 | 196 | IRLIEGLTFQGLNS | 14 | 0.52 |
| 10 | A | 207 | 220 | ISKLTDGAFWGLSK | 14 | 0.514 |
| 11 | A | 158 | 170 | NRITQLPVRAFKL | 13 | 0.501 |
| 12 | A | 96 | 101 | KAYLSL | 6 | 0.5 |
| 13 | A | 531 | 559 | KKDNEVLTNADMENFVHVHAVMEYT | 25 | 0.82 |
| 14 | A | 517 | 527 | SAASSSSSFMT | 11 | 0.817 |
| 15 | A | 727 | 744 | FKGDRPLSLTERHHLTPD | 18 | 0.781 |
| 16 | A | 777 | 786 | QLSVLLENLY | 10 | 0.772 |
| 17 | A | 494 | 501 | KFQIITQP | 8 | 0.732 |
| 18 | A | 697 | 711 | VPLEDRVVSVGETVA | 15 | 0.721 |
| 19 | A | 849 | 858 | HVMPQDDVFF | 10 | 0.69 |
| 20 | A | 579 | 590 | ITNHFGSTYSHK | 12 | 0.676 |
| 21 | A | 746 | 760 | QLLVVQNVVAEDAGR | 15 | 0.669 |
| 22 | A | 563 | 570 | HLRQVTFG | 8 | 0.564 |

FIG. 3

| No. | Discontiguous epitope positions | Number of Residue | Score |
|---|---|---|---|
| 1 | C1, P2, S3, R4, C5, T6, C7, S8, G9, D10, S11, L12, D13, C14, G15, G16, R17, G18, L19, A20, A21, L22, P23, G24, D25, L26, P27, S28, S29, T30, R31, S32, L33, N34, L35, S36, Y37, N38, K39, L40, S41, E42, I43, D44, P45, A46, G47, F48, E49, D50, L51, P52, N53, L54, Q55, E56, L58, N60, N61, N62, E63, L64, T65, A66, P68, S69, L70, G71, A72, A73, S74, S75, H76, V79, H84, N85, K86, I87, R88, S89, K96, A97, Y98, L99, S100, L101, P120, H121, G122, P123, P124 | 91 | 0.747 |
| 2 | N109, N110, I111, T112, E113, R115, N116, T117, N133, R134, I135, G136, T137, E139, L140, G141, A142, N158, R159, I160, T161, Q162, L163, P164, V165, R166, A167, K169, L170, P171, R182, I183, L185, E187, G188, L189, T190, Q192, G193, L194, N195, S196, I207, S208, K209, T211, D212, G213, A214, F215, W216, G217, L218, S219, K220, S230, L231, V232, E233, V234, N235, S236, G237, Y240, G241, L242, T243, A244, A256, R257, R260, K261, S264, F266, Q267, E284, E285, S286, L287, A288, E289, L290, S291, A307, E308, G309, K312, G313, R315, S316, S335, G336, S339, G340, L341, D342, S343, I354, K356, K359, G364, L365, E366, G367, E369, N376, A377, I378, R379, S380, V381, Q382, F383, D384, A385, V387, K388, M389, K390, N391, L392, K393, S399, D400, S401, F402, L403, C404, D405, C406, Q407, L408, K409, W410, L411, P412, P413, W414, L415, I416, G417, R418, L420, Q421, A422, F423, V424, T425, A426, T427, C428, A429, H430, P431, E432, S433, L434, K435, G436, Q437, S438, I439, F440, S441, V442, P443, P444, E445, S446, F447, V448, C449, D450, D451, F452, L453, K454, A455 | 178 | 0.636 |
| 1 | N784, L785, Y786 | 3 | 0.877 |
| 2 | K494, P495, Q496, I497, I498, T499, Q500, P501, S517, A518, A519, S520, S521, S522, S523, S524, P525, M526, T527, E543, N544, F545, V546, H547, V548, H549, V555, M556, E557, Y558, T559, E79, T580, N581, H582, F583, G584, S585, T586, Y587, S588, H589 | 42 | 0.788 |
| 3 | V697, P698, L699, E700, D701, R702, V703, V704, S705, V706, G707, E708, T709, V710, A711, F727, K728, G729, D730, R731, P732, L733, S734, L735, T736, E737, R738, H739, H740, L741, T742, P743, D744, N745, L747, V749, V750, Q751, N752, V753, V754, A755, E756, D757, A758, R760, Q777, L778, S779, V780, L781, L782, E783 | 53 | 0.739 |
| 4 | D511, K531, K532, D533, N534, E535, V536, L537, T538, N539, A540, D541, M542, H583, R565 | 15 | 0.699 |
| 5 | T614, M615, H649, V650, M651, P652, D653, D654, D655, V656, F658, T660 | 12 | 0.669 |
| 6 | V508, G509, K510, Q566, V567, T568, F569, G570 | 8 | 0.529 |

FIG. 4

| Gene | Fold change | Reference |
|---|---|---|
| GPR83 | 29.5 | J. Immunol. 2006 |
| Nrp1 | 23.7 | Eur. J. Immunol. 2004 |
| Lag3 | 3.1 | Immunity, 2003 |
| Ikzf4 | 4.2 | Science, 2009 |

| | Lrig1-IgG |
|---|---|
| B16F10 | --- |

√ Degree of decrease in cancer size as compared with control (0~30 %: ---, 31~70 %: --, 71~100 %: -)
√ Degree of increase in cancer size as compared with control (100~130 %: +, 131~170 %: ++, or higher: +++)

SEQUENCE LISTING

```
<160> NUMBER OF SEQ ID NOS: 118

<210> SEQ ID NO 1
<211> LENGTH: 762
<212> TYPE: PRT
<213> ORGANISM: Homo sapiens

<400> SEQUENCE: 1

Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60
```

-continued

```
Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
```

```
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe
        755                 760


<210> SEQ ID NO 2
<211> LENGTH: 2286
<212> TYPE: DNA
<213> ORGANISM: Homo sapiens

<400> SEQUENCE: 2

gctgggcctc gggctccttg tgctgccgcc tgcacatgtg caggcgattc cctggactgc      60

ggcggcagag gcctggccgc cctgcctggc gatctgccat cctggacccg gagcctgaac     120

ctgagctaca acaagctgag cgagatcgat cccgccggct ttgaggacct gcctaacctg     180

caggaggtgt atctgaacaa taacgagctg accgcggtac catccctggg cgctgcttca     240

tcacatgtcg tctctctctt tctgcagcac aacaagattc gcagcgtgga ggggagccag     300

ctgaaggcct acctttcctt agaagtgtta gatctgagtt tgaacaacat cacggaagtg     360

cggaacacct gctttccaca cggaccgcct ataaaggagc tcaacctggc aggcaatcgg     420

attggcaccc tggagttggg agcatttgat ggtctgtcac ggtcgctgct aactcttcgc     480

ctgagcaaaa acaggatcac ccagcttcct gtaagagcat tcaagctacc caggctgaca     540
```

-continued

```
caactggacc tcaatcggaa caggattcgg ctgatagagg gcctcacctt ccaggggctc    600

aacagcttgg aggtgctgaa gcttcagcga aacaacatca gcaaactgac agatggggcc    660

ttctggggac tgtccaagat gcatgtgctg cacctggagt acaacagcct ggtagaagtg    720

aacagcggct cgctctacgg cctcacggcc ctgcatcagc tccacctcag caacaattcc    780

atcgctcgca ttcaccgcaa gggctggagc ttctgccaga agctgcatga gttggtcctg    840

tccttcaaca acctgacacg gctggacgag gagagcctgg ccgagctgag cagcctgagt    900

gtcctgcgtc tcagccacaa ttccatcagc cacattgcgg agggtgcctt caagggactc    960

aggagcctgc gagtcttgga tctggaccat aacgagattt cgggcacaat agaggacacg   1020

agcggcgcct tctcagggct cgacagcctc agcaagctga ctctgtttgg aaacaagatc   1080

aagtctgtgg ctaagagagc attctcgggg ctggaaggcc tggagcacct gaaccttgga   1140

gggaatgcga tcagatctgt ccagtttgat gcctttgtga agatgaagaa tcttaaagag   1200

ctccatatca gcagcgacag cttcctgtgt gactgccagc tgaagtggct gcccccgtgg   1260

ctaattggca ggatgctgca ggcctttgtg acagccacct gtgcccaccc agaatcactg   1320

aagggtcaga gcattttctc tgtgccacca gagagtttcg tgtgcgatga cttcctgaag   1380

ccacagatca tcacccagcc agaaaccacc atggctatgg tgggcaagga catccggttt   1440

acatgctcag cagccagcag cagcagctcc cccatgacct ttgcctggaa gaaagacaat   1500

gaagtcctga ccaatgcaga catggagaac tttgtccacg tccacgcgca ggacggggaa   1560

gtgatggagt acaccaccat cctgcacctc cgtcaggtca ctttcgggca cgagggccgc   1620

taccaatgtg tcatcaccaa ccactttggc tccacctatt cacataaggc caggctcacc   1680

gtgaatgtgt tgccatcatt caccaaaacg ccccacgaca taaccatccg gaccaccacc   1740

gtggcccgcc tcgaatgtgc tgccacaggt cacccaaacc ctcagattgc ctggcagaag   1800

gatggaggca cggatttccc cgctgcccgt gagcgacgca tgcatgtcat gccggatgac   1860

gacgtgtttt tcatcactga tgtgaaaata gatgacgcag gggtttacag ctgtactgct   1920

cagaactcag ccggttctat ttcagctaat gccaccctga ctgtcctaga gaccccatcc   1980

ttggtggtcc ccttggaaga ccgtgtggta tctgtgggag aaacagtggc cctccaatgc   2040

aaagccacgg ggaaccctcc gccccgcatc acctggttca aggggggaccg cccgctgagc   2100

ctcactgagc ggcaccacct gacccctgac aaccagctcc tggtggttca gaacgtggtg   2160

gcagaggatg cgggccgata tacctgtgag atgtccaaca ccctgggcac ggagcgagct   2220

cacagccagc tgagcgtcct gcccgcagca ggctgcagga aggatgggac cacggtaggc   2280

atcttc                                                              2286
```

```
<210> SEQ ID NO 3
<211> LENGTH: 760
<212> TYPE: PRT
<213> ORGANISM: Mus musculus

<400> SEQUENCE: 3

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60
```

-continued

```
Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480
```

-continued

```
Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr
        755                 760


<210> SEQ ID NO 4
<211> LENGTH: 2280
<212> TYPE: DNA
<213> ORGANISM: Mus musculus

<400> SEQUENCE: 4

gctcaggctg gacctagggc tccttgcgct gccgcctgca cctgtgcagg cgattctctg      60

gactgcagcg gccggggcct ggccacactg cccagggacc tgccttcctg gaccagatct     120

ctgaacctga gctacaatcg gctgtccgag atcgattctg ccgcctttga ggacctgaca     180

aatctgcagg aggtgtatct gaacagcaat gagctgaccg caatcccctc cctgggagca     240

gcctctatcg gcgtggtgag cctgttcctg cagcacaaca agatcctgag cgtggatggc     300

tcccagctga agagctacct gtctctggag gtgctggacc tgagctccaa caatatcacc     360

gagatcagat ctagctgttt tcctaatggc ctgcggatca gagagctgaa cctggcctct     420

aatcggatca gcatcctgga gtccggcgcc ttcgatggcc tgagcagatc cctgctgaca     480

ctgcgcctgt ccaagaaccg gatcacccag ctgcccgtga aggcctttaa gctgcctagg     540
```

```
ctgacacagc tggacctgaa ccggaataga atcaggctga tcgagggcct gaccttccag    600

ggcctggata gcctggaggt gctgcgcctg cagcggaaca atatctcccg cctgacagac    660

ggagcatttt ggggcctgtc taagatgcac gtgctgcacc tggagtacaa tagcctggtg    720

gaggtgaact ctggcagcct gtatggcctg accgccctgc accagctgca cctgtccaac    780

aatagcatca gcagaatcca gagggatggc tggtccttct gccagaagct gcacgagctg    840

atcctgtctt ttaacaatct gaccaggctg gacgaggaga gcctggcaga gctgtcctct    900

ctgtccatcc tgcgcctgtc tcacaatgcc atcagccaca tcgccgaggg cgcctttaag    960

ggcctgaaga gcctgagggt gctggatctg gaccacaacg agatctctgg caccatcgag   1020

gatacaagcg gcgccttcac aggcctggac aatctgtcca agctgaccct gtttggcaac   1080

aagatcaagt ctgtggccaa gcgggccttc tctggcctgg agagcctgga gcacctgaac   1140

ctgggcgaga atgccatcag atccgtgcag ttcgatgcct ttgccaagat gaagaatctg   1200

aaggagctgt acatcagctc cgagagcttc ctgtgcgact gtcagctgaa gtggctgcca   1260

ccttggctga tgggaaggat gctgcaggcc tttgtgaccg ccacatgcgc ccacccagag   1320

agcctgaagg gccagagcat cttctccgtg ctgcccgata gcttcgtgtg cgacgatttt   1380

cctaagccac agatcatcac ccagccagag acaacaatgg ccgtggtggg caaggacatc   1440

cggtttacat gttccgccgc ctctagctcc tctagcccca tgaccttcgc ctggaagaag   1500

gataacgagg tgctggccaa tgccgacatg gagaacttcg cccacgtgag agcccaggat   1560

ggcgaagtga tggagtatac cacaatcctg cacctgcggc acgtgacctt tggccacgag   1620

ggcagatacc agtgcatcat cacaaatcac ttcggctcta cctatagcca caaggccagg   1680

ctgacagtga acgtgctgcc tagctttacc aagatcccac acgacatcgc catcagaaca   1740

ggcaccacag caaggctgga gtgtgcagca accggacacc caaaccctca gatcgcatgg   1800

cagaaggatg gaggcacaga cttccctgca gcccgcgaga ggagaatgca cgtgatgcca   1860

gacgatgacg tgttctttat cacagatgtg aagatcgatg acatgggcgt gtactcctgc   1920

accgcacaga acagcgccgg cagcgtgtcc gccaacgcca ccctgaccgt gctggagaca   1980

ccatccctgg ccgtgcccct ggaggacagg gtggtgaccg tgggcgagac agtggccttt   2040

cagtgtaagg ccaccggctc tccaacacca aggatcacct ggctgaaggg cggcaggccc   2100

ctgagcctga cagagcgcca ccacttcacc cctggcaatc agctgctggt ggtgcagaac   2160

gtgatgatcg atgacgccgg caggtataca tgcgagatga gcaatcctct gggcaccgag   2220

agggcacact cccagctgtc tatcctgcct accccaggct gccggaagga tggcaccaca   2280
```

<210> SEQ ID NO 5
<211> LENGTH: 206
<212> TYPE: PRT
<213> ORGANISM: Homo sapiens

<400> SEQUENCE: 5

```
Leu Phe Pro Pro Lys Pro Lys Asp Thr Leu Met Ile Ser Arg Thr Pro
1               5                   10                  15

Glu Val Thr Cys Val Val Val Asp Val Ser His Glu Asp Pro Glu Val
            20                  25                  30

Lys Phe Asn Trp Tyr Val Asp Gly Val Glu Val His Asn Ala Lys Thr
        35                  40                  45

Lys Pro Arg Glu Glu Gln Tyr Asn Ser Thr Tyr Arg Val Val Ser Val
    50                  55                  60
```

```
Leu Thr Val Leu His Gln Asp Trp Leu Asn Gly Lys Glu Tyr Lys Cys
65                  70                  75                  80

Lys Val Ser Asn Lys Ala Leu Pro Ala Pro Ile Glu Lys Thr Ile Ser
                85                  90                  95

Lys Ala Lys Gly Gln Pro Arg Glu Pro Gln Val Tyr Thr Leu Pro Pro
            100                 105                 110

Ser Arg Asp Glu Leu Thr Lys Asn Gln Val Ser Leu Thr Cys Leu Val
        115                 120                 125

Lys Gly Phe Tyr Pro Ser Asp Ile Ala Val Glu Trp Glu Ser Asn Gly
    130                 135                 140

Gln Pro Glu Asn Asn Tyr Lys Thr Thr Pro Pro Val Leu Asp Ser Asp
145                 150                 155                 160

Gly Ser Phe Phe Leu Tyr Ser Lys Leu Thr Val Asp Lys Ser Arg Trp
                165                 170                 175

Gln Gln Gly Asn Val Phe Ser Cys Ser Val Met His Glu Ala Leu His
            180                 185                 190

Asn His Tyr Thr Gln Lys Ser Leu Ser Leu Ser Pro Gly Lys
        195                 200                 205


<210> SEQ ID NO 6
<211> LENGTH: 206
<212> TYPE: PRT
<213> ORGANISM: Mus musculus

<400> SEQUENCE: 6

Ile Phe Pro Pro Lys Ile Lys Asp Val Leu Met Ile Ser Leu Ser Pro
1               5                   10                  15

Ile Val Thr Cys Val Val Val Asp Val Ser Glu Asp Asp Pro Asp Val
            20                  25                  30

Gln Ile Ser Trp Phe Val Asn Asn Val Glu Val His Thr Ala Gln Thr
        35                  40                  45

Gln Thr His Arg Glu Asp Tyr Asn Ser Thr Leu Arg Val Val Ser Ala
    50                  55                  60

Leu Pro Ile Gln His Gln Asp Trp Met Ser Gly Lys Glu Phe Lys Cys
65                  70                  75                  80

Lys Val Asn Asn Lys Asp Leu Pro Ala Pro Ile Glu Arg Thr Ile Ser
                85                  90                  95

Lys Pro Lys Gly Ser Val Arg Ala Pro Gln Val Tyr Val Leu Pro Pro
            100                 105                 110

Pro Glu Glu Glu Met Thr Lys Lys Gln Val Thr Leu Thr Cys Met Val
        115                 120                 125

Thr Asp Phe Met Pro Glu Asp Ile Tyr Val Glu Trp Thr Asn Asn Gly
    130                 135                 140

Lys Thr Glu Leu Asn Tyr Lys Asn Thr Glu Pro Val Leu Asp Ser Asp
145                 150                 155                 160

Gly Ser Tyr Phe Met Tyr Ser Lys Leu Arg Val Glu Lys Lys Asn Trp
                165                 170                 175

Val Glu Arg Asn Ser Tyr Ser Cys Ser Val Val His Glu Gly Leu His
            180                 185                 190

Asn His His Thr Thr Lys Ser Phe Ser Arg Thr Pro Gly Lys
        195                 200                 205


<210> SEQ ID NO 7
<211> LENGTH: 26
<212> TYPE: PRT
<213> ORGANISM: Homo sapiens
```

<400> SEQUENCE: 7

Glu Pro Lys Ser Ser Asp Lys Thr His Thr Ser Pro Pro Cys Pro Ala
1 5 10 15

Pro Glu Leu Leu Gly Gly Pro Ser Val Phe
20 25

<210> SEQ ID NO 8
<211> LENGTH: 27
<212> TYPE: PRT
<213> ORGANISM: Mus musculus

<400> SEQUENCE: 8

Glu Pro Arg Gly Pro Thr Ile Lys Pro Cys Pro Pro Cys Lys Cys Pro
1 5 10 15

Ala Pro Asn Leu Leu Gly Gly Pro Ser Val Phe
20 25

<210> SEQ ID NO 9
<211> LENGTH: 39
<212> TYPE: PRT
<213> ORGANISM: Homo sapiens

<400> SEQUENCE: 9

Arg Asn Thr Gly Arg Gly Gly Glu Glu Lys Lys Lys Glu Lys Glu Lys
1 5 10 15

Glu Glu Gln Glu Glu Arg Glu Thr Lys Thr Pro Glu Cys Pro Ser His
20 25 30

Thr Gln Pro Leu Gly Val Phe
35

<210> SEQ ID NO 10
<211> LENGTH: 26
<212> TYPE: PRT
<213> ORGANISM: Artificial Sequence
<220> FEATURE:
<223> OTHER INFORMATION: Abatacept hinge

<400> SEQUENCE: 10

Glu Pro Lys Ser Ser Asp Lys Thr His Thr Ser Pro Pro Ser Pro Ala
1 5 10 15

Pro Glu Leu Leu Gly Gly Ser Ser Val Phe
20 25

<210> SEQ ID NO 11
<211> LENGTH: 2
<212> TYPE: PRT
<213> ORGANISM: Artificial Sequence
<220> FEATURE:
<223> OTHER INFORMATION: linker

<400> SEQUENCE: 11

Gly Ser
1

<210> SEQ ID NO 12
<211> LENGTH: 3
<212> TYPE: PRT
<213> ORGANISM: Artificial Sequence
<220> FEATURE:
<223> OTHER INFORMATION: linker

<400> SEQUENCE: 12

Gly Gly Gly
1

<210> SEQ ID NO 13
<211> LENGTH: 994
<212> TYPE: PRT
<213> ORGANISM: Artificial Sequence
<220> FEATURE:
<223> OTHER INFORMATION: fusion protein

<400> SEQUENCE: 13

Ala Gly Pro Arg Ala Pro Cys Ala Ala Ala Cys Thr Cys Ala Gly Asp
1 5 10 15

Ser Leu Asp Cys Gly Gly Arg Gly Leu Ala Ala Leu Pro Gly Asp Leu
20 25 30

Pro Ser Trp Thr Arg Ser Leu Asn Leu Ser Tyr Asn Lys Leu Ser Glu
35 40 45

Ile Asp Pro Ala Gly Phe Glu Asp Leu Pro Asn Leu Gln Glu Val Tyr
50 55 60

Leu Asn Asn Asn Glu Leu Thr Ala Val Pro Ser Leu Gly Ala Ala Ser
65 70 75 80

Ser His Val Val Ser Leu Phe Leu Gln His Asn Lys Ile Arg Ser Val
85 90 95

Glu Gly Ser Gln Leu Lys Ala Tyr Leu Ser Leu Glu Val Leu Asp Leu
100 105 110

Ser Leu Asn Asn Ile Thr Glu Val Arg Asn Thr Cys Phe Pro His Gly
115 120 125

Pro Pro Ile Lys Glu Leu Asn Leu Ala Gly Asn Arg Ile Gly Thr Leu
130 135 140

Glu Leu Gly Ala Phe Asp Gly Leu Ser Arg Ser Leu Leu Thr Leu Arg
145 150 155 160

Leu Ser Lys Asn Arg Ile Thr Gln Leu Pro Val Arg Ala Phe Lys Leu
165 170 175

Pro Arg Leu Thr Gln Leu Asp Leu Asn Arg Asn Arg Ile Arg Leu Ile
180 185 190

Glu Gly Leu Thr Phe Gln Gly Leu Asn Ser Leu Glu Val Leu Lys Leu
195 200 205

Gln Arg Asn Asn Ile Ser Lys Leu Thr Asp Gly Ala Phe Trp Gly Leu
210 215 220

Ser Lys Met His Val Leu His Leu Glu Tyr Asn Ser Leu Val Glu Val
225 230 235 240

Asn Ser Gly Ser Leu Tyr Gly Leu Thr Ala Leu His Gln Leu His Leu
245 250 255

Ser Asn Asn Ser Ile Ala Arg Ile His Arg Lys Gly Trp Ser Phe Cys
260 265 270

Gln Lys Leu His Glu Leu Val Leu Ser Phe Asn Asn Leu Thr Arg Leu
275 280 285

Asp Glu Glu Ser Leu Ala Glu Leu Ser Ser Leu Ser Val Leu Arg Leu
290 295 300

Ser His Asn Ser Ile Ser His Ile Ala Glu Gly Ala Phe Lys Gly Leu
305 310 315 320

Arg Ser Leu Arg Val Leu Asp Leu Asp His Asn Glu Ile Ser Gly Thr
325 330 335

Ile Glu Asp Thr Ser Gly Ala Phe Ser Gly Leu Asp Ser Leu Ser Lys
340 345 350

```
Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Glu Pro Lys Ser Ser Asp
        755                 760                 765

Lys Thr His Thr Ser Pro Pro Cys Pro Ala Pro Glu Leu Leu Gly Gly
```

-continued 770 775 780

Pro Ser Val Phe Leu Phe Pro Pro Lys Pro Lys Asp Thr Leu Met Ile
785 790 795 800

Ser Arg Thr Pro Glu Val Thr Cys Val Val Val Asp Val Ser His Glu
805 810 815

Asp Pro Glu Val Lys Phe Asn Trp Tyr Val Asp Gly Val Glu Val His
820 825 830

Asn Ala Lys Thr Lys Pro Arg Glu Glu Gln Tyr Asn Ser Thr Tyr Arg
835 840 845

Val Val Ser Val Leu Thr Val Leu His Gln Asp Trp Leu Asn Gly Lys
850 855 860

Glu Tyr Lys Cys Lys Val Ser Asn Lys Ala Leu Pro Ala Pro Ile Glu
865 870 875 880

Lys Thr Ile Ser Lys Ala Lys Gly Gln Pro Arg Glu Pro Gln Val Tyr
885 890 895

Thr Leu Pro Pro Ser Arg Asp Glu Leu Thr Lys Asn Gln Val Ser Leu
900 905 910

Thr Cys Leu Val Lys Gly Phe Tyr Pro Ser Asp Ile Ala Val Glu Trp
915 920 925

Glu Ser Asn Gly Gln Pro Glu Asn Asn Tyr Lys Thr Thr Pro Pro Val
930 935 940

Leu Asp Ser Asp Gly Ser Phe Phe Leu Tyr Ser Lys Leu Thr Val Asp
945 950 955 960

Lys Ser Arg Trp Gln Gln Gly Asn Val Phe Ser Cys Ser Val Met His
965 970 975

Glu Ala Leu His Asn His Tyr Thr Gln Lys Ser Leu Ser Leu Ser Pro
980 985 990

Gly Lys

<210> SEQ ID NO 14
<211> LENGTH: 995
<212> TYPE: PRT
<213> ORGANISM: Artificial Sequence
<220> FEATURE:
<223> OTHER INFORMATION: fusion protein

<400> SEQUENCE: 14

Ala Gly Pro Arg Ala Pro Cys Ala Ala Ala Cys Thr Cys Ala Gly Asp
1 5 10 15

Ser Leu Asp Cys Gly Gly Arg Gly Leu Ala Ala Leu Pro Gly Asp Leu
20 25 30

Pro Ser Trp Thr Arg Ser Leu Asn Leu Ser Tyr Asn Lys Leu Ser Glu
35 40 45

Ile Asp Pro Ala Gly Phe Glu Asp Leu Pro Asn Leu Gln Glu Val Tyr
50 55 60

Leu Asn Asn Asn Glu Leu Thr Ala Val Pro Ser Leu Gly Ala Ala Ser
65 70 75 80

Ser His Val Val Ser Leu Phe Leu Gln His Asn Lys Ile Arg Ser Val
85 90 95

Glu Gly Ser Gln Leu Lys Ala Tyr Leu Ser Leu Glu Val Leu Asp Leu
100 105 110

Ser Leu Asn Asn Ile Thr Glu Val Arg Asn Thr Cys Phe Pro His Gly
115 120 125

Pro Pro Ile Lys Glu Leu Asn Leu Ala Gly Asn Arg Ile Gly Thr Leu
130 135 140

```
Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560
```

-continued

```
Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Glu Pro Arg Gly Pro Thr
        755                 760                 765

Ile Lys Pro Cys Pro Pro Cys Lys Cys Pro Ala Pro Asn Leu Leu Gly
    770                 775                 780

Gly Pro Ser Val Phe Leu Phe Pro Pro Lys Pro Lys Asp Thr Leu Met
785                 790                 795                 800

Ile Ser Arg Thr Pro Glu Val Thr Cys Val Val Val Asp Val Ser His
                805                 810                 815

Glu Asp Pro Glu Val Lys Phe Asn Trp Tyr Val Asp Gly Val Glu Val
            820                 825                 830

His Asn Ala Lys Thr Lys Pro Arg Glu Glu Gln Tyr Asn Ser Thr Tyr
        835                 840                 845

Arg Val Val Ser Val Leu Thr Val Leu His Gln Asp Trp Leu Asn Gly
    850                 855                 860

Lys Glu Tyr Lys Cys Lys Val Ser Asn Lys Ala Leu Pro Ala Pro Ile
865                 870                 875                 880

Glu Lys Thr Ile Ser Lys Ala Lys Gly Gln Pro Arg Glu Pro Gln Val
                885                 890                 895

Tyr Thr Leu Pro Pro Ser Arg Asp Glu Leu Thr Lys Asn Gln Val Ser
            900                 905                 910

Leu Thr Cys Leu Val Lys Gly Phe Tyr Pro Ser Asp Ile Ala Val Glu
        915                 920                 925

Trp Glu Ser Asn Gly Gln Pro Glu Asn Asn Tyr Lys Thr Thr Pro Pro
    930                 935                 940

Val Leu Asp Ser Asp Gly Ser Phe Phe Leu Tyr Ser Lys Leu Thr Val
945                 950                 955                 960

Asp Lys Ser Arg Trp Gln Gln Gly Asn Val Phe Ser Cys Ser Val Met
                965                 970                 975

His Glu Ala Leu His Asn His Tyr Thr Gln Lys Ser Leu Ser Leu Ser
```

980 985 990

Pro Gly Lys
995

<210> SEQ ID NO 15
<211> LENGTH: 1007
<212> TYPE: PRT
<213> ORGANISM: Artificial Sequence
<220> FEATURE:
<223> OTHER INFORMATION: fusion protein

<400> SEQUENCE: 15

Ala Gly Pro Arg Ala Pro Cys Ala Ala Ala Cys Thr Cys Ala Gly Asp
1 5 10 15

Ser Leu Asp Cys Gly Gly Arg Gly Leu Ala Ala Leu Pro Gly Asp Leu
20 25 30

Pro Ser Trp Thr Arg Ser Leu Asn Leu Ser Tyr Asn Lys Leu Ser Glu
35 40 45

Ile Asp Pro Ala Gly Phe Glu Asp Leu Pro Asn Leu Gln Glu Val Tyr
50 55 60

Leu Asn Asn Asn Glu Leu Thr Ala Val Pro Ser Leu Gly Ala Ala Ser
65 70 75 80

Ser His Val Val Ser Leu Phe Leu Gln His Asn Lys Ile Arg Ser Val
85 90 95

Glu Gly Ser Gln Leu Lys Ala Tyr Leu Ser Leu Glu Val Leu Asp Leu
100 105 110

Ser Leu Asn Asn Ile Thr Glu Val Arg Asn Thr Cys Phe Pro His Gly
115 120 125

Pro Pro Ile Lys Glu Leu Asn Leu Ala Gly Asn Arg Ile Gly Thr Leu
130 135 140

Glu Leu Gly Ala Phe Asp Gly Leu Ser Arg Ser Leu Leu Thr Leu Arg
145 150 155 160

Leu Ser Lys Asn Arg Ile Thr Gln Leu Pro Val Arg Ala Phe Lys Leu
165 170 175

Pro Arg Leu Thr Gln Leu Asp Leu Asn Arg Asn Arg Ile Arg Leu Ile
180 185 190

Glu Gly Leu Thr Phe Gln Gly Leu Asn Ser Leu Glu Val Leu Lys Leu
195 200 205

Gln Arg Asn Asn Ile Ser Lys Leu Thr Asp Gly Ala Phe Trp Gly Leu
210 215 220

Ser Lys Met His Val Leu His Leu Glu Tyr Asn Ser Leu Val Glu Val
225 230 235 240

Asn Ser Gly Ser Leu Tyr Gly Leu Thr Ala Leu His Gln Leu His Leu
245 250 255

Ser Asn Asn Ser Ile Ala Arg Ile His Arg Lys Gly Trp Ser Phe Cys
260 265 270

Gln Lys Leu His Glu Leu Val Leu Ser Phe Asn Asn Leu Thr Arg Leu
275 280 285

Asp Glu Glu Ser Leu Ala Glu Leu Ser Ser Leu Ser Val Leu Arg Leu
290 295 300

Ser His Asn Ser Ile Ser His Ile Ala Glu Gly Ala Phe Lys Gly Leu
305 310 315 320

Arg Ser Leu Arg Val Leu Asp Leu Asp His Asn Glu Ile Ser Gly Thr
325 330 335

Ile Glu Asp Thr Ser Gly Ala Phe Ser Gly Leu Asp Ser Leu Ser Lys

-continued

```
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Arg Asn Thr Gly Arg Gly
        755                 760                 765
```

-continued

Gly Glu Glu Lys Lys Lys Glu Lys Glu Lys Glu Glu Gln Glu Glu Arg
    770                 775                 780

Glu Thr Lys Thr Pro Glu Cys Pro Ser His Thr Gln Pro Leu Gly Val
785                 790                 795                 800

Phe Leu Phe Pro Pro Lys Pro Lys Asp Thr Leu Met Ile Ser Arg Thr
                805                 810                 815

Pro Glu Val Thr Cys Val Val Val Asp Val Ser His Glu Asp Pro Glu
            820                 825                 830

Val Lys Phe Asn Trp Tyr Val Asp Gly Val Glu Val His Asn Ala Lys
        835                 840                 845

Thr Lys Pro Arg Glu Glu Gln Tyr Asn Ser Thr Tyr Arg Val Val Ser
    850                 855                 860

Val Leu Thr Val Leu His Gln Asp Trp Leu Asn Gly Lys Glu Tyr Lys
865                 870                 875                 880

Cys Lys Val Ser Asn Lys Ala Leu Pro Ala Pro Ile Glu Lys Thr Ile
                885                 890                 895

Ser Lys Ala Lys Gly Gln Pro Arg Glu Pro Gln Val Tyr Thr Leu Pro
            900                 905                 910

Pro Ser Arg Asp Glu Leu Thr Lys Asn Gln Val Ser Leu Thr Cys Leu
        915                 920                 925

Val Lys Gly Phe Tyr Pro Ser Asp Ile Ala Val Glu Trp Glu Ser Asn
    930                 935                 940

Gly Gln Pro Glu Asn Asn Tyr Lys Thr Thr Pro Pro Val Leu Asp Ser
945                 950                 955                 960

Asp Gly Ser Phe Phe Leu Tyr Ser Lys Leu Thr Val Asp Lys Ser Arg
                965                 970                 975

Trp Gln Gln Gly Asn Val Phe Ser Cys Ser Val Met His Glu Ala Leu
            980                 985                 990

His Asn His Tyr Thr Gln Lys Ser  Leu Ser Leu Ser Pro  Gly Lys
        995                 1000                1005

<210> SEQ ID NO 16
<211> LENGTH: 994
<212> TYPE: PRT
<213> ORGANISM: Artificial Sequence
<220> FEATURE:
<223> OTHER INFORMATION: fusion protein

<400> SEQUENCE: 16

Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

-continued

```
Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540
```

-continued

```
Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Glu Pro Lys Ser Ser Asp
        755                 760                 765

Lys Thr His Thr Ser Pro Pro Ser Pro Ala Pro Glu Leu Leu Gly Gly
    770                 775                 780

Ser Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
                805                 810                 815

Asp Pro Glu Val Lys Phe Asn Trp Tyr Val Asp Gly Val Glu Val His
            820                 825                 830

Asn Ala Lys Thr Lys Pro Arg Glu Glu Gln Tyr Asn Ser Thr Tyr Arg
        835                 840                 845

Val Val Ser Val Leu Thr Val Leu His Gln Asp Trp Leu Asn Gly Lys
    850                 855                 860

Glu Tyr Lys Cys Lys Val Ser Asn Lys Ala Leu Pro Ala Pro Ile Glu
865                 870                 875                 880

Lys Thr Ile Ser Lys Ala Lys Gly Gln Pro Arg Glu Pro Gln Val Tyr
                885                 890                 895

Thr Leu Pro Pro Ser Arg Asp Glu Leu Thr Lys Asn Gln Val Ser Leu
            900                 905                 910

Thr Cys Leu Val Lys Gly Phe Tyr Pro Ser Asp Ile Ala Val Glu Trp
        915                 920                 925

Glu Ser Asn Gly Gln Pro Glu Asn Asn Tyr Lys Thr Thr Pro Pro Val
    930                 935                 940

Leu Asp Ser Asp Gly Ser Phe Phe Leu Tyr Ser Lys Leu Thr Val Asp
945                 950                 955                 960

Lys Ser Arg Trp Gln Gln Gly Asn Val Phe Ser Cys Ser Val Met His
```

-continued

```
                965                 970                 975

Glu Ala Leu His Asn His Tyr Thr Gln Lys Ser Leu Ser Leu Ser Pro
            980                 985                 990

Gly Lys


<210> SEQ ID NO 17
<211> LENGTH: 2982
<212> TYPE: DNA
<213> ORGANISM: Artificial Sequence
<220> FEATURE:
<223> OTHER INFORMATION: fusion protein

<400> SEQUENCE: 17

gctgggcctc gggctccttg tgctgccgcc tgcacatgtg caggcgattc cctggactgc     60

ggcggcagag gcctggccgc cctgcctggc gatctgccat cctggacccg gagcctgaac    120

ctgagctaca acaagctgag cgagatcgat cccgccggct ttgaggacct gcctaacctg    180

caggaggtgt atctgaacaa taacgagctg accgcggtac catccctggg cgctgcttca    240

tcacatgtcg tctctctctt tctgcagcac aacaagattc gcagcgtgga ggggagccag    300

ctgaaggcct acctttcctt agaagtgtta gatctgagtt tgaacaacat cacggaagtg    360

cggaacacct gctttccaca cggaccgcct ataaaggagc tcaacctggc aggcaatcgg    420

attggcaccc tggagttggg agcatttgat ggtctgtcac ggtcgctgct aactcttcgc    480

ctgagcaaaa acaggatcac ccagcttcct gtaagagcat tcaagctacc caggctgaca    540

caactggacc tcaatcggaa caggattcgg ctgatagagg gcctcacctt ccaggggctc    600

aacagcttgg aggtgctgaa gcttcagcga aacaacatca gcaaactgac agatggggcc    660

ttctggggac tgtccaagat gcatgtgctg cacctggagt acaacagcct ggtagaagtg    720

aacagcggct cgctctacgg cctcacggcc ctgcatcagc tccacctcag caacaattcc    780

atcgctcgca ttcaccgcaa gggctggagc ttctgccaga agctgcatga gttggtcctg    840

tccttcaaca acctgacacg gctggacgag gagagcctgg ccgagctgag cagcctgagt    900

gtcctgcgtc tcagccacaa ttccatcagc cacattgcgg agggtgcctt caagggactc    960

aggagcctgc gagtcttgga tctggaccat aacgagattt cgggcacaat agaggacacg   1020

agcggcgcct tctcagggct cgacagcctc agcaagctga ctctgtttgg aaacaagatc   1080

aagtctgtgg ctaagagagc attctcgggg ctggaaggcc tggagcacct gaaccttgga   1140

gggaatgcga tcagatctgt ccagtttgat gcctttgtga agatgaagaa tcttaaagag   1200

ctccatatca gcagcgacag cttcctgtgt gactgccagc tgaagtggct gccccgtgg   1260

ctaattggca ggatgctgca ggcctttgtg acagccacct gtgcccaccc agaatcactg   1320

aagggtcaga gcattttctc tgtgccacca gagagtttcg tgtgcgatga cttcctgaag   1380

ccacagatca tcacccagcc agaaaccacc atggctatgg tgggcaagga catccggttt   1440

acatgctcag cagccagcag cagcagctcc cccatgacct ttgcctggaa gaaagacaat   1500

gaagtcctga ccaatgcaga catggagaac tttgtccacg tccacgcgca ggacggggaa   1560

gtgatggagt acaccaccat cctgcacctc cgtcaggtca ctttcgggca cgagggccgc   1620

taccaatgtg tcatcaccaa ccactttggc tccacctatt cacataaggc caggctcacc   1680

gtgaatgtgt tgccatcatt caccaaaacg ccccacgaca taaccatccg gaccaccacc   1740

gtggcccgcc tcgaatgtgc tgccacaggt cacccaaacc ctcagattgc ctggcagaag   1800

gatggaggca cggatttccc cgctgcccgt gagcgacgca tgcatgtcat gccggatgac   1860
```

```
gacgtgtttt tcatcactga tgtgaaaata gatgacgcag gggtttacag ctgtactgct   1920
cagaactcag ccggttctat ttcagctaat gccaccctga ctgtcctaga gaccccatcc   1980
ttggtggtcc ccttggaaga ccgtgtggta tctgtgggag aaacagtggc cctccaatgc   2040
aaagccacgg ggaaccctcc gccccgcatc acctggttca aggggaccg  cccgctgagc   2100
ctcactgagc ggcaccacct gacccctgac aaccagctcc tggtggttca gaacgtggtg   2160
gcagaggatg cgggccgata tacctgtgag atgtccaaca ccctgggcac ggagcgagct   2220
cacagccagc tgagcgtcct gcccgcagca ggctgcagga aggatgggac cacggtaggc   2280
atcttcgagc caaagtcctc tgataagaca cacacctctc caccatgccc agcaccagag   2340
ctgctgggag gaccaagcgt gttcctgttt cctccaaagc ccaaggacac actgatgatc   2400
tccaggacac cagaggtgac ctgcgtggtg gtggacgtga gccacgagga ccccgaggtg   2460
aagttcaact ggtacgtgga tggcgtggag gtgcacaatg ccaagaccaa gcccagagag   2520
gagcagtaca actctaccta tagggtggtg agcgtgctga cagtgctgca ccaggactgg   2580
ctgaacggca aggagtataa gtgcaaggtg agcaataagg ccctgcctgc cccaatcgag   2640
aagacaatct ccaaggccaa gggccagcca agagagcccc aggtgtacac cctgccccct   2700
agcagggatg agctgacaaa gaaccaggtg tccctgacct gtctggtgaa gggcttttat   2760
ccctccgaca tcgccgtgga gtgggagtct aatggccagc ctgagaataa ctacaagaca   2820
accccacccg tgctggattc tgacggcagc ttctttctgt attctaagct gaccgtggac   2880
aagagcaggt ggcagcaggg caacgtgttc agctgctccg tgatgcacga agcactgcac   2940
aatcactaca cccagaaatc actgtcactg agccctggca aa                      2982
```

```
<210> SEQ ID NO 18
<211> LENGTH: 2985
<212> TYPE: DNA
<213> ORGANISM: Artificial Sequence
<220> FEATURE:
<223> OTHER INFORMATION: fusion protein

<400> SEQUENCE: 18
```

```
gctgggcctc gggctccttg tgctgccgcc tgcacatgtg caggcgattc cctggactgc     60
ggcggcagag gcctggccgc cctgcctggc gatctgccat cctggacccg gagcctgaac    120
ctgagctaca acaagctgag cgagatcgat cccgccggct ttgaggacct gcctaacctg    180
caggaggtgt atctgaacaa taacgagctg accgcggtac catccctggg cgctgcttca    240
tcacatgtcg tctctctctt tctgcagcac aacaagattc gcagcgtgga ggggagccag    300
ctgaaggcct acctttcctt agaagtgtta gatctgagtt tgaacaacat cacggaagtg    360
cggaacacct gctttccaca cggaccgcct ataaaggagc tcaacctggc aggcaatcgg    420
attggcaccc tggagttggg agcatttgat ggtctgtcac ggtcgctgct aactcttcgc    480
ctgagcaaaa acaggatcac ccagcttcct gtaagagcat tcaagctacc caggctgaca    540
caactggacc tcaatcggaa caggattcgg ctgatagagg gcctcacctt ccaggggctc    600
aacagcttgg aggtgctgaa gcttcagcga aacaacatca gcaaactgac agatggggcc    660
ttctggggac tgtccaagat gcatgtgctg cacctggagt acaacagcct ggtagaagtg    720
aacagcggct cgctctacgg cctcacggcc ctgcatcagc tccacctcag caacaattcc    780
atcgctcgca ttcaccgcaa gggctggagc ttctgccaga agctgcatga gttggtcctg    840
tccttcaaca acctgacacg gctggacgag gagagcctgg ccgagctgag cagcctgagt    900
gtcctgcgtc tcagccacaa ttccatcagc cacattgcgg agggtgcctt caagggactc    960
```

```
aggagcctgc gagtcttgga tctggaccat aacgagattt cgggcacaat agaggacacg   1020
agcggcgcct tctcagggct cgacagcctc agcaagctga ctctgtttgg aaacaagatc   1080
aagtctgtgg ctaagagagc attctcgggg ctggaaggcc tggagcacct gaaccttgga   1140
gggaatgcga tcagatctgt ccagtttgat gcctttgtga agatgaagaa tcttaaagag   1200
ctccatatca gcagcgacag cttcctgtgt gactgccagc tgaagtggct gcccccgtgg   1260
ctaattggca ggatgctgca ggcctttgtg acagccacct gtgcccaccc agaatcactg   1320
aagggtcaga gcattttctc tgtgccacca gagagtttcg tgtgcgatga cttcctgaag   1380
ccacagatca tcacccagcc agaaaccacc atggctatgg tgggcaagga catccggttt   1440
acatgctcag cagccagcag cagcagctcc cccatgacct ttgcctggaa gaaagacaat   1500
gaagtcctga ccaatgcaga catggagaac tttgtccacg tccacgcgca ggacggggaa   1560
gtgatggagt acaccaccat cctgcacctc cgtcaggtca ctttcgggca cgagggccgc   1620
taccaatgtg tcatcaccaa ccactttggc tccacctatt cacataaggc caggctcacc   1680
gtgaatgtgt tgccatcatt caccaaaacg ccccacgaca taaccatccg gaccaccacc   1740
gtggcccgcc tcgaatgtgc tgccacaggt cacccaaacc ctcagattgc ctggcagaag   1800
gatggaggca cggatttccc cgctgcccgt gagcgacgca tgcatgtcat gccggatgac   1860
gacgtgtttt tcatcactga tgtgaaaata gatgacgcag ggtttacag ctgtactgct   1920
cagaactcag ccggttctat ttcagctaat gccaccctga ctgtcctaga gaccccatcc   1980
ttggtggtcc ccttggaaga ccgtgtggta tctgtgggag aaacagtggc cctccaatgc   2040
aaagccacgg ggaaccctcc gccccgcatc acctggttca aggggaccg cccgctgagc   2100
ctcactgagc ggcaccacct gacccctgac aaccagctcc tggtggttca gaacgtggtg   2160
gcagaggatg cgggccgata tacctgtgag atgtccaaca ccctgggcac ggagcgagct   2220
cacagccagc tgagcgtcct gcccgcagca ggctgcagga aggatgggac cacggtaggc   2280
atcttcgagc ctcggggccc taccatcaag ccctgccccc cttgcaagtg ccctgcccct   2340
aatctgctgg gcggaccctc cgtgttcctg tttcctccaa agcccaagga cacactgatg   2400
atctccagga caccagaggt gacctgcgtg gtggtggacg tgagccacga ggaccccgag   2460
gtgaagttca actggtacgt ggatggcgtg gaggtgcaca atgccaagac caagcccaga   2520
gaggagcagt acaactctac ctatagggtg gtgagcgtgc tgacagtgct gcaccaggac   2580
tggctgaacg gcaaggagta taagtgcaag gtgagcaata aggccctgcc tgccccaatc   2640
gagaagacaa tctccaaggc caagggccag ccaagagagc cccaggtgta caccctgccc   2700
cctagcaggg atgagctgac aaagaaccag gtgtccctga cctgtctggt gaagggcttt   2760
tatccctccg acatcgccgt ggagtgggag tctaatggcc agcctgagaa taactacaag   2820
acaaccccac ccgtgctgga ttctgacggc agcttctttc tgtattctaa gctgaccgtg   2880
gacaagagca ggtggcagca gggcaacgtg ttcagctgct ccgtgatgca cgaagcactg   2940
cacaatcact acacccagaa atcactgtca ctgagccctg gcaaa                   2985
```

<210> SEQ ID NO 19
<211> LENGTH: 3021
<212> TYPE: DNA
<213> ORGANISM: Artificial Sequence
<220> FEATURE:
<223> OTHER INFORMATION: fusion protein

<400> SEQUENCE: 19

-continued

```
gctgggcctc gggctccttg tgctgccgcc tgcacatgtg caggcgattc cctggactgc     60
ggcggcagag gcctggccgc cctgcctggc gatctgccat cctggacccg gagcctgaac    120
ctgagctaca acaagctgag cgagatcgat cccgccggct ttgaggacct gcctaacctg    180
caggaggtgt atctgaacaa taacgagctg accgcggtac catccctggg cgctgcttca    240
tcacatgtcg tctctctctt tctgcagcac aacaagattc gcagcgtgga ggggagccag    300
ctgaaggcct acctttcctt agaagtgtta gatctgagtt tgaacaacat cacggaagtg    360
cggaacacct gctttccaca cggaccgcct ataaaggagc tcaacctggc aggcaatcgg    420
attggcaccc tggagttggg agcatttgat ggtctgtcac ggtcgctgct aactcttcgc    480
ctgagcaaaa acaggatcac ccagcttcct gtaagagcat tcaagctacc caggctgaca    540
caactggacc tcaatcggaa caggattcgg ctgatagagg gcctcacctt ccaggggctc    600
aacagcttgg aggtgctgaa gcttcagcga aacaacatca gcaaactgac agatggggcc    660
ttctggggac tgtccaagat gcatgtgctg cacctggagt acaacagcct ggtagaagtg    720
aacagcggct cgctctacgg cctcacggcc ctgcatcagc tccacctcag caacaattcc    780
atcgctcgca ttcaccgcaa gggctggagc ttctgccaga agctgcatga gttggtcctg    840
tccttcaaca acctgacacg gctggacgag gagagcctgg ccgagctgag cagcctgagt    900
gtcctgcgtc tcagccacaa ttccatcagc cacattgcgg agggtgcctt caagggactc    960
aggagcctgc gagtcttgga tctggaccat aacgagattt cgggcacaat agaggacacg   1020
agcggcgcct tctcagggct cgacagcctc agcaagctga ctctgtttgg aaacaagatc   1080
aagtctgtgg ctaagagagc attctcgggg ctggaaggcc tggagcacct gaaccttgga   1140
gggaatgcga tcagatctgt ccagtttgat gcctttgtga agatgaagaa tcttaaagag   1200
ctccatatca gcagcgacag cttcctgtgt gactgccagc tgaagtggct gcccccgtgg   1260
ctaattggca ggatgctgca ggcctttgtg acagccacct gtgcccaccc agaatcactg   1320
aagggtcaga gcattttctc tgtgccacca gagagtttcg tgtgcgatga cttcctgaag   1380
ccacagatca tcacccagcc agaaaccacc atggctatgg tgggcaagga catccggttt   1440
acatgctcag cagccagcag cagcagctcc cccatgacct ttgcctggaa gaaagacaat   1500
gaagtcctga ccaatgcaga catggagaac tttgtccacg tccacgcgca ggacggggaa   1560
gtgatggagt acaccaccat cctgcacctc cgtcaggtca ctttcgggca cgagggccgc   1620
taccaatgtg tcatcaccaa ccactttggc tccacctatt cacataaggc caggctcacc   1680
gtgaatgtgt tgccatcatt caccaaaacg ccccacgaca taaccatccg gaccaccacc   1740
gtggcccgcc tcgaatgtgc tgccacaggt cacccaaacc ctcagattgc ctggcagaag   1800
gatggaggca cggatttccc cgctgcccgt gagcgacgca tgcatgtcat gccggatgac   1860
gacgtgtttt tcatcactga tgtgaaaata gatgacgcag gggtttacag ctgtactgct   1920
cagaactcag ccggttctat ttcagctaat gccaccctga ctgtcctaga gaccccatcc   1980
ttggtggtcc ccttggaaga ccgtgtggta tctgtgggag aaacagtggc cctccaatgc   2040
aaagccacgg ggaaccctcc gccccgcatc acctggttca agggggaccg cccgctgagc   2100
ctcactgagc ggcaccacct gacccctgac aaccagctcc tggtggttca gaacgtggtg   2160
gcagaggatg cgggccgata tacctgtgag atgtccaaca ccctgggcac ggagcgagct   2220
cacagccagc tgagcgtcct gcccgcagca ggctgcagga aggatgggac cacggtaggc   2280
atcttccgca acaccggccg cggcggcgag gagaagaaga aggagaagga gaaggaggag   2340
caggaggagc gcgagaccaa gacccccgag tgccccagcc acacccagcc cctgggcgtg   2400
```

ttcctgtttc ctccaaagcc caaggacaca ctgatgatct ccaggacacc agaggtgacc 2460
tgcgtggtgg tggacgtgag ccacgaggac cccgaggtga agttcaactg gtacgtggat 2520
ggcgtggagg tgcacaatgc caagaccaag cccagagagg agcagtacaa ctctacctat 2580
agggtggtga gcgtgctgac agtgctgcac caggactggc tgaacggcaa ggagtataag 2640
tgcaaggtga gcaataaggc cctgcctgcc ccaatcgaga agacaatctc caaggccaag 2700
ggccagccaa gagagcccca ggtgtacacc ctgcccccta gcagggatga gctgacaaag 2760
aaccaggtgt ccctgacctg tctggtgaag ggcttttatc cctccgacat cgccgtggag 2820
tgggagtcta atggccagcc tgagaataac tacaagacaa ccccacccgt gctggattct 2880
gacggcagct tctttctgta ttctaagctg accgtggaca agagcaggtg gcagcagggc 2940
aacgtgttca gctgctccgt gatgcacgaa gcactgcaca atcactacac ccagaaatca 3000
ctgtcactga gccctggcaa a 3021

<210> SEQ ID NO 20
<211> LENGTH: 2982
<212> TYPE: DNA
<213> ORGANISM: Artificial Sequence
<220> FEATURE:
<223> OTHER INFORMATION: fusion protein

<400> SEQUENCE: 20
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cgggcacaat agaggacacg 1020
agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260
ctaattggca ggatgctgca ggcctttgtg acagccacct gtgcccaccc agaatcactg 1320
aagggtcaga gcattttctc tgtgccacca gagagtttcg tgtgcgatga cttcctgaag 1380

-continued

```
ccacagatca tcacccagcc agaaaccacc atggctatgg tgggcaagga catccggttt   1440

acatgctcag cagccagcag cagcagctcc cccatgacct ttgcctggaa gaaagacaat   1500

gaagtcctga ccaatgcaga catggagaac tttgtccacg tccacgcgca ggacggggaa   1560

gtgatggagt acaccaccat cctgcacctc cgtcaggtca ctttcgggca cgagggccgc   1620

taccaatgtg tcatcaccaa ccactttggc tccacctatt cacataaggc caggctcacc   1680

gtgaatgtgt tgccatcatt caccaaaacg ccccacgaca taaccatccg gaccaccacc   1740

gtggcccgcc tcgaatgtgc tgccacaggt cacccaaacc ctcagattgc ctggcagaag   1800

gatggaggca cggatttccc cgctgcccgt gagcgacgca tgcatgtcat gccggatgac   1860

gacgtgtttt tcatcactga tgtgaaaata gatgacgcag ggtttacag ctgtactgct   1920

cagaactcag ccggttctat ttcagctaat gccaccctga ctgtcctaga gaccccatcc   1980

ttggtggtcc ccttggaaga ccgtgtggta tctgtgggag aaacagtggc cctccaatgc   2040

aaagccacgg ggaaccctcc gccccgcatc acctggttca aggggggaccg cccgctgagc   2100

ctcactgagc ggcaccacct gacccctgac aaccagctcc tggtggttca gaacgtggtg   2160

gcagaggatg cgggccgata tacctgtgag atgtccaaca ccctgggcac ggagcgagct   2220

cacagccagc tgagcgtcct gcccgcagca ggctgcagga aggatgggac cacggtaggc   2280

atcttcgaac cgaaatcttc tgacaaaacc cacacctctc cgccgtctcc ggctccggaa   2340

ctgctgggtg gttcttctgt tttcctgttt cctccaaagc ccaaggacac actgatgatc   2400

tccaggacac cagaggtgac ctgcgtggtg gtggacgtga gccacgagga ccccgaggtg   2460

aagttcaact ggtacgtgga tggcgtggag gtgcacaatg ccaagaccaa gcccagagag   2520

gagcagtaca actctaccta tagggtggtg agcgtgctga cagtgctgca ccaggactgg   2580

ctgaacggca aggagtataa gtgcaaggtg agcaataagg ccctgcctgc cccaatcgag   2640

aagacaatct ccaaggccaa gggccagcca agagagcccc aggtgtacac cctgccccct   2700

agcagggatg agctgacaaa gaaccaggtg tccctgacct gtctggtgaa gggcttttat   2760

ccctccgaca tcgccgtgga gtgggagtct aatggccagc ctgagaataa ctacaagaca   2820

accccacccg tgctggattc tgacggcagc ttctttctgt attctaagct gaccgtggac   2880

aagagcaggt ggcagcaggg caacgtgttc agctgctccg tgatgcacga agcactgcac   2940

aatcactaca cccagaaatc actgtcactg agccctggca aa                     2982
```

<210> SEQ ID NO 21
<211> LENGTH: 992
<212> TYPE: PRT
<213> ORGANISM: Artificial Sequence
<220> FEATURE:
<223> OTHER INFORMATION: fusion protein

<400> SEQUENCE: 21

```
Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80
```

-continued

```
Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
```

-continued

```
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Glu Pro Lys Ser Ser Asp Lys Thr
        755                 760                 765

His Thr Ser Pro Pro Cys Pro Ala Pro Glu Leu Leu Gly Gly Pro Ser
    770                 775                 780

Val Phe Leu Phe Pro Pro Lys Pro Lys Asp Thr Leu Met Ile Ser Arg
785                 790                 795                 800

Thr Pro Glu Val Thr Cys Val Val Val Asp Val Ser His Glu Asp Pro
                805                 810                 815

Glu Val Lys Phe Asn Trp Tyr Val Asp Gly Val Glu Val His Asn Ala
            820                 825                 830

Lys Thr Lys Pro Arg Glu Glu Gln Tyr Asn Ser Thr Tyr Arg Val Val
        835                 840                 845

Ser Val Leu Thr Val Leu His Gln Asp Trp Leu Asn Gly Lys Glu Tyr
    850                 855                 860

Lys Cys Lys Val Ser Asn Lys Ala Leu Pro Ala Pro Ile Glu Lys Thr
865                 870                 875                 880

Ile Ser Lys Ala Lys Gly Gln Pro Arg Glu Pro Gln Val Tyr Thr Leu
                885                 890                 895

Pro Pro Ser Arg Asp Glu Leu Thr Lys Asn Gln Val Ser Leu Thr Cys
            900                 905                 910

Leu Val Lys Gly Phe Tyr Pro Ser Asp Ile Ala Val Glu Trp Glu Ser
        915                 920                 925
```

```
Asn Gly Gln Pro Glu Asn Asn Tyr Lys Thr Thr Pro Pro Val Leu Asp
    930                 935                 940

Ser Asp Gly Ser Phe Phe Leu Tyr Ser Lys Leu Thr Val Asp Lys Ser
945                 950                 955                 960

Arg Trp Gln Gln Gly Asn Val Phe Ser Cys Ser Val Met His Glu Ala
                965                 970                 975

Leu His Asn His Tyr Thr Gln Lys Ser Leu Ser Leu Ser Pro Gly Lys
            980                 985                 990


<210> SEQ ID NO 22
<211> LENGTH: 993
<212> TYPE: PRT
<213> ORGANISM: Artificial Sequence
<220> FEATURE:
<223> OTHER INFORMATION: fusion protein

<400> SEQUENCE: 22

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300
```

```
Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720
```

Val Met Ile Asp Asp Ala Gly Arg Tyr Thr Cys Glu Met Ser Asn Pro
725 730 735

Leu Gly Thr Glu Arg Ala His Ser Gln Leu Ser Ile Leu Pro Thr Pro
740 745 750

Gly Cys Arg Lys Asp Gly Thr Thr Glu Pro Arg Gly Pro Thr Ile Lys
755 760 765

Pro Cys Pro Pro Cys Lys Cys Pro Ala Pro Asn Leu Leu Gly Gly Pro
770 775 780

Ser Val Phe Leu Phe Pro Pro Lys Pro Lys Asp Thr Leu Met Ile Ser
785 790 795 800

Arg Thr Pro Glu Val Thr Cys Val Val Val Asp Val Ser His Glu Asp
805 810 815

Pro Glu Val Lys Phe Asn Trp Tyr Val Asp Gly Val Glu Val His Asn
820 825 830

Ala Lys Thr Lys Pro Arg Glu Glu Gln Tyr Asn Ser Thr Tyr Arg Val
835 840 845

Val Ser Val Leu Thr Val Leu His Gln Asp Trp Leu Asn Gly Lys Glu
850 855 860

Tyr Lys Cys Lys Val Ser Asn Lys Ala Leu Pro Ala Pro Ile Glu Lys
865 870 875 880

Thr Ile Ser Lys Ala Lys Gly Gln Pro Arg Glu Pro Gln Val Tyr Thr
885 890 895

Leu Pro Pro Ser Arg Asp Glu Leu Thr Lys Asn Gln Val Ser Leu Thr
900 905 910

Cys Leu Val Lys Gly Phe Tyr Pro Ser Asp Ile Ala Val Glu Trp Glu
915 920 925

Ser Asn Gly Gln Pro Glu Asn Asn Tyr Lys Thr Thr Pro Pro Val Leu
930 935 940

Asp Ser Asp Gly Ser Phe Phe Leu Tyr Ser Lys Leu Thr Val Asp Lys
945 950 955 960

Ser Arg Trp Gln Gln Gly Asn Val Phe Ser Cys Ser Val Met His Glu
965 970 975

Ala Leu His Asn His Tyr Thr Gln Lys Ser Leu Ser Leu Ser Pro Gly
980 985 990

Lys

<210> SEQ ID NO 23
<211> LENGTH: 1005
<212> TYPE: PRT
<213> ORGANISM: Artificial Sequence
<220> FEATURE:
<223> OTHER INFORMATION: fusion protein

<400> SEQUENCE: 23

Ala Gln Ala Gly Pro Arg Ala Pro Cys Ala Ala Ala Cys Thr Cys Ala
1 5 10 15

Gly Asp Ser Leu Asp Cys Ser Gly Arg Gly Leu Ala Thr Leu Pro Arg
20 25 30

Asp Leu Pro Ser Trp Thr Arg Ser Leu Asn Leu Ser Tyr Asn Arg Leu
35 40 45

Ser Glu Ile Asp Ser Ala Ala Phe Glu Asp Leu Thr Asn Leu Gln Glu
50 55 60

Val Tyr Leu Asn Ser Asn Glu Leu Thr Ala Ile Pro Ser Leu Gly Ala
65 70 75 80

Ala Ser Ile Gly Val Val Ser Leu Phe Leu Gln His Asn Lys Ile Leu

-continued

```
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510
```

```
Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Arg Asn Thr Gly Arg Gly Gly Glu
        755                 760                 765

Glu Lys Lys Lys Glu Lys Glu Lys Glu Glu Gln Glu Glu Arg Glu Thr
    770                 775                 780

Lys Thr Pro Glu Cys Pro Ser His Thr Gln Pro Leu Gly Val Phe Leu
785                 790                 795                 800

Phe Pro Pro Lys Pro Lys Asp Thr Leu Met Ile Ser Arg Thr Pro Glu
                805                 810                 815

Val Thr Cys Val Val Val Asp Val Ser His Glu Asp Pro Glu Val Lys
            820                 825                 830

Phe Asn Trp Tyr Val Asp Gly Val Glu Val His Asn Ala Lys Thr Lys
        835                 840                 845

Pro Arg Glu Glu Gln Tyr Asn Ser Thr Tyr Arg Val Val Ser Val Leu
    850                 855                 860

Thr Val Leu His Gln Asp Trp Leu Asn Gly Lys Glu Tyr Lys Cys Lys
865                 870                 875                 880

Val Ser Asn Lys Ala Leu Pro Ala Pro Ile Glu Lys Thr Ile Ser Lys
                885                 890                 895

Ala Lys Gly Gln Pro Arg Glu Pro Gln Val Tyr Thr Leu Pro Pro Ser
            900                 905                 910

Arg Asp Glu Leu Thr Lys Asn Gln Val Ser Leu Thr Cys Leu Val Lys
        915                 920                 925
```

```
Gly Phe Tyr Pro Ser Asp Ile Ala Val Glu Trp Glu Ser Asn Gly Gln
    930                 935                 940

Pro Glu Asn Asn Tyr Lys Thr Thr Pro Pro Val Leu Asp Ser Asp Gly
945                 950                 955                 960

Ser Phe Phe Leu Tyr Ser Lys Leu Thr Val Asp Lys Ser Arg Trp Gln
                965                 970                 975

Gln Gly Asn Val Phe Ser Cys Ser Val Met His Glu Ala Leu His Asn
            980                 985                 990

His Tyr Thr Gln Lys Ser Leu Ser  Leu Ser Pro Gly Lys
        995                 1000                1005


<210> SEQ ID NO 24
<211> LENGTH: 992
<212> TYPE: PRT
<213> ORGANISM: Artificial Sequence
<220> FEATURE:
<223> OTHER INFORMATION: fusion protein

<400> SEQUENCE: 24

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285
```

```
Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
```

-continued

```
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Glu Pro Lys Ser Ser Asp Lys Thr
        755                 760                 765

His Thr Ser Pro Pro Ser Pro Ala Pro Glu Leu Leu Gly Gly Ser Ser
    770                 775                 780

Val Phe Leu Phe Pro Pro Lys Pro Lys Asp Thr Leu Met Ile Ser Arg
785                 790                 795                 800

Thr Pro Glu Val Thr Cys Val Val Val Asp Val Ser His Glu Asp Pro
                805                 810                 815

Glu Val Lys Phe Asn Trp Tyr Val Asp Gly Val Glu Val His Asn Ala
            820                 825                 830

Lys Thr Lys Pro Arg Glu Glu Gln Tyr Asn Ser Thr Tyr Arg Val Val
        835                 840                 845

Ser Val Leu Thr Val Leu His Gln Asp Trp Leu Asn Gly Lys Glu Tyr
    850                 855                 860

Lys Cys Lys Val Ser Asn Lys Ala Leu Pro Ala Pro Ile Glu Lys Thr
865                 870                 875                 880

Ile Ser Lys Ala Lys Gly Gln Pro Arg Glu Pro Gln Val Tyr Thr Leu
                885                 890                 895

Pro Pro Ser Arg Asp Glu Leu Thr Lys Asn Gln Val Ser Leu Thr Cys
            900                 905                 910

Leu Val Lys Gly Phe Tyr Pro Ser Asp Ile Ala Val Glu Trp Glu Ser
        915                 920                 925

Asn Gly Gln Pro Glu Asn Asn Tyr Lys Thr Thr Pro Pro Val Leu Asp
    930                 935                 940

Ser Asp Gly Ser Phe Phe Leu Tyr Ser Lys Leu Thr Val Asp Lys Ser
945                 950                 955                 960

Arg Trp Gln Gln Gly Asn Val Phe Ser Cys Ser Val Met His Glu Ala
                965                 970                 975

Leu His Asn His Tyr Thr Gln Lys Ser Leu Ser Leu Ser Pro Gly Lys
            980                 985                 990


<210> SEQ ID NO 25
<211> LENGTH: 2976
<212> TYPE: DNA
<213> ORGANISM: Artificial Sequence
<220> FEATURE:
<223> OTHER INFORMATION: fusion protein

<400> SEQUENCE: 25

gctcaggctg gacctagggc tccttgcgct gccgcctgca cctgtgcagg cgattctctg      60

gactgcagcg gccggggcct ggccacactg cccagggacc tgccttcctg gaccagatct     120

ctgaacctga gctacaatcg gctgtccgag atcgattctg ccgcctttga ggacctgaca     180

aatctgcagg aggtgtatct gaacagcaat gagctgaccg caatcccctc cctgggagca     240

gcctctatcg gcgtggtgag cctgttcctg cagcacaaca agatcctgag cgtggatggc     300

tcccagctga agagctacct gtctctggag gtgctggacc tgagctccaa caatatcacc     360

gagatcagat ctagctgttt tcctaatggc ctgcggatca gagagctgaa cctggcctct     420

aatcggatca gcatcctgga gtccggcgcc ttcgatggcc tgagcagatc cctgctgaca     480
```

-continued

```
ctgcgcctgt ccaagaaccg gatcacccag ctgcccgtga aggcctttaa gctgcctagg    540
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
gagccaaagt cctctgataa gacacacacc tctccaccat gcccagcacc agagctgctg   2340
ggaggaccaa gcgtgttcct gtttcctcca aagcccaagg acacactgat gatctccagg   2400
acaccagagg tgacctgcgt ggtggtggac gtgagccacg aggaccccga ggtgaagttc   2460
aactggtacg tggatggcgt ggaggtgcac aatgccaaga ccaagcccag agaggagcag   2520
tacaactcta cctatagggt ggtgagcgtg ctgacagtgc tgcaccagga ctggctgaac   2580
ggcaaggagt ataagtgcaa ggtgagcaat aaggccctgc ctgccccaat cgagaagaca   2640
atctccaagg ccaagggcca gccaagagag ccccaggtgt acaccctgcc ccctagcagg   2700
gatgagctga caaagaacca ggtgtccctg acctgtctgg tgaagggctt ttatccctcc   2760
gacatcgccg tggagtggga gtctaatggc cagcctgaga ataactacaa gacaacccca   2820
cccgtgctgg attctgacgg cagcttcttt ctgtattcta agctgaccgt ggacaagagc   2880
```

aggtggcagc agggcaacgt gttcagctgc tccgtgatgc acgaagcact gcacaatcac 2940
tacacccaga aatcactgtc actgagccct ggcaaa 2976

<210> SEQ ID NO 26
<211> LENGTH: 2979
<212> TYPE: DNA
<213> ORGANISM: Artificial Sequence
<220> FEATURE:
<223> OTHER INFORMATION: fusion protein

<400> SEQUENCE: 26
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
gagcctcggg gccctaccat caagccctgc cccccttgca agtgccctgc ccctaatctg 2340
ctgggcggac cctccgtgtt cctgtttcct ccaaagccca aggacacact gatgatctcc 2400
aggacaccag aggtgacctg cgtggtggtg gacgtgagcc acgaggaccc cgaggtgaag 2460
ttcaactggt acgtggatgg cgtggaggtg cacaatgcca agaccaagcc cagagaggag 2520
cagtacaact ctacctatag ggtggtgagc gtgctgacag tgctgcacca ggactggctg 2580
aacggcaagg agtataagtg caaggtgagc aataaggccc tgcctgcccc aatcgagaag 2640
acaatctcca aggccaaggg ccagccaaga gagccccagg tgtacaccct gccccctagc 2700
agggatgagc tgacaaagaa ccaggtgtcc ctgacctgtc tggtgaaggg cttttatccc 2760
tccgacatcg ccgtggagtg ggagtctaat ggccagcctg agaataacta caagacaacc 2820
ccacccgtgc tggattctga cggcagcttc tttctgtatt ctaagctgac cgtggacaag 2880
agcaggtggc agcagggcaa cgtgttcagc tgctccgtga tgcacgaagc actgcacaat 2940
cactacaccc agaaatcact gtcactgagc cctggcaaa 2979

<210> SEQ ID NO 27
<211> LENGTH: 3015
<212> TYPE: DNA
<213> ORGANISM: Artificial Sequence
<220> FEATURE:
<223> OTHER INFORMATION: fusion protein

<400> SEQUENCE: 27
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020

```
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
cgcaacaccg gccgcggcgg cgaggagaag aagaaggaga aggagaagga ggagcaggag   2340
gagcgcgaga ccaagacccc cgagtgcccc agccacaccc agcccctggg cgtgttcctg   2400
tttcctccaa agcccaagga cacactgatg atctccagga caccagaggt gacctgcgtg   2460
gtggtggacg tgagccacga ggaccccgag gtgaagttca actggtacgt ggatggcgtg   2520
gaggtgcaca atgccaagac caagcccaga gaggagcagt acaactctac ctatagggtg   2580
gtgagcgtgc tgacagtgct gcaccaggac tggctgaacg gcaaggagta taagtgcaag   2640
gtgagcaata aggccctgcc tgccccaatc gagaagacaa tctccaaggc caagggccag   2700
ccaagagagc cccaggtgta caccctgccc cctagcaggg atgagctgac aaagaaccag   2760
gtgtccctga cctgtctggt gaagggcttt tatccctccg acatcgccgt ggagtgggag   2820
tctaatggcc agcctgagaa taactacaag acaaccccac ccgtgctgga ttctgacggc   2880
agcttctttc tgtattctaa gctgaccgtg gacaagagca ggtggcagca gggcaacgtg   2940
ttcagctgct ccgtgatgca cgaagcactg cacaatcact acacccagaa atcactgtca   3000
ctgagccctg gcaaa                                                    3015
```

<210> SEQ ID NO 28
<211> LENGTH: 2976
<212> TYPE: DNA
<213> ORGANISM: Artificial Sequence
<220> FEATURE:
<223> OTHER INFORMATION: fusion protein

<400> SEQUENCE: 28

-continued

```
gctcaggctg gacctagggc tccttgcgct gccgcctgca cctgtgcagg cgattctctg     60
gactgcagcg gccggggcct ggccacactg cccagggacc tgccttcctg gaccagatct    120
ctgaacctga gctacaatcg gctgtccgag atcgattctg ccgcctttga ggacctgaca    180
aatctgcagg aggtgtatct gaacagcaat gagctgaccg caatcccctc cctgggagca    240
gcctctatcg gcgtggtgag cctgttcctg cagcacaaca agatcctgag cgtggatggc    300
tcccagctga agagctacct gtctctggag gtgctggacc tgagctccaa caatatcacc    360
gagatcagat ctagctgttt tcctaatggc ctgcggatca gagagctgaa cctggcctct    420
aatcggatca gcatcctgga gtccggcgcc ttcgatggcc tgagcagatc cctgctgaca    480
ctgcgcctgt ccaagaaccg gatcacccag ctgcccgtga aggcctttaa gctgcctagg    540
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
gaaccgaaat cttctgacaa aacccacacc tctccgccgt ctccggctcc ggaactgctg   2340
ggtggttctt ctgttttcct gtttcctcca aagcccaagg acacactgat gatctccagg   2400
```

```
acaccagagg tgacctgcgt ggtggtggac gtgagccacg aggaccccga ggtgaagttc   2460

aactggtacg tggatggcgt ggaggtgcac aatgccaaga ccaagcccag agaggagcag   2520

tacaactcta cctatagggt ggtgagcgtg ctgacagtgc tgcaccagga ctggctgaac   2580

ggcaaggagt ataagtgcaa ggtgagcaat aaggccctgc ctgcccccaat cgagaagaca  2640

atctccaagg ccaagggcca gccaagagag ccccaggtgt acaccctgcc ccctagcagg   2700

gatgagctga caaagaacca ggtgtccctg acctgtctgg tgaagggctt ttatccctcc   2760

gacatcgccg tggagtggga gtctaatggc cagcctgaga ataactacaa gacaacccca   2820

cccgtgctgg attctgacgg cagcttcttt ctgtattcta agctgaccgt ggacaagagc   2880

aggtggcagc agggcaacgt gttcagctgc tccgtgatgc acgaagcact gcacaatcac   2940

tacacccaga aatcactgtc actgagccct ggcaaa                             2976


<210> SEQ ID NO 29
<211> LENGTH: 992
<212> TYPE: PRT
<213> ORGANISM: Artificial Sequence
<220> FEATURE:
<223> OTHER INFORMATION: fusion protein

<400> SEQUENCE: 29

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255
```

```
His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
```

```
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Glu Pro Lys Ser Ser Asp Lys Thr
        755                 760                 765

His Thr Ser Pro Pro Cys Pro Ala Pro Glu Leu Leu Gly Gly Pro Ser
    770                 775                 780

Val Phe Ile Phe Pro Pro Lys Ile Lys Asp Val Leu Met Ile Ser Leu
785                 790                 795                 800

Ser Pro Ile Val Thr Cys Val Val Val Asp Val Ser Glu Asp Asp Pro
                805                 810                 815

Asp Val Gln Ile Ser Trp Phe Val Asn Asn Val Glu Val His Thr Ala
            820                 825                 830

Gln Thr Gln Thr His Arg Glu Asp Tyr Asn Ser Thr Leu Arg Val Val
        835                 840                 845

Ser Ala Leu Pro Ile Gln His Gln Asp Trp Met Ser Gly Lys Glu Phe
    850                 855                 860

Lys Cys Lys Val Asn Asn Lys Asp Leu Pro Ala Pro Ile Glu Arg Thr
865                 870                 875                 880

Ile Ser Lys Pro Lys Gly Ser Val Arg Ala Pro Gln Val Tyr Val Leu
                885                 890                 895

Pro Pro Pro Glu Glu Glu Met Thr Lys Lys Gln Val Thr Leu Thr Cys
            900                 905                 910

Met Val Thr Asp Phe Met Pro Glu Asp Ile Tyr Val Glu Trp Thr Asn
        915                 920                 925

Asn Gly Lys Thr Glu Leu Asn Tyr Lys Asn Thr Glu Pro Val Leu Asp
    930                 935                 940

Ser Asp Gly Ser Tyr Phe Met Tyr Ser Lys Leu Arg Val Glu Lys Lys
945                 950                 955                 960

Asn Trp Val Glu Arg Asn Ser Tyr Ser Cys Ser Val Val His Glu Gly
                965                 970                 975

Leu His Asn His His Thr Thr Lys Ser Phe Ser Arg Thr Pro Gly Lys
            980                 985                 990


<210> SEQ ID NO 30
<211> LENGTH: 993
<212> TYPE: PRT
<213> ORGANISM: Artificial Sequence
<220> FEATURE:
<223> OTHER INFORMATION: fusion protein

<400> SEQUENCE: 30

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
```

```
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480
```

-continued

```
Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Glu Pro Arg Gly Pro Thr Ile Lys
        755                 760                 765

Pro Cys Pro Pro Cys Lys Cys Pro Ala Pro Asn Leu Leu Gly Gly Pro
    770                 775                 780

Ser Val Phe Ile Phe Pro Pro Lys Ile Lys Asp Val Leu Met Ile Ser
785                 790                 795                 800

Leu Ser Pro Ile Val Thr Cys Val Val Val Asp Val Ser Glu Asp Asp
                805                 810                 815

Pro Asp Val Gln Ile Ser Trp Phe Val Asn Asn Val Glu Val His Thr
            820                 825                 830

Ala Gln Thr Gln Thr His Arg Glu Asp Tyr Asn Ser Thr Leu Arg Val
        835                 840                 845

Val Ser Ala Leu Pro Ile Gln His Gln Asp Trp Met Ser Gly Lys Glu
    850                 855                 860

Phe Lys Cys Lys Val Asn Asn Lys Asp Leu Pro Ala Pro Ile Glu Arg
865                 870                 875                 880

Thr Ile Ser Lys Pro Lys Gly Ser Val Arg Ala Pro Gln Val Tyr Val
                885                 890                 895
```

```
Leu Pro Pro Pro Glu Glu Glu Met Thr Lys Lys Gln Val Thr Leu Thr
            900                 905                 910

Cys Met Val Thr Asp Phe Met Pro Glu Asp Ile Tyr Val Glu Trp Thr
        915                 920                 925

Asn Asn Gly Lys Thr Glu Leu Asn Tyr Lys Asn Thr Glu Pro Val Leu
    930                 935                 940

Asp Ser Asp Gly Ser Tyr Phe Met Tyr Ser Lys Leu Arg Val Glu Lys
945                 950                 955                 960

Lys Asn Trp Val Glu Arg Asn Ser Tyr Ser Cys Ser Val Val His Glu
                965                 970                 975

Gly Leu His Asn His His Thr Thr Lys Ser Phe Ser Arg Thr Pro Gly
            980                 985                 990

Lys


<210> SEQ ID NO 31
<211> LENGTH: 1005
<212> TYPE: PRT
<213> ORGANISM: Artificial Sequence
<220> FEATURE:
<223> OTHER INFORMATION: fusion protein

<400> SEQUENCE: 31

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
```

```
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685
```

```
Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Arg Asn Thr Gly Arg Gly Gly Glu
        755                 760                 765

Glu Lys Lys Lys Glu Lys Glu Lys Glu Glu Gln Glu Glu Arg Glu Thr
    770                 775                 780

Lys Thr Pro Glu Cys Pro Ser His Thr Gln Pro Leu Gly Val Phe Ile
785                 790                 795                 800

Phe Pro Pro Lys Ile Lys Asp Val Leu Met Ile Ser Leu Ser Pro Ile
                805                 810                 815

Val Thr Cys Val Val Val Asp Val Ser Glu Asp Asp Pro Asp Val Gln
            820                 825                 830

Ile Ser Trp Phe Val Asn Asn Val Glu Val His Thr Ala Gln Thr Gln
        835                 840                 845

Thr His Arg Glu Asp Tyr Asn Ser Thr Leu Arg Val Val Ser Ala Leu
    850                 855                 860

Pro Ile Gln His Gln Asp Trp Met Ser Gly Lys Glu Phe Lys Cys Lys
865                 870                 875                 880

Val Asn Asn Lys Asp Leu Pro Ala Pro Ile Glu Arg Thr Ile Ser Lys
                885                 890                 895

Pro Lys Gly Ser Val Arg Ala Pro Gln Val Tyr Val Leu Pro Pro Pro
            900                 905                 910

Glu Glu Glu Met Thr Lys Lys Gln Val Thr Leu Thr Cys Met Val Thr
        915                 920                 925

Asp Phe Met Pro Glu Asp Ile Tyr Val Glu Trp Thr Asn Asn Gly Lys
    930                 935                 940

Thr Glu Leu Asn Tyr Lys Asn Thr Glu Pro Val Leu Asp Ser Asp Gly
945                 950                 955                 960

Ser Tyr Phe Met Tyr Ser Lys Leu Arg Val Glu Lys Lys Asn Trp Val
                965                 970                 975

Glu Arg Asn Ser Tyr Ser Cys Ser Val Val His Glu Gly Leu His Asn
            980                 985                 990

His His Thr Thr Lys Ser Phe Ser  Arg Thr Pro Gly Lys
        995                 1000                1005


<210> SEQ ID NO 32
<211> LENGTH: 992
<212> TYPE: PRT
<213> ORGANISM: Artificial Sequence
<220> FEATURE:
<223> OTHER INFORMATION: fusion protein

<400> SEQUENCE: 32

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45
```

-continued

```
Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460
```

-continued

```
Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Glu Pro Lys Ser Ser Asp Lys Thr
        755                 760                 765

His Thr Ser Pro Pro Ser Pro Ala Pro Glu Leu Leu Gly Gly Ser Ser
    770                 775                 780

Val Phe Ile Phe Pro Pro Lys Ile Lys Asp Val Leu Met Ile Ser Leu
785                 790                 795                 800

Ser Pro Ile Val Thr Cys Val Val Val Asp Val Ser Glu Asp Asp Pro
                805                 810                 815

Asp Val Gln Ile Ser Trp Phe Val Asn Asn Val Glu Val His Thr Ala
            820                 825                 830

Gln Thr Gln Thr His Arg Glu Asp Tyr Asn Ser Thr Leu Arg Val Val
        835                 840                 845

Ser Ala Leu Pro Ile Gln His Gln Asp Trp Met Ser Gly Lys Glu Phe
    850                 855                 860

Lys Cys Lys Val Asn Asn Lys Asp Leu Pro Ala Pro Ile Glu Arg Thr
865                 870                 875                 880

Ile Ser Lys Pro Lys Gly Ser Val Arg Ala Pro Gln Val Tyr Val Leu
```

```
                885                 890                 895

Pro Pro Pro Glu Glu Glu Met Thr Lys Lys Gln Val Thr Leu Thr Cys
            900                 905                 910

Met Val Thr Asp Phe Met Pro Glu Asp Ile Tyr Val Glu Trp Thr Asn
        915                 920                 925

Asn Gly Lys Thr Glu Leu Asn Tyr Lys Asn Thr Glu Pro Val Leu Asp
    930                 935                 940

Ser Asp Gly Ser Tyr Phe Met Tyr Ser Lys Leu Arg Val Glu Lys Lys
945                 950                 955                 960

Asn Trp Val Glu Arg Asn Ser Tyr Ser Cys Ser Val Val His Glu Gly
                965                 970                 975

Leu His Asn His His Thr Thr Lys Ser Phe Ser Arg Thr Pro Gly Lys
            980                 985                 990


<210> SEQ ID NO 33
<211> LENGTH: 2976
<212> TYPE: DNA
<213> ORGANISM: Artificial Sequence
<220> FEATURE:
<223> OTHER INFORMATION: fusion protein

<400> SEQUENCE: 33

gctcaggctg gacctagggc tccttgcgct gccgcctgca cctgtgcagg cgattctctg      60

gactgcagcg gccggggcct ggccacactg cccagggacc tgccttcctg gaccagatct     120

ctgaacctga gctacaatcg gctgtccgag atcgattctg ccgcctttga ggacctgaca     180

aatctgcagg aggtgtatct gaacagcaat gagctgaccg caatcccctc cctgggagca     240

gcctctatcg gcgtggtgag cctgttcctg cagcacaaca agatcctgag cgtggatggc     300

tcccagctga agagctacct gtctctggag gtgctggacc tgagctccaa caatatcacc     360

gagatcagat ctagctgttt tcctaatggc ctgcggatca gagagctgaa cctggcctct     420

aatcggatca gcatcctgga gtccggcgcc ttcgatggcc tgagcagatc cctgctgaca     480

ctgcgcctgt ccaagaaccg gatcacccag ctgcccgtga aggcctttaa gctgcctagg     540

ctgacacagc tggacctgaa ccggaataga atcaggctga tcgagggcct gaccttccag     600

ggcctggata gcctggaggt gctgcgcctg cagcggaaca atatctcccg cctgacagac     660

ggagcatttt ggggcctgtc taagatgcac gtgctgcacc tggagtacaa tagcctggtg     720

gaggtgaact ctggcagcct gtatggcctg accgccctgc accagctgca cctgtccaac     780

aatagcatca gcagaatcca gagggatggc tggtccttct gccagaagct gcacgagctg     840

atcctgtctt ttaacaatct gaccaggctg gacgaggaga gcctggcaga gctgtcctct     900

ctgtccatcc tgcgcctgtc tcacaatgcc atcagccaca tcgccgaggg cgcctttaag     960

ggcctgaaga gcctgagggt gctggatctg gaccacaacg agatctctgg caccatcgag    1020

gatacaagcg gcgccttcac aggcctggac aatctgtcca agctgaccct gtttggcaac    1080

aagatcaagt ctgtggccaa gcgggccttc tctggcctgg agagcctgga gcacctgaac    1140

ctgggcgaga atgccatcag atccgtgcag ttcgatgcct ttgccaagat gaagaatctg    1200

aaggagctgt acatcagctc cgagagcttc ctgtgcgact gtcagctgaa gtggctgcca    1260

ccttggctga tgggaaggat gctgcaggcc tttgtgaccg ccacatgcgc ccacccagag    1320

agcctgaagg gccagagcat cttctccgtg ctgcccgata gcttcgtgtg cgacgatttt    1380

cctaagccac agatcatcac ccagccagag acaacaatgg ccgtggtggg caaggacatc    1440

cggtttacat gttccgccgc ctctagctcc tctagcccca tgaccttcgc ctggaagaag    1500
```

gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
gagccaaagt cctctgataa gacacacacc tctccaccat gcccagcacc agagctgctg 2340
ggaggaccaa gcgtgttcat cttcccaccc aagatcaagg acgtgctgat gatctccctg 2400
tcccccatcg tgacctgcgt ggtggtggac gtgtccgagg acgaccccga cgtgcagatc 2460
agttggttcg tgaacaacgt ggaagtgcac accgcccaga cccagaccca cagagaggac 2520
tacaactcca ccctgcgggt ggtgtccgcc ctgcccatcc agcaccagga ctggatgtcc 2580
ggcaaagaat tcaagtgcaa agtgaacaac aaggacctgc ctgcccccat cgagcggacc 2640
atctccaagc ccaagggctc cgtgcgggct ccccaggtgt acgtgctgcc ccctccagag 2700
gaagagatga ccaagaagca ggtcacactg acctgcatgg tcaccgactt catgcccgag 2760
gacatctacg tggaatggac caacaatggc aagaccgagc tgaactacaa gaacaccgag 2820
cctgtgctgg actccgacgg ctcctacttc atgtactcca agctgcgggt ggaaaagaag 2880
aactgggtcg agcggaactc ctactcctgc tccgtggtgc acgagggcct gcacaaccac 2940
cacaccacca agtccttctc ccggaccccc ggcaaa 2976

<210> SEQ ID NO 34
<211> LENGTH: 2979
<212> TYPE: DNA
<213> ORGANISM: Artificial Sequence
<220> FEATURE:
<223> OTHER INFORMATION: fusion protein

<400> SEQUENCE: 34
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540

-continued

```
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
gagcctcggg gccctaccat caagccctgc ccccttgca agtgccctgc ccctaatctg    2340
ctgggcggac cctccgtgtt catcttccca cccaagatca aggacgtgct gatgatctcc   2400
ctgtccccca tcgtgacctg cgtggtggtg gacgtgtccg aggacgaccc cgacgtgcag   2460
atcagttggt tcgtgaacaa cgtggaagtg cacaccgccc agacccagac ccacagagag   2520
gactacaact ccaccctgcg ggtggtgtcc gccctgccca tccagcacca ggactggatg   2580
tccggcaaag aattcaagtg caaagtgaac aacaaggacc tgcctgcccc catcgagcgg   2640
accatctcca agcccaaggg ctccgtgcgg gctccccagg tgtacgtgct gcccccctcca   2700
gaggaagaga tgaccaagaa gcaggtcaca ctgacctgca tggtcaccga cttcatgccc   2760
gaggacatct acgtggaatg gaccaacaat ggcaagaccg agctgaacta caagaacacc   2820
gagcctgtgc tggactccga cggctcctac ttcatgtact ccaagctgcg ggtggaaaag   2880
aagaactggg tcgagcggaa ctcctactcc tgctccgtgg tgcacgaggg cctgcacaac   2940
```

caccacacca ccaagtcctt ctcccggacc cccggcaaa 2979

<210> SEQ ID NO 35
<211> LENGTH: 3015
<212> TYPE: DNA
<213> ORGANISM: Artificial Sequence
<220> FEATURE:
<223> OTHER INFORMATION: fusion protein

<400> SEQUENCE: 35
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980

-continued ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
cgcaacaccg gccgcggcgg cgaggagaag aagaaggaga aggagaagga ggagcaggag 2340
gagcgcgaga ccaagacccc cgagtgcccc agccacaccc agcccctggg cgtgttcatc 2400
ttcccaccca agatcaagga cgtgctgatg atctccctgt cccccatcgt gacctgcgtg 2460
gtggtggacg tgtccgagga cgaccccgac gtgcagatca gttggttcgt gaacaacgtg 2520
gaagtgcaca ccgcccagac ccagacccac agagaggact acaactccac cctgcgggtg 2580
gtgtccgccc tgcccatcca gcaccaggac tggatgtccg gcaaagaatt caagtgcaaa 2640
gtgaacaaca aggacctgcc tgcccccatc gagcggacca tctccaagcc caagggctcc 2700
gtgcgggctc cccaggtgta cgtgctgccc cctccagagg aagagatgac caagaagcag 2760
gtcacactga cctgcatggt caccgacttc atgcccgagg acatctacgt ggaatggacc 2820
aacaatggca agaccgagct gaactacaag aacaccgagc ctgtgctgga ctccgacggc 2880
tcctacttca tgtactccaa gctgcgggtg gaaaagaaga actgggtcga gcggaactcc 2940
tactcctgct ccgtggtgca cgagggcctg cacaaccacc acaccaccaa gtccttctcc 3000
cggacccccg gcaaa 3015

<210> SEQ ID NO 36
<211> LENGTH: 2976
<212> TYPE: DNA
<213> ORGANISM: Artificial Sequence
<220> FEATURE:
<223> OTHER INFORMATION: fusion protein

<400> SEQUENCE: 36
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
gaaccgaaat cttctgacaa aacccacacc tctccgccgt ctccggctcc ggaactgctg 2340
ggtggttctt ctgttttcat cttcccaccc aagatcaagg acgtgctgat gatctccctg 2400
tcccccatcg tgacctgcgt ggtggtggac gtgtccgagg acgaccccga cgtgcagatc 2460
agttggttcg tgaacaacgt ggaagtgcac accgcccaga cccagaccca cagagaggac 2520
tacaactcca ccctgcgggt ggtgtccgcc ctgcccatcc agcaccagga ctggatgtcc 2580
ggcaaagaat tcaagtgcaa agtgaacaac aaggacctgc ctgcccccat cgagcggacc 2640
atctccaagc ccaagggctc cgtgcgggct ccccaggtgt acgtgctgcc ccctccagag 2700
gaagagatga ccaagaagca ggtcacactg acctgcatgg tcaccgactt catgcccgag 2760
gacatctacg tggaatggac caacaatggc aagaccgagc tgaactacaa gaacaccgag 2820
cctgtgctgg actccgacgg ctcctacttc atgtactcca agctgcgggt ggaaaagaag 2880
aactgggtcg agcggaactc ctactcctgc tccgtggtgc acgagggcct gcacaaccac 2940
cacaccacca agtccttctc ccggaccccc ggcaaa 2976

<210> SEQ ID NO 37
<211> LENGTH: 996
<212> TYPE: PRT
<213> ORGANISM: Artificial Sequence
<220> FEATURE:
<223> OTHER INFORMATION: fusion protein

<400> SEQUENCE: 37

Ala Gly Pro Arg Ala Pro Cys Ala Ala Ala Cys Thr Cys Ala Gly Asp
1 5 10 15

```
Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430
```

```
Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Ser Glu Pro Lys Ser
        755                 760                 765

Ser Asp Lys Thr His Thr Ser Pro Pro Cys Pro Ala Pro Glu Leu Leu
    770                 775                 780

Gly Gly Pro Ser Val Phe Leu Phe Pro Pro Lys Pro Lys Asp Thr Leu
785                 790                 795                 800

Met Ile Ser Arg Thr Pro Glu Val Thr Cys Val Val Val Asp Val Ser
                805                 810                 815

His Glu Asp Pro Glu Val Lys Phe Asn Trp Tyr Val Asp Gly Val Glu
            820                 825                 830

Val His Asn Ala Lys Thr Lys Pro Arg Glu Glu Gln Tyr Asn Ser Thr
        835                 840                 845

Tyr Arg Val Val Ser Val Leu Thr Val Leu His Gln Asp Trp Leu Asn
```

-continued

```
    850                 855                 860

Gly Lys Glu Tyr Lys Cys Lys Val Ser Asn Lys Ala Leu Pro Ala Pro
865                 870                 875                 880

Ile Glu Lys Thr Ile Ser Lys Ala Lys Gly Gln Pro Arg Glu Pro Gln
                885                 890                 895

Val Tyr Thr Leu Pro Pro Ser Arg Asp Glu Leu Thr Lys Asn Gln Val
            900                 905                 910

Ser Leu Thr Cys Leu Val Lys Gly Phe Tyr Pro Ser Asp Ile Ala Val
        915                 920                 925

Glu Trp Glu Ser Asn Gly Gln Pro Glu Asn Asn Tyr Lys Thr Thr Pro
    930                 935                 940

Pro Val Leu Asp Ser Asp Gly Ser Phe Phe Leu Tyr Ser Lys Leu Thr
945                 950                 955                 960

Val Asp Lys Ser Arg Trp Gln Gln Gly Asn Val Phe Ser Cys Ser Val
                965                 970                 975

Met His Glu Ala Leu His Asn His Tyr Thr Gln Lys Ser Leu Ser Leu
            980                 985                 990

Ser Pro Gly Lys
        995


<210> SEQ ID NO 38
<211> LENGTH: 997
<212> TYPE: PRT
<213> ORGANISM: Artificial Sequence
<220> FEATURE:
<223> OTHER INFORMATION: fusion protein

<400> SEQUENCE: 38

Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
```

-continued

```
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640
```

```
Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Ser Glu Pro Arg Gly
        755                 760                 765

Pro Thr Ile Lys Pro Cys Pro Pro Cys Lys Cys Pro Ala Pro Asn Leu
    770                 775                 780

Leu Gly Gly Pro Ser Val Phe Leu Phe Pro Pro Lys Pro Lys Asp Thr
785                 790                 795                 800

Leu Met Ile Ser Arg Thr Pro Glu Val Thr Cys Val Val Val Asp Val
                805                 810                 815

Ser His Glu Asp Pro Glu Val Lys Phe Asn Trp Tyr Val Asp Gly Val
            820                 825                 830

Glu Val His Asn Ala Lys Thr Lys Pro Arg Glu Glu Gln Tyr Asn Ser
        835                 840                 845

Thr Tyr Arg Val Val Ser Val Leu Thr Val Leu His Gln Asp Trp Leu
    850                 855                 860

Asn Gly Lys Glu Tyr Lys Cys Lys Val Ser Asn Lys Ala Leu Pro Ala
865                 870                 875                 880

Pro Ile Glu Lys Thr Ile Ser Lys Ala Lys Gly Gln Pro Arg Glu Pro
                885                 890                 895

Gln Val Tyr Thr Leu Pro Pro Ser Arg Asp Glu Leu Thr Lys Asn Gln
            900                 905                 910

Val Ser Leu Thr Cys Leu Val Lys Gly Phe Tyr Pro Ser Asp Ile Ala
        915                 920                 925

Val Glu Trp Glu Ser Asn Gly Gln Pro Glu Asn Asn Tyr Lys Thr Thr
    930                 935                 940

Pro Pro Val Leu Asp Ser Asp Gly Ser Phe Phe Leu Tyr Ser Lys Leu
945                 950                 955                 960

Thr Val Asp Lys Ser Arg Trp Gln Gln Gly Asn Val Phe Ser Cys Ser
                965                 970                 975

Val Met His Glu Ala Leu His Asn His Tyr Thr Gln Lys Ser Leu Ser
            980                 985                 990

Leu Ser Pro Gly Lys
        995
```

<210> SEQ ID NO 39
<211> LENGTH: 1009
<212> TYPE: PRT
<213> ORGANISM: Artificial Sequence
<220> FEATURE:
<223> OTHER INFORMATION: fusion protein

<400> SEQUENCE: 39

```
Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415
```

-continued

```
Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Ser Arg Asn Thr Gly
        755                 760                 765

Arg Gly Gly Glu Glu Lys Lys Lys Glu Lys Glu Lys Glu Glu Gln Glu
    770                 775                 780

Glu Arg Glu Thr Lys Thr Pro Glu Cys Pro Ser His Thr Gln Pro Leu
785                 790                 795                 800

Gly Val Phe Leu Phe Pro Pro Lys Pro Lys Asp Thr Leu Met Ile Ser
                805                 810                 815

Arg Thr Pro Glu Val Thr Cys Val Val Val Asp Val Ser His Glu Asp
            820                 825                 830

Pro Glu Val Lys Phe Asn Trp Tyr Val Asp Gly Val Glu Val His Asn
```

```
        835                 840                 845

Ala Lys Thr Lys Pro Arg Glu Glu Gln Tyr Asn Ser Thr Tyr Arg Val
    850                 855                 860

Val Ser Val Leu Thr Val Leu His Gln Asp Trp Leu Asn Gly Lys Glu
865                 870                 875                 880

Tyr Lys Cys Lys Val Ser Asn Lys Ala Leu Pro Ala Pro Ile Glu Lys
                885                 890                 895

Thr Ile Ser Lys Ala Lys Gly Gln Pro Arg Glu Pro Gln Val Tyr Thr
            900                 905                 910

Leu Pro Pro Ser Arg Asp Glu Leu Thr Lys Asn Gln Val Ser Leu Thr
        915                 920                 925

Cys Leu Val Lys Gly Phe Tyr Pro Ser Asp Ile Ala Val Glu Trp Glu
    930                 935                 940

Ser Asn Gly Gln Pro Glu Asn Asn Tyr Lys Thr Thr Pro Pro Val Leu
945                 950                 955                 960

Asp Ser Asp Gly Ser Phe Phe Leu Tyr Ser Lys Leu Thr Val Asp Lys
                965                 970                 975

Ser Arg Trp Gln Gln Gly Asn Val Phe Ser Cys Ser Val Met His Glu
            980                 985                 990

Ala Leu His Asn His Tyr Thr Gln  Lys Ser Leu Ser Leu  Ser Pro Gly
        995                 1000                1005

Lys


<210> SEQ ID NO 40
<211> LENGTH: 996
<212> TYPE: PRT
<213> ORGANISM: Artificial Sequence
<220> FEATURE:
<223> OTHER INFORMATION: fusion protein

<400> SEQUENCE: 40

Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190
```

-continued

```
Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605
```

```
Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Ser Glu Pro Lys Ser
        755                 760                 765

Ser Asp Lys Thr His Thr Ser Pro Pro Ser Pro Ala Pro Glu Leu Leu
    770                 775                 780

Gly Gly Ser Ser Val Phe Leu Phe Pro Pro Lys Pro Lys Asp Thr Leu
785                 790                 795                 800

Met Ile Ser Arg Thr Pro Glu Val Thr Cys Val Val Val Asp Val Ser
                805                 810                 815

His Glu Asp Pro Glu Val Lys Phe Asn Trp Tyr Val Asp Gly Val Glu
            820                 825                 830

Val His Asn Ala Lys Thr Lys Pro Arg Glu Glu Gln Tyr Asn Ser Thr
        835                 840                 845

Tyr Arg Val Val Ser Val Leu Thr Val Leu His Gln Asp Trp Leu Asn
    850                 855                 860

Gly Lys Glu Tyr Lys Cys Lys Val Ser Asn Lys Ala Leu Pro Ala Pro
865                 870                 875                 880

Ile Glu Lys Thr Ile Ser Lys Ala Lys Gly Gln Pro Arg Glu Pro Gln
                885                 890                 895

Val Tyr Thr Leu Pro Pro Ser Arg Asp Glu Leu Thr Lys Asn Gln Val
            900                 905                 910

Ser Leu Thr Cys Leu Val Lys Gly Phe Tyr Pro Ser Asp Ile Ala Val
        915                 920                 925

Glu Trp Glu Ser Asn Gly Gln Pro Glu Asn Asn Tyr Lys Thr Thr Pro
    930                 935                 940

Pro Val Leu Asp Ser Asp Gly Ser Phe Phe Leu Tyr Ser Lys Leu Thr
945                 950                 955                 960

Val Asp Lys Ser Arg Trp Gln Gln Gly Asn Val Phe Ser Cys Ser Val
                965                 970                 975

Met His Glu Ala Leu His Asn His Tyr Thr Gln Lys Ser Leu Ser Leu
            980                 985                 990

Ser Pro Gly Lys
        995
```

<210> SEQ ID NO 41
<211> LENGTH: 2988
<212> TYPE: DNA

-continued

<213> ORGANISM: Artificial Sequence
<220> FEATURE:
<223> OTHER INFORMATION: fusion protein

<400> SEQUENCE: 41
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cggcacaat agaggacacg 1020
agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260
ctaattggca ggatgctgca ggcctttgtg acagccacct gtgcccaccc agaatcactg 1320
aagggtcaga gcattttctc tgtgccacca gagagtttcg tgtgcgatga cttcctgaag 1380
ccacagatca tcacccagcc agaaaccacc atggctatgg tgggcaagga catccggttt 1440
acatgctcag cagccagcag cagcagctcc cccatgacct ttgcctggaa gaaagacaat 1500
gaagtcctga ccaatgcaga catggagaac tttgtccacg tccacgcgca ggacggggaa 1560
gtgatggagt acaccaccat cctgcacctc cgtcaggtca ctttcgggca cgagggccgc 1620
taccaatgtg tcatcaccaa ccactttggc tccacctatt cacataaggc caggctcacc 1680
gtgaatgtgt tgccatcatt caccaaaacg ccccacgaca taaccatccg gaccaccacc 1740
gtggcccgcc tcgaatgtgc tgccacaggt cacccaaacc ctcagattgc ctggcagaag 1800
gatggaggca cggatttccc cgctgcccgt gagcgacgca tgcatgtcat gccggatgac 1860
gacgtgtttt tcatcactga tgtgaaaata gatgacgcag ggtttacag ctgtactgct 1920
cagaactcag ccggttctat ttcagctaat gccaccctga ctgtcctaga gaccccatcc 1980
ttggtggtcc ccttggaaga ccgtgtggta tctgtgggag aaacagtggc cctccaatgc 2040
aaagccacgg ggaaccctcc gccccgcatc acctggttca agggggaccg cccgctgagc 2100
ctcactgagc ggcaccacct gacccctgac aaccagctcc tggtggttca gaacgtggtg 2160
gcagaggatg cgggccgata tacctgtgag atgtccaaca ccctgggcac ggagcgagct 2220
cacagccagc tgagcgtcct gcccgcagca ggctgcagga aggatgggac cacggtaggc 2280
atcttcggat ccgagccaaa gtcctctgat aagacacaca cctctccacc atgcccagca 2340
ccagagctgc tgggaggacc aagcgtgttc ctgtttcctc caaagcccaa ggacacactg 2400
atgatctcca ggacaccaga ggtgacctgc gtggtggtgg acgtgagcca cgaggacccc 2460
gaggtgaagt tcaactggta cgtggatggc gtggaggtgc acaatgccaa gaccaagccc 2520
agagaggagc agtacaactc tacctatagg gtggtgagcg tgctgacagt gctgcaccag 2580
gactggctga acggcaagga gtataagtgc aaggtgagca ataaggccct gcctgcccca 2640
atcgagaaga caatctccaa ggccaagggc cagccaagag agccccaggt gtacaccctg 2700
ccccctagca gggatgagct gacaaagaac caggtgtccc tgacctgtct ggtgaagggc 2760
ttttatccct ccgacatcgc cgtggagtgg gagtctaatg gccagcctga gaataactac 2820
aagacaaccc cacccgtgct ggattctgac ggcagcttct ttctgtattc taagctgacc 2880
gtggacaaga gcaggtggca gcagggcaac gtgttcagct gctccgtgat gcacgaagca 2940
ctgcacaatc actacaccca gaaatcactg tcactgagcc ctggcaaa 2988

<210> SEQ ID NO 42
<211> LENGTH: 2991
<212> TYPE: DNA
<213> ORGANISM: Artificial Sequence
<220> FEATURE:
<223> OTHER INFORMATION: fusion protein

<400> SEQUENCE: 42
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cgggcacaat agaggacacg 1020
agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260

-continued

```
ctaattggca ggatgctgca ggcctttgtg acagccacct gtgcccaccc agaatcactg   1320

aagggtcaga gcattttctc tgtgccacca gagagtttcg tgtgcgatga cttcctgaag   1380

ccacagatca tcacccagcc agaaaccacc atggctatgg tgggcaagga catccggttt   1440

acatgctcag cagccagcag cagcagctcc cccatgacct ttgcctggaa gaaagacaat   1500

gaagtcctga ccaatgcaga catggagaac tttgtccacg tccacgcgca ggacggggaa   1560

gtgatggagt acaccaccat cctgcacctc cgtcaggtca ctttcgggca cgagggccgc   1620

taccaatgtg tcatcaccaa ccactttggc tccacctatt cacataaggc caggctcacc   1680

gtgaatgtgt tgccatcatt caccaaaacg ccccacgaca taaccatccg gaccaccacc   1740

gtggcccgcc tcgaatgtgc tgccacaggt cacccaaacc ctcagattgc ctggcagaag   1800

gatggaggca cggatttccc cgctgcccgt gagcgacgca tgcatgtcat gccggatgac   1860

gacgtgtttt tcatcactga tgtgaaaata gatgacgcag gggtttacag ctgtactgct   1920

cagaactcag ccggttctat ttcagctaat gccaccctga ctgtcctaga gaccccatcc   1980

ttggtggtcc ccttggaaga ccgtgtggta tctgtgggag aaacagtggc cctccaatgc   2040

aaagccacgg ggaaccctcc gccccgcatc acctggttca agggggaccg cccgctgagc   2100

ctcactgagc ggcaccacct gacccctgac aaccagctcc tggtggttca gaacgtggtg   2160

gcagaggatg cgggccgata tacctgtgag atgtccaaca ccctgggcac ggagcgagct   2220

cacagccagc tgagcgtcct gcccgcagca ggctgcagga aggatgggac cacggtaggc   2280

atcttcggat ccgagcctcg ggccctacc atcaagccct gcccccccttg caagtgccct   2340

gcccctaatc tgctgggcgg accctccgtg ttcctgtttc ctccaaagcc caaggacaca   2400

ctgatgatct ccaggacacc agaggtgacc tgcgtggtgg tggacgtgag ccacgaggac   2460

cccgaggtga agttcaactg gtacgtggat ggcgtggagg tgcacaatgc caagaccaag   2520

cccagagagg agcagtacaa ctctacctat agggtggtga gcgtgctgac agtgctgcac   2580

caggactggc tgaacggcaa ggagtataag tgcaaggtga gcaataaggc cctgcctgcc   2640

ccaatcgaga agacaatctc caaggccaag ggccagccaa gagagcccca ggtgtacacc   2700

ctgccccccta gcagggatga gctgacaaag aaccaggtgt ccctgacctg tctggtgaag   2760

ggcttttatc cctccgacat cgccgtggag tgggagtcta atggccagcc tgagaataac   2820

tacaagacaa ccccacccgt gctggattct gacggcagct tctttctgta ttctaagctg   2880

accgtggaca agagcaggtg gcagcagggc aacgtgttca gctgctccgt gatgcacgaa   2940

gcactgcaca atcactacac ccagaaatca ctgtcactga gccctggcaa a            2991
```

```
<210> SEQ ID NO 43
<211> LENGTH: 3027
<212> TYPE: DNA
<213> ORGANISM: Artificial Sequence
<220> FEATURE:
<223> OTHER INFORMATION: fusion protein

<400> SEQUENCE: 43

gctgggcctc gggctccttg tgctgccgcc tgcacatgtg caggcgattc cctggactgc     60

ggcggcagag gcctggccgc cctgcctggc gatctgccat cctggacccg gagcctgaac    120

ctgagctaca acaagctgag cgagatcgat cccgccggct ttgaggacct gcctaacctg    180

caggaggtgt atctgaacaa taacgagctg accgcggtac catccctggg cgctgcttca    240

tcacatgtcg tctctctctt tctgcagcac aacaagattc gcagcgtgga ggggagccag    300

ctgaaggcct acctttcctt agaagtgtta gatctgagtt tgaacaacat cacggaagtg    360
```

```
cggaacacct gctttccaca cggaccgcct ataaaggagc tcaacctggc aggcaatcgg    420
attggcaccc tggagttggg agcatttgat ggtctgtcac ggtcgctgct aactcttcgc    480
ctgagcaaaa acaggatcac ccagcttcct gtaagagcat tcaagctacc caggctgaca    540
caactggacc tcaatcggaa caggattcgg ctgatagagg gcctcacctt ccaggggctc    600
aacagcttgg aggtgctgaa gcttcagcga aacaacatca gcaaactgac agatggggcc    660
ttctggggac tgtccaagat gcatgtgctg cacctggagt acaacagcct ggtagaagtg    720
aacagcggct cgctctacgg cctcacggcc ctgcatcagc tccacctcag caacaattcc    780
atcgctcgca ttcaccgcaa gggctggagc ttctgccaga agctgcatga gttggtcctg    840
tccttcaaca acctgacacg gctggacgag gagagcctgg ccgagctgag cagcctgagt    900
gtcctgcgtc tcagccacaa ttccatcagc cacattgcgg agggtgcctt caagggactc    960
aggagcctgc gagtcttgga tctggaccat aacgagattt cgggcacaat agaggacacg   1020
agcggcgcct tctcagggct cgacagcctc agcaagctga ctctgtttgg aaacaagatc   1080
aagtctgtgg ctaagagagc attctcgggg ctggaaggcc tggagcacct gaaccttgga   1140
gggaatgcga tcagatctgt ccagtttgat gcctttgtga agatgaagaa tcttaaagag   1200
ctccatatca gcagcgacag cttcctgtgt gactgccagc tgaagtggct gcccccgtgg   1260
ctaattggca ggatgctgca ggcctttgtg acagccacct gtgcccaccc agaatcactg   1320
aagggtcaga gcattttctc tgtgccacca gagagtttcg tgtgcgatga cttcctgaag   1380
ccacagatca tcacccagcc agaaaccacc atggctatgg tgggcaagga catccggttt   1440
acatgctcag cagccagcag cagcagctcc cccatgacct ttgcctggaa gaaagacaat   1500
gaagtcctga ccaatgcaga catggagaac tttgtccacg tccacgcgca ggacggggaa   1560
gtgatggagt acaccaccat cctgcacctc cgtcaggtca ctttcgggca cgagggccgc   1620
taccaatgtg tcatcaccaa ccactttggc tccacctatt cacataaggc caggctcacc   1680
gtgaatgtgt tgccatcatt caccaaaacg ccccacgaca taaccatccg gaccaccacc   1740
gtggcccgcc tcgaatgtgc tgccacaggt cacccaaacc ctcagattgc ctggcagaag   1800
gatggaggca cggatttccc cgctgcccgt gagcgacgca tgcatgtcat gccggatgac   1860
gacgtgtttt tcatcactga tgtgaaaata gatgacgcag ggtttacag ctgtactgct   1920
cagaactcag ccggttctat ttcagctaat gccaccctga ctgtcctaga gaccccatcc   1980
ttggtggtcc ccttggaaga ccgtgtggta tctgtgggag aaacagtggc cctccaatgc   2040
aaagccacgg ggaaccctcc gccccgcatc acctggttca agggggaccg cccgctgagc   2100
ctcactgagc ggcaccacct gaccccctgac aaccagctcc tggtggttca gaacgtggtg   2160
gcagaggatg cgggccgata tacctgtgag atgtccaaca ccctgggcac ggagcgagct   2220
cacagccagc tgagcgtcct gcccgcagca ggctgcagga aggatgggac cacggtaggc   2280
atcttcggat cccgcaacac cggccgcggc ggcgaggaga agaagaagga gaaggagaag   2340
gaggagcagg aggagcgcga gaccaagacc cccgagtgcc ccagccacac ccagcccctg   2400
ggcgtgttcc tgtttcctcc aaagcccaag gacacactga tgatctccag gacaccagag   2460
gtgacctgcg tggtggtgga cgtgagccac gaggaccccg aggtgaagtt caactggtac   2520
gtggatggcg tggaggtgca caatgccaag accaagccca gagaggagca gtacaactct   2580
acctataggg tggtgagcgt gctgacagtg ctgcaccagg actggctgaa cggcaaggag   2640
tataagtgca aggtgagcaa taaggccctg cctgccccaa tcgagaagac aatctccaag   2700
```

gccaagggcc agccaagaga gccccaggtg tacaccctgc cccctagcag ggatgagctg 2760
acaaagaacc aggtgtccct gacctgtctg gtgaagggct tttatccctc cgacatcgcc 2820
gtggagtggg agtctaatgg ccagcctgag aataactaca agacaacccc acccgtgctg 2880
gattctgacg gcagcttctt tctgtattct aagctgaccg tggacaagag caggtggcag 2940
cagggcaacg tgttcagctg ctccgtgatg cacgaagcac tgcacaatca ctacacccag 3000
aaatcactgt cactgagccc tggcaaa 3027

<210> SEQ ID NO 44
<211> LENGTH: 2988
<212> TYPE: DNA
<213> ORGANISM: Artificial Sequence
<220> FEATURE:
<223> OTHER INFORMATION: fusion protein

<400> SEQUENCE: 44
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cgggcacaat agaggacacg 1020
agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260
ctaattggca ggatgctgca ggcctttgtg acagccacct gtgcccaccc agaatcactg 1320
aagggtcaga gcattttctc tgtgccacca gagagtttcg tgtgcgatga cttcctgaag 1380
ccacagatca tcacccagcc agaaaccacc atggctatgg tgggcaagga catccggttt 1440
acatgctcag cagccagcag cagcagctcc cccatgacct ttgcctggaa gaaagacaat 1500
gaagtcctga ccaatgcaga catggagaac tttgtccacg tccacgcgca ggacggggaa 1560
gtgatggagt acaccaccat cctgcacctc cgtcaggtca ctttcgggca cgagggccgc 1620
taccaatgtg tcatcaccaa ccactttggc tccacctatt cacataaggc caggctcacc 1680
gtgaatgtgt tgccatcatt caccaaaacg ccccacgaca taaccatccg gaccaccacc 1740

```
gtggcccgcc tcgaatgtgc tgccacaggt cacccaaacc ctcagattgc ctggcagaag   1800

gatggaggca cggatttccc cgctgcccgt gagcgacgca tgcatgtcat gccggatgac   1860

gacgtgtttt tcatcactga tgtgaaaata gatgacgcag ggtttacag ctgtactgct    1920

cagaactcag ccggttctat ttcagctaat gccaccctga ctgtcctaga gaccccatcc   1980

ttggtggtcc ccttggaaga ccgtgtggta tctgtgggag aaacagtggc cctccaatgc   2040

aaagccacgg ggaaccctcc gccccgcatc acctggttca agggggaccg cccgctgagc   2100

ctcactgagc ggcaccacct gacccctgac aaccagctcc tggtggttca gaacgtggtg   2160

gcagaggatg cgggccgata tacctgtgag atgtccaaca ccctgggcac ggagcgagct   2220

cacagccagc tgagcgtcct gcccgcagca ggctgcagga aggatgggac cacggtaggc   2280

atcttcggat ccgaaccgaa atcttctgac aaaacccaca cctctccgcc gtctccggct   2340

ccggaactgc tgggtggttc ttctgttttc ctgtttcctc caaagcccaa ggacacactg   2400

atgatctcca ggacaccaga ggtgacctgc gtggtggtgg acgtgagcca cgaggacccc   2460

gaggtgaagt tcaactggta cgtggatggc gtggaggtgc acaatgccaa gaccaagccc   2520

agagaggagc agtacaactc tacctatagg gtggtgagcg tgctgacagt gctgcaccag   2580

gactggctga acggcaagga gtataagtgc aaggtgagca ataaggccct gcctgcccca   2640

atcgagaaga caatctccaa ggccaagggc cagccaagag agccccaggt gtacaccctg   2700

ccccctagca gggatgagct gacaaagaac caggtgtccc tgacctgtct ggtgaagggc   2760

ttttatccct ccgacatcgc cgtggagtgg gagtctaatg gccagcctga gaataactac   2820

aagacaaccc cacccgtgct ggattctgac ggcagcttct ttctgtattc taagctgacc   2880

gtggacaaga gcaggtggca gcagggcaac gtgttcagct gctccgtgat gcacgaagca   2940

ctgcacaatc actacaccca gaaatcactg tcactgagcc ctggcaaa                 2988
```

<210> SEQ ID NO 45
<211> LENGTH: 994
<212> TYPE: PRT
<213> ORGANISM: Artificial Sequence
<220> FEATURE:
<223> OTHER INFORMATION: fusion protein

<400> SEQUENCE: 45

```
Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140
```

```
Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560
```

```
Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Ser Glu Pro Lys Ser Ser Asp
        755                 760                 765

Lys Thr His Thr Ser Pro Pro Cys Pro Ala Pro Glu Leu Leu Gly Gly
    770                 775                 780

Pro Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
                805                 810                 815

Asp Pro Glu Val Lys Phe Asn Trp Tyr Val Asp Gly Val Glu Val His
            820                 825                 830

Asn Ala Lys Thr Lys Pro Arg Glu Glu Gln Tyr Asn Ser Thr Tyr Arg
        835                 840                 845

Val Val Ser Val Leu Thr Val Leu His Gln Asp Trp Leu Asn Gly Lys
    850                 855                 860

Glu Tyr Lys Cys Lys Val Ser Asn Lys Ala Leu Pro Ala Pro Ile Glu
865                 870                 875                 880

Lys Thr Ile Ser Lys Ala Lys Gly Gln Pro Arg Glu Pro Gln Val Tyr
                885                 890                 895

Thr Leu Pro Pro Ser Arg Asp Glu Leu Thr Lys Asn Gln Val Ser Leu
            900                 905                 910

Thr Cys Leu Val Lys Gly Phe Tyr Pro Ser Asp Ile Ala Val Glu Trp
        915                 920                 925

Glu Ser Asn Gly Gln Pro Glu Asn Asn Tyr Lys Thr Thr Pro Pro Val
    930                 935                 940

Leu Asp Ser Asp Gly Ser Phe Phe Leu Tyr Ser Lys Leu Thr Val Asp
945                 950                 955                 960

Lys Ser Arg Trp Gln Gln Gly Asn Val Phe Ser Cys Ser Val Met His
                965                 970                 975

Glu Ala Leu His Asn His Tyr Thr Gln Lys Ser Leu Ser Leu Ser Pro
```

980 985 990

Gly Lys

<210> SEQ ID NO 46
<211> LENGTH: 995
<212> TYPE: PRT
<213> ORGANISM: Artificial Sequence
<220> FEATURE:
<223> OTHER INFORMATION: fusion protein

<400> SEQUENCE: 46

Ala Gln Ala Gly Pro Arg Ala Pro Cys Ala Ala Ala Cys Thr Cys Ala
1 5 10 15

Gly Asp Ser Leu Asp Cys Ser Gly Arg Gly Leu Ala Thr Leu Pro Arg
20 25 30

Asp Leu Pro Ser Trp Thr Arg Ser Leu Asn Leu Ser Tyr Asn Arg Leu
35 40 45

Ser Glu Ile Asp Ser Ala Ala Phe Glu Asp Leu Thr Asn Leu Gln Glu
50 55 60

Val Tyr Leu Asn Ser Asn Glu Leu Thr Ala Ile Pro Ser Leu Gly Ala
65 70 75 80

Ala Ser Ile Gly Val Val Ser Leu Phe Leu Gln His Asn Lys Ile Leu
85 90 95

Ser Val Asp Gly Ser Gln Leu Lys Ser Tyr Leu Ser Leu Glu Val Leu
100 105 110

Asp Leu Ser Ser Asn Asn Ile Thr Glu Ile Arg Ser Ser Cys Phe Pro
115 120 125

Asn Gly Leu Arg Ile Arg Glu Leu Asn Leu Ala Ser Asn Arg Ile Ser
130 135 140

Ile Leu Glu Ser Gly Ala Phe Asp Gly Leu Ser Arg Ser Leu Leu Thr
145 150 155 160

Leu Arg Leu Ser Lys Asn Arg Ile Thr Gln Leu Pro Val Lys Ala Phe
165 170 175

Lys Leu Pro Arg Leu Thr Gln Leu Asp Leu Asn Arg Asn Arg Ile Arg
180 185 190

Leu Ile Glu Gly Leu Thr Phe Gln Gly Leu Asp Ser Leu Glu Val Leu
195 200 205

Arg Leu Gln Arg Asn Asn Ile Ser Arg Leu Thr Asp Gly Ala Phe Trp
210 215 220

Gly Leu Ser Lys Met His Val Leu His Leu Glu Tyr Asn Ser Leu Val
225 230 235 240

Glu Val Asn Ser Gly Ser Leu Tyr Gly Leu Thr Ala Leu His Gln Leu
245 250 255

His Leu Ser Asn Asn Ser Ile Ser Arg Ile Gln Arg Asp Gly Trp Ser
260 265 270

Phe Cys Gln Lys Leu His Glu Leu Ile Leu Ser Phe Asn Asn Leu Thr
275 280 285

Arg Leu Asp Glu Glu Ser Leu Ala Glu Leu Ser Ser Leu Ser Ile Leu
290 295 300

Arg Leu Ser His Asn Ala Ile Ser His Ile Ala Glu Gly Ala Phe Lys
305 310 315 320

Gly Leu Lys Ser Leu Arg Val Leu Asp Leu Asp His Asn Glu Ile Ser
325 330 335

Gly Thr Ile Glu Asp Thr Ser Gly Ala Phe Thr Gly Leu Asp Asn Leu
340 345 350

Ser Lys Leu Thr Leu Phe Gly Asn Lys Ile Lys Ser Val Ala Lys Arg
355 360 365

Ala Phe Ser Gly Leu Glu Ser Leu Glu His Leu Asn Leu Gly Glu Asn
370 375 380

Ala Ile Arg Ser Val Gln Phe Asp Ala Phe Ala Lys Met Lys Asn Leu
385 390 395 400

Lys Glu Leu Tyr Ile Ser Ser Glu Ser Phe Leu Cys Asp Cys Gln Leu
405 410 415

Lys Trp Leu Pro Pro Trp Leu Met Gly Arg Met Leu Gln Ala Phe Val
420 425 430

Thr Ala Thr Cys Ala His Pro Glu Ser Leu Lys Gly Gln Ser Ile Phe
435 440 445

Ser Val Leu Pro Asp Ser Phe Val Cys Asp Asp Phe Pro Lys Pro Gln
450 455 460

Ile Ile Thr Gln Pro Glu Thr Thr Met Ala Val Val Gly Lys Asp Ile
465 470 475 480

Arg Phe Thr Cys Ser Ala Ala Ser Ser Ser Ser Ser Pro Met Thr Phe
485 490 495

Ala Trp Lys Lys Asp Asn Glu Val Leu Ala Asn Ala Asp Met Glu Asn
500 505 510

Phe Ala His Val Arg Ala Gln Asp Gly Glu Val Met Glu Tyr Thr Thr
515 520 525

Ile Leu His Leu Arg His Val Thr Phe Gly His Glu Gly Arg Tyr Gln
530 535 540

Cys Ile Ile Thr Asn His Phe Gly Ser Thr Tyr Ser His Lys Ala Arg
545 550 555 560

Leu Thr Val Asn Val Leu Pro Ser Phe Thr Lys Ile Pro His Asp Ile
565 570 575

Ala Ile Arg Thr Gly Thr Thr Ala Arg Leu Glu Cys Ala Ala Thr Gly
580 585 590

His Pro Asn Pro Gln Ile Ala Trp Gln Lys Asp Gly Gly Thr Asp Phe
595 600 605

Pro Ala Ala Arg Glu Arg Arg Met His Val Met Pro Asp Asp Asp Val
610 615 620

Phe Phe Ile Thr Asp Val Lys Ile Asp Asp Met Gly Val Tyr Ser Cys
625 630 635 640

Thr Ala Gln Asn Ser Ala Gly Ser Val Ser Ala Asn Ala Thr Leu Thr
645 650 655

Val Leu Glu Thr Pro Ser Leu Ala Val Pro Leu Glu Asp Arg Val Val
660 665 670

Thr Val Gly Glu Thr Val Ala Phe Gln Cys Lys Ala Thr Gly Ser Pro
675 680 685

Thr Pro Arg Ile Thr Trp Leu Lys Gly Gly Arg Pro Leu Ser Leu Thr
690 695 700

Glu Arg His His Phe Thr Pro Gly Asn Gln Leu Leu Val Val Gln Asn
705 710 715 720

Val Met Ile Asp Asp Ala Gly Arg Tyr Thr Cys Glu Met Ser Asn Pro
725 730 735

Leu Gly Thr Glu Arg Ala His Ser Gln Leu Ser Ile Leu Pro Thr Pro
740 745 750

Gly Cys Arg Lys Asp Gly Thr Thr Gly Ser Glu Pro Arg Gly Pro Thr
755 760 765

-continued

```
Ile Lys Pro Cys Pro Pro Cys Lys Cys Pro Ala Pro Asn Leu Leu Gly
    770                 775                 780

Gly Pro Ser Val Phe Leu Phe Pro Pro Lys Pro Lys Asp Thr Leu Met
785                 790                 795                 800

Ile Ser Arg Thr Pro Glu Val Thr Cys Val Val Val Asp Val Ser His
                805                 810                 815

Glu Asp Pro Glu Val Lys Phe Asn Trp Tyr Val Asp Gly Val Glu Val
            820                 825                 830

His Asn Ala Lys Thr Lys Pro Arg Glu Glu Gln Tyr Asn Ser Thr Tyr
        835                 840                 845

Arg Val Val Ser Val Leu Thr Val Leu His Gln Asp Trp Leu Asn Gly
    850                 855                 860

Lys Glu Tyr Lys Cys Lys Val Ser Asn Lys Ala Leu Pro Ala Pro Ile
865                 870                 875                 880

Glu Lys Thr Ile Ser Lys Ala Lys Gly Gln Pro Arg Glu Pro Gln Val
                885                 890                 895

Tyr Thr Leu Pro Pro Ser Arg Asp Glu Leu Thr Lys Asn Gln Val Ser
            900                 905                 910

Leu Thr Cys Leu Val Lys Gly Phe Tyr Pro Ser Asp Ile Ala Val Glu
        915                 920                 925

Trp Glu Ser Asn Gly Gln Pro Glu Asn Asn Tyr Lys Thr Thr Pro Pro
    930                 935                 940

Val Leu Asp Ser Asp Gly Ser Phe Phe Leu Tyr Ser Lys Leu Thr Val
945                 950                 955                 960

Asp Lys Ser Arg Trp Gln Gln Gly Asn Val Phe Ser Cys Ser Val Met
                965                 970                 975

His Glu Ala Leu His Asn His Tyr Thr Gln Lys Ser Leu Ser Leu Ser
            980                 985                 990

Pro Gly Lys
        995


<210> SEQ ID NO 47
<211> LENGTH: 1007
<212> TYPE: PRT
<213> ORGANISM: Artificial Sequence
<220> FEATURE:
<223> OTHER INFORMATION: fusion protein

<400> SEQUENCE: 47

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125
```

```
Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
```

-continued

```
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Ser Arg Asn Thr Gly Arg Gly
        755                 760                 765

Gly Glu Glu Lys Lys Lys Glu Lys Glu Lys Glu Glu Gln Glu Glu Arg
    770                 775                 780

Glu Thr Lys Thr Pro Glu Cys Pro Ser His Thr Gln Pro Leu Gly Val
785                 790                 795                 800

Phe Leu Phe Pro Pro Lys Pro Lys Asp Thr Leu Met Ile Ser Arg Thr
                805                 810                 815

Pro Glu Val Thr Cys Val Val Val Asp Val Ser His Glu Asp Pro Glu
            820                 825                 830

Val Lys Phe Asn Trp Tyr Val Asp Gly Val Glu Val His Asn Ala Lys
        835                 840                 845

Thr Lys Pro Arg Glu Glu Gln Tyr Asn Ser Thr Tyr Arg Val Val Ser
    850                 855                 860

Val Leu Thr Val Leu His Gln Asp Trp Leu Asn Gly Lys Glu Tyr Lys
865                 870                 875                 880

Cys Lys Val Ser Asn Lys Ala Leu Pro Ala Pro Ile Glu Lys Thr Ile
                885                 890                 895

Ser Lys Ala Lys Gly Gln Pro Arg Glu Pro Gln Val Tyr Thr Leu Pro
            900                 905                 910

Pro Ser Arg Asp Glu Leu Thr Lys Asn Gln Val Ser Leu Thr Cys Leu
        915                 920                 925

Val Lys Gly Phe Tyr Pro Ser Asp Ile Ala Val Glu Trp Glu Ser Asn
    930                 935                 940

Gly Gln Pro Glu Asn Asn Tyr Lys Thr Thr Pro Pro Val Leu Asp Ser
945                 950                 955                 960

Asp Gly Ser Phe Phe Leu Tyr Ser Lys Leu Thr Val Asp Lys Ser Arg
                965                 970                 975
```

Trp Gln Gln Gly Asn Val Phe Ser Cys Ser Val Met His Glu Ala Leu
980 985 990

His Asn His Tyr Thr Gln Lys Ser Leu Ser Leu Ser Pro Gly Lys
995 1000 1005

<210> SEQ ID NO 48
<211> LENGTH: 994
<212> TYPE: PRT
<213> ORGANISM: Artificial Sequence
<220> FEATURE:
<223> OTHER INFORMATION: fusion protein

<400> SEQUENCE: 48

Ala Gln Ala Gly Pro Arg Ala Pro Cys Ala Ala Ala Cys Thr Cys Ala
1 5 10 15

Gly Asp Ser Leu Asp Cys Ser Gly Arg Gly Leu Ala Thr Leu Pro Arg
20 25 30

Asp Leu Pro Ser Trp Thr Arg Ser Leu Asn Leu Ser Tyr Asn Arg Leu
35 40 45

Ser Glu Ile Asp Ser Ala Ala Phe Glu Asp Leu Thr Asn Leu Gln Glu
50 55 60

Val Tyr Leu Asn Ser Asn Glu Leu Thr Ala Ile Pro Ser Leu Gly Ala
65 70 75 80

Ala Ser Ile Gly Val Val Ser Leu Phe Leu Gln His Asn Lys Ile Leu
85 90 95

Ser Val Asp Gly Ser Gln Leu Lys Ser Tyr Leu Ser Leu Glu Val Leu
100 105 110

Asp Leu Ser Ser Asn Asn Ile Thr Glu Ile Arg Ser Ser Cys Phe Pro
115 120 125

Asn Gly Leu Arg Ile Arg Glu Leu Asn Leu Ala Ser Asn Arg Ile Ser
130 135 140

Ile Leu Glu Ser Gly Ala Phe Asp Gly Leu Ser Arg Ser Leu Leu Thr
145 150 155 160

Leu Arg Leu Ser Lys Asn Arg Ile Thr Gln Leu Pro Val Lys Ala Phe
165 170 175

Lys Leu Pro Arg Leu Thr Gln Leu Asp Leu Asn Arg Asn Arg Ile Arg
180 185 190

Leu Ile Glu Gly Leu Thr Phe Gln Gly Leu Asp Ser Leu Glu Val Leu
195 200 205

Arg Leu Gln Arg Asn Asn Ile Ser Arg Leu Thr Asp Gly Ala Phe Trp
210 215 220

Gly Leu Ser Lys Met His Val Leu His Leu Glu Tyr Asn Ser Leu Val
225 230 235 240

Glu Val Asn Ser Gly Ser Leu Tyr Gly Leu Thr Ala Leu His Gln Leu
245 250 255

His Leu Ser Asn Asn Ser Ile Ser Arg Ile Gln Arg Asp Gly Trp Ser
260 265 270

Phe Cys Gln Lys Leu His Glu Leu Ile Leu Ser Phe Asn Asn Leu Thr
275 280 285

Arg Leu Asp Glu Glu Ser Leu Ala Glu Leu Ser Ser Leu Ser Ile Leu
290 295 300

Arg Leu Ser His Asn Ala Ile Ser His Ile Ala Glu Gly Ala Phe Lys
305 310 315 320

Gly Leu Lys Ser Leu Arg Val Leu Asp Leu Asp His Asn Glu Ile Ser
325 330 335

```
Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750
```

```
Gly Cys Arg Lys Asp Gly Thr Thr Gly Ser Glu Pro Lys Ser Ser Asp
        755                 760                 765

Lys Thr His Thr Ser Pro Pro Ser Pro Ala Pro Glu Leu Leu Gly Gly
    770                 775                 780

Ser Ser Val Phe Leu Phe Pro Pro Lys Pro Lys Asp Thr Leu Met Ile
785                 790                 795                 800

Ser Arg Thr Pro Glu Val Thr Cys Val Val Val Asp Val Ser His Glu
                805                 810                 815

Asp Pro Glu Val Lys Phe Asn Trp Tyr Val Asp Gly Val Glu Val His
            820                 825                 830

Asn Ala Lys Thr Lys Pro Arg Glu Glu Gln Tyr Asn Ser Thr Tyr Arg
        835                 840                 845

Val Val Ser Val Leu Thr Val Leu His Gln Asp Trp Leu Asn Gly Lys
    850                 855                 860

Glu Tyr Lys Cys Lys Val Ser Asn Lys Ala Leu Pro Ala Pro Ile Glu
865                 870                 875                 880

Lys Thr Ile Ser Lys Ala Lys Gly Gln Pro Arg Glu Pro Gln Val Tyr
                885                 890                 895

Thr Leu Pro Pro Ser Arg Asp Glu Leu Thr Lys Asn Gln Val Ser Leu
            900                 905                 910

Thr Cys Leu Val Lys Gly Phe Tyr Pro Ser Asp Ile Ala Val Glu Trp
        915                 920                 925

Glu Ser Asn Gly Gln Pro Glu Asn Asn Tyr Lys Thr Thr Pro Pro Val
    930                 935                 940

Leu Asp Ser Asp Gly Ser Phe Phe Leu Tyr Ser Lys Leu Thr Val Asp
945                 950                 955                 960

Lys Ser Arg Trp Gln Gln Gly Asn Val Phe Ser Cys Ser Val Met His
                965                 970                 975

Glu Ala Leu His Asn His Tyr Thr Gln Lys Ser Leu Ser Leu Ser Pro
            980                 985                 990

Gly Lys


<210> SEQ ID NO 49
<211> LENGTH: 2982
<212> TYPE: DNA
<213> ORGANISM: Artificial Sequence
<220> FEATURE:
<223> OTHER INFORMATION: fusion protein

<400> SEQUENCE: 49

gctcaggctg gacctagggc tccttgcgct gccgcctgca cctgtgcagg cgattctctg      60

gactgcagcg gccggggcct ggccacactg cccagggacc tgccttcctg gaccagatct     120

ctgaacctga gctacaatcg gctgtccgag atcgattctg ccgcctttga ggacctgaca     180

aatctgcagg aggtgtatct gaacagcaat gagctgaccg caatcccctc cctgggagca     240

gcctctatcg gcgtggtgag cctgttcctg cagcacaaca agatcctgag cgtggatggc     300

tcccagctga agagctacct gtctctggag gtgctggacc tgagctccaa caatatcacc     360

gagatcagat ctagctgttt tcctaatggc ctgcggatca gagagctgaa cctggcctct     420

aatcggatca gcatcctgga gtccggcgcc ttcgatggcc tgagcagatc cctgctgaca     480

ctgcgcctgt ccaagaaccg gatcacccag ctgcccgtga aggcctttaa gctgcctagg     540

ctgacacagc tggacctgaa ccggaataga atcaggctga tcgagggcct gaccttccag     600

ggcctggata gcctggaggt gctgcgcctg cagcggaaca atatctcccg cctgacagac     660
```

-continued

```
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggatccgagc caaagtcctc tgataagaca cacacctctc caccatgccc agcaccagag   2340
ctgctgggag gaccaagcgt gttcctgttt cctccaaagc ccaaggacac actgatgatc   2400
tccaggacac cagaggtgac ctgcgtggtg gtggacgtga gccacgagga ccccgaggtg   2460
aagttcaact ggtacgtgga tggcgtggag gtgcacaatg ccaagaccaa gcccagagag   2520
gagcagtaca actctaccta tagggtggtg agcgtgctga cagtgctgca ccaggactgg   2580
ctgaacggca aggagtataa gtgcaaggtg agcaataagg ccctgcctgc cccaatcgag   2640
aagacaatct ccaaggccaa gggccagcca agagagcccc aggtgtacac cctgccccct   2700
agcagggatg agctgacaaa gaaccaggtg tccctgacct gtctggtgaa gggcttttat   2760
ccctccgaca tcgccgtgga gtgggagtct aatggccagc ctgagaataa ctacaagaca   2820
accccacccg tgctggattc tgacggcagc ttctttctgt attctaagct gaccgtggac   2880
aagagcaggt ggcagcaggg caacgtgttc agctgctccg tgatgcacga agcactgcac   2940
aatcactaca cccagaaatc actgtcactg agccctggca aa                      2982
```

<210> SEQ ID NO 50
<211> LENGTH: 2985
<212> TYPE: DNA
<213> ORGANISM: Artificial Sequence
<220> FEATURE:
<223> OTHER INFORMATION: fusion protein

<400> SEQUENCE: 50
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100

-continued

```
ctgagcctga cagagcgcca ccacttcacc cctggcaatc agctgctggt ggtgcagaac   2160

gtgatgatcg atgacgccgg caggtataca tgcgagatga gcaatcctct gggcaccgag   2220

agggcacact cccagctgtc tatcctgcct accccaggct gccggaagga tggcaccaca   2280

ggatccgagc ctcggggccc taccatcaag ccctgccccc cttgcaagtg ccctgcccct   2340

aatctgctgg gcggaccctc cgtgttcctg tttcctccaa agcccaagga cacactgatg   2400

atctccagga caccagaggt gacctgcgtg gtggtggacg tgagccacga ggaccccgag   2460

gtgaagttca actggtacgt ggatggcgtg gaggtgcaca atgccaagac caagcccaga   2520

gaggagcagt acaactctac ctatagggtg gtgagcgtgc tgacagtgct gcaccaggac   2580

tggctgaacg gcaaggagta taagtgcaag gtgagcaata aggccctgcc tgccccaatc   2640

gagaagacaa tctccaaggc caagggccag ccaagagagc cccaggtgta caccctgccc   2700

cctagcaggg atgagctgac aaagaaccag gtgtccctga cctgtctggt gaagggcttt   2760

tatccctccg acatcgccgt ggagtgggag tctaatggcc agcctgagaa taactacaag   2820

acaaccccac ccgtgctgga ttctgacggc agcttctttc tgtattctaa gctgaccgtg   2880

gacaagagca ggtggcagca gggcaacgtg ttcagctgct ccgtgatgca cgaagcactg   2940

cacaatcact acacccagaa atcactgtca ctgagccctg gcaaa                    2985
```

<210> SEQ ID NO 51
<211> LENGTH: 3021
<212> TYPE: DNA
<213> ORGANISM: Artificial Sequence
<220> FEATURE:
<223> OTHER INFORMATION: fusion protein

<400> SEQUENCE: 51

```
gctcaggctg gacctagggc tccttgcgct gccgcctgca cctgtgcagg cgattctctg     60

gactgcagcg gccggggcct ggccacactg cccagggacc tgccttcctg gaccagatct    120

ctgaacctga gctacaatcg gctgtccgag atcgattctg ccgcctttga ggacctgaca    180

aatctgcagg aggtgtatct gaacagcaat gagctgaccg caatcccctc cctgggagca    240

gcctctatcg gcgtggtgag cctgttcctg cagcacaaca agatcctgag cgtggatggc    300

tcccagctga agagctacct gtctctggag gtgctggacc tgagctccaa caatatcacc    360

gagatcagat ctagctgttt tcctaatggc ctgcggatca gagagctgaa cctggcctct    420

aatcggatca gcatcctgga gtccggcgcc ttcgatggcc tgagcagatc cctgctgaca    480

ctgcgcctgt ccaagaaccg gatcacccag ctgcccgtga aggcctttaa gctgcctagg    540

ctgacacagc tggacctgaa ccggaataga atcaggctga tcgagggcct gaccttccag    600

ggcctggata gcctggaggt gctgcgcctg cagcggaaca atatctcccg cctgacagac    660

ggagcatttt ggggcctgtc taagatgcac gtgctgcacc tggagtacaa tagcctggtg    720

gaggtgaact ctggcagcct gtatggcctg accgccctgc accagctgca cctgtccaac    780

aatagcatca gcagaatcca gagggatggc tggtccttct gccagaagct gcacgagctg    840

atcctgtctt ttaacaatct gaccaggctg gacgaggaga gcctggcaga gctgtcctct    900

ctgtccatcc tgcgcctgtc tcacaatgcc atcagccaca tcgccgaggg cgcctttaag    960

ggcctgaaga gcctgagggt gctggatctg gaccacaacg agatctctgg caccatcgag   1020

gatacaagcg gcgccttcac aggcctggac aatctgtcca agctgaccct gtttggcaac   1080

aagatcaagt ctgtggccaa gcgggccttc tctggcctgg agagcctgga gcacctgaac   1140

ctgggcgaga atgccatcag atccgtgcag ttcgatgcct ttgccaagat gaagaatctg   1200
```

aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
ggatcccgca acaccggccg cggcggcgag gagaagaaga aggagaagga gaaggaggag 2340
caggaggagc gcgagaccaa gacccccgag tgccccagcc acacccagcc cctgggcgtg 2400
ttcctgtttc ctccaaagcc caaggacaca ctgatgatct ccaggacacc agaggtgacc 2460
tgcgtggtgg tggacgtgag ccacgaggac cccgaggtga agttcaactg gtacgtggat 2520
ggcgtggagg tgcacaatgc caagaccaag cccagagagg agcagtacaa ctctacctat 2580
agggtggtga gcgtgctgac agtgctgcac caggactggc tgaacggcaa ggagtataag 2640
tgcaaggtga gcaataaggc cctgcctgcc ccaatcgaga agacaatctc caaggccaag 2700
ggccagccaa gagagcccca ggtgtacacc ctgcccccta gcagggatga gctgacaaag 2760
aaccaggtgt ccctgacctg tctggtgaag ggcttttatc cctccgacat cgccgtggag 2820
tgggagtcta atggccagcc tgagaataac tacaagacaa ccccacccgt gctggattct 2880
gacggcagct tctttctgta ttctaagctg accgtggaca agagcaggtg gcagcagggc 2940
aacgtgttca gctgctccgt gatgcacgaa gcactgcaca atcactacac ccagaaatca 3000
ctgtcactga gccctggcaa a 3021

<210> SEQ ID NO 52
<211> LENGTH: 2982
<212> TYPE: DNA
<213> ORGANISM: Artificial Sequence
<220> FEATURE:
<223> OTHER INFORMATION: fusion protein

<400> SEQUENCE: 52
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180

-continued

```
aatctgcagg aggtgtatct gaacagcaat gagctgaccg caatcccctc cctgggagca    240
gcctctatcg gcgtggtgag cctgttcctg cagcacaaca agatcctgag cgtggatggc    300
tcccagctga agagctacct gtctctggag gtgctggacc tgagctccaa caatatcacc    360
gagatcagat ctagctgttt tcctaatggc ctgcggatca gagagctgaa cctggcctct    420
aatcggatca gcatcctgga gtccggcgcc ttcgatggcc tgagcagatc cctgctgaca    480
ctgcgcctgt ccaagaaccg gatcacccag ctgcccgtga aggcctttaa gctgcctagg    540
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggatccgaac cgaaatcttc tgacaaaacc cacacctctc cgccgtctcc ggctccggaa   2340
ctgctgggtg gttcttctgt tttcctgttt cctccaaagc ccaaggacac actgatgatc   2400
tccaggacac cagaggtgac ctgcgtggtg gtggacgtga gccacgagga ccccgaggtg   2460
aagttcaact ggtacgtgga tggcgtggag gtgcacaatg ccaagaccaa gcccagagag   2520
gagcagtaca actctaccta tagggtggtg agcgtgctga cagtgctgca ccaggactgg   2580
```

```
ctgaacggca aggagtataa gtgcaaggtg agcaataagg ccctgcctgc cccaatcgag   2640

aagacaatct ccaaggccaa gggccagcca agagagcccc aggtgtacac cctgccccct   2700

agcagggatg agctgacaaa gaaccaggtg tccctgacct gtctggtgaa gggcttttat   2760

ccctccgaca tcgccgtgga gtgggagtct aatggccagc ctgagaataa ctacaagaca   2820

accccacccg tgctggattc tgacggcagc ttctttctgt attctaagct gaccgtggac   2880

aagagcaggt ggcagcaggg caacgtgttc agctgctccg tgatgcacga agcactgcac   2940

aatcactaca cccagaaatc actgtcactg agccctggca aa                      2982


<210> SEQ ID NO 53
<211> LENGTH: 994
<212> TYPE: PRT
<213> ORGANISM: Artificial Sequence
<220> FEATURE:
<223> OTHER INFORMATION: fusion protein

<400> SEQUENCE: 53

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285
```

-continued

```
Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
```

705 710 715 720

Val Met Ile Asp Asp Ala Gly Arg Tyr Thr Cys Glu Met Ser Asn Pro
725 730 735

Leu Gly Thr Glu Arg Ala His Ser Gln Leu Ser Ile Leu Pro Thr Pro
740 745 750

Gly Cys Arg Lys Asp Gly Thr Thr Gly Ser Glu Pro Lys Ser Ser Asp
755 760 765

Lys Thr His Thr Ser Pro Pro Cys Pro Ala Pro Glu Leu Leu Gly Gly
770 775 780

Pro Ser Val Phe Ile Phe Pro Pro Lys Ile Lys Asp Val Leu Met Ile
785 790 795 800

Ser Leu Ser Pro Ile Val Thr Cys Val Val Val Asp Val Ser Glu Asp
805 810 815

Asp Pro Asp Val Gln Ile Ser Trp Phe Val Asn Asn Val Glu Val His
820 825 830

Thr Ala Gln Thr Gln Thr His Arg Glu Asp Tyr Asn Ser Thr Leu Arg
835 840 845

Val Val Ser Ala Leu Pro Ile Gln His Gln Asp Trp Met Ser Gly Lys
850 855 860

Glu Phe Lys Cys Lys Val Asn Asn Lys Asp Leu Pro Ala Pro Ile Glu
865 870 875 880

Arg Thr Ile Ser Lys Pro Lys Gly Ser Val Arg Ala Pro Gln Val Tyr
885 890 895

Val Leu Pro Pro Pro Glu Glu Glu Met Thr Lys Lys Gln Val Thr Leu
900 905 910

Thr Cys Met Val Thr Asp Phe Met Pro Glu Asp Ile Tyr Val Glu Trp
915 920 925

Thr Asn Asn Gly Lys Thr Glu Leu Asn Tyr Lys Asn Thr Glu Pro Val
930 935 940

Leu Asp Ser Asp Gly Ser Tyr Phe Met Tyr Ser Lys Leu Arg Val Glu
945 950 955 960

Lys Lys Asn Trp Val Glu Arg Asn Ser Tyr Ser Cys Ser Val Val His
965 970 975

Glu Gly Leu His Asn His His Thr Thr Lys Ser Phe Ser Arg Thr Pro
980 985 990

Gly Lys

<210> SEQ ID NO 54
<211> LENGTH: 995
<212> TYPE: PRT
<213> ORGANISM: Artificial Sequence
<220> FEATURE:
<223> OTHER INFORMATION: fusion protein

<400> SEQUENCE: 54

Ala Gln Ala Gly Pro Arg Ala Pro Cys Ala Ala Ala Cys Thr Cys Ala
1 5 10 15

Gly Asp Ser Leu Asp Cys Ser Gly Arg Gly Leu Ala Thr Leu Pro Arg
20 25 30

Asp Leu Pro Ser Trp Thr Arg Ser Leu Asn Leu Ser Tyr Asn Arg Leu
35 40 45

Ser Glu Ile Asp Ser Ala Ala Phe Glu Asp Leu Thr Asn Leu Gln Glu
50 55 60

Val Tyr Leu Asn Ser Asn Glu Leu Thr Ala Ile Pro Ser Leu Gly Ala
65 70 75 80

```
Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495
```

-continued

```
Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Ser Glu Pro Arg Gly Pro Thr
        755                 760                 765

Ile Lys Pro Cys Pro Pro Cys Lys Cys Pro Ala Pro Asn Leu Leu Gly
    770                 775                 780

Gly Pro Ser Val Phe Ile Phe Pro Pro Lys Ile Lys Asp Val Leu Met
785                 790                 795                 800

Ile Ser Leu Ser Pro Ile Val Thr Cys Val Val Val Asp Val Ser Glu
                805                 810                 815

Asp Asp Pro Asp Val Gln Ile Ser Trp Phe Val Asn Asn Val Glu Val
            820                 825                 830

His Thr Ala Gln Thr Gln Thr His Arg Glu Asp Tyr Asn Ser Thr Leu
        835                 840                 845

Arg Val Val Ser Ala Leu Pro Ile Gln His Gln Asp Trp Met Ser Gly
    850                 855                 860

Lys Glu Phe Lys Cys Lys Val Asn Asn Lys Asp Leu Pro Ala Pro Ile
865                 870                 875                 880

Glu Arg Thr Ile Ser Lys Pro Lys Gly Ser Val Arg Ala Pro Gln Val
                885                 890                 895

Tyr Val Leu Pro Pro Pro Glu Glu Glu Met Thr Lys Lys Gln Val Thr
            900                 905                 910

Leu Thr Cys Met Val Thr Asp Phe Met Pro Glu Asp Ile Tyr Val Glu
```

```
        915                 920                 925

Trp Thr Asn Asn Gly Lys Thr Glu Leu Asn Tyr Lys Asn Thr Glu Pro
    930                 935                 940

Val Leu Asp Ser Asp Gly Ser Tyr Phe Met Tyr Ser Lys Leu Arg Val
945                 950                 955                 960

Glu Lys Lys Asn Trp Val Glu Arg Asn Ser Tyr Ser Cys Ser Val Val
                965                 970                 975

His Glu Gly Leu His Asn His His Thr Thr Lys Ser Phe Ser Arg Thr
            980                 985                 990

Pro Gly Lys
        995


<210> SEQ ID NO 55
<211> LENGTH: 1007
<212> TYPE: PRT
<213> ORGANISM: Artificial Sequence
<220> FEATURE:
<223> OTHER INFORMATION: fusion protein

<400> SEQUENCE: 55

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
```

```
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700
```

```
Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Ser Arg Asn Thr Gly Arg Gly
        755                 760                 765

Gly Glu Glu Lys Lys Lys Glu Lys Glu Lys Glu Glu Gln Glu Glu Arg
    770                 775                 780

Glu Thr Lys Thr Pro Glu Cys Pro Ser His Thr Gln Pro Leu Gly Val
785                 790                 795                 800

Phe Ile Phe Pro Pro Lys Ile Lys Asp Val Leu Met Ile Ser Leu Ser
                805                 810                 815

Pro Ile Val Thr Cys Val Val Val Asp Val Ser Glu Asp Asp Pro Asp
            820                 825                 830

Val Gln Ile Ser Trp Phe Val Asn Asn Val Glu Val His Thr Ala Gln
        835                 840                 845

Thr Gln Thr His Arg Glu Asp Tyr Asn Ser Thr Leu Arg Val Val Ser
    850                 855                 860

Ala Leu Pro Ile Gln His Gln Asp Trp Met Ser Gly Lys Glu Phe Lys
865                 870                 875                 880

Cys Lys Val Asn Asn Lys Asp Leu Pro Ala Pro Ile Glu Arg Thr Ile
                885                 890                 895

Ser Lys Pro Lys Gly Ser Val Arg Ala Pro Gln Val Tyr Val Leu Pro
            900                 905                 910

Pro Pro Glu Glu Glu Met Thr Lys Lys Gln Val Thr Leu Thr Cys Met
        915                 920                 925

Val Thr Asp Phe Met Pro Glu Asp Ile Tyr Val Glu Trp Thr Asn Asn
    930                 935                 940

Gly Lys Thr Glu Leu Asn Tyr Lys Asn Thr Glu Pro Val Leu Asp Ser
945                 950                 955                 960

Asp Gly Ser Tyr Phe Met Tyr Ser Lys Leu Arg Val Glu Lys Lys Asn
                965                 970                 975

Trp Val Glu Arg Asn Ser Tyr Ser Cys Ser Val Val His Glu Gly Leu
            980                 985                 990

His Asn His His Thr Thr Lys Ser  Phe Ser Arg Thr Pro  Gly Lys
        995                 1000                1005
```

<210> SEQ ID NO 56
<211> LENGTH: 994
<212> TYPE: PRT
<213> ORGANISM: Artificial Sequence
<220> FEATURE:
<223> OTHER INFORMATION: fusion protein

<400> SEQUENCE: 56

```
Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60
```

```
Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480
```

-continued

```
Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Ser Glu Pro Lys Ser Ser Asp
        755                 760                 765

Lys Thr His Thr Ser Pro Pro Ser Pro Ala Pro Glu Leu Leu Gly Gly
    770                 775                 780

Ser Ser Val Phe Ile Phe Pro Pro Lys Ile Lys Asp Val Leu Met Ile
785                 790                 795                 800

Ser Leu Ser Pro Ile Val Thr Cys Val Val Val Asp Val Ser Glu Asp
                805                 810                 815

Asp Pro Asp Val Gln Ile Ser Trp Phe Val Asn Asn Val Glu Val His
            820                 825                 830

Thr Ala Gln Thr Gln Thr His Arg Glu Asp Tyr Asn Ser Thr Leu Arg
        835                 840                 845

Val Val Ser Ala Leu Pro Ile Gln His Gln Asp Trp Met Ser Gly Lys
    850                 855                 860

Glu Phe Lys Cys Lys Val Asn Asn Lys Asp Leu Pro Ala Pro Ile Glu
865                 870                 875                 880

Arg Thr Ile Ser Lys Pro Lys Gly Ser Val Arg Ala Pro Gln Val Tyr
                885                 890                 895

Val Leu Pro Pro Pro Glu Glu Glu Met Thr Lys Lys Gln Val Thr Leu
```

```
            900                 905                 910

Thr Cys Met Val Thr Asp Phe Met Pro Glu Asp Ile Tyr Val Glu Trp
        915                 920                 925

Thr Asn Asn Gly Lys Thr Glu Leu Asn Tyr Lys Asn Thr Glu Pro Val
    930                 935                 940

Leu Asp Ser Asp Gly Ser Tyr Phe Met Tyr Ser Lys Leu Arg Val Glu
945                 950                 955                 960

Lys Lys Asn Trp Val Glu Arg Asn Ser Tyr Ser Cys Ser Val Val His
                965                 970                 975

Glu Gly Leu His Asn His His Thr Thr Lys Ser Phe Ser Arg Thr Pro
            980                 985                 990

Gly Lys


<210> SEQ ID NO 57
<211> LENGTH: 2982
<212> TYPE: DNA
<213> ORGANISM: Artificial Sequence
<220> FEATURE:
<223> OTHER INFORMATION: fusion protein

<400> SEQUENCE: 57

gctcaggctg gacctagggc tccttgcgct gccgcctgca cctgtgcagg cgattctctg     60

gactgcagcg gccggggcct ggccacactg cccagggacc tgccttcctg gaccagatct    120

ctgaacctga gctacaatcg gctgtccgag atcgattctg ccgcctttga ggacctgaca    180

aatctgcagg aggtgtatct gaacagcaat gagctgaccg caatcccctc cctgggagca    240

gcctctatcg gcgtggtgag cctgttcctg cagcacaaca agatcctgag cgtggatggc    300

tcccagctga agagctacct gtctctggag gtgctggacc tgagctccaa caatatcacc    360

gagatcagat ctagctgttt tcctaatggc ctgcggatca gagagctgaa cctggcctct    420

aatcggatca gcatcctgga gtccggcgcc ttcgatggcc tgagcagatc cctgctgaca    480

ctgcgcctgt ccaagaaccg gatcacccag ctgcccgtga aggcctttaa gctgcctagg    540

ctgacacagc tggacctgaa ccggaataga atcaggctga tcgagggcct gaccttccag    600

ggcctggata gcctggaggt gctgcgcctg cagcggaaca atatctcccg cctgacagac    660

ggagcatttt ggggcctgtc taagatgcac gtgctgcacc tggagtacaa tagcctggtg    720

gaggtgaact ctggcagcct gtatggcctg accgccctgc accagctgca cctgtccaac    780

aatagcatca gcagaatcca gagggatggc tggtccttct gccagaagct gcacgagctg    840

atcctgtctt ttaacaatct gaccaggctg gacgaggaga gcctggcaga gctgtcctct    900

ctgtccatcc tgcgcctgtc tcacaatgcc atcagccaca tcgccgaggg cgcctttaag    960

ggcctgaaga gcctgagggt gctggatctg gaccacaacg agatctctgg caccatcgag   1020

gatacaagcg gcgccttcac aggcctggac aatctgtcca agctgaccct gtttggcaac   1080

aagatcaagt ctgtggccaa gcgggccttc tctggcctgg agagcctgga gcacctgaac   1140

ctgggcgaga atgccatcag atccgtgcag ttcgatgcct ttgccaagat gaagaatctg   1200

aaggagctgt acatcagctc cgagagcttc ctgtgcgact gtcagctgaa gtggctgcca   1260

ccttggctga tgggaaggat gctgcaggcc tttgtgaccg ccacatgcgc ccacccagag   1320

agcctgaagg gccagagcat cttctccgtg ctgcccgata gcttcgtgtg cgacgatttt   1380

cctaagccac agatcatcac ccagccagag acaacaatgg ccgtggtggg caaggacatc   1440

cggtttacat gttccgccgc ctctagctcc tctagcccca tgaccttcgc ctggaagaag   1500
```

```
gataacgagg tgctggccaa tgccgacatg gagaacttcg cccacgtgag agcccaggat   1560

ggcgaagtga tggagtatac cacaatcctg cacctgcggc acgtgacctt tggccacgag   1620

ggcagatacc agtgcatcat cacaaatcac ttcggctcta cctatagcca caaggccagg   1680

ctgacagtga acgtgctgcc tagctttacc aagatcccac acgacatcgc catcagaaca   1740

ggcaccacag caaggctgga gtgtgcagca accggacacc caaaccctca gatcgcatgg   1800

cagaaggatg gaggcacaga cttccctgca gcccgcgaga ggagaatgca cgtgatgcca   1860

gacgatgacg tgttctttat cacagatgtg aagatcgatg acatgggcgt gtactcctgc   1920

accgcacaga acagcgccgg cagcgtgtcc gccaacgcca ccctgaccgt gctggagaca   1980

ccatccctgg ccgtgcccct ggaggacagg gtggtgaccg tgggcgagac agtggccttt   2040

cagtgtaagg ccaccggctc tccaacacca aggatcacct ggctgaaggg cggcaggccc   2100

ctgagcctga cagagcgcca ccacttcacc cctggcaatc agctgctggt ggtgcagaac   2160

gtgatgatcg atgacgccgg caggtataca tgcgagatga gcaatcctct gggcaccgag   2220

agggcacact cccagctgtc tatcctgcct accccaggct gccggaagga tggcaccaca   2280

ggatccgagc caaagtcctc tgataagaca cacacctctc caccatgccc agcaccagag   2340

ctgctgggag gaccaagcgt gttcatcttc ccacccaaga tcaaggacgt gctgatgatc   2400

tccctgtccc ccatcgtgac ctgcgtggtg gtggacgtgt ccgaggacga ccccgacgtg   2460

cagatcagtt ggttcgtgaa caacgtggaa gtgcacaccg cccagaccca gacccacaga   2520

gaggactaca actccaccct gcgggtggtg tccgccctgc ccatccagca ccaggactgg   2580

atgtccggca aagaattcaa gtgcaaagtg aacaacaagg acctgcctgc ccccatcgag   2640

cggaccatct ccaagcccaa gggctccgtg cgggctcccc aggtgtacgt gctgcccccct  2700

ccagaggaag agatgaccaa gaagcaggtc acactgacct gcatggtcac cgacttcatg   2760

cccgaggaca tctacgtgga atggaccaac aatggcaaga ccgagctgaa ctacaagaac   2820

accgagcctg tgctggactc cgacggctcc tacttcatgt actccaagct gcgggtggaa   2880

aagaagaact gggtcgagcg gaactcctac tcctgctccg tggtgcacga gggcctgcac   2940

aaccaccaca ccaccaagtc cttctcccgg acccccggca aa                      2982
```

<210> SEQ ID NO 58
<211> LENGTH: 2985
<212> TYPE: DNA
<213> ORGANISM: Artificial Sequence
<220> FEATURE:
<223> OTHER INFORMATION: fusion protein

<400> SEQUENCE: 58

```
gctcaggctg gacctagggc tccttgcgct gccgcctgca cctgtgcagg cgattctctg     60

gactgcagcg gccggggcct ggccacactg cccagggacc tgccttcctg gaccagatct    120

ctgaacctga gctacaatcg gctgtccgag atcgattctg ccgcctttga ggacctgaca    180

aatctgcagg aggtgtatct gaacagcaat gagctgaccg caatcccctc cctgggagca    240

gcctctatcg gcgtggtgag cctgttcctg cagcacaaca agatcctgag cgtggatggc    300

tcccagctga agagctacct gtctctggag gtgctggacc tgagctccaa caatatcacc    360

gagatcagat ctagctgttt tcctaatggc ctgcggatca gagagctgaa cctggcctct    420

aatcggatca gcatcctgga gtccggcgcc ttcgatggcc tgagcagatc cctgctgaca    480

ctgcgcctgt ccaagaaccg gatcacccag ctgcccgtga aggcctttaa gctgcctagg    540

ctgacacagc tggacctgaa ccggaataga atcaggctga tcgagggcct gaccttccag    600
```

-continued

```
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggatccgagc ctcggggccc taccatcaag ccctgccccc cttgcaagtg ccctgcccct   2340
aatctgctgg gcggaccctc cgtgttcatc ttcccaccca agatcaagga cgtgctgatg   2400
atctccctgt cccccatcgt gacctgcgtg gtggtggacg tgtccgagga cgaccccgac   2460
gtgcagatca gttggttcgt gaacaacgtg gaagtgcaca ccgcccagac ccagacccac   2520
agagaggact acaactccac cctgcgggtg gtgtccgccc tgcccatcca gcaccaggac   2580
tggatgtccg gcaaagaatt caagtgcaaa gtgaacaaca aggacctgcc tgcccccatc   2640
gagcggacca tctccaagcc caagggctcc gtgcgggctc cccaggtgta cgtgctgccc   2700
cctccagagg aagagatgac caagaagcag gtcacactga cctgcatggt caccgacttc   2760
atgcccgagg acatctacgt ggaatggacc aacaatggca agaccgagct gaactacaag   2820
aacaccgagc ctgtgctgga ctccgacggc tcctacttca tgtactccaa gctgcgggtg   2880
gaaaagaaga actgggtcga gcggaactcc tactcctgct ccgtggtgca cgagggcctg   2940
```

cacaaccacc acaccaccaa gtccttctcc cggacccccg gcaaa 2985

<210> SEQ ID NO 59
<211> LENGTH: 3021
<212> TYPE: DNA
<213> ORGANISM: Artificial Sequence
<220> FEATURE:
<223> OTHER INFORMATION: fusion protein

<400> SEQUENCE: 59
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
ggatcccgca acaccggccg cggcggcgag gagaagaaga aggagaagga gaaggaggag 2340
caggaggagc gcgagaccaa gacccccgag tgccccagcc acacccagcc cctgggcgtg 2400
ttcatcttcc cacccaagat caaggacgtg ctgatgatct ccctgtcccc catcgtgacc 2460
tgcgtggtgg tggacgtgtc cgaggacgac cccgacgtgc agatcagttg gttcgtgaac 2520
aacgtggaag tgcacaccgc ccagacccag acccacagag aggactacaa ctccaccctg 2580
cgggtggtgt ccgccctgcc catccagcac caggactgga tgtccggcaa agaattcaag 2640
tgcaaagtga acaacaagga cctgcctgcc cccatcgagc ggaccatctc caagcccaag 2700
ggctccgtgc gggctcccca ggtgtacgtg ctgccccctc cagaggaaga gatgaccaag 2760
aagcaggtca cactgacctg catggtcacc gacttcatgc ccgaggacat ctacgtggaa 2820
tggaccaaca atggcaagac cgagctgaac tacaagaaca ccgagcctgt gctggactcc 2880
gacggctcct acttcatgta ctccaagctg cgggtggaaa agaagaactg ggtcgagcgg 2940
aactcctact cctgctccgt ggtgcacgag ggcctgcaca accaccacac caccaagtcc 3000
ttctcccgga cccccggcaa a 3021

<210> SEQ ID NO 60
<211> LENGTH: 2982
<212> TYPE: DNA
<213> ORGANISM: Artificial Sequence
<220> FEATURE:
<223> OTHER INFORMATION: fusion protein

<400> SEQUENCE: 60
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
ggatccgaac cgaaatcttc tgacaaaacc cacacctctc cgccgtctcc ggctccggaa 2340
ctgctgggtg gttcttctgt tttcatcttc ccacccaaga tcaaggacgt gctgatgatc 2400
tccctgtccc ccatcgtgac ctgcgtggtg gtggacgtgt ccgaggacga ccccgacgtg 2460
cagatcagtt ggttcgtgaa caacgtggaa gtgcacaccg cccagaccca gacccacaga 2520
gaggactaca actccaccct gcgggtggtg tccgccctgc ccatccagca ccaggactgg 2580
atgtccggca aagaattcaa gtgcaaagtg aacaacaagg acctgcctgc ccccatcgag 2640
cggaccatct ccaagcccaa gggctccgtg cgggctcccc aggtgtacgt gctgccccct 2700
ccagaggaag agatgaccaa gaagcaggtc acactgacct gcatggtcac cgacttcatg 2760
cccgaggaca tctacgtgga atggaccaac aatggcaaga ccgagctgaa ctacaagaac 2820
accgagcctg tgctggactc cgacggctcc tacttcatgt actccaagct gcgggtggaa 2880
aagaagaact gggtcgagcg gaactcctac tcctgctccg tggtgcacga gggcctgcac 2940
aaccaccaca ccaccaagtc cttctcccgg acccccggca aa 2982

<210> SEQ ID NO 61
<211> LENGTH: 999
<212> TYPE: PRT
<213> ORGANISM: Artificial Sequence
<220> FEATURE:
<223> OTHER INFORMATION: fusion protein

<400> SEQUENCE: 61

Ala Gly Pro Arg Ala Pro Cys Ala Ala Ala Cys Thr Cys Ala Gly Asp
1 5 10 15

-continued

```
Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
```

```
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Gly Gly Gly Ser Glu
        755                 760                 765

Pro Lys Ser Ser Asp Lys Thr His Thr Ser Pro Pro Cys Pro Ala Pro
    770                 775                 780

Glu Leu Leu Gly Gly Pro Ser Val Phe Leu Phe Pro Pro Lys Pro Lys
785                 790                 795                 800

Asp Thr Leu Met Ile Ser Arg Thr Pro Glu Val Thr Cys Val Val Val
                805                 810                 815

Asp Val Ser His Glu Asp Pro Glu Val Lys Phe Asn Trp Tyr Val Asp
            820                 825                 830

Gly Val Glu Val His Asn Ala Lys Thr Lys Pro Arg Glu Glu Gln Tyr
        835                 840                 845

Asn Ser Thr Tyr Arg Val Val Ser Val Leu Thr Val Leu His Gln Asp
    850                 855                 860
```

```
Trp Leu Asn Gly Lys Glu Tyr Lys Cys Lys Val Ser Asn Lys Ala Leu
865                 870                 875                 880

Pro Ala Pro Ile Glu Lys Thr Ile Ser Lys Ala Lys Gly Gln Pro Arg
                885                 890                 895

Glu Pro Gln Val Tyr Thr Leu Pro Pro Ser Arg Asp Glu Leu Thr Lys
            900                 905                 910

Asn Gln Val Ser Leu Thr Cys Leu Val Lys Gly Phe Tyr Pro Ser Asp
        915                 920                 925

Ile Ala Val Glu Trp Glu Ser Asn Gly Gln Pro Glu Asn Asn Tyr Lys
    930                 935                 940

Thr Thr Pro Pro Val Leu Asp Ser Asp Gly Ser Phe Phe Leu Tyr Ser
945                 950                 955                 960

Lys Leu Thr Val Asp Lys Ser Arg Trp Gln Gln Gly Asn Val Phe Ser
                965                 970                 975

Cys Ser Val Met His Glu Ala Leu His Asn His Tyr Thr Gln Lys Ser
            980                 985                 990

Leu Ser Leu Ser Pro Gly Lys
        995


<210> SEQ ID NO 62
<211> LENGTH: 1000
<212> TYPE: PRT
<213> ORGANISM: Artificial Sequence
<220> FEATURE:
<223> OTHER INFORMATION: fusion protein

<400> SEQUENCE: 62

Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220
```

```
Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640
```

```
Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Gly Gly Gly Ser Glu
        755                 760                 765

Pro Arg Gly Pro Thr Ile Lys Pro Cys Pro Pro Cys Lys Cys Pro Ala
    770                 775                 780

Pro Asn Leu Leu Gly Gly Pro Ser Val Phe Leu Phe Pro Pro Lys Pro
785                 790                 795                 800

Lys Asp Thr Leu Met Ile Ser Arg Thr Pro Glu Val Thr Cys Val Val
                805                 810                 815

Val Asp Val Ser His Glu Asp Pro Glu Val Lys Phe Asn Trp Tyr Val
            820                 825                 830

Asp Gly Val Glu Val His Asn Ala Lys Thr Lys Pro Arg Glu Glu Gln
        835                 840                 845

Tyr Asn Ser Thr Tyr Arg Val Val Ser Val Leu Thr Val Leu His Gln
    850                 855                 860

Asp Trp Leu Asn Gly Lys Glu Tyr Lys Cys Lys Val Ser Asn Lys Ala
865                 870                 875                 880

Leu Pro Ala Pro Ile Glu Lys Thr Ile Ser Lys Ala Lys Gly Gln Pro
                885                 890                 895

Arg Glu Pro Gln Val Tyr Thr Leu Pro Pro Ser Arg Asp Glu Leu Thr
            900                 905                 910

Lys Asn Gln Val Ser Leu Thr Cys Leu Val Lys Gly Phe Tyr Pro Ser
        915                 920                 925

Asp Ile Ala Val Glu Trp Glu Ser Asn Gly Gln Pro Glu Asn Asn Tyr
    930                 935                 940

Lys Thr Thr Pro Pro Val Leu Asp Ser Asp Gly Ser Phe Phe Leu Tyr
945                 950                 955                 960

Ser Lys Leu Thr Val Asp Lys Ser Arg Trp Gln Gln Gly Asn Val Phe
                965                 970                 975

Ser Cys Ser Val Met His Glu Ala Leu His Asn His Tyr Thr Gln Lys
            980                 985                 990

Ser Leu Ser Leu Ser Pro Gly Lys
        995                 1000
```

<210> SEQ ID NO 63
<211> LENGTH: 1012
<212> TYPE: PRT
<213> ORGANISM: Artificial Sequence
<220> FEATURE:
<223> OTHER INFORMATION: fusion protein

<400> SEQUENCE: 63

-continued

```
Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190

Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
```

-continued

```
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605

Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Gly Gly Gly Ser Arg
        755                 760                 765

Asn Thr Gly Arg Gly Gly Glu Glu Lys Lys Lys Glu Lys Glu Lys Glu
    770                 775                 780

Glu Gln Glu Glu Arg Glu Thr Lys Thr Pro Glu Cys Pro Ser His Thr
785                 790                 795                 800

Gln Pro Leu Gly Val Phe Leu Phe Pro Pro Lys Pro Lys Asp Thr Leu
                805                 810                 815

Met Ile Ser Arg Thr Pro Glu Val Thr Cys Val Val Val Asp Val Ser
            820                 825                 830

His Glu Asp Pro Glu Val Lys Phe Asn Trp Tyr Val Asp Gly Val Glu
        835                 840                 845
```

```
Val His Asn Ala Lys Thr Lys Pro Arg Glu Glu Gln Tyr Asn Ser Thr
    850                 855                 860

Tyr Arg Val Val Ser Val Leu Thr Val Leu His Gln Asp Trp Leu Asn
865                 870                 875                 880

Gly Lys Glu Tyr Lys Cys Lys Val Ser Asn Lys Ala Leu Pro Ala Pro
                885                 890                 895

Ile Glu Lys Thr Ile Ser Lys Ala Lys Gly Gln Pro Arg Glu Pro Gln
            900                 905                 910

Val Tyr Thr Leu Pro Pro Ser Arg Asp Glu Leu Thr Lys Asn Gln Val
        915                 920                 925

Ser Leu Thr Cys Leu Val Lys Gly Phe Tyr Pro Ser Asp Ile Ala Val
    930                 935                 940

Glu Trp Glu Ser Asn Gly Gln Pro Glu Asn Asn Tyr Lys Thr Thr Pro
945                 950                 955                 960

Pro Val Leu Asp Ser Asp Gly Ser Phe Phe Leu Tyr Ser Lys Leu Thr
                965                 970                 975

Val Asp Lys Ser Arg Trp Gln Gln Gly Asn Val Phe Ser Cys Ser Val
            980                 985                 990

Met His Glu Ala Leu His Asn His  Tyr Thr Gln Lys Ser  Leu Ser Leu
        995                 1000                1005

Ser Pro  Gly Lys
    1010


<210> SEQ ID NO 64
<211> LENGTH: 999
<212> TYPE: PRT
<213> ORGANISM: Artificial Sequence
<220> FEATURE:
<223> OTHER INFORMATION: fusion protein

<400> SEQUENCE: 64

Ala Gly Pro Arg Ala Pro Cys Ala Ala Ala Cys Thr Cys Ala Gly Asp
1               5                   10                  15

Ser Leu Asp Cys Gly Gly Arg Gly Leu Ala Ala Leu Pro Gly Asp Leu
            20                  25                  30

Pro Ser Trp Thr Arg Ser Leu Asn Leu Ser Tyr Asn Lys Leu Ser Glu
        35                  40                  45

Ile Asp Pro Ala Gly Phe Glu Asp Leu Pro Asn Leu Gln Glu Val Tyr
    50                  55                  60

Leu Asn Asn Asn Glu Leu Thr Ala Val Pro Ser Leu Gly Ala Ala Ser
65                  70                  75                  80

Ser His Val Val Ser Leu Phe Leu Gln His Asn Lys Ile Arg Ser Val
                85                  90                  95

Glu Gly Ser Gln Leu Lys Ala Tyr Leu Ser Leu Glu Val Leu Asp Leu
            100                 105                 110

Ser Leu Asn Asn Ile Thr Glu Val Arg Asn Thr Cys Phe Pro His Gly
        115                 120                 125

Pro Pro Ile Lys Glu Leu Asn Leu Ala Gly Asn Arg Ile Gly Thr Leu
    130                 135                 140

Glu Leu Gly Ala Phe Asp Gly Leu Ser Arg Ser Leu Leu Thr Leu Arg
145                 150                 155                 160

Leu Ser Lys Asn Arg Ile Thr Gln Leu Pro Val Arg Ala Phe Lys Leu
                165                 170                 175

Pro Arg Leu Thr Gln Leu Asp Leu Asn Arg Asn Arg Ile Arg Leu Ile
            180                 185                 190
```

-continued

```
Glu Gly Leu Thr Phe Gln Gly Leu Asn Ser Leu Glu Val Leu Lys Leu
        195                 200                 205

Gln Arg Asn Asn Ile Ser Lys Leu Thr Asp Gly Ala Phe Trp Gly Leu
    210                 215                 220

Ser Lys Met His Val Leu His Leu Glu Tyr Asn Ser Leu Val Glu Val
225                 230                 235                 240

Asn Ser Gly Ser Leu Tyr Gly Leu Thr Ala Leu His Gln Leu His Leu
                245                 250                 255

Ser Asn Asn Ser Ile Ala Arg Ile His Arg Lys Gly Trp Ser Phe Cys
            260                 265                 270

Gln Lys Leu His Glu Leu Val Leu Ser Phe Asn Asn Leu Thr Arg Leu
        275                 280                 285

Asp Glu Glu Ser Leu Ala Glu Leu Ser Ser Leu Ser Val Leu Arg Leu
    290                 295                 300

Ser His Asn Ser Ile Ser His Ile Ala Glu Gly Ala Phe Lys Gly Leu
305                 310                 315                 320

Arg Ser Leu Arg Val Leu Asp Leu Asp His Asn Glu Ile Ser Gly Thr
                325                 330                 335

Ile Glu Asp Thr Ser Gly Ala Phe Ser Gly Leu Asp Ser Leu Ser Lys
            340                 345                 350

Leu Thr Leu Phe Gly Asn Lys Ile Lys Ser Val Ala Lys Arg Ala Phe
        355                 360                 365

Ser Gly Leu Glu Gly Leu Glu His Leu Asn Leu Gly Gly Asn Ala Ile
    370                 375                 380

Arg Ser Val Gln Phe Asp Ala Phe Val Lys Met Lys Asn Leu Lys Glu
385                 390                 395                 400

Leu His Ile Ser Ser Asp Ser Phe Leu Cys Asp Cys Gln Leu Lys Trp
                405                 410                 415

Leu Pro Pro Trp Leu Ile Gly Arg Met Leu Gln Ala Phe Val Thr Ala
            420                 425                 430

Thr Cys Ala His Pro Glu Ser Leu Lys Gly Gln Ser Ile Phe Ser Val
        435                 440                 445

Pro Pro Glu Ser Phe Val Cys Asp Asp Phe Leu Lys Pro Gln Ile Ile
    450                 455                 460

Thr Gln Pro Glu Thr Thr Met Ala Met Val Gly Lys Asp Ile Arg Phe
465                 470                 475                 480

Thr Cys Ser Ala Ala Ser Ser Ser Ser Ser Pro Met Thr Phe Ala Trp
                485                 490                 495

Lys Lys Asp Asn Glu Val Leu Thr Asn Ala Asp Met Glu Asn Phe Val
            500                 505                 510

His Val His Ala Gln Asp Gly Glu Val Met Glu Tyr Thr Thr Ile Leu
        515                 520                 525

His Leu Arg Gln Val Thr Phe Gly His Glu Gly Arg Tyr Gln Cys Val
    530                 535                 540

Ile Thr Asn His Phe Gly Ser Thr Tyr Ser His Lys Ala Arg Leu Thr
545                 550                 555                 560

Val Asn Val Leu Pro Ser Phe Thr Lys Thr Pro His Asp Ile Thr Ile
                565                 570                 575

Arg Thr Thr Thr Val Ala Arg Leu Glu Cys Ala Ala Thr Gly His Pro
            580                 585                 590

Asn Pro Gln Ile Ala Trp Gln Lys Asp Gly Gly Thr Asp Phe Pro Ala
        595                 600                 605
```

```
Ala Arg Glu Arg Arg Met His Val Met Pro Asp Asp Asp Val Phe Phe
    610                 615                 620

Ile Thr Asp Val Lys Ile Asp Asp Ala Gly Val Tyr Ser Cys Thr Ala
625                 630                 635                 640

Gln Asn Ser Ala Gly Ser Ile Ser Ala Asn Ala Thr Leu Thr Val Leu
                645                 650                 655

Glu Thr Pro Ser Leu Val Val Pro Leu Glu Asp Arg Val Val Ser Val
            660                 665                 670

Gly Glu Thr Val Ala Leu Gln Cys Lys Ala Thr Gly Asn Pro Pro Pro
        675                 680                 685

Arg Ile Thr Trp Phe Lys Gly Asp Arg Pro Leu Ser Leu Thr Glu Arg
    690                 695                 700

His His Leu Thr Pro Asp Asn Gln Leu Leu Val Val Gln Asn Val Val
705                 710                 715                 720

Ala Glu Asp Ala Gly Arg Tyr Thr Cys Glu Met Ser Asn Thr Leu Gly
                725                 730                 735

Thr Glu Arg Ala His Ser Gln Leu Ser Val Leu Pro Ala Ala Gly Cys
            740                 745                 750

Arg Lys Asp Gly Thr Thr Val Gly Ile Phe Gly Gly Gly Gly Ser Glu
        755                 760                 765

Pro Lys Ser Ser Asp Lys Thr His Thr Ser Pro Pro Ser Pro Ala Pro
    770                 775                 780

Glu Leu Leu Gly Gly Ser Ser Val Phe Leu Phe Pro Pro Lys Pro Lys
785                 790                 795                 800

Asp Thr Leu Met Ile Ser Arg Thr Pro Glu Val Thr Cys Val Val Val
                805                 810                 815

Asp Val Ser His Glu Asp Pro Glu Val Lys Phe Asn Trp Tyr Val Asp
            820                 825                 830

Gly Val Glu Val His Asn Ala Lys Thr Lys Pro Arg Glu Glu Gln Tyr
        835                 840                 845

Asn Ser Thr Tyr Arg Val Val Ser Val Leu Thr Val Leu His Gln Asp
    850                 855                 860

Trp Leu Asn Gly Lys Glu Tyr Lys Cys Lys Val Ser Asn Lys Ala Leu
865                 870                 875                 880

Pro Ala Pro Ile Glu Lys Thr Ile Ser Lys Ala Lys Gly Gln Pro Arg
                885                 890                 895

Glu Pro Gln Val Tyr Thr Leu Pro Pro Ser Arg Asp Glu Leu Thr Lys
            900                 905                 910

Asn Gln Val Ser Leu Thr Cys Leu Val Lys Gly Phe Tyr Pro Ser Asp
        915                 920                 925

Ile Ala Val Glu Trp Glu Ser Asn Gly Gln Pro Glu Asn Asn Tyr Lys
    930                 935                 940

Thr Thr Pro Pro Val Leu Asp Ser Asp Gly Ser Phe Phe Leu Tyr Ser
945                 950                 955                 960

Lys Leu Thr Val Asp Lys Ser Arg Trp Gln Gln Gly Asn Val Phe Ser
                965                 970                 975

Cys Ser Val Met His Glu Ala Leu His Asn His Tyr Thr Gln Lys Ser
            980                 985                 990

Leu Ser Leu Ser Pro Gly Lys
        995
```

<210> SEQ ID NO 65
<211> LENGTH: 2997
<212> TYPE: DNA

<213> ORGANISM: Artificial Sequence
<220> FEATURE:
<223> OTHER INFORMATION: fusion protein

<400> SEQUENCE: 65
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cggcacaat agaggacacg 1020 agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260
ctaattggca ggatgctgca ggcctttgtg acagccacct gtgcccaccc agaatcactg 1320
aagggtcaga gcattttctc tgtgccacca gagagtttcg tgtgcgatga cttcctgaag 1380
ccacagatca tcacccagcc agaaaccacc atggctatgg tgggcaagga catccggttt 1440
acatgctcag cagccagcag cagcagctcc cccatgacct ttgcctggaa gaaagacaat 1500
gaagtcctga ccaatgcaga catggagaac tttgtccacg tccacgcgca ggacggggaa 1560
gtgatggagt acaccaccat cctgcacctc cgtcaggtca ctttcgggca cgagggccgc 1620
taccaatgtg tcatcaccaa ccactttggc tccacctatt cacataaggc caggctcacc 1680
gtgaatgtgt tgccatcatt caccaaaacg ccccacgaca taaccatccg gaccaccacc 1740
gtggcccgcc tcgaatgtgc tgccacaggt cacccaaacc ctcagattgc ctggcagaag 1800
gatggaggca cggatttccc cgctgcccgt gagcgacgca tgcatgtcat gccggatgac 1860
gacgtgtttt tcatcactga tgtgaaaata gatgacgcag gggtttacag ctgtactgct 1920
cagaactcag ccggttctat ttcagctaat gccaccctga ctgtcctaga gaccccatcc 1980
ttggtggtcc ccttggaaga ccgtgtggta tctgtgggag aaacagtggc cctccaatgc 2040
aaagccacgg ggaaccctcc gccccgcatc acctggttca agggggaccg cccgctgagc 2100
ctcactgagc ggcaccacct gaccccctgac aaccagctcc tggtggttca gaacgtggtg 2160
gcagaggatg cgggccgata tacctgtgag atgtccaaca ccctgggcac ggagcgagct 2220
cacagccagc tgagcgtcct gcccgcagca ggctgcagga aggatgggac cacggtaggc 2280
atcttcggcg gtggcggatc cgagccaaag tcctctgata agacacacac ctctccacca 2340
tgcccagcac cagagctgct gggaggacca agcgtgttcc tgtttcctcc aaagcccaag 2400
gacacactga tgatctccag gacaccagag gtgacctgcg tggtggtgga cgtgagccac 2460
gaggaccccg aggtgaagtt caactggtac gtggatggcg tggaggtgca caatgccaag 2520
accaagccca gagaggagca gtacaactct acctataggg tggtgagcgt gctgacagtg 2580
ctgcaccagg actggctgaa cggcaaggag tataagtgca aggtgagcaa taaggccctg 2640
cctgccccaa tcgagaagac aatctccaag gccaagggcc agccaagaga gccccaggtg 2700
tacaccctgc cccctagcag ggatgagctg acaaagaacc aggtgtccct gacctgtctg 2760
gtgaagggct tttatccctc cgacatcgcc gtggagtggg agtctaatgg ccagcctgag 2820
aataactaca agacaacccc acccgtgctg gattctgacg gcagcttctt tctgtattct 2880
aagctgaccg tggacaagag caggtggcag cagggcaacg tgttcagctg ctccgtgatg 2940
cacgaagcac tgcacaatca ctacacccag aaatcactgt cactgagccc tggcaaa 2997

<210> SEQ ID NO 66
<211> LENGTH: 3000
<212> TYPE: DNA
<213> ORGANISM: Artificial Sequence
<220> FEATURE:
<223> OTHER INFORMATION: fusion protein

<400> SEQUENCE: 66
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cgggcacaat agaggacacg 1020
agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260
ctaattggca ggatgctgca ggcctttgtg acagccacct gtgcccaccc agaatcactg 1320
aagggtcaga gcattttctc tgtgccacca gagagtttcg tgtgcgatga cttcctgaag 1380
ccacagatca tcacccagcc agaaaccacc atggctatgg tgggcaagga catccggttt 1440
acatgctcag cagccagcag cagcagctcc cccatgacct ttgcctggaa gaaagacaat 1500
gaagtcctga ccaatgcaga catggagaac tttgtccacg tccacgcgca ggacggggaa 1560
gtgatggagt acaccaccat cctgcacctc cgtcaggtca ctttcgggca cgagggccgc 1620
taccaatgtg tcatcaccaa ccactttggc tccacctatt cacataaggc caggctcacc 1680
gtgaatgtgt tgccatcatt caccaaaacg ccccacgaca taaccatccg gaccaccacc 1740
gtggcccgcc tcgaatgtgc tgccacaggt cacccaaacc ctcagattgc ctggcagaag 1800
gatggaggca cggatttccc cgctgcccgt gagcgacgca tgcatgtcat gccggatgac 1860
gacgtgtttt tcatcactga tgtgaaaata gatgacgcag gggtttacag ctgtactgct 1920
cagaactcag ccggttctat ttcagctaat gccaccctga ctgtcctaga gaccccatcc 1980
ttggtggtcc ccttggaaga ccgtgtggta tctgtgggag aaacagtggc cctccaatgc 2040
aaagccacgg ggaaccctcc gccccgcatc acctggttca agggggaccg cccgctgagc 2100
ctcactgagc ggcaccacct gacccctgac aaccagctcc tggtggttca gaacgtggtg 2160
gcagaggatg cgggccgata tacctgtgag atgtccaaca ccctgggcac ggagcgagct 2220
cacagccagc tgagcgtcct gcccgcagca ggctgcagga aggatgggac cacggtaggc 2280
atcttcggcg gtggcggatc cgagcctcgg ggccctacca tcaagccctg ccccccttgc 2340
aagtgccctg cccctaatct gctgggcgga ccctccgtgt tcctgtttcc tccaaagccc 2400
aaggacacac tgatgatctc caggacacca gaggtgacct gcgtggtggt ggacgtgagc 2460
cacgaggacc ccgaggtgaa gttcaactgg tacgtggatg gcgtggaggt gcacaatgcc 2520
aagaccaagc ccagagagga gcagtacaac tctacctata gggtggtgag cgtgctgaca 2580
gtgctgcacc aggactggct gaacggcaag gagtataagt gcaaggtgag caataaggcc 2640
ctgcctgccc caatcgagaa gacaatctcc aaggccaagg gccagccaag agagccccag 2700
gtgtacaccc tgccccctag cagggatgag ctgacaaaga accaggtgtc cctgacctgt 2760
ctggtgaagg gcttttatcc ctccgacatc gccgtggagt gggagtctaa tggccagcct 2820
gagaataact acaagacaac ccccacccgtg ctggattctg acggcagctt ctttctgtat 2880
tctaagctga ccgtggacaa gagcaggtgg cagcagggca acgtgttcag ctgctccgtg 2940
atgcacgaag cactgcacaa tcactacacc cagaaatcac tgtcactgag ccctggcaaa 3000

<210> SEQ ID NO 67
<211> LENGTH: 3036
<212> TYPE: DNA
<213> ORGANISM: Artificial Sequence
<220> FEATURE:
<223> OTHER INFORMATION: fusion protein

<400> SEQUENCE: 67
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360

```
cggaacacct gctttccaca cggaccgcct ataaaggagc tcaacctggc aggcaatcgg    420
attggcaccc tggagttggg agcatttgat ggtctgtcac ggtcgctgct aactcttcgc    480
ctgagcaaaa acaggatcac ccagcttcct gtaagagcat tcaagctacc caggctgaca    540
caactggacc tcaatcggaa caggattcgg ctgatagagg gcctcacctt ccaggggctc    600
aacagcttgg aggtgctgaa gcttcagcga aacaacatca gcaaactgac agatggggcc    660
ttctggggac tgtccaagat gcatgtgctg cacctggagt acaacagcct ggtagaagtg    720
aacagcggct cgctctacgg cctcacggcc ctgcatcagc tccacctcag caacaattcc    780
atcgctcgca ttcaccgcaa gggctggagc ttctgccaga agctgcatga gttggtcctg    840
tccttcaaca acctgacacg gctggacgag gagagcctgg ccgagctgag cagcctgagt    900
gtcctgcgtc tcagccacaa ttccatcagc cacattgcgg agggtgcctt caagggactc    960
aggagcctgc gagtcttgga tctggaccat aacgagattt cgggcacaat agaggacacg   1020
agcggcgcct tctcagggct cgacagcctc agcaagctga ctctgtttgg aaacaagatc   1080
aagtctgtgg ctaagagagc attctcgggg ctggaaggcc tggagcacct gaaccttgga   1140
gggaatgcga tcagatctgt ccagtttgat gcctttgtga agatgaagaa tcttaaagag   1200
ctccatatca gcagcgacag cttcctgtgt gactgccagc tgaagtggct gccccccgtgg   1260
ctaattggca ggatgctgca ggcctttgtg acagccacct gtgcccaccc agaatcactg   1320
aagggtcaga gcattttctc tgtgccacca gagagtttcg tgtgcgatga cttcctgaag   1380
ccacagatca tcacccagcc agaaaccacc atggctatgg tgggcaagga catccggttt   1440
acatgctcag cagccagcag cagcagctcc cccatgacct ttgcctggaa gaaagacaat   1500
gaagtcctga ccaatgcaga catggagaac tttgtccacg tccacgcgca ggacggggaa   1560
gtgatggagt acaccaccat cctgcacctc cgtcaggtca ctttcgggca cgagggccgc   1620
taccaatgtg tcatcaccaa ccactttggc tccacctatt cacataaggc caggctcacc   1680
gtgaatgtgt tgccatcatt caccaaaacg ccccacgaca taaccatccg gaccaccacc   1740
gtggcccgcc tcgaatgtgc tgccacaggt cacccaaacc ctcagattgc ctggcagaag   1800
gatggaggca cggatttccc cgctgcccgt gagcgacgca tgcatgtcat gccggatgac   1860
gacgtgtttt tcatcactga tgtgaaaata gatgacgcag ggtttacag ctgtactgct   1920
cagaactcag ccggttctat ttcagctaat gccaccctga ctgtcctaga gaccccatcc   1980
ttggtggtcc ccttggaaga ccgtgtggta tctgtgggag aaacagtggc cctccaatgc   2040
aaagccacgg ggaaccctcc gccccgcatc acctggttca aggggggaccg cccgctgagc   2100
ctcactgagc ggcaccacct gacccctgac aaccagctcc tggtggttca gaacgtggtg   2160
gcagaggatg cgggccgata tacctgtgag atgtccaaca ccctgggcac ggagcgagct   2220
cacagccagc tgagcgtcct gcccgcagca ggctgcagga aggatgggac cacggtaggc   2280
atcttcggcg gtggcggatc ccgcaacacc ggccgcggcg gcgaggagaa gaagaaggag   2340
aaggagaagg aggagcagga ggagcgcgag accaagaccc ccgagtgccc cagccacacc   2400
cagcccctgg gcgtgttcct gtttcctcca aagcccaagg acacactgat gatctccagg   2460
acaccagagg tgacctgcgt ggtggtggac gtgagccacg aggaccccga ggtgaagttc   2520
aactggtacg tggatggcgt ggaggtgcac aatgccaaga ccaagcccag agaggagcag   2580
tacaactcta cctatagggt ggtgagcgtg ctgacagtgc tgcaccagga ctggctgaac   2640
ggcaaggagt ataagtgcaa ggtgagcaat aaggccctgc ctgccccaat cgagaagaca   2700
```

atctccaagg ccaagggcca gccaagagag ccccaggtgt acaccctgcc ccctagcagg 2760
gatgagctga caaagaacca ggtgtccctg acctgtctgg tgaagggctt ttatccctcc 2820
gacatcgccg tggagtggga gtctaatggc cagcctgaga ataactacaa gacaacccca 2880
cccgtgctgg attctgacgg cagcttcttt ctgtattcta agctgaccgt ggacaagagc 2940
aggtggcagc agggcaacgt gttcagctgc tccgtgatgc acgaagcact gcacaatcac 3000
tacacccaga aatcactgtc actgagccct ggcaaa 3036

<210> SEQ ID NO 68
<211> LENGTH: 2997
<212> TYPE: DNA
<213> ORGANISM: Artificial Sequence
<220> FEATURE:
<223> OTHER INFORMATION: fusion protein

<400> SEQUENCE: 68
gctgggcctc gggctccttg tgctgccgcc tgcacatgtg caggcgattc cctggactgc 60
ggcggcagag gcctggccgc cctgcctggc gatctgccat cctggacccg gagcctgaac 120
ctgagctaca acaagctgag cgagatcgat cccgccggct ttgaggacct gcctaacctg 180
caggaggtgt atctgaacaa taacgagctg accgcggtac catccctggg cgctgcttca 240
tcacatgtcg tctctctctt tctgcagcac aacaagattc gcagcgtgga ggggagccag 300
ctgaaggcct acctttcctt agaagtgtta gatctgagtt tgaacaacat cacggaagtg 360
cggaacacct gctttccaca cggaccgcct ataaaggagc tcaacctggc aggcaatcgg 420
attggcaccc tggagttggg agcatttgat ggtctgtcac ggtcgctgct aactcttcgc 480
ctgagcaaaa acaggatcac ccagcttcct gtaagagcat tcaagctacc caggctgaca 540
caactggacc tcaatcggaa caggattcgg ctgatagagg gcctcacctt ccaggggctc 600
aacagcttgg aggtgctgaa gcttcagcga aacaacatca gcaaactgac agatggggcc 660
ttctggggac tgtccaagat gcatgtgctg cacctggagt acaacagcct ggtagaagtg 720
aacagcggct cgctctacgg cctcacggcc ctgcatcagc tccacctcag caacaattcc 780
atcgctcgca ttcaccgcaa gggctggagc ttctgccaga agctgcatga gttggtcctg 840
tccttcaaca acctgacacg gctggacgag gagagcctgg ccgagctgag cagcctgagt 900
gtcctgcgtc tcagccacaa ttccatcagc cacattgcgg agggtgcctt caagggactc 960
aggagcctgc gagtcttgga tctggaccat aacgagattt cgggcacaat agaggacacg 1020
agcggcgcct tctcagggct cgacagcctc agcaagctga ctctgtttgg aaacaagatc 1080
aagtctgtgg ctaagagagc attctcgggg ctggaaggcc tggagcacct gaaccttgga 1140
gggaatgcga tcagatctgt ccagtttgat gcctttgtga agatgaagaa tcttaaagag 1200
ctccatatca gcagcgacag cttcctgtgt gactgccagc tgaagtggct gcccccgtgg 1260
ctaattggca ggatgctgca ggcctttgtg acagccacct gtgcccaccc agaatcactg 1320
aagggtcaga gcattttctc tgtgccacca gagagtttcg tgtgcgatga cttcctgaag 1380
ccacagatca tcacccagcc agaaaccacc atggctatgg tgggcaagga catccggttt 1440
acatgctcag cagccagcag cagcagctcc cccatgacct ttgcctggaa gaaagacaat 1500
gaagtcctga ccaatgcaga catggagaac tttgtccacg tccacgcgca ggacggggaa 1560
gtgatggagt acaccaccat cctgcacctc cgtcaggtca ctttcgggca cgagggccgc 1620
taccaatgtg tcatcaccaa ccactttggc tccacctatt cacataaggc caggctcacc 1680
gtgaatgtgt tgccatcatt caccaaaacg ccccacgaca taaccatccg gaccaccacc 1740

```
gtggcccgcc tcgaatgtgc tgccacaggt cacccaaacc ctcagattgc ctggcagaag   1800

gatggaggca cggatttccc cgctgcccgt gagcgacgca tgcatgtcat gccggatgac   1860

gacgtgtttt tcatcactga tgtgaaaata gatgacgcag ggtttacag ctgtactgct    1920

cagaactcag ccggttctat ttcagctaat gccaccctga ctgtcctaga gaccccatcc   1980

ttggtggtcc ccttggaaga ccgtgtggta tctgtgggag aaacagtggc cctccaatgc   2040

aaagccacgg ggaaccctcc gccccgcatc acctggttca agggggaccg cccgctgagc   2100

ctcactgagc ggcaccacct gacccctgac aaccagctcc tggtggttca gaacgtggtg   2160

gcagaggatg cgggccgata tacctgtgag atgtccaaca ccctgggcac ggagcgagct   2220

cacagccagc tgagcgtcct gcccgcagca ggctgcagga aggatgggac cacggtaggc   2280

atcttcggcg gtggcggatc cgaaccgaaa tcttctgaca aaacccacac ctctccgccg   2340

tctccggctc cggaactgct gggtggttct tctgttttcc tgtttcctcc aaagcccaag   2400

gacacactga tgatctccag gacaccagag gtgacctgcg tggtggtgga cgtgagccac   2460

gaggaccccg aggtgaagtt caactggtac gtggatggcg tggaggtgca caatgccaag   2520

accaagccca gagaggagca gtacaactct acctataggg tggtgagcgt gctgacagtg   2580

ctgcaccagg actggctgaa cggcaaggag tataagtgca aggtgagcaa taaggccctg   2640

cctgccccaa tcgagaagac aatctccaag gccaagggcc agccaagaga gccccaggtg   2700

tacaccctgc cccctagcag ggatgagctg acaaagaacc aggtgtccct gacctgtctg   2760

gtgaagggct tttatccctc cgacatcgcc gtggagtggg agtctaatgg ccagcctgag   2820

aataactaca agacaacccc acccgtgctg gattctgacg gcagcttctt tctgtattct   2880

aagctgaccg tggacaagag caggtggcag cagggcaacg tgttcagctg ctccgtgatg   2940

cacgaagcac tgcacaatca ctacacccag aaatcactgt cactgagccc tggcaaa      2997
```

```
<210> SEQ ID NO 69
<211> LENGTH: 997
<212> TYPE: PRT
<213> ORGANISM: Artificial Sequence
<220> FEATURE:
<223> OTHER INFORMATION: fusion protein

<400> SEQUENCE: 69

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140
```

```
Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560
```

-continued

```
Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Glu Pro Lys
        755                 760                 765

Ser Ser Asp Lys Thr His Thr Ser Pro Pro Cys Pro Ala Pro Glu Leu
    770                 775                 780

Leu Gly Gly Pro Ser Val Phe Leu Phe Pro Pro Lys Pro Lys Asp Thr
785                 790                 795                 800

Leu Met Ile Ser Arg Thr Pro Glu Val Thr Cys Val Val Val Asp Val
                805                 810                 815

Ser His Glu Asp Pro Glu Val Lys Phe Asn Trp Tyr Val Asp Gly Val
            820                 825                 830

Glu Val His Asn Ala Lys Thr Lys Pro Arg Glu Glu Gln Tyr Asn Ser
        835                 840                 845

Thr Tyr Arg Val Val Ser Val Leu Thr Val Leu His Gln Asp Trp Leu
    850                 855                 860

Asn Gly Lys Glu Tyr Lys Cys Lys Val Ser Asn Lys Ala Leu Pro Ala
865                 870                 875                 880

Pro Ile Glu Lys Thr Ile Ser Lys Ala Lys Gly Gln Pro Arg Glu Pro
                885                 890                 895

Gln Val Tyr Thr Leu Pro Pro Ser Arg Asp Glu Leu Thr Lys Asn Gln
            900                 905                 910

Val Ser Leu Thr Cys Leu Val Lys Gly Phe Tyr Pro Ser Asp Ile Ala
        915                 920                 925

Val Glu Trp Glu Ser Asn Gly Gln Pro Glu Asn Asn Tyr Lys Thr Thr
    930                 935                 940

Pro Pro Val Leu Asp Ser Asp Gly Ser Phe Phe Leu Tyr Ser Lys Leu
945                 950                 955                 960

Thr Val Asp Lys Ser Arg Trp Gln Gln Gly Asn Val Phe Ser Cys Ser
                965                 970                 975

Val Met His Glu Ala Leu His Asn His Tyr Thr Gln Lys Ser Leu Ser
```

```
            980                 985                 990

Leu Ser Pro Gly Lys
        995


<210> SEQ ID NO 70
<211> LENGTH: 998
<212> TYPE: PRT
<213> ORGANISM: Artificial Sequence
<220> FEATURE:
<223> OTHER INFORMATION: fusion protein

<400> SEQUENCE: 70

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
```

```
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Glu Pro Arg
        755                 760                 765
```

```
Gly Pro Thr Ile Lys Pro Cys Pro Pro Cys Lys Cys Pro Ala Pro Asn
    770                 775                 780

Leu Leu Gly Gly Pro Ser Val Phe Leu Phe Pro Pro Lys Pro Lys Asp
785                 790                 795                 800

Thr Leu Met Ile Ser Arg Thr Pro Glu Val Thr Cys Val Val Val Asp
                805                 810                 815

Val Ser His Glu Asp Pro Glu Val Lys Phe Asn Trp Tyr Val Asp Gly
            820                 825                 830

Val Glu Val His Asn Ala Lys Thr Lys Pro Arg Glu Glu Gln Tyr Asn
        835                 840                 845

Ser Thr Tyr Arg Val Val Ser Val Leu Thr Val Leu His Gln Asp Trp
    850                 855                 860

Leu Asn Gly Lys Glu Tyr Lys Cys Lys Val Ser Asn Lys Ala Leu Pro
865                 870                 875                 880

Ala Pro Ile Glu Lys Thr Ile Ser Lys Ala Lys Gly Gln Pro Arg Glu
                885                 890                 895

Pro Gln Val Tyr Thr Leu Pro Pro Ser Arg Asp Glu Leu Thr Lys Asn
            900                 905                 910

Gln Val Ser Leu Thr Cys Leu Val Lys Gly Phe Tyr Pro Ser Asp Ile
        915                 920                 925

Ala Val Glu Trp Glu Ser Asn Gly Gln Pro Glu Asn Asn Tyr Lys Thr
    930                 935                 940

Thr Pro Pro Val Leu Asp Ser Asp Gly Ser Phe Phe Leu Tyr Ser Lys
945                 950                 955                 960

Leu Thr Val Asp Lys Ser Arg Trp Gln Gln Gly Asn Val Phe Ser Cys
                965                 970                 975

Ser Val Met His Glu Ala Leu His Asn His Tyr Thr Gln Lys Ser Leu
            980                 985                 990

Ser Leu Ser Pro Gly Lys
        995


<210> SEQ ID NO 71
<211> LENGTH: 1010
<212> TYPE: PRT
<213> ORGANISM: Artificial Sequence
<220> FEATURE:
<223> OTHER INFORMATION: fusion protein

<400> SEQUENCE: 71

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125
```

-continued

```
Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540
```

-continued

```
Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Arg Asn Thr
        755                 760                 765

Gly Arg Gly Gly Glu Glu Lys Lys Lys Glu Lys Glu Lys Glu Glu Gln
    770                 775                 780

Glu Glu Arg Glu Thr Lys Thr Pro Glu Cys Pro Ser His Thr Gln Pro
785                 790                 795                 800

Leu Gly Val Phe Leu Phe Pro Pro Lys Pro Lys Asp Thr Leu Met Ile
                805                 810                 815

Ser Arg Thr Pro Glu Val Thr Cys Val Val Val Asp Val Ser His Glu
            820                 825                 830

Asp Pro Glu Val Lys Phe Asn Trp Tyr Val Asp Gly Val Glu Val His
        835                 840                 845

Asn Ala Lys Thr Lys Pro Arg Glu Glu Gln Tyr Asn Ser Thr Tyr Arg
    850                 855                 860

Val Val Ser Val Leu Thr Val Leu His Gln Asp Trp Leu Asn Gly Lys
865                 870                 875                 880

Glu Tyr Lys Cys Lys Val Ser Asn Lys Ala Leu Pro Ala Pro Ile Glu
                885                 890                 895

Lys Thr Ile Ser Lys Ala Lys Gly Gln Pro Arg Glu Pro Gln Val Tyr
            900                 905                 910

Thr Leu Pro Pro Ser Arg Asp Glu Leu Thr Lys Asn Gln Val Ser Leu
        915                 920                 925

Thr Cys Leu Val Lys Gly Phe Tyr Pro Ser Asp Ile Ala Val Glu Trp
    930                 935                 940

Glu Ser Asn Gly Gln Pro Glu Asn Asn Tyr Lys Thr Thr Pro Pro Val
945                 950                 955                 960

Leu Asp Ser Asp Gly Ser Phe Phe Leu Tyr Ser Lys Leu Thr Val Asp
```

```
                965                 970                 975

Lys Ser Arg Trp Gln Gln Gly Asn Val Phe Ser Cys Ser Val Met His
            980                 985                 990

Glu Ala Leu His Asn His Tyr Thr  Gln Lys Ser Leu Ser  Leu Ser Pro
        995                 1000                1005

Gly Lys
    1010


<210> SEQ ID NO 72
<211> LENGTH: 997
<212> TYPE: PRT
<213> ORGANISM: Artificial Sequence
<220> FEATURE:
<223> OTHER INFORMATION: fusion protein

<400> SEQUENCE: 72

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
```

-continued

```
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735
```

```
Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Glu Pro Lys
        755                 760                 765

Ser Ser Asp Lys Thr His Thr Ser Pro Pro Ser Pro Ala Pro Glu Leu
    770                 775                 780

Leu Gly Gly Ser Ser Val Phe Leu Phe Pro Pro Lys Pro Lys Asp Thr
785                 790                 795                 800

Leu Met Ile Ser Arg Thr Pro Glu Val Thr Cys Val Val Val Asp Val
                805                 810                 815

Ser His Glu Asp Pro Glu Val Lys Phe Asn Trp Tyr Val Asp Gly Val
            820                 825                 830

Glu Val His Asn Ala Lys Thr Lys Pro Arg Glu Glu Gln Tyr Asn Ser
        835                 840                 845

Thr Tyr Arg Val Val Ser Val Leu Thr Val Leu His Gln Asp Trp Leu
    850                 855                 860

Asn Gly Lys Glu Tyr Lys Cys Lys Val Ser Asn Lys Ala Leu Pro Ala
865                 870                 875                 880

Pro Ile Glu Lys Thr Ile Ser Lys Ala Lys Gly Gln Pro Arg Glu Pro
                885                 890                 895

Gln Val Tyr Thr Leu Pro Pro Ser Arg Asp Glu Leu Thr Lys Asn Gln
            900                 905                 910

Val Ser Leu Thr Cys Leu Val Lys Gly Phe Tyr Pro Ser Asp Ile Ala
        915                 920                 925

Val Glu Trp Glu Ser Asn Gly Gln Pro Glu Asn Asn Tyr Lys Thr Thr
    930                 935                 940

Pro Pro Val Leu Asp Ser Asp Gly Ser Phe Phe Leu Tyr Ser Lys Leu
945                 950                 955                 960

Thr Val Asp Lys Ser Arg Trp Gln Gln Gly Asn Val Phe Ser Cys Ser
                965                 970                 975

Val Met His Glu Ala Leu His Asn His Tyr Thr Gln Lys Ser Leu Ser
            980                 985                 990

Leu Ser Pro Gly Lys
        995


<210> SEQ ID NO 73
<211> LENGTH: 2991
<212> TYPE: DNA
<213> ORGANISM: Artificial Sequence
<220> FEATURE:
<223> OTHER INFORMATION: fusion protein

<400> SEQUENCE: 73

gctcaggctg gacctagggc tccttgcgct gccgcctgca cctgtgcagg cgattctctg      60

gactgcagcg gccggggcct ggccacactg cccagggacc tgccttcctg gaccagatct     120

ctgaacctga gctacaatcg gctgtccgag atcgattctg ccgcctttga ggacctgaca     180

aatctgcagg aggtgtatct gaacagcaat gagctgaccg caatcccctc cctgggagca     240

gcctctatcg gcgtggtgag cctgttcctg cagcacaaca agatcctgag cgtggatggc     300

tcccagctga agagctacct gtctctggag gtgctggacc tgagctccaa caatatcacc     360

gagatcagat ctagctgttt tcctaatggc ctgcggatca gagagctgaa cctggcctct     420

aatcggatca gcatcctgga gtccggcgcc ttcgatggcc tgagcagatc cctgctgaca     480

ctgcgcctgt ccaagaaccg gatcacccag ctgcccgtga aggcctttaa gctgcctagg     540
```

```
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggcggtggcg gatccgagcc aaagtcctct gataagacac acacctctcc accatgccca   2340
gcaccagagc tgctgggagg accaagcgtg ttcctgtttc ctccaaagcc caaggacaca   2400
ctgatgatct ccaggacacc agaggtgacc tgcgtggtgg tggacgtgag ccacgaggac   2460
cccgaggtga agttcaactg gtacgtggat ggcgtggagg tgcacaatgc caagaccaag   2520
cccagagagg agcagtacaa ctctacctat agggtggtga gcgtgctgac agtgctgcac   2580
caggactggc tgaacggcaa ggagtataag tgcaaggtga gcaataaggc cctgcctgcc   2640
ccaatcgaga agacaatctc caaggccaag ggccagccaa gagagcccca ggtgtacacc   2700
ctgcccccta gcagggatga gctgacaaag aaccaggtgt ccctgacctg tctggtgaag   2760
ggcttttatc cctccgacat cgccgtggag tgggagtcta atggccagcc tgagaataac   2820
tacaagacaa ccccacccgt gctggattct gacggcagct tctttctgta ttctaagctg   2880
```

accgtggaca agagcaggtg gcagcagggc aacgtgttca gctgctccgt gatgcacgaa 2940
gcactgcaca atcactacac ccagaaatca ctgtcactga gccctggcaa a 2991

<210> SEQ ID NO 74
<211> LENGTH: 2994
<212> TYPE: DNA
<213> ORGANISM: Artificial Sequence
<220> FEATURE:
<223> OTHER INFORMATION: fusion protein

<400> SEQUENCE: 74
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980

```
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggcggtggcg gatccgagcc tcggggccct accatcaagc cctgcccccc ttgcaagtgc   2340
cctgccccta atctgctggg cggaccctcc gtgttcctgt ttcctccaaa gcccaaggac   2400
acactgatga tctccaggac accagaggtg acctgcgtgg tggtggacgt gagccacgag   2460
gaccccgagg tgaagttcaa ctggtacgtg gatggcgtgg aggtgcacaa tgccaagacc   2520
aagcccagag aggagcagta caactctacc tatagggtgg tgagcgtgct gacagtgctg   2580
caccaggact ggctgaacgg caaggagtat aagtgcaagg tgagcaataa ggccctgcct   2640
gccccaatcg agaagacaat ctccaaggcc aagggccagc caagagagcc ccaggtgtac   2700
accctgcccc ctagcaggga tgagctgaca aagaaccagg tgtccctgac ctgtctggtg   2760
aagggctttt atccctccga catcgccgtg gagtgggagt ctaatggcca gcctgagaat   2820
aactacaaga caaccccacc cgtgctggat tctgacggca gcttctttct gtattctaag   2880
ctgaccgtgg acaagagcag gtggcagcag ggcaacgtgt tcagctgctc cgtgatgcac   2940
gaagcactgc acaatcacta cacccagaaa tcactgtcac tgagccctgg caaa         2994
```

<210> SEQ ID NO 75
<211> LENGTH: 3030
<212> TYPE: DNA
<213> ORGANISM: Artificial Sequence
<220> FEATURE:
<223> OTHER INFORMATION: fusion protein

<400> SEQUENCE: 75

```
gctcaggctg gacctagggc tccttgcgct gccgcctgca cctgtgcagg cgattctctg     60
gactgcagcg gccggggcct ggccacactg cccagggacc tgccttcctg gaccagatct    120
ctgaacctga gctacaatcg gctgtccgag atcgattctg ccgcctttga ggacctgaca    180
aatctgcagg aggtgtatct gaacagcaat gagctgaccg caatcccctc cctgggagca    240
gcctctatcg gcgtggtgag cctgttcctg cagcacaaca agatcctgag cgtggatggc    300
tcccagctga agagctacct gtctctggag gtgctggacc tgagctccaa caatatcacc    360
gagatcagat ctagctgttt tcctaatggc ctgcggatca gagagctgaa cctggcctct    420
aatcggatca gcatcctgga gtccggcgcc ttcgatggcc tgagcagatc cctgctgaca    480
ctgcgcctgt ccaagaaccg gatcacccag ctgcccgtga aggcctttaa gctgcctagg    540
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
```

gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
ggcggtggcg gatcccgcaa caccggccgc ggcggcgagg agaagaagaa ggagaaggag 2340
aaggaggagc aggaggagcg cgagaccaag acccccgagt gccccagcca cacccagccc 2400
ctgggcgtgt tcctgtttcc tccaaagccc aaggacacac tgatgatctc caggacacca 2460
gaggtgacct gcgtggtggt ggacgtgagc cacgaggacc ccgaggtgaa gttcaactgg 2520
tacgtggatg gcgtggaggt gcacaatgcc aagaccaagc ccagagagga gcagtacaac 2580
tctacctata gggtggtgag cgtgctgaca gtgctgcacc aggactggct gaacggcaag 2640
gagtataagt gcaaggtgag caataaggcc ctgcctgccc caatcgagaa gacaatctcc 2700
aaggccaagg gccagccaag agagccccag gtgtacaccc tgccccctag cagggatgag 2760
ctgacaaaga accaggtgtc cctgacctgt ctggtgaagg gcttttatcc ctccgacatc 2820
gccgtggagt gggagtctaa tggccagcct gagaataact acaagacaac cccacccgtg 2880
ctggattctg acggcagctt ctttctgtat tctaagctga ccgtggacaa gagcaggtgg 2940
cagcagggca acgtgttcag ctgctccgtg atgcacgaag cactgcacaa tcactacacc 3000
cagaaatcac tgtcactgag ccctggcaaa 3030

<210> SEQ ID NO 76
<211> LENGTH: 2991
<212> TYPE: DNA
<213> ORGANISM: Artificial Sequence
<220> FEATURE:
<223> OTHER INFORMATION: fusion protein

<400> SEQUENCE: 76
gctcaggctg gacctagggc tccttgcgct gccgcctgca cctgtgcagg cgattctctg 60

```
gactgcagcg gccggggcct ggccacactg cccagggacc tgccttcctg gaccagatct    120
ctgaacctga gctacaatcg gctgtccgag atcgattctg ccgcctttga ggacctgaca    180
aatctgcagg aggtgtatct gaacagcaat gagctgaccg caatcccctc cctgggagca    240
gcctctatcg gcgtggtgag cctgttcctg cagcacaaca agatcctgag cgtggatggc    300
tcccagctga agagctacct gtctctggag gtgctggacc tgagctccaa caatatcacc    360
gagatcagat ctagctgttt tcctaatggc ctgcggatca gagagctgaa cctggcctct    420
aatcggatca gcatcctgga gtccggcgcc ttcgatggcc tgagcagatc cctgctgaca    480
ctgcgcctgt ccaagaaccg gatcacccag ctgcccgtga aggcctttaa gctgcctagg    540
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggcggtggcg gatccgaacc gaaatcttct gacaaaaccc acacctctcc gccgtctccg   2340
gctccggaac tgctgggtgg ttcttctgtt ttcctgtttc ctccaaagcc caaggacaca   2400
```

-continued

```
ctgatgatct ccaggacacc agaggtgacc tgcgtggtgg tggacgtgag ccacgaggac   2460

cccgaggtga agttcaactg gtacgtggat ggcgtggagg tgcacaatgc caagaccaag   2520

cccagagagg agcagtacaa ctctacctat agggtggtga gcgtgctgac agtgctgcac   2580

caggactggc tgaacggcaa ggagtataag tgcaaggtga gcaataaggc cctgcctgcc   2640

ccaatcgaga agacaatctc caaggccaag ggccagccaa gagagcccca ggtgtacacc   2700

ctgcccccta gcagggatga gctgacaaag aaccaggtgt ccctgacctg tctggtgaag   2760

ggcttttatc cctccgacat cgccgtggag tgggagtcta atggccagcc tgagaataac   2820

tacaagacaa ccccacccgt gctggattct gacggcagct tctttctgta ttctaagctg   2880

accgtggaca agagcaggtg gcagcagggc aacgtgttca gctgctccgt gatgcacgaa   2940

gcactgcaca atcactacac ccagaaatca ctgtcactga gccctggcaa a            2991
```

```
<210> SEQ ID NO 77
<211> LENGTH: 997
<212> TYPE: PRT
<213> ORGANISM: Artificial Sequence
<220> FEATURE:
<223> OTHER INFORMATION: fusion protein

<400> SEQUENCE: 77

Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
```

-continued

```
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685
```

```
Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Glu Pro Lys
        755                 760                 765

Ser Ser Asp Lys Thr His Thr Ser Pro Pro Cys Pro Ala Pro Glu Leu
    770                 775                 780

Leu Gly Gly Pro Ser Val Phe Ile Phe Pro Pro Lys Ile Lys Asp Val
785                 790                 795                 800

Leu Met Ile Ser Leu Ser Pro Ile Val Thr Cys Val Val Val Asp Val
                805                 810                 815

Ser Glu Asp Asp Pro Asp Val Gln Ile Ser Trp Phe Val Asn Asn Val
            820                 825                 830

Glu Val His Thr Ala Gln Thr Gln Thr His Arg Glu Asp Tyr Asn Ser
        835                 840                 845

Thr Leu Arg Val Val Ser Ala Leu Pro Ile Gln His Gln Asp Trp Met
    850                 855                 860

Ser Gly Lys Glu Phe Lys Cys Lys Val Asn Asn Lys Asp Leu Pro Ala
865                 870                 875                 880

Pro Ile Glu Arg Thr Ile Ser Lys Pro Lys Gly Ser Val Arg Ala Pro
                885                 890                 895

Gln Val Tyr Val Leu Pro Pro Pro Glu Glu Glu Met Thr Lys Lys Gln
            900                 905                 910

Val Thr Leu Thr Cys Met Val Thr Asp Phe Met Pro Glu Asp Ile Tyr
        915                 920                 925

Val Glu Trp Thr Asn Asn Gly Lys Thr Glu Leu Asn Tyr Lys Asn Thr
    930                 935                 940

Glu Pro Val Leu Asp Ser Asp Gly Ser Tyr Phe Met Tyr Ser Lys Leu
945                 950                 955                 960

Arg Val Glu Lys Lys Asn Trp Val Glu Arg Asn Ser Tyr Ser Cys Ser
                965                 970                 975

Val Val His Glu Gly Leu His Asn His His Thr Thr Lys Ser Phe Ser
            980                 985                 990

Arg Thr Pro Gly Lys
        995
```

<210> SEQ ID NO 78
<211> LENGTH: 998
<212> TYPE: PRT
<213> ORGANISM: Artificial Sequence
<220> FEATURE:
<223> OTHER INFORMATION: fusion protein

<400> SEQUENCE: 78

```
Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45
```

```
Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460
```

-continued

```
Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Glu Pro Arg
        755                 760                 765

Gly Pro Thr Ile Lys Pro Cys Pro Pro Cys Lys Cys Pro Ala Pro Asn
    770                 775                 780

Leu Leu Gly Gly Pro Ser Val Phe Ile Phe Pro Pro Lys Ile Lys Asp
785                 790                 795                 800

Val Leu Met Ile Ser Leu Ser Pro Ile Val Thr Cys Val Val Val Asp
                805                 810                 815

Val Ser Glu Asp Asp Pro Asp Val Gln Ile Ser Trp Phe Val Asn Asn
            820                 825                 830

Val Glu Val His Thr Ala Gln Thr Gln Thr His Arg Glu Asp Tyr Asn
        835                 840                 845

Ser Thr Leu Arg Val Val Ser Ala Leu Pro Ile Gln His Gln Asp Trp
    850                 855                 860

Met Ser Gly Lys Glu Phe Lys Cys Lys Val Asn Asn Lys Asp Leu Pro
865                 870                 875                 880

Ala Pro Ile Glu Arg Thr Ile Ser Lys Pro Lys Gly Ser Val Arg Ala
```

```
                885                 890                 895

Pro Gln Val Tyr Val Leu Pro Pro Pro Glu Glu Glu Met Thr Lys Lys
            900                 905                 910

Gln Val Thr Leu Thr Cys Met Val Thr Asp Phe Met Pro Glu Asp Ile
        915                 920                 925

Tyr Val Glu Trp Thr Asn Asn Gly Lys Thr Glu Leu Asn Tyr Lys Asn
    930                 935                 940

Thr Glu Pro Val Leu Asp Ser Asp Gly Ser Tyr Phe Met Tyr Ser Lys
945                 950                 955                 960

Leu Arg Val Glu Lys Lys Asn Trp Val Glu Arg Asn Ser Tyr Ser Cys
                965                 970                 975

Ser Val Val His Glu Gly Leu His Asn His His Thr Thr Lys Ser Phe
            980                 985                 990

Ser Arg Thr Pro Gly Lys
        995
```

<210> SEQ ID NO 79
<211> LENGTH: 1010
<212> TYPE: PRT
<213> ORGANISM: Artificial Sequence
<220> FEATURE:
<223> OTHER INFORMATION: fusion protein

<400> SEQUENCE: 79

```
Ala Gln Ala Gly Pro Arg Ala Pro Cys Ala Ala Ala Cys Thr Cys Ala
1               5                   10                  15

Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
```

```
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430

Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670
```

```
Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Arg Asn Thr
        755                 760                 765

Gly Arg Gly Gly Glu Glu Lys Lys Lys Glu Lys Glu Lys Glu Glu Gln
    770                 775                 780

Glu Glu Arg Glu Thr Lys Thr Pro Glu Cys Pro Ser His Thr Gln Pro
785                 790                 795                 800

Leu Gly Val Phe Ile Phe Pro Pro Lys Ile Lys Asp Val Leu Met Ile
                805                 810                 815

Ser Leu Ser Pro Ile Val Thr Cys Val Val Val Asp Val Ser Glu Asp
            820                 825                 830

Asp Pro Asp Val Gln Ile Ser Trp Phe Val Asn Asn Val Glu Val His
        835                 840                 845

Thr Ala Gln Thr Gln Thr His Arg Glu Asp Tyr Asn Ser Thr Leu Arg
    850                 855                 860

Val Val Ser Ala Leu Pro Ile Gln His Gln Asp Trp Met Ser Gly Lys
865                 870                 875                 880

Glu Phe Lys Cys Lys Val Asn Asn Lys Asp Leu Pro Ala Pro Ile Glu
                885                 890                 895

Arg Thr Ile Ser Lys Pro Lys Gly Ser Val Arg Ala Pro Gln Val Tyr
            900                 905                 910

Val Leu Pro Pro Pro Glu Glu Glu Met Thr Lys Lys Gln Val Thr Leu
        915                 920                 925

Thr Cys Met Val Thr Asp Phe Met Pro Glu Asp Ile Tyr Val Glu Trp
    930                 935                 940

Thr Asn Asn Gly Lys Thr Glu Leu Asn Tyr Lys Asn Thr Glu Pro Val
945                 950                 955                 960

Leu Asp Ser Asp Gly Ser Tyr Phe Met Tyr Ser Lys Leu Arg Val Glu
                965                 970                 975

Lys Lys Asn Trp Val Glu Arg Asn Ser Tyr Ser Cys Ser Val Val His
            980                 985                 990

Glu Gly Leu His Asn His His Thr  Thr Lys Ser Phe Ser  Arg Thr Pro
        995                 1000                1005

Gly Lys
    1010


<210> SEQ ID NO 80
<211> LENGTH: 997
<212> TYPE: PRT
<213> ORGANISM: Artificial Sequence
<220> FEATURE:
<223> OTHER INFORMATION: fusion protein

<400> SEQUENCE: 80

Ala Gln Ala Gly Pro Arg Ala Pro Cys Ala Ala Ala Cys Thr Cys Ala
1               5                   10                  15
```

-continued

```
Gly Asp Ser Leu Asp Cys Ser Gly Arg Gly Leu Ala Thr Leu Pro Arg
            20                  25                  30

Asp Leu Pro Ser Trp Thr Arg Ser Leu Asn Leu Ser Tyr Asn Arg Leu
        35                  40                  45

Ser Glu Ile Asp Ser Ala Ala Phe Glu Asp Leu Thr Asn Leu Gln Glu
    50                  55                  60

Val Tyr Leu Asn Ser Asn Glu Leu Thr Ala Ile Pro Ser Leu Gly Ala
65                  70                  75                  80

Ala Ser Ile Gly Val Val Ser Leu Phe Leu Gln His Asn Lys Ile Leu
                85                  90                  95

Ser Val Asp Gly Ser Gln Leu Lys Ser Tyr Leu Ser Leu Glu Val Leu
            100                 105                 110

Asp Leu Ser Ser Asn Asn Ile Thr Glu Ile Arg Ser Ser Cys Phe Pro
        115                 120                 125

Asn Gly Leu Arg Ile Arg Glu Leu Asn Leu Ala Ser Asn Arg Ile Ser
    130                 135                 140

Ile Leu Glu Ser Gly Ala Phe Asp Gly Leu Ser Arg Ser Leu Leu Thr
145                 150                 155                 160

Leu Arg Leu Ser Lys Asn Arg Ile Thr Gln Leu Pro Val Lys Ala Phe
                165                 170                 175

Lys Leu Pro Arg Leu Thr Gln Leu Asp Leu Asn Arg Asn Arg Ile Arg
            180                 185                 190

Leu Ile Glu Gly Leu Thr Phe Gln Gly Leu Asp Ser Leu Glu Val Leu
        195                 200                 205

Arg Leu Gln Arg Asn Asn Ile Ser Arg Leu Thr Asp Gly Ala Phe Trp
    210                 215                 220

Gly Leu Ser Lys Met His Val Leu His Leu Glu Tyr Asn Ser Leu Val
225                 230                 235                 240

Glu Val Asn Ser Gly Ser Leu Tyr Gly Leu Thr Ala Leu His Gln Leu
                245                 250                 255

His Leu Ser Asn Asn Ser Ile Ser Arg Ile Gln Arg Asp Gly Trp Ser
            260                 265                 270

Phe Cys Gln Lys Leu His Glu Leu Ile Leu Ser Phe Asn Asn Leu Thr
        275                 280                 285

Arg Leu Asp Glu Glu Ser Leu Ala Glu Leu Ser Ser Leu Ser Ile Leu
    290                 295                 300

Arg Leu Ser His Asn Ala Ile Ser His Ile Ala Glu Gly Ala Phe Lys
305                 310                 315                 320

Gly Leu Lys Ser Leu Arg Val Leu Asp Leu Asp His Asn Glu Ile Ser
                325                 330                 335

Gly Thr Ile Glu Asp Thr Ser Gly Ala Phe Thr Gly Leu Asp Asn Leu
            340                 345                 350

Ser Lys Leu Thr Leu Phe Gly Asn Lys Ile Lys Ser Val Ala Lys Arg
        355                 360                 365

Ala Phe Ser Gly Leu Glu Ser Leu Glu His Leu Asn Leu Gly Glu Asn
    370                 375                 380

Ala Ile Arg Ser Val Gln Phe Asp Ala Phe Ala Lys Met Lys Asn Leu
385                 390                 395                 400

Lys Glu Leu Tyr Ile Ser Ser Glu Ser Phe Leu Cys Asp Cys Gln Leu
                405                 410                 415

Lys Trp Leu Pro Pro Trp Leu Met Gly Arg Met Leu Gln Ala Phe Val
            420                 425                 430
```

```
Thr Ala Thr Cys Ala His Pro Glu Ser Leu Lys Gly Gln Ser Ile Phe
        435                 440                 445

Ser Val Leu Pro Asp Ser Phe Val Cys Asp Asp Phe Pro Lys Pro Gln
    450                 455                 460

Ile Ile Thr Gln Pro Glu Thr Thr Met Ala Val Val Gly Lys Asp Ile
465                 470                 475                 480

Arg Phe Thr Cys Ser Ala Ala Ser Ser Ser Ser Ser Pro Met Thr Phe
                485                 490                 495

Ala Trp Lys Lys Asp Asn Glu Val Leu Ala Asn Ala Asp Met Glu Asn
            500                 505                 510

Phe Ala His Val Arg Ala Gln Asp Gly Glu Val Met Glu Tyr Thr Thr
        515                 520                 525

Ile Leu His Leu Arg His Val Thr Phe Gly His Glu Gly Arg Tyr Gln
    530                 535                 540

Cys Ile Ile Thr Asn His Phe Gly Ser Thr Tyr Ser His Lys Ala Arg
545                 550                 555                 560

Leu Thr Val Asn Val Leu Pro Ser Phe Thr Lys Ile Pro His Asp Ile
                565                 570                 575

Ala Ile Arg Thr Gly Thr Thr Ala Arg Leu Glu Cys Ala Ala Thr Gly
            580                 585                 590

His Pro Asn Pro Gln Ile Ala Trp Gln Lys Asp Gly Gly Thr Asp Phe
        595                 600                 605

Pro Ala Ala Arg Glu Arg Arg Met His Val Met Pro Asp Asp Asp Val
    610                 615                 620

Phe Phe Ile Thr Asp Val Lys Ile Asp Asp Met Gly Val Tyr Ser Cys
625                 630                 635                 640

Thr Ala Gln Asn Ser Ala Gly Ser Val Ser Ala Asn Ala Thr Leu Thr
                645                 650                 655

Val Leu Glu Thr Pro Ser Leu Ala Val Pro Leu Glu Asp Arg Val Val
            660                 665                 670

Thr Val Gly Glu Thr Val Ala Phe Gln Cys Lys Ala Thr Gly Ser Pro
        675                 680                 685

Thr Pro Arg Ile Thr Trp Leu Lys Gly Gly Arg Pro Leu Ser Leu Thr
    690                 695                 700

Glu Arg His His Phe Thr Pro Gly Asn Gln Leu Leu Val Val Gln Asn
705                 710                 715                 720

Val Met Ile Asp Asp Ala Gly Arg Tyr Thr Cys Glu Met Ser Asn Pro
                725                 730                 735

Leu Gly Thr Glu Arg Ala His Ser Gln Leu Ser Ile Leu Pro Thr Pro
            740                 745                 750

Gly Cys Arg Lys Asp Gly Thr Thr Gly Gly Gly Gly Ser Glu Pro Lys
        755                 760                 765

Ser Ser Asp Lys Thr His Thr Ser Pro Pro Ser Pro Ala Pro Glu Leu
    770                 775                 780

Leu Gly Gly Ser Ser Val Phe Ile Phe Pro Pro Lys Ile Lys Asp Val
785                 790                 795                 800

Leu Met Ile Ser Leu Ser Pro Ile Val Thr Cys Val Val Val Asp Val
                805                 810                 815

Ser Glu Asp Asp Pro Asp Val Gln Ile Ser Trp Phe Val Asn Asn Val
            820                 825                 830

Glu Val His Thr Ala Gln Thr Gln Thr His Arg Glu Asp Tyr Asn Ser
        835                 840                 845

Thr Leu Arg Val Val Ser Ala Leu Pro Ile Gln His Gln Asp Trp Met
```

850 855 860

Ser Gly Lys Glu Phe Lys Cys Lys Val Asn Asn Lys Asp Leu Pro Ala
865 870 875 880

Pro Ile Glu Arg Thr Ile Ser Lys Pro Lys Gly Ser Val Arg Ala Pro
885 890 895

Gln Val Tyr Val Leu Pro Pro Pro Glu Glu Glu Met Thr Lys Lys Gln
900 905 910

Val Thr Leu Thr Cys Met Val Thr Asp Phe Met Pro Glu Asp Ile Tyr
915 920 925

Val Glu Trp Thr Asn Asn Gly Lys Thr Glu Leu Asn Tyr Lys Asn Thr
930 935 940

Glu Pro Val Leu Asp Ser Asp Gly Ser Tyr Phe Met Tyr Ser Lys Leu
945 950 955 960

Arg Val Glu Lys Lys Asn Trp Val Glu Arg Asn Ser Tyr Ser Cys Ser
965 970 975

Val Val His Glu Gly Leu His Asn His His Thr Thr Lys Ser Phe Ser
980 985 990

Arg Thr Pro Gly Lys
995

<210> SEQ ID NO 81
<211> LENGTH: 2991
<212> TYPE: DNA
<213> ORGANISM: Artificial Sequence
<220> FEATURE:
<223> OTHER INFORMATION: fusion protein

<400> SEQUENCE: 81
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
ggcggtggcg gatccgagcc aaagtcctct gataagacac acacctctcc accatgccca 2340
gcaccagagc tgctgggagg accaagcgtg ttcatcttcc cacccaagat caaggacgtg 2400
ctgatgatct ccctgtcccc catcgtgacc tgcgtggtgg tggacgtgtc cgaggacgac 2460
cccgacgtgc agatcagttg gttcgtgaac aacgtggaag tgcacaccgc ccagacccag 2520
acccacagag aggactacaa ctccaccctg cgggtggtgt ccgccctgcc catccagcac 2580
caggactgga tgtccggcaa agaattcaag tgcaaagtga acaacaagga cctgcctgcc 2640
cccatcgagc ggaccatctc caagcccaag ggctccgtgc gggctcccca ggtgtacgtg 2700
ctgccccctc cagaggaaga gatgaccaag aagcaggtca cactgacctg catggtcacc 2760
gacttcatgc ccgaggacat ctacgtggaa tggaccaaca atggcaagac cgagctgaac 2820
tacaagaaca ccgagcctgt gctggactcc gacggctcct acttcatgta ctccaagctg 2880
cgggtggaaa agaagaactg ggtcgagcgg aactcctact cctgctccgt ggtgcacgag 2940
ggcctgcaca accaccacac caccaagtcc ttctcccgga cccccggcaa a 2991

<210> SEQ ID NO 82
<211> LENGTH: 2994
<212> TYPE: DNA
<213> ORGANISM: Artificial Sequence
<220> FEATURE:
<223> OTHER INFORMATION: fusion protein

<400> SEQUENCE: 82
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300

-continued

```
tcccagctga agagctacct gtctctggag gtgctggacc tgagctccaa caatatcacc    360
gagatcagat ctagctgttt tcctaatggc ctgcggatca gagagctgaa cctggcctct    420
aatcggatca gcatcctgga gtccggcgcc ttcgatggcc tgagcagatc cctgctgaca    480
ctgcgcctgt ccaagaaccg gatcacccag ctgcccgtga aggcctttaa gctgcctagg    540
ctgacacagc tggacctgaa ccggaataga atcaggctga tcgagggcct gaccttccag    600
ggcctggata gcctggaggt gctgcgcctg cagcggaaca atatctcccg cctgacagac    660
ggagcatttt ggggcctgtc taagatgcac gtgctgcacc tggagtacaa tagcctggtg    720
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggcggtggcg gatccgagcc tcggggccct accatcaagc cctgcccccc ttgcaagtgc   2340
cctgccccta atctgctggg cggaccctcc gtgttcatct tcccacccaa gatcaaggac   2400
gtgctgatga tctccctgtc ccccatcgtg acctgcgtgg tggtggacgt gtccgaggac   2460
gaccccgacg tgcagatcag ttggttcgtg aacaacgtgg aagtgcacac cgcccagacc   2520
cagacccaca gagaggacta caactccacc ctgcgggtgg tgtccgccct gcccatccag   2580
caccaggact ggatgtccgg caaagaattc aagtgcaaag tgaacaacaa ggacctgcct   2640
```

gcccccatcg agcggaccat ctccaagccc aagggctccg tgcgggctcc ccaggtgtac 2700
gtgctgcccc ctccagagga agagatgacc aagaagcagg tcacactgac ctgcatggtc 2760
accgacttca tgcccgagga catctacgtg gaatggacca acaatggcaa gaccgagctg 2820
aactacaaga acaccgagcc tgtgctggac tccgacggct cctacttcat gtactccaag 2880
ctgcgggtgg aaaagaagaa ctgggtcgag cggaactcct actcctgctc cgtggtgcac 2940
gagggcctgc acaaccacca caccaccaag tccttctccc ggacccccgg caaa 2994

<210> SEQ ID NO 83
<211> LENGTH: 3030
<212> TYPE: DNA
<213> ORGANISM: Artificial Sequence
<220> FEATURE:
<223> OTHER INFORMATION: fusion protein

<400> SEQUENCE: 83
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720
gaggtgaact ctggcagcct gtatggcctg accgccctgc accagctgca cctgtccaac 780
aatagcatca gcagaatcca gagggatggc tggtccttct gccagaagct gcacgagctg 840
atcctgtctt ttaacaatct gaccaggctg gacgaggaga gcctggcaga gctgtcctct 900
ctgtccatcc tgcgcctgtc tcacaatgcc atcagccaca tcgccgaggg cgcctttaag 960
ggcctgaaga gcctgagggt gctggatctg gaccacaacg agatctctgg caccatcgag 1020
gatacaagcg gcgccttcac aggcctggac aatctgtcca agctgaccct gtttggcaac 1080
aagatcaagt ctgtggccaa gcgggccttc tctggcctgg agagcctgga gcacctgaac 1140
ctgggcgaga atgccatcag atccgtgcag ttcgatgcct ttgccaagat gaagaatctg 1200
aaggagctgt acatcagctc cgagagcttc ctgtgcgact gtcagctgaa gtggctgcca 1260
ccttggctga tgggaaggat gctgcaggcc tttgtgaccg ccacatgcgc ccacccagag 1320
agcctgaagg gccagagcat cttctccgtg ctgcccgata gcttcgtgtg cgacgatttt 1380
cctaagccac agatcatcac ccagccagag acaacaatgg ccgtggtggg caaggacatc 1440
cggtttacat gttccgccgc ctctagctcc tctagcccca tgaccttcgc ctggaagaag 1500
gataacgagg tgctggccaa tgccgacatg gagaacttcg cccacgtgag agcccaggat 1560
ggcgaagtga tggagtatac cacaatcctg cacctgcggc acgtgacctt tggccacgag 1620
ggcagatacc agtgcatcat cacaaatcac ttcggctcta cctatagcca caaggccagg 1680
ctgacagtga acgtgctgcc tagctttacc aagatcccac acgacatcgc catcagaaca 1740
ggcaccacag caaggctgga gtgtgcagca accggacacc caaaccctca gatcgcatgg 1800
cagaaggatg gaggcacaga cttccctgca gcccgcgaga ggagaatgca cgtgatgcca 1860
gacgatgacg tgttctttat cacagatgtg aagatcgatg acatgggcgt gtactcctgc 1920
accgcacaga acagcgccgg cagcgtgtcc gccaacgcca ccctgaccgt gctggagaca 1980
ccatccctgg ccgtgcccct ggaggacagg gtggtgaccg tgggcgagac agtggccttt 2040
cagtgtaagg ccaccggctc tccaacacca aggatcacct ggctgaaggg cggcaggccc 2100
ctgagcctga cagagcgcca ccacttcacc cctggcaatc agctgctggt ggtgcagaac 2160
gtgatgatcg atgacgccgg caggtataca tgcgagatga gcaatcctct gggcaccgag 2220
agggcacact cccagctgtc tatcctgcct accccaggct gccggaagga tggcaccaca 2280
ggcggtggcg gatcccgcaa caccggccgc ggcggcgagg agaagaagaa ggagaaggag 2340
aaggaggagc aggaggagcg cgagaccaag acccccgagt gccccagcca cacccagccc 2400
ctgggcgtgt tcatcttccc acccaagatc aaggacgtgc tgatgatctc cctgtccccc 2460
atcgtgacct gcgtggtggt ggacgtgtcc gaggacgacc ccgacgtgca gatcagttgg 2520
ttcgtgaaca acgtggaagt gcacaccgcc cagacccaga cccacagaga ggactacaac 2580
tccaccctgc gggtggtgtc cgccctgccc atccagcacc aggactggat gtccggcaaa 2640
gaattcaagt gcaaagtgaa caacaaggac ctgcctgccc ccatcgagcg gaccatctcc 2700
aagcccaagg gctccgtgcg ggctccccag gtgtacgtgc tgccccctcc agaggaagag 2760
atgaccaaga agcaggtcac actgacctgc atggtcaccg acttcatgcc cgaggacatc 2820
tacgtggaat ggaccaacaa tggcaagacc gagctgaact acaagaacac cgagcctgtg 2880
ctggactccg acggctccta cttcatgtac tccaagctgc gggtggaaaa gaagaactgg 2940
gtcgagcgga actcctactc ctgctccgtg gtgcacgagg gcctgcacaa ccaccacacc 3000
accaagtcct tctcccggac ccccggcaaa 3030

<210> SEQ ID NO 84
<211> LENGTH: 2991
<212> TYPE: DNA
<213> ORGANISM: Artificial Sequence
<220> FEATURE:
<223> OTHER INFORMATION: fusion protein

<400> SEQUENCE: 84
gctcaggctg gacctagggc tccttgcgct gccgcctgca cctgtgcagg cgattctctg 60
gactgcagcg gccggggcct ggccacactg cccagggacc tgccttcctg gaccagatct 120
ctgaacctga gctacaatcg gctgtccgag atcgattctg ccgcctttga ggacctgaca 180
aatctgcagg aggtgtatct gaacagcaat gagctgaccg caatcccctc cctgggagca 240
gcctctatcg gcgtggtgag cctgttcctg cagcacaaca agatcctgag cgtggatggc 300
tcccagctga agagctacct gtctctggag gtgctggacc tgagctccaa caatatcacc 360
gagatcagat ctagctgttt tcctaatggc ctgcggatca gagagctgaa cctggcctct 420
aatcggatca gcatcctgga gtccggcgcc ttcgatggcc tgagcagatc cctgctgaca 480
ctgcgcctgt ccaagaaccg gatcacccag ctgcccgtga aggcctttaa gctgcctagg 540
ctgacacagc tggacctgaa ccggaataga atcaggctga tcgagggcct gaccttccag 600
ggcctggata gcctggaggt gctgcgcctg cagcggaaca atatctcccg cctgacagac 660
ggagcatttt ggggcctgtc taagatgcac gtgctgcacc tggagtacaa tagcctggtg 720

-continued

```
gaggtgaact ctggcagcct gtatggcctg accgccctgc accagctgca cctgtccaac    780
aatagcatca gcagaatcca gagggatggc tggtccttct gccagaagct gcacgagctg    840
atcctgtctt ttaacaatct gaccaggctg gacgaggaga gcctggcaga gctgtcctct    900
ctgtccatcc tgcgcctgtc tcacaatgcc atcagccaca tcgccgaggg cgcctttaag    960
ggcctgaaga gcctgagggt gctggatctg gaccacaacg agatctctgg caccatcgag   1020
gatacaagcg gcgccttcac aggcctggac aatctgtcca agctgaccct gtttggcaac   1080
aagatcaagt ctgtggccaa gcgggccttc tctggcctgg agagcctgga gcacctgaac   1140
ctgggcgaga atgccatcag atccgtgcag ttcgatgcct ttgccaagat gaagaatctg   1200
aaggagctgt acatcagctc cgagagcttc ctgtgcgact gtcagctgaa gtggctgcca   1260
ccttggctga tgggaaggat gctgcaggcc tttgtgaccg ccacatgcgc ccacccagag   1320
agcctgaagg gccagagcat cttctccgtg ctgcccgata gcttcgtgtg cgacgatttt   1380
cctaagccac agatcatcac ccagccagag acaacaatgg ccgtggtggg caaggacatc   1440
cggtttacat gttccgccgc ctctagctcc tctagcccca tgaccttcgc ctggaagaag   1500
gataacgagg tgctggccaa tgccgacatg gagaacttcg cccacgtgag agcccaggat   1560
ggcgaagtga tggagtatac cacaatcctg cacctgcggc acgtgacctt tggccacgag   1620
ggcagatacc agtgcatcat cacaaatcac ttcggctcta cctatagcca caaggccagg   1680
ctgacagtga acgtgctgcc tagctttacc aagatcccac acgacatcgc catcagaaca   1740
ggcaccacag caaggctgga gtgtgcagca accggacacc caaaccctca gatcgcatgg   1800
cagaaggatg gaggcacaga cttccctgca gcccgcgaga ggagaatgca cgtgatgcca   1860
gacgatgacg tgttctttat cacagatgtg aagatcgatg acatgggcgt gtactcctgc   1920
accgcacaga acagcgccgg cagcgtgtcc gccaacgcca ccctgaccgt gctggagaca   1980
ccatccctgg ccgtgcccct ggaggacagg gtggtgaccg tgggcgagac agtggccttt   2040
cagtgtaagg ccaccggctc tccaacacca aggatcacct ggctgaaggg cggcaggccc   2100
ctgagcctga cagagcgcca ccacttcacc cctggcaatc agctgctggt ggtgcagaac   2160
gtgatgatcg atgacgccgg caggtataca tgcgagatga gcaatcctct gggcaccgag   2220
agggcacact cccagctgtc tatcctgcct accccaggct gccggaagga tggcaccaca   2280
ggcggtggcg gatccgaacc gaaatcttct gacaaaaccc acacctctcc gccgtctccg   2340
gctccggaac tgctgggtgg ttcttctgtt ttcatcttcc cacccaagat caaggacgtg   2400
ctgatgatct ccctgtcccc catcgtgacc tgcgtggtgg tggacgtgtc cgaggacgac   2460
cccgacgtgc agatcagttg gttcgtgaac aacgtggaag tgcacaccgc ccagacccag   2520
acccacagag aggactacaa ctccaccctg cgggtggtgt ccgccctgcc catccagcac   2580
caggactgga tgtccggcaa agaattcaag tgcaaagtga acaacaagga cctgcctgcc   2640
cccatcgagc ggaccatctc caagcccaag ggctccgtgc gggctcccca ggtgtacgtg   2700
ctgccccctc cagaggaaga gatgaccaag aagcaggtca cactgacctg catggtcacc   2760
gacttcatgc ccgaggacat ctacgtggaa tggaccaaca atggcaagac cgagctgaac   2820
tacaagaaca ccgagcctgt gctggactcc gacggctcct acttcatgta ctccaagctg   2880
cgggtggaaa agaagaactg ggtcgagcgg aactcctact cctgctccgt ggtgcacgag   2940
ggcctgcaca accaccacac caccaagtcc ttctcccgga cccccggcaa a            2991
```

<210> SEQ ID NO 85
<211> LENGTH: 24

<212> TYPE: DNA
<213> ORGANISM: Artificial Sequence
<220> FEATURE:
<223> OTHER INFORMATION: Mouse Lrig-1 forward primer

<400> SEQUENCE: 85
gacggaattc agtgaggaga acct 24

<210> SEQ ID NO 86
<211> LENGTH: 24
<212> TYPE: DNA
<213> ORGANISM: Artificial Sequence
<220> FEATURE:
<223> OTHER INFORMATION: Mouse Lrig-1 reverse primer

<400> SEQUENCE: 86
caactggtag tggcagcttg tagg 24

<210> SEQ ID NO 87
<211> LENGTH: 24
<212> TYPE: DNA
<213> ORGANISM: Artificial Sequence
<220> FEATURE:
<223> OTHER INFORMATION: Mouse Lrig-2 forward primer

<400> SEQUENCE: 87
tcacaaggaa cattgtctga acca 24

<210> SEQ ID NO 88
<211> LENGTH: 24
<212> TYPE: DNA
<213> ORGANISM: Artificial Sequence
<220> FEATURE:
<223> OTHER INFORMATION: Mouse Lrig-2 reverse primer

<400> SEQUENCE: 88
gcctgatcta acacatcctc ctca 24

<210> SEQ ID NO 89
<211> LENGTH: 24
<212> TYPE: DNA
<213> ORGANISM: Artificial Sequence
<220> FEATURE:
<223> OTHER INFORMATION: Mouse Lrig-3 forward primer

<400> SEQUENCE: 89
cagcaccttg agctgaacag aaac 24

<210> SEQ ID NO 90
<211> LENGTH: 24
<212> TYPE: DNA
<213> ORGANISM: Artificial Sequence
<220> FEATURE:
<223> OTHER INFORMATION: Mouse Lrig-3 reverse primer

<400> SEQUENCE: 90
ccagcctttg gtaatctcgg ttag 24

<210> SEQ ID NO 91
<211> LENGTH: 24
<212> TYPE: DNA
<213> ORGANISM: Artificial Sequence
<220> FEATURE:
<223> OTHER INFORMATION: Mouse FOXP3 forward primer

<400> SEQUENCE: 91
ctttcaccta tcccaccctt atcc 24

<210> SEQ ID NO 92
<211> LENGTH: 24
<212> TYPE: DNA
<213> ORGANISM: Artificial Sequence
<220> FEATURE:
<223> OTHER INFORMATION: Mouse FOXP3 reverse primer

<400> SEQUENCE: 92
attcatctac ggtccacact gctc 24

<210> SEQ ID NO 93
<211> LENGTH: 20
<212> TYPE: DNA
<213> ORGANISM: Artificial Sequence
<220> FEATURE:
<223> OTHER INFORMATION: ACTG1 forward primer

<400> SEQUENCE: 93
ggcgtcatgg tgggcatggg 20

<210> SEQ ID NO 94
<211> LENGTH: 20
<212> TYPE: DNA
<213> ORGANISM: Artificial Sequence
<220> FEATURE:
<223> OTHER INFORMATION: ACTG1 reverse primer

<400> SEQUENCE: 94
atggcgtggg gaagggcgta 20

<210> SEQ ID NO 95
<211> LENGTH: 60
<212> TYPE: DNA
<213> ORGANISM: Artificial Sequence
<220> FEATURE:
<223> OTHER INFORMATION: signal sequence

<400> SEQUENCE: 95
atggaaaccg atactctgct gctgtgggtg ctgctgctgt gggtgccagg ctctaccggg 60

<210> SEQ ID NO 96
<211> LENGTH: 48
<212> TYPE: PRT
<213> ORGANISM: Artificial Sequence
<220> FEATURE:
<223> OTHER INFORMATION: epitope

<400> SEQUENCE: 96

```
Gly Asp Ser Leu Asp Cys Gly Gly Arg Gly Leu Ala Ala Leu Pro Gly
1               5                   10                  15

Asp Leu Pro Ser Ser Thr Arg Ser Leu Asn Leu Ser Tyr Asn Lys Leu
            20                  25                  30

Ser Glu Ile Asp Pro Ala Gly Phe Glu Asp Leu Pro Asn Leu Gln Glu
        35                  40                  45
```

<210> SEQ ID NO 97
<211> LENGTH: 57
<212> TYPE: PRT
<213> ORGANISM: Artificial Sequence
<220> FEATURE:
<223> OTHER INFORMATION: epitope

<400> SEQUENCE: 97

Ser Asp Ser Phe Leu Cys Asp Cys Gln Leu Lys Trp Leu Pro Pro Trp
1 5 10 15

Leu Ile Gly Arg Met Leu Gln Ala Phe Val Thr Ala Thr Cys Ala His
20 25 30

Pro Glu Ser Leu Lys Gly Gln Ser Ile Phe Ser Val Pro Pro Glu Ser
35 40 45

Phe Val Cys Asp Asp Phe Leu Lys Ala
50 55

<210> SEQ ID NO 98
<211> LENGTH: 7
<212> TYPE: PRT
<213> ORGANISM: Artificial Sequence
<220> FEATURE:
<223> OTHER INFORMATION: epitope

<400> SEQUENCE: 98

Asn Asn Asn Glu Leu Thr Ala
1 5

<210> SEQ ID NO 99
<211> LENGTH: 18
<212> TYPE: PRT
<213> ORGANISM: Artificial Sequence
<220> FEATURE:
<223> OTHER INFORMATION: epitope

<400> SEQUENCE: 99

Asn Ala Ile Arg Ser Val Gln Phe Asp Ala Phe Val Lys Met Lys Asn
1 5 10 15

Leu Lys

<210> SEQ ID NO 100
<211> LENGTH: 5
<212> TYPE: PRT
<213> ORGANISM: Artificial Sequence
<220> FEATURE:
<223> OTHER INFORMATION: epitope

<400> SEQUENCE: 100

Asn Lys Ile Arg Ser
1 5

<210> SEQ ID NO 101
<211> LENGTH: 6
<212> TYPE: PRT
<213> ORGANISM: Artificial Sequence
<220> FEATURE:
<223> OTHER INFORMATION: epitope

<400> SEQUENCE: 101

Val Glu Val Asn Ser Gly
1 5

<210> SEQ ID NO 102
<211> LENGTH: 6
<212> TYPE: PRT
<213> ORGANISM: Artificial Sequence
<220> FEATURE:
<223> OTHER INFORMATION: epitope

<400> SEQUENCE: 102

Ala Arg Ile His Arg Lys
1 5

<210> SEQ ID NO 103
<211> LENGTH: 9
<212> TYPE: PRT
<213> ORGANISM: Artificial Sequence
<220> FEATURE:
<223> OTHER INFORMATION: epitope

<400> SEQUENCE: 103

Asn Asn Ile Thr Glu Val Arg Asn Thr
1 5

<210> SEQ ID NO 104
<211> LENGTH: 14
<212> TYPE: PRT
<213> ORGANISM: Artificial Sequence
<220> FEATURE:
<223> OTHER INFORMATION: epitope

<400> SEQUENCE: 104

Ile Arg Leu Ile Glu Gly Leu Thr Phe Gln Gly Leu Asn Ser
1 5 10

<210> SEQ ID NO 105
<211> LENGTH: 14
<212> TYPE: PRT
<213> ORGANISM: Artificial Sequence
<220> FEATURE:
<223> OTHER INFORMATION: epitope

<400> SEQUENCE: 105

Ile Ser Lys Leu Thr Asp Gly Ala Phe Trp Gly Leu Ser Lys
1 5 10

<210> SEQ ID NO 106
<211> LENGTH: 13
<212> TYPE: PRT
<213> ORGANISM: Artificial Sequence
<220> FEATURE:
<223> OTHER INFORMATION: epitope

<400> SEQUENCE: 106

Asn Arg Ile Thr Gln Leu Pro Val Arg Ala Phe Lys Leu
1 5 10

<210> SEQ ID NO 107
<211> LENGTH: 6
<212> TYPE: PRT
<213> ORGANISM: Artificial Sequence
<220> FEATURE:
<223> OTHER INFORMATION: epitope

<400> SEQUENCE: 107

Lys Ala Tyr Leu Ser Leu
1 5

<210> SEQ ID NO 108
<211> LENGTH: 25
<212> TYPE: PRT
<213> ORGANISM: Artificial Sequence
<220> FEATURE:
<223> OTHER INFORMATION: epitope

<400> SEQUENCE: 108

Lys Lys Asp Asn Glu Val Leu Thr Asn Ala Asp Met Glu Asn Phe Val
1 5 10 15

His Val His Ala Val Met Glu Tyr Thr 20 25

<210> SEQ ID NO 109
<211> LENGTH: 11
<212> TYPE: PRT
<213> ORGANISM: Artificial Sequence
<220> FEATURE:
<223> OTHER INFORMATION: epitope

<400> SEQUENCE: 109

Ser Ala Ala Ser Ser Ser Ser Ser Pro Met Thr
1 5 10

<210> SEQ ID NO 110
<211> LENGTH: 18
<212> TYPE: PRT
<213> ORGANISM: Artificial Sequence
<220> FEATURE:
<223> OTHER INFORMATION: epitope

<400> SEQUENCE: 110

Phe Lys Gly Asp Arg Pro Leu Ser Leu Thr Glu Arg His His Leu Thr
1 5 10 15

Pro Asp

<210> SEQ ID NO 111
<211> LENGTH: 10
<212> TYPE: PRT
<213> ORGANISM: Artificial Sequence
<220> FEATURE:
<223> OTHER INFORMATION: epitope

<400> SEQUENCE: 111

Gln Leu Ser Val Leu Leu Glu Asn Leu Tyr
1 5 10

<210> SEQ ID NO 112
<211> LENGTH: 8
<212> TYPE: PRT
<213> ORGANISM: Artificial Sequence
<220> FEATURE:
<223> OTHER INFORMATION: epitope

<400> SEQUENCE: 112

Lys Pro Gln Ile Ile Thr Gln Pro
1 5

<210> SEQ ID NO 113
<211> LENGTH: 15
<212> TYPE: PRT
<213> ORGANISM: Artificial Sequence
<220> FEATURE:
<223> OTHER INFORMATION: epitope

<400> SEQUENCE: 113

Val Pro Leu Glu Asp Arg Val Val Ser Val Gly Glu Thr Val Ala
1 5 10 15

<210> SEQ ID NO 114
<211> LENGTH: 10
<212> TYPE: PRT
<213> ORGANISM: Artificial Sequence
<220> FEATURE:
<223> OTHER INFORMATION: epitope

<400> SEQUENCE: 114

-continued

```
His Val Met Pro Asp Asp Asp Val Phe Phe
1               5                   10


<210> SEQ ID NO 115
<211> LENGTH: 12
<212> TYPE: PRT
<213> ORGANISM: Artificial Sequence
<220> FEATURE:
<223> OTHER INFORMATION: epitope

<400> SEQUENCE: 115

Ile Thr Asn His Phe Gly Ser Thr Tyr Ser His Lys
1               5                   10


<210> SEQ ID NO 116
<211> LENGTH: 15
<212> TYPE: PRT
<213> ORGANISM: Artificial Sequence
<220> FEATURE:
<223> OTHER INFORMATION: epitope

<400> SEQUENCE: 116

Gln Leu Leu Val Val Gln Asn Val Val Ala Glu Asp Ala Gly Arg
1               5                   10                  15


<210> SEQ ID NO 117
<211> LENGTH: 8
<212> TYPE: PRT
<213> ORGANISM: Artificial Sequence
<220> FEATURE:
<223> OTHER INFORMATION: epitope

<400> SEQUENCE: 117

His Leu Arg Val Gln Thr Phe Gly
1               5


<210> SEQ ID NO 118
<211> LENGTH: 5
<212> TYPE: PRT
<213> ORGANISM: Artificial Sequence
<220> FEATURE:
<223> OTHER INFORMATION: linker

<400> SEQUENCE: 118

Gly Gly Gly Gly Ser
1               5
```

FUSION PROTEIN, AND PHARMACEUTICAL COMPOSITION FOR PREVENTING OR TREATING CANCER, CONTAINING SAME

CROSS-REFERENCE TO RELATED APPLICATIONS

This application is a U.S. National Stage entry of International Patent Application no. PCT/KR2019/005096, filed Apr. 26, 2019, which claims the benefit of priority to Korean Patent Application no. 10-2018-0048343, filed Apr. 26, 2018.

REFERENCE TO AN ELECTRONIC SEQUENCE LISTING

The instant application contains an electronic Sequence Listing text file in ASCII format that has been submitted electronically and is hereby incorporated by reference in its entirety. The Sequence Listing text file was created on May 8, 2023, is named "20-1686-WO-US_SubstituteSequenceListing_ST25.txt" and is 487,216 bytes in size.

TECHNICAL FIELD

The present invention relates to a novel fusion protein comprising an extracellular domain of leucine-rich and immunoglobulin-like domains 1 (Lrig-1) protein and an immunoglobulin Fc region, and to a use thereof.

BACKGROUND ART

Immunoglobulin comprises four polypeptide chains, that is, two heavy chains and two light chains which are associated with each other via interchain disulfide bonds. Each light chain has two domains, that is, a variable light domain (VL) and a constant light domain (CL); and each heavy chain has two regions, that is, a variable heavy region (VH) and a constant heavy region (CH). The constant heavy region (CH) consists of constant heavy regions (for example, CH1, CH2, CH3, and the like) designated by the number (see, for example, U.S. Pat. No. 6,086,875 (Blumberg R. S. et al.), U.S. Pat. No. 5,624,821 (Winter G. P. et al.), and U.S. Pat. No. 5,116,964 (Capon D. J. and Lasky L. A.)). Immunoglobulins are classified into different isotypes (that is, IgG, IgM, IgA, IgD, and IgE) based on their biological properties, location within an organism, and ability to process different antigens. Depending on the immunoglobulin isotype, the constant heavy region (CH) may have 3 or 4 CH domains. In addition, in some isotypes (IgA, IgD, and IgG), the heavy chain contains a hinge region that adds flexibility to the molecule (Janeway et al. 2001, Immunobiology, Garland Publishing, N.Y., N.Y).

In humans, there are four IgG subclasses (IgG1, 2, 3, and 4), which are named in the order of their abundance in serum (IgG1 is most abundant). The IgG isotype consists of two light chains and two heavy chains, in which each heavy chain includes three constant heavy domains (CH1, CH2, and CH3). The two heavy chains of IgG are linked to each other by disulfide bonds (—S—S—) and each heavy chain is linked to a light chain by disulfide bonds. The antigen binding site of IgG is located in the fragment antigen binding region (Fab region) that includes the variable domains of light chain (VL) and heavy chain (VH) as well as the constant domains of light chain (CL) and heavy chain (CH1). The fragment crystallizable region (Fc region) of IgG is a portion of the heavy chain containing the CH2 and CH3 domains which bind to Fc receptors found on the surface of certain cells, including a neonatal Fc receptor (FcRn). The heavy chain of IgG also has a hinge region (hinge) between CH1 and CH2 which separates the Fab region from the Fc region and participates in linking the two heavy chains together via disulfide bonds. The structure of the hinge region contributes to unique biological properties of each of the four IgG subclasses.

IgG is secreted as a monomer that is small in size, allowing it to easily perfuse tissues. It is the only isotype that has a receptor (neonatal Fc receptor (FcRn)) to facilitate passage through the human placenta, thereby providing protection to the fetus in utero. IgG absorbed through the placenta provides the neonate with humoral immunity before its own immune system develops.

The IgG neonatal Fc receptor (FcRn) binding site is located in the Fc region of the antibody. FcRn is normally expressed in human placenta and epithelial cells and participates in an endocytic salvage pathway that prevents degradation of IgG. This salvage pathway is mediated by the highly pH-dependent binding affinity of IgG to FcRn at acidic pH. The high affinity of IgG to FcRn at acidic pH is believed to result in binding of internalized IgG to FcRn following its uptake into acidic endosomes (Goebl N A et al., 2008; Junghans R P et al., 1996). Most soluble proteins are directed to lysosomes after internalization; however, internalized FcRn-bound IgG returns to the plasma membrane and is effectively rescued from the underlying degradation pathway. Upon exposure to neutral pH in the extracellular space, IgG can dissociate from FcRn and return to the circulation. Thus, the extended serum half-life property of the antibody is retained in the Fc fragment.

The salvage pathway provides one mechanism for developing next-generation protein drugs with an extended half-life in blood circulation as compared with unmodified protein drugs. In particular, unmodified protein drugs have a short circulating half-life, and thus require frequent administration over a long-term treatment period that is needed. Extensive efforts have been made to extend the half-life of the protein drugs using a large number of approaches including PEGylation and fusion-protein technology (U.S. Food and Drug Administration; Osborn B L et al., 2002); however, these efforts have not produced ideal results.

Technical Problem

An object of the present invention is to provide a novel fusion protein, comprising an extracellular domain of leucine-rich and immunoglobulin-like domains 1 (Lrig-1) protein and an immunoglobulin Fc region.

Another object of the present invention is to provide a nucleic acid molecule, which encodes the fusion protein according to the present invention.

Yet another object of the present invention is to provide an expression vector, into which the nucleic acid molecule according to the present invention is inserted.

Still yet another object of the present invention is to provide a host cell line, transfected with the expression vector according to the present invention.

Still yet another object of the present invention is to provide a pharmaceutical composition for preventing or treating cancer, comprising the fusion protein according to the present invention.

However, the technical problem to be achieved by the present invention is not limited to the above-mentioned problems, and other problems that are not mentioned will be clearly understood by those of ordinary skill in the art from the following description.

Solution to Problem

According to an embodiment of the present invention, there is provided a fusion protein, comprising an extracellular domain of leucine-rich and immunoglobulin-like domains 1 (Lrig-1) protein and an immunoglobulin Fc region.

In the present invention, the "Lrig-1 protein" is a transmembrane protein consisting of 1091 amino acids present on the surface of regulatory T cells, and is composed of leucine-rich repeats (LRRs) and three immunoglobulin-like domains on the extracellular or lumen side, a cell transmembrane sequence, and a cytoplasmic tail portion. The LRIG gene family includes LRIG1, LRIG2, and LRIG3, and the amino acids therebetween are highly conserved.

In an example of the present invention, the extracellular domain of the Lrig-1 protein may be an extracellular domain of Lrig-1 protein derived from mammals, including primates such as humans and monkeys, rodents such as mice and rats, and the like.

In an example of the present invention, the extracellular domain of the Lrig-1 protein may be represented by, but is not limited to, SEQ ID NO: 1 that corresponds to a sequence of amino acids 35 to 794 of the human-derived Lrig-1 protein and can be encoded by the nucleic acid sequence represented by SEQ ID NO: 2 (see Table 1).

TABLE 1

| SEQ ID NO | Sequence information |
|---|---|
| SEQ ID NO: 1 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMHV<br>MPDDDVFFITDVKIDDAGVYSCTAQNSAGSISANATLTVLETPSLVVPLEDR<br>VVSVGETVALQCKATGNPPPRITWFKGDRPLSLTERHHLTPDNQLLVVQNV<br>VAEDAGRYTCEMSNTLGTERAHSQLSVLPAAGCRKDGTTVGIF |
| SEQ ID NO: 2 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGCC<br>ATCCTGGACCCGGAGCCTGAACCTGAGCTACAACAAGCTGAGCGAGAT<br>CGATCCCGCCGGCTTTGAGGACCTGCCTAACCTGCAGGAGGTGTATCTG<br>AACAATAACGAGCTGACCGCGGTACCatccctgggcgctgcttcatcacatgtcgtctctctcttt<br>ctgcagcacaacaagattcgcagcgtggaggggagccagctgaaggcctacctttccttagaagtgttagatctgagtt<br>tgaacaacatcacggaagtgcggaacacctgctttccacacggaccgcctataaaggagctcaacctggcaggcaat<br>cggattggcaccctggagttgggagcatttgatggtctgtcacggtcgctgctaactcttcgcctgagcaaaaacagga<br>tcacccagcttcctgtaagagcattcaagctacccaggctgacacaactggacctcaatcggaacaggattcggctgat<br>agagggcctcaccttccaggggctcaacagcttggaggtgctgaagcttcagcgaaacaacatcagcaaactgacag<br>atggggccttctggggactgtccaagatgcatgtgctgcacctggagtacaacagcctggtagaagtgaacagcggc<br>tcgctctacggcctcacggccctgcatcagctccacctcagcaacaattccatcgctcgcattcaccgcaagggctgg<br>agcttctgccagaagctgcatgagttggtcctgtccttcaacaacctgacacggctggacgaggagagcctggccga<br>gctgagcagcctgagtgtcctgcgtctcagccacaattccatcagccacattgcggagggtgccttcaagggactcag<br>gagcctgcgagtcttggatctggaccataacgagatttcgggcacaatagaggacacgagcggcgccttctcagggc<br>tcgacagcctcagcaagctgactctgtttggaaacaagatcaagtctgtggctaagagagcattctcggggctggaag<br>gcctggagcacctgaaccttggagggaatgcgatcagatctgtccagtttgatgcctttgtgaagatgaagaatcttaaa<br>gagctccatatcagcagcgacagcttcctgtgtgactgccagctgaagtggctgcccccgtggctaattggcaggatg<br>ctgcaggcctttgtgacagccacctgtgcccacccagaatcactgaagggtcagagcattttctctgtgccaccagaga<br>gtttcgtgtgcgatgacttcctgaagccacagatcatcacccagccagaaaccaccatggctatggtgggcaaggaca<br>tccggtttacatgctcagcagccagcagcagcagctcccccatgacctttgcctggaagaaagacaatgaagtcctga<br>ccaatgcagacatggagaactttgtccacgtccacgcgcaggacggggaagtgatggagtacaccaccatcctgcac<br>ctccgtcaggtcactttcgggcacgagggccgctaccaatgtgtcatcaccaaccactttggctccacctattcacataa<br>ggccaggctcaccgtgaatgtgttgccatcattcaccaaaacgccccacgacataaccatccggaccaccaccgtgg<br>cccgcctcgaatgtgctgccacaggtcacccaaaccctcagattgcctggcagaaggatggaggcacggatttcccc<br>gctgcccgtgagcgacgcatgcatgtcatgccggatgacgacgtgtttttcatcactgatgtgaaaatagatgacgcag<br>gggtttacagctgtactgctcagaactcagccggttctatttcagctaatgccaccctgactgtcctagagaccccatcct<br>tggtggtccccttggaagaccgtgtggtatctgtgggagaaacagtggccctccaatgcaaagccacggggaaccct<br>ccgccccgcatcacctggttcaagggggaccgcccgctgagcctcactgagcggcaccacctgacccctgacaacc<br>agctcctggtggttcagaacgtggtggcagaggatgcgggccgatatacctgtgagatgtccaacaccctgggcacg<br>gagcgagctcacagccagctgagcgtcctgcccgcagcaggctgcaggaaggatgggaccacggtaggcatcttc |

In another example of the present invention, the extracellular domain of the Lrig-1 protein may be represented by, but is not limited to, SEQ ID NO: 3 that corresponds to a sequence of amino acids 35 to 794 of the mouse-derived Lrig-1 protein and can be encoded by the nucleic acid sequence represented by SEQ ID NO: 4 (see Table 2).

TABLE 2

| SEQ ID NO | Sequence information |
|---|---|
| SEQ ID NO: 3 | AQAGPRAPCA AACTCAGDSL DCSGRGLATL PRDLPSWTRS LNLSYNRLSE<br>IDSAAFEDLT NLQEVYLNSN ELTAIPSLGA ASIGVVSLFL QHNKILSVDG<br>SQLKSYLSLE VLDLSSNNIT EIRSSCFPNG LRIRELNLAS NRISILESGA<br>FDGLSRSLLT LRLSKNRITQ LPVKAFKLPR LTQLDLNRNR IRLIEGLTFQ<br>GLDSLEVLRL QRNNISRLTD GAFWGLSKMH VLHLEYNSLV<br>EVNSGSLYGL TALHQLHLSN NSISRIQRDG WSFCQKLHEL ILSFNNLTRL<br>DEESLAELSS LSILRLSHNA ISHIAEGAFK GLKSLRVLDL DHNEISGTIE<br>DTSGAFTGLD NLSKLTLFGN KIKSVAKRAF SGLESLEHLN LGENAIRSVQ<br>FDAFAKMKNL KELYISSESF LCDCQLKWLP PWLMGRMLQA<br>FVTATCAHPE SLKGQSIFSV LPDSFVCDDF PKPQIITQPE TTMAVVGKDI<br>RFTCSAASSS SSPMTFAWKK DNEVLANADM ENFAHVRAQD<br>GEVMEYTTIL HLRHVTFGHE GRYQCIITNH FGSTYSHKAR LTVNVLPSFT<br>KIPHDIAIRT GTTARLECAA TGHPNPQIAW QKDGGTDFPA ARERRMHVMP<br>DDDVFFITDV KIDDMGVYSC TAQNSAGSVS ANATLTVLET PSLAVPLEDR<br>VVTVGETVAF QCKATGSPTP RITWLKGGRP LSLTERHHFT PGNQLLVVQN<br>VMIDDAGRYT CEMSNPLGTE RAHSQLSILP TPGCRKDGTT |
| SEQ ID NO: 4 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTAG<br>GCTGACACAGCTGGACCTGAACCGGAATAGAATCAGGCTGATCGAGGG<br>CCTGACCTTCCAGGGCCTGGATAGCCTGGAGGTGCTGCGCCTGCAGCGG<br>AACAATATCTCCCGCCTGACAGACGGAGCATTTTGGGGCCTGTCTAAGA<br>TGCACGTGCTGCACCTGGAGTACAATAGCCTGGTGGAGGTGAACTCTGG<br>CAGCCTGTATGGCCTGACCGCCCTGCACCAGCTGCACCTGTCCAACAAT<br>AGCATCAGCAGAATCCAGAGGGATGGCTGGTCCTTCTGCCAGAAGCTGC<br>ACGAGCTGATCCTGTCTTTTAACAATCTGACCAGGCTGGACGAGGAGAG<br>CCTGGCAGAGCTGTCCTCTCTGTCCATCCTGCGCCTGTCTCACAATGCCA<br>TCAGCCACATCGCCGAGGGCGCCTTTAAGGGCCTGAAGAGCCTGAGGG<br>TGCTGGATCTGGACCACAACGAGATCTCTGGCACCATCGAGGATACAAG<br>CGGCGCCTTCACAGGCCTGGACAATCTGTCCAAGCTGACCCTGTTTGGC<br>AACAAGATCAAGTCTGTGGCCAAGCGGGCCTTCTCTGGCCTGGAGAGC<br>CTGGAGCACCTGAACCTGGGCGAGAATGCCATCAGATCCGTGCAGTTCG<br>ATGCCTTTGCCAAGATGAAGAATCTGAAGGAGCTGTACATCAGCTCCGA<br>GAGCTTCCTGTGCGACTGTCAGCTGAAGTGGCTGCCACCTTGGCTGATG<br>GGAAGGATGCTGCAGGCCTTTGTGACCGCCACATGCGCCCACCCAGAG<br>AGCCTGAAGGGCCAGAGCATCTTCTCCGTGCTGCCCGATAGCTTCGTGT<br>GCGACGATTTTCCTAAGCCACAGATCATCACCCAGCCAGAGACAACAAT<br>GGCCGTGGTGGGCAAGGACATCCGGTTTACATGTTCCGCCGCCTCTAGC<br>TCCTCTAGCCCCATGACCTTCGCCTGGAAGAAGGATAACGAGGTGCTGG<br>CCAATGCCGACATGGAGAACTTCGCCCACGTGAGAGCCCAGGATGGCG<br>AAGTGATGGAGTATACCACAATCCTGCACCTGCGGCACGTGACCTTTGG<br>CCACGAGGGCAGATACCAGTGCATCATCACAAATCACTTCGGCTCTACC<br>TATAGCCACAAGGCCAGGCTGACAGTGAACGTGCTGCCTAGCTTTACCA<br>AGATCCCACACGACATCGCCATCAGAACAGGCACCACAGCAAGGCTGG<br>AGTGTGCAGCAACCGGACACCCAAACCCTCAGATCGCATGGCAGAAGG<br>ATGGAGGCACAGACTTCCCTGCAGCCCGCGAGAGGAGAATGCACGTGA<br>TGCCAGACGATGACGTGTTCTTTATCACAGATGTGAAGATCGATGACATG<br>GGCGTGTACTCCTGCACCGCACAGAACAGCGCCGGCAGCGTGTCCGCC<br>AACGCCACCCTGACCGTGCTGGAGACACCATCCCTGGCCGTGCCCCTGG<br>AGGACAGGGTGGTGACCGTGGGCGAGACAGTGGCCTTTCAGTGTAAGG<br>CCACCGGCTCTCCAACACCAAGGATCACCTGGCTGAAGGGCGGCAGGC<br>CCCTGAGCCTGACAGAGCGCCACCACTTCACCCCTGGCAATCAGCTGCT<br>GGTGGTGCAGAACGTGATGATCGATGACGCCGGCAGGTATACATGCGAG<br>ATGAGCAATCCTCTGGGCACCGAGAGGGCACACTCCCAGCTGTCTATCC<br>TGCCTACCCCAGGCTGCCGGAAGGATGGCACCACA |

As used herein, the term "immunoglobulin Fc region" refers to a region of immunoglobulin which includes the heavy chain constant region 2 (CH2) and/or the heavy chain constant region 3 (CH3), excluding the heavy and light chain variable regions. The immunoglobulin Fc region may be a component that constitutes a moiety in the protein combination of the present invention.

The immunoglobulin Fc region may include a hinge portion in the heavy chain constant region so as to not only affect structural flexibility of the fusion protein to be finally prepared, but also further increase productivity and stability of the fusion protein. However, the present invention is not limited thereto In addition, the immunoglobulin Fc region of the present invention may be an extended Fc region of immunoglobulin which includes some or all of the heavy chain constant region 1 (CH1) and/or the light chain constant region 1 (CL1), excluding only the heavy and light chain variable regions, as long as the immunoglobulin Fc region has an effect that is substantially the same or improved as compared with its native type. In addition, the immunoglobulin Fc region may be a region obtained by removal of a significantly long partial amino acid sequence that corresponds to CH2 and/or CH3.

For example, the immunoglobulin Fc region of the present invention may be 1) CH1 domain, CH2 domain, CH3 domain, and CH4 domain; 2) CH1 domain and CH2 domain; 3) CH1 domain and CH3 domain; 4) CH2 domain and CH3 domain; 5) a combination of an immunoglobulin hinge region (or part of the hinge region) with one or two or more domains of CH1 domain, CH2 domain, CH3 domain, and CH4 domain and; and 6) a dimer formed of each domain of the heavy chain constant region and the light chain constant region. However, the present invention is not limited thereto.

In addition, the immunoglobulin Fc region of the present invention includes its native amino acid sequence as well as a sequence derivative thereof. An amino acid sequence derivative refers to an amino acid sequence that differs from its native amino acid sequence by deletion, insertion, or non-conservative or conservative substitution of at least one amino acid residue, or a combination thereof.

For example, for IgG Fc, the amino acid residues at positions 214 to 238, 297 to 299, 318 to 322, or 327 to 331, which are known to be important for binding, may be used as suitable sites for modification.

In addition, various types of derivatives are possible, including one obtained by deletion of a site capable of forming a disulfide bond, one obtained by deletion of some amino acid residues at the N-terminus of native Fc, one obtained by addition of a methionine residue at the N-terminus of native Fc, and the like. In addition, in order to remove an effector function therein, a complement-binding site, such as a C1q-binding site, may be deleted, or an antibody dependent cell mediated cytotoxicity (ADCC) site may be deleted. Techniques for preparing such sequence derivatives of the immunoglobulin Fc region are disclosed in International Patent Publication Nos. WO 97/34631 and WO 96/32478, and the like.

Amino acid exchanges in proteins and peptides, which do not alter the molecular activity as a whole, are known in the art (H. Neurath, R. L. Hill, The Proteins, Academic Press, New York, 1979). The most common exchanges are exchanges occurring between the amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, or Asp/Gly. As the case may be, modification may be achieved by phosphorylation, sulfation, acrylation, glycosylation, methylation, farnesylation, acetylation, amidation, and the like.

The above-described Fc derivatives exhibit biological activity equivalent to that of the Fc region of the present invention, and may be those having increased structural stability against heat, pH, or the like.

In addition, these Fc regions may be obtained from native types isolated in vivo from animals such as humans, cows, goats, pigs, mice, rabbits, hamsters, rats, or guinea pigs, or may be recombinants, which are obtained from transformed animal cells or microorganisms, or derivatives thereof. Here, the method of obtaining the Fc region from the native types may be a method in which the entire immunoglobulin is isolated from a living human or animal body, and then treated with protease to obtain the Fc region. In a case of being treated with papain, the entire immunoglobulin is cleaved into Fab and Fc; and in a case of being treated with pepsin, the entire immunoglobulin is cleaved into pF'c and $F(ab)_2$. Fc or pF'c may be isolated using size-exclusion chromatography or the like. In a more specific embodiment, the immunoglobulin Fc region is a recombinant immunoglobulin Fc region obtained from a microorganism using a human- or mouse-derived Fc region.

In addition, the immunoglobulin Fc region may have native-type glycan, or increased or decreased level of glycan as compared with the native-type, or may be in a deglycosylated form. Conventional methods such as chemical methods, enzymatic methods, and genetic engineering methods using microorganisms may be used for such increase or decrease of glycan or deglycosylation in the immunoglobulin Fc. Here, the immunoglobulin Fc region, in which glycan has been removed on Fc, exhibits remarkably decreased binding capacity with a complement (C1 q) and has decreased or eliminated antibody-dependent cytotoxicity or complement-dependent cytotoxicity; and therefore does not cause any unnecessary immune responses in vivo. In this viewpoint, the deglycosylated or aglycosylated immunoglobulin Fc region would be a more suitable form for the original purpose as a drug carrier.

As used herein, the term "deglycosylation" refers to an Fc region from which sugar is enzymatically removed, and the term "aglycosylation" refers to an Fc region that is not glycosylated by being produced in a prokaryote that is *E. coli* in a more specific embodiment.

Meanwhile, the immunoglobulin Fc region may be derived from humans or other animals such as cows, goats, pigs, mice, rabbits, hamsters, rats, and guinea pigs. In a more specific embodiment, it is derived from humans.

In addition, the immunoglobulin Fc region of the present invention may be IgG-, IgA-, IgD-, IgE-, or IgM-derived Fc region, heavy chain constant region 2 (CH2), heavy chain constant region 3 (CH3), hinge, a fragment thereof, or a combination thereof, or a hybrid Fc including the combination.

Meanwhile, as used herein, the term "combination" means that a polypeptide coding for single-chain immunoglobulin Fc region, heavy chain constant region 2 (CH2), or heavy chain constant region 3 (CH3), which is of the same origin, forms a bond with a single-chain polypeptide of a different origin when they form a dimer or multimer. That is, it is possible to prepare a dimer or a multimer from two or more fragments selected from IgG-, IgA-, IgD-, IgE-, or IgM-derived Fc region, heavy chain constant region 2 (CH2), or heavy chain constant region 3 (CH3).

In the present invention, the "hybrid Fc" may be derived from combinations of human IgG subclasses or combinations of human IgD and IgG. In an embodiment, the hybrid Fc may include, for example, an IgD hinge region, and a CH2 N-terminal region+IgG4 CH2 and CH3 regions. For example, a hybrid Fc form disclosed in Korean Patent No. 0897938, which is incorporated herein by reference, may be adopted and used in the same manner. In the present invention, in a case where the hybrid Fc binds to a biologically active molecule, a polypeptide, or the like, it has an effect of increasing the serum half-life of the biologically active molecule as well as an effect of increasing an expression level of the polypeptide when the polypeptide is expressed by a nucleotide sequence encoding an Fc-polypeptide fusion protein.

As an example of the present invention, the immunoglobulin Fc region may be an IgG-, IgA-, IgM-, IgD-, or IgE-derived Fc region, or may include IgG-, IgA-, IgM-, IgD-, or IgE-derived heavy chain constant region 2 (CH2) and heavy chain constant region 3 (CH3). However, the present invention is not limited thereto.

As an example of the present invention, the immunoglobulin Fc region may be an IgG- or IgM-derived Fc region which is most abundant in human blood, or may include IgG- or IgM-derived heavy chain constant region 2 (CH2) and heavy chain constant region 3 (CH3). As another example, the immunoglobulin Fc region may be an IgG-derived Fc region known to enhance the half-life of a ligand-binding protein, or may include IgG-derived heavy chain constant region 2 (CH2) and heavy chain constant region 3 (CH3). As yet another example, the immunoglobulin Fc region may be an IgG1-, IgG2-, IgG3-, or IgG4-derived Fc region, or may include the IgG1-, IgG2-, IgG3-, or IgG4-derived heavy chain constant region 2 (CH2) and heavy chain constant region 3 (CH3). As still yet another example, the immunoglobulin Fc region may include IgG1- or IgG2-derived heavy chain constant region 2 (CH2) and heavy chain constant region 3 (CH3).

As a preferred example in the present invention, the immunoglobulin Fc region may include, but is not limited to, human IgG1-derived heavy chain constant region 2 (CH2) and heavy chain constant region 3 (CH3), which are represented by SEQ ID NO: 5, or mouse IgG2-derived heavy chain constant region 2 (CH2) and heavy chain constant region 3 (CH3), which are represented by SEQ ID NO: 6 (see Table 3 below).

TABLE 3

| SEQ ID NO | Sequence information |
|---|---|
| SEQ ID NO: 5 | LFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGS FFLYSKLTVDKSRWQQGNVFSCSVMHEALHNHYTQKSLSLSPGK |
| SEQ ID NO: 6 | IFPPKIKDVLMISLSPIVTCVVVDVSEDDPDVQISWFVNNVEVHTAQTQTHREDY NSTLRVVSALPIQHQDWMSGKEFKCKVNNKDLPAPIERTISKPKGSVRAPQVYV LPPPEEEMTKKQVTLTCMVTDFMPEDIYVEWTNNGKTELNYKNTEPVLDSDGS YFMYSKLRVEKKNWVERNSYSCSVVHEGLHNHHTTKSFSRTPGK |

As an example of the present invention, the immunoglobulin Fc region may include an IgG-, IgA-, IgM-, IgD-, IgE-, or Abatacept-derived hinge region; and as another example, the immunoglobulin Fc region may include an IgG-, IgD-, or Abatacept-derived hinge region, or may include an IgG1-, IgG2-, IgG3-, IgG4-, IgD-, or Abatacept-derived hinge region. However, the present invention is not limited thereto.

As a preferred example in the present invention, the immunoglobulin Fc region may include one or more selected from the group consisting of a human IgG1-derived hinge region represented by SEQ ID NO: 7; a human IgG2-derived hinge region represented by SEQ ID NO: 8; a human IgD-derived hinge region represented by SEQ ID NO: 9; and a hinge region of Abatacept represented by SEQ ID NO: 10 (see Table 4 below), thereby increasing structural flexibility of the fusion protein to be finally prepared and remarkably enhancing productivity and stability of the fusion protein. However, the present invention is not limited thereto.

TABLE 4

| SEQ ID NO | Sequence information |
|---|---|
| SEQ ID NO: 7 | EPKSSDKTHTSPPCPAPELLGGPSVF |
| SEQ ID NO: 8 | EPRGPTIKPCPPCKCPAPNLLGGPSVF |
| SEQ ID NO: 9 | RNTGRGGEEKKKEKEKEEQEERETKTPECPSHTQPL GVF |
| SEQ ID NO: 10 | EPKSSDKTHTSPPSPAPELLGGSSVF |

In the present invention, in a case where the extracellular domain of the Lrig-1 protein and the Fc region are connected via a linker, the linker may be linked to the N-terminus, C-terminus, or free radical of the Fc fragment and may be linked to the N-terminus, C-terminus, or free radical of the extracellular domain of the Lrig-1 protein. In a case where the linker is a peptide linker, linkage may occur at any site. For example, the linker may be linked to the C-terminus of the extracellular domain of the Lrig-1 protein and the N-terminus of the immunoglobulin Fc region, or may be linked to the C-terminus of the immunoglobulin Fc region and the N-terminus of the extracellular domain of the Lrig-1 protein.

In the present invention, the "linker" can decrease interference between the extracellular domain of the Lrig-1 protein and the immunoglobulin Fc region in the fusion protein, thereby increasing the desired activity of the extracellular domain of the Lrig-1 protein in target cells. In addition, in the present invention, the linker may include a sequence that can be cleaved by an enzyme overexpressed in the tissue or cell with the target disease. In a case where the linker can be cleaved by the enzyme overexpressed as described above, it is possible to effectively prevent the activity of the polypeptide from being decreased due to the Fc portion.

As an example of the present invention, the linker preferably has 1 to 100 amino acids; however, the present invention is not limited thereto. Any peptide, which is capable of separating the extracellular domain of the Lrig-1 protein from the immunoglobulin Fc region, may be used. Although there is no particular limitation on the amino acid sequence that constitutes the linker, it is preferable to include glycine (G) and serine (S), or to include them in a repeated or random pattern. As such an example, the linker may include at least one of a peptide linker represented by SEQ ID NO: 11 and a peptide linker represented by SEQ ID NO: 12, or may include the amino acid sequence $(GGGGS)_N$ (SEQ ID NO: 118; N is an integer of 1 or more, preferably an integer of 1 to 20) (see Table 5 below), thereby increasing stability of the active substance in a cell and further enhancing productivity thereof.

TABLE 5

| SEQ ID NO | Sequence information |
|---|---|
| SEQ ID NO: 11 | GS |
| SEQ ID NO: 12 | GGG |

In addition, as an example of the linker in the present invention, a peptide linker consisting of 33 amino acids located at positions 282 to 314, more preferably 13 amino acids located at positions 292 to 304, of human albumin, which is most abundant in the blood, may be mentioned. Such a portion is exposed in most parts to the outside as viewed in a three-dimensional structure, and thus has minimized possibility of inducing an immune response in the body. However, the present invention is not limited thereto.

In addition, in the present invention, in a case where the linker and the Fc region are separately expressed and then jointed to each other, the linker may be a crosslinking agent known in the art. The crosslinking agent may be, for example, 1,1-bis(diazoacetyl)-2-phenylethane, glutaraldehyde, N-hydroxysuccinimide esters such as 4-azidosalicylic acid, imidoestesr including disuccinimidyl esters such as 3,3'-dithiobis(succinimidylpropionate), and bifunctional maleimide such as bis-N-maleimido-1,8-octane. However, the crosslinking agent is not limited thereto.

As an example of the fusion protein provided in the present invention, a fusion protein, comprising the extracellular domain of the Lrig-1 protein represented by SEQ ID NO: 1; the hinge region represented by any one of SEQ ID NOs: 7 to 10; and the human IgG1-derived heavy chain constant region 2 (CH2) and heavy chain constant region 3 (CH3) which are represented by SEQ ID NO: 5, may be mentioned (see Table 6 below). The fusion proteins represented by SEQ ID NOs: 13 to 16 in Table 6 below may be encoded by the nucleic acid sequences represented by SEQ ID NOs: 17 to 20 in Table 7 below (see Table 7 below).

TABLE 6

| SEQ ID NO | Sequence information |
|---|---|
| SEQ ID NO: 13 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>EPKSSDKTHT SPPCPAPELL GGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 14 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>EPRGPTIKPCPPCKCPAPNLLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 15 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS |

TABLE 6-continued

| SEQ ID NO | Sequence information |
|---|---|
| | RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>RNTGRGGEEKKKEKEKEEQEERETKTPECPSHTQPLGVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 16 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>EPKSSDKTHTSPPSPAPELLGGSSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |

TABLE 7

| SEQ ID NO | Sequence information |
|---|---|
| SEQ ID NO: 17 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGC GAGA<br>TCGATCCCGCCGGCTTTGAGGACCTGCCTAACCTGCAGGAGGTGTATCT<br>GAACAATAACGAGCTGACCGCGGTACCatccctgggcgctgatcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca |

TABLE 7-continued

| SEQ ID NO | Sequence information |
|---|---|
| | ccctgggcacggagcgagctcacagccagctgagcgtcctgcccgcagcaggctgcaggaaggatgggaccacg<br>gtaggcatcttc<br>GAGCCAAAGTCCTCTGATAAGACACACACCTCTCCACCATGCCCAGCAC<br>CAGAGCTGCTGGGAGGACCAAGCGTGTTC<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 18 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>Gagcctcggggccctaccatcaagccctgcccccttgcaagtgccctgcccctaatctgctgggcggaccctccgt<br>gttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 19 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag |

TABLE 7-continued

| SEQ ID NO | Sequence information |
|---|---|
| | ggctggagcttctgccagaagctgcatgagttggtcctgtccttcaacaacctgacacggctggacgaggagagcct ggccgagctgagcagcctgagtgtcctgcgtctcagccacaattccatcagccacattgcggagggtgccttcaagg gactcaggagcctgcgagtcttggatctggaccataacgagatttcgggcacaatagaggacacgagcggcgccttc tcagggctcgacagcctcagcaagctgactctgtttggaaacaagatcaagtctgtggctaagagagcattctcgggg ctggaaggcctggagcacctgaaccttggagggaatgcgatcagatctgtccagtttgatgcctttgtgaagatgaag aatcttaaagagctccatatcagcagcgacagcttcctgtgtgactgccagctgaagtggctgcccccgtggctaattg gcaggatgctgcaggcctttgtgacagccacctgtgcccacccagaatcactgaagggtcagagcattttctctgtgcc accagagagtttcgtgtgcgatgacttcctgaagccacagatcatcacccagccagaaaccaccatggctatggtggg caaggacatccggtttacatgctcagcagccagcagcagcagctcccccatgacctttgcctggaagaaagacaatg aagtcctgaccaatgcagacatggagaactttgtccacgtccacgcgcaggacggggaagtgatggagtacaccac catcctgcacctccgtcaggtcactttcgggcacgagggccgctaccaatgtgtcatcaccaaccactttggctccacc tattcacataaggccaggctcaccgtgaatgtgttgccatcattcaccaaaacgccccacgacataaccatccggacc accaccgtggcccgcctcgaatgtgctgccacaggtcacccaaaccctcagattgcctggcagaaggatggaggca cggatttccccgctgcccgtgagcgacgcatgcatgtcatgccggatgacgacgtgtttttcatcactgatgtgaaaata gatgacgcaggggtttacagctgtactgctcagaactcagccggttctatttcagctaatgccaccctgactgtcctaga gaccccatccttggtggtccccttggaagaccgtgtggtatctgtgggagaaacagtggccctccaatgcaaagccac ggggaaccctccgccccgcatcacctggttcaagggggaccgcccgctgagcctcactgagcggcaccacctgac ccctgacaaccagctcctggtggttcagaacgtggtggcagaggatgcgggccgatatacctgtgagatgtccaaca ccctgggcacggagcgagctcacagccagctgagcgtcctgcccgcagcaggctgcaggaaggatgggaccacg gtaggcatcttc<br>cgcaacaccggccgcggcggcgaggagaagaagaaggagaaggagaaggaggagcaggaggagcgcgaga ccaagacccccgagtgccccagccacacccagcccctgggcgtgttc<br>CTGTTTCCTCCAAAGCCCAAGGACACACTGATGATCTCCAGGACACCAG AGGTGACCTGCGTGGTGGTGGACGTGAGCCACGAGGACCCCGAGGTG AAGTTCAACTGGTACGTGGATGGCGTGGAGGTGCACAATGCCAAGACC AAGCCCAGAGAGGAGCAGTACAACTCTACCTATAGGGTGGTGAGCGTG CTGACAGTGCTGCACCAGGACTGGCTGAACGGCAAGGAGTATAAGTGC AAGGTGAGCAATAAGGCCCTGCCTGCCCCAATCGAGAAGACAATCTCC AAGGCCAAGGGCCAGCCAAGAGAGCCCCAGGTGTACACCCTGCCCCCT AGCAGGGATGAGCTGACAAAGAACCAGGTGTCCCTGACCTGTCTGGTG AAGGGCTTTTATCCCTCCGACATCGCCGTGGAGTGGGAGTCTAATGGCC AGCCTGAGAATAACTACAAGACAACCCCACCCGTGCTGGATTCTGACG GCAGCTTCTTTCTGTATTCTAAGCTGACCGTGGACAAGAGCAGGTGGCA GCAGGGCAACGTGTTCAGCTGCTCCGTGATGCACGAAGCACTGCACAA TCACTACACCCAGAAATCACTGTCACTGAGCCCTGGCAAA |
| SEQ ID NO: 20 | GCTGGGCCTCGGGCTCCTTGTGCTGCCGCCTGCACATGTGCAGGCGATT CCCTGGACTGCGGCGGCAGAGGCCTGGCCGCCCTGCCTGGCGATCTGC CATCCTGGACCCGGAGCCTGAACCTGAGCTACAACAAGCTGAGCGAGA TCGATCCCGCCGGCTTTGAGGACCTGCCTAACCTGCAGGAGGTGTATCT GAACAATAACGAGCTGACCGCGGTACCatccctgggcgctgcttcatcacatgtcgtctctct ctttctgcagcacaacaagattcgcagcgtggaggggagccagctgaaggcctacctttccttagaagtgttagatctg agtttgaacaacatcacggaagtgcggaacacctgctttccacacggaccgcctataaaggagctcaacctggcagg caatcggattggcaccctggagttgggagcatttgatggtctgtcacggtcgctgctaactcttcgcctgagcaaaaac aggatcacccagcttcctgtaagagcattcaagctacccaggctgacacaactggacctcaatcggaacaggattcg gctgatagagggcctcaccttccaggggctcaacagcttggaggtgctgaagcttcagcgaaacaacatcagcaaac tgacagatggggccttctggggactgtccaagatgcatgtgctgcacctggagtacaacagcctggtagaagtgaac agcggctcgctctacggcctcacggccctgcatcagctccacctcagcaacaattccatcgctcgcattcaccgcaag ggctggagcttctgccagaagctgcatgagttggtcctgtccttcaacaacctgacacggctggacgaggagagcct ggccgagctgagcagcctgagtgtcctgcgtctcagccacaattccatcagccacattgcggagggtgccttcaagg gactcaggagcctgcgagtcttggatctggaccataacgagatttcgggcacaatagaggacacgagcggcgccttc tcagggctcgacagcctcagcaagctgactctgtttggaaacaagatcaagtctgtggctaagagagcattctcgggg ctggaaggcctggagcacctgaaccttggagggaatgcgatcagatctgtccagtttgatgcctttgtgaagatgaag aatcttaaagagctccatatcagcagcgacagcttcctgtgtgactgccagctgaagtggctgcccccgtggctaattg gcaggatgctgcaggcctttgtgacagccacctgtgcccacccagaatcactgaagggtcagagcattttctctgtgcc accagagagtttcgtgtgcgatgacttcctgaagccacagatcatcacccagccagaaaccaccatggctatggtggg caaggacatccggtttacatgctcagcagccagcagcagcagctcccccatgacctttgcctggaagaaagacaatg aagtcctgaccaatgcagacatggagaactttgtccacgtccacgcgcaggacggggaagtgatggagtacaccac catcctgcacctccgtcaggtcactttcgggcacgagggccgctaccaatgtgtcatcaccaaccactttggctccacc tattcacataaggccaggctcaccgtgaatgtgttgccatcattcaccaaaacgccccacgacataaccatccggacc accaccgtggcccgcctcgaatgtgctgccacaggtcacccaaaccctcagattgcctggcagaaggatggaggca cggatttccccgctgcccgtgagcgacgcatgcatgtcatgccggatgacgacgtgtttttcatcactgatgtgaaaata gatgacgcaggggtttacagctgtactgctcagaactcagccggttctatttcagctaatgccaccctgactgtcctaga gaccccatccttggtggtccccttggaagaccgtgtggtatctgtgggagaaacagtggccctccaatgcaaagccac ggggaaccctccgccccgcatcacctggttcaagggggaccgcccgctgagcctcactgagcggcaccacctgac ccctgacaaccagctcctggtggttcagaacgtggtggcagaggatgcgggccgatatacctgtgagatgtccaaca ccctgggcacggagcgagctcacagccagctgagcgtcctgcccgcagcaggctgcaggaaggatgggaccacg gtaggcatcttc<br>gaaccgaaatcttctgacaaaacccacacctctccgccgtctccggctccggaactgctgggtggttcttctgttttc<br>CTGTTTCCTCCAAAGCCCAAGGACACACTGATGATCTCCAGGACACCAG AGGTGACCTGCGTGGTGGTGGACGTGAGCCACGAGGACCCCGAGGTG AAGTTCAACTGGTACGTGGATGGCGTGGAGGTGCACAATGCCAAGACC AAGCCCAGAGAGGAGCAGTACAACTCTACCTATAGGGTGGTGAGCGTG CTGACAGTGCTGCACCAGGACTGGCTGAACGGCAAGGAGTATAAGTGC AAGGTGAGCAATAAGGCCCTGCCTGCCCCAATCGAGAAGACAATCTCC AAGGCCAAGGGCCAGCCAAGAGAGCCCCAGGTGTACACCCTGCCCCCT AGCAGGGATGAGCTGACAAAGAACCAGGTGTCCCTGACCTGTCTGGTG AAGGGCTTTTATCCCTCCGACATCGCCGTGGAGTGGGAGTCTAATGGCC |

TABLE 7-continued

| SEQ ID NO | Sequence information |
|---|---|
| | AGCCTGAGAATAACTACAAGACAACCCCACCCGTGCTGGATTCTGACG GCAGCTTCTTTCTGTATTCTAAGCTGACCGTGGACAAGAGCAGGTGGCA GCAGGGCAACGTGTTCAGCTGCTCCGTGATGCACGAAGCACTGCACAA TCACTACACCCAGAAATCACTGTCACTGAGCCCTGGCAAA |

As an example of the fusion protein provided in the present invention, a fusion protein, comprising the extracellular domain of the Lrig-1 protein represented by SEQ ID NO: 3; the hinge region represented by any one of SEQ ID NOs: 7 to 10; and the human IgG1-derived heavy chain constant region 2 (CH2) and heavy chain constant region 3 (CH3) which are represented by SEQ ID NO: 5, may be mentioned (see Table 8 below). The fusion proteins represented by SEQ ID NOs: 21 to 24 in Table 8 below may be encoded by the nucleic acid sequences represented by SEQ ID NOs: 25 to 28 in Table 9 below (see Table 9 below).

TABLE 8

| SEQ ID NO | Sequence information |
|---|---|
| SEQ ID NO: 21 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT EPKSSDKTHT SPPCPAPELL GGPSVF LFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLS LSPGK |
| SEQ ID NO: 22 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT EPRGPTIKPCPPCKCPAPNLLGGPSVF LFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLS LSPGK |
| SEQ ID NO: 23 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ |

TABLE 8-continued

| SEQ ID NO | Sequence information |
|---|---|
| | PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT RNTGRGGEEKKKEKEKEEQEERETKTPECPSHTQPLGVF LFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLS LSPGK |
| SEQ ID NO: 24 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT EPKSSDKTHTSPPSPAPELLGGSSVF LFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLS LSPGK |

TABLE 9

| SEQ ID NO | Sequence information |
|---|---|
| SEQ ID NO: 25 | GCTCAGGCTGGACCTAGGGCTCCTTGCGCTGCCGCCTGCACCTGTGCA GGCGATTCTCTGGACTGCAGCGGCCGGGGCCTGGCCACACTGCCCAG GGACCTGCCTTCCTGGACCAGATCTCTGAACCTGAGCTACAATCGGCT GTCCGAGATCGATTCTGCCGCCTTTGAGGACCTGACAAATCTGCAGGA GGTGTATCTGAACAGCAATGAGCTGACCGCAATCCCCTCCCTGGGAGC AGCCTCTATCGGCGTGGTGAGCCTGTTCCTGCAGCACAACAAGATCCT GAGCGTGGATGGCTCCCAGCTGAAGAGCTACCTGTCTCTGGAGGTGCT GGACCTGAGCTCCAACAATATCACCGAGATCAGATCTAGCTGTTTTCCT AATGGCCTGCGGATCAGAGAGCTGAACCTGGCCTCTAATCGGATCAGC ATCCTGGAGTCCGGCGCCTTCGATGGCCTGAGCAGATCCCTGCTGACA CTGCGCCTGTCCAAGAACCGGATCACCCAGCTGCCCGTGAAGGCCTTT AAGCTGCCTAGGCTGACACAGCTGGACCTGAACCGGAATAGAATCAG GCTGATCGAGGGCCTGACCTTCCAGGGCCTGGATAGCCTGGAGGTGCT GCGCCTGCAGCGGAACAATATCTCCCGCCTGACAGACGGAGCATTTTG GGGCCTGTCTAAGATGCACGTGCTGCACCTGGAGTACAATAGCCTGGT GGAGGTGAACTCTGGCAGCCTGTATGGCCTGACCGCCCTGCACCAGCT GCACCTGTCCAACAATAGCATCAGCAGAATCCAGAGGGATGGCTGGTC CTTCTGCCAGAAGCTGCACGAGCTGATCCTGTCTTTTAACAATCTGAC CAGGCTGGACGAGGAGAGCCTGGCAGAGCTGTCCTCTCTGTCCATCCT GCGCCTGTCTCACAATGCCATCAGCCACATCGCCGAGGGCGCCTTTAA GGGCCTGAAGAGCCTGAGGGTGCTGGATCTGGACCACAACGAGATCT CTGGCACCATCGAGGATACAAGCGGCGCCTTCACAGGCCTGGACAATC TGTCCAAGCTGACCCTGTTTGGCAACAAGATCAAGTCTGTGGCCAAGC GGGCCTTCTCTGGCCTGGAGAGCCTGGAGCACCTGAACCTGGGCGAG AATGCCATCAGATCCGTGCAGTTCGATGCCTTTGCCAAGATGAAGAAT CTGAAGGAGCTGTACATCAGCTCCGAGAGCTTCCTGTGCGACTGTCAG CTGAAGTGGCTGCCACCTTGGCTGATGGGAAGGATGCTGCAGGCCTTT GTGACCGCCACATGCGCCCACCCAGAGAGCCTGAAGGGCCAGAGCAT CTTCTCCGTGCTGCCCGATAGCTTCGTGTGCGACGATTTTCCTAAGCCA CAGATCATCACCCAGCCAGAGACAACAATGGCCGTGGTGGGCAAGGA CATCCGGTTTACATGTTCCGCCGCCTCTAGCTCCTCTAGCCCCATGACC TTCGCCTGGAAGAAGGATAACGAGGTGCTGGCCAATGCCGACATGGA GAACTTCGCCCACGTGAGAGCCCAGGATGGCGAAGTGATGGAGTATA CCACAATCCTGCACCTGCGGCACGTGACCTTTGGCCACGAGGGCAGAT ACCAGTGCATCATCACAAATCACTTCGGCTCTACCTATAGCCACAAGGC CAGGCTGACAGTGAACGTGCTGCCTAGCTTTACCAAGATCCCACACGA |

TABLE 9-continued

| SEQ ID NO | Sequence information |
|---|---|
| | CATCGCCATCAGAACAGGCACCACAGCAAGGCTGGAGTGTGCAGCAA<br>CCGGACACCCAAACCCTCAGATCGCATGGCAGAAGGATGGAGGCACA<br>GACTTCCCTGCAGCCCGCGAGAGGAGAATGCACGTGATGCCAGACGA<br>TGACGTGTTCTTTATCACAGATGTGAAGATCGATGACATGGGCGTGTAC<br>TCCTGCACCGCACAGAACAGCGCCGGCAGCGTGTCCGCCAACGCCAC<br>CCTGACCGTGCTGGAGACACCATCCCTGGCCGTGCCCCTGGAGGACA<br>GGGTGGTGACCGTGGGCGAGACAGTGGCCTTTCAGTGTAAGGCCACC<br>GGCTCTCCAACACCAAGGATCACCTGGCTGAAGGGCGGCAGGCCCCT<br>GAGCCTGACAGAGCGCCACCACTTCACCCCTGGCAATCAGCTGCTGG<br>TGGTGCAGAACGTGATGATCGATGACGCCGGCAGGTATACATGCGAGA<br>TGAGCAATCCTCTGGGCACCGAGAGGGCACACTCCCAGCTGTCTATCC<br>TGCCTACCCCAGGCTGCCGGAAGGATGGCACCACA<br>GAGCCAAAGTCCTCTGATAAGACACACACCTCTCCACCATGCCCAGCA<br>CCAGAGCTGCTGGGAGGACCAAGCGTGTTC<br>CTGTTTCCTCCAAAGCCCAAGGACACACTGATGATCTCCAGGACACCA<br>GAGGTGACCTGCGTGGTGGTGGACGTGAGCCACGAGGACCCCGAGGT<br>GAAGTTCAACTGGTACGTGGATGGCGTGGAGGTGCACAATGCCAAGA<br>CCAAGCCCAGAGAGGAGCAGTACAACTCTACCTATAGGGTGGTGAGC<br>GTGCTGACAGTGCTGCACCAGGACTGGCTGAACGGCAAGGAGTATAA<br>GTGCAAGGTGAGCAATAAGGCCCTGCCTGCCCCAATCGAGAAGACAA<br>TCTCCAAGGCCAAGGGCCAGCCAAGAGAGCCCCAGGTGTACACCCTG<br>CCCCCTAGCAGGGATGAGCTGACAAAGAACCAGGTGTCCCTGACCTG<br>TCTGGTGAAGGGCTTTTATCCCTCCGACATCGCCGTGGAGTGGGAGTC<br>TAATGGCCAGCCTGAGAATAACTACAAGACAACCCCACCCGTGCTGGA<br>TTCTGACGGCAGCTTCTTTCTGTATTCTAAGCTGACCGTGGACAAGAG<br>CAGGTGGCAGCAGGGCAACGTGTTCAGCTGCTCCGTGATGCACGAAG<br>CACTGCACAATCACTACACCCAGAAATCACTGTCACTGAGCCCTGGCA<br>AA |
| SEQ ID NO: 26 | GCTCAGGCTGGACCTAGGGCTCCTTGCGCTGCCGCCTGCACCTGTGCA<br>GGCGATTCTCTGGACTGCAGCGGCCGGGGCCTGGCCACACTGCCCAG<br>GGACCTGCCTTCCTGGACCAGATCTCTGAACCTGAGCTACAATCGGCT<br>GTCCGAGATCGATTCTGCCGCCTTTGAGGACCTGACAAATCTGCAGGA<br>GGTGTATCTGAACAGCAATGAGCTGACCGCAATCCCCTCCCTGGGAGC<br>AGCCTCTATCGGCGTGGTGAGCCTGTTCCTGCAGCACAACAAGATCCT<br>GAGCGTGGATGGCTCCCAGCTGAAGAGCTACCTGTCTCTGGAGGTGCT<br>GGACCTGAGCTCCAACAATATCACCGAGATCAGATCTAGCTGTTTTCCT<br>AATGGCCTGCGGATCAGAGAGCTGAACCTGGCCTCTAATCGGATCAGC<br>ATCCTGGAGTCCGGCGCCTTCGATGGCCTGAGCAGATCCCTGCTGACA<br>CTGCGCCTGTCCAAGAACCGGATCACCCAGCTGCCCGTGAAGGCCTTT<br>AAGCTGCCTAGGCTGACACAGCTGGACCTGAACCGGAATAGAATCAG<br>GCTGATCGAGGGCCTGACCTTCCAGGGCCTGGATAGCCTGGAGGTGCT<br>GCGCCTGCAGCGGAACAATATCTCCCGCCTGACAGACGGAGCATTTTG<br>GGGCCTGTCTAAGATGCACGTGCTGCACCTGGAGTACAATAGCCTGGT<br>GGAGGTGAACTCTGGCAGCCTGTATGGCCTGACCGCCCTGCACCAGCT<br>GCACCTGTCCAACAATAGCATCAGCAGAATCCAGAGGGATGGCTGGTC<br>CTTCTGCCAGAAGCTGCACGAGCTGATCCTGTCTTTTAACAATCTGAC<br>CAGGCTGGACGAGGAGAGCCTGGCAGAGCTGTCCTCTCTGTCCATCCT<br>GCGCCTGTCTCACAATGCCATCAGCCACATCGCCGAGGGCGCCTTTAA<br>GGGCCTGAAGAGCCTGAGGGTGCTGGATCTGGACCACAACGAGATCT<br>CTGGCACCATCGAGGATACAAGCGGCGCCTTCACAGGCCTGGACAATC<br>TGTCCAAGCTGACCCTGTTTGGCAACAAGATCAAGTCTGTGGCCAAGC<br>GGGCCTTCTCTGGCCTGGAGAGCCTGGAGCACCTGAACCTGGGCGAG<br>AATGCCATCAGATCCGTGCAGTTCGATGCCTTTGCCAAGATGAAGAAT<br>CTGAAGGAGCTGTACATCAGCTCCGAGAGCTTCCTGTGCGACTGTCAG<br>CTGAAGTGGCTGCCACCTTGGCTGATGGGAAGGATGCTGCAGGCCTTT<br>GTGACCGCCACATGCGCCCACCCAGAGAGCCTGAAGGGCCAGAGCAT<br>CTTCTCCGTGCTGCCCGATAGCTTCGTGTGCGACGATTTTCCTAAGCCA<br>CAGATCATCACCCAGCCAGAGACAACAATGGCCGTGGTGGGCAAGGA<br>CATCCGGTTTACATGTTCCGCCGCCTCTAGCTCCTCTAGCCCCATGACC<br>TTCGCCTGGAAGAAGGATAACGAGGTGCTGGCCAATGCCGACATGGA<br>GAACTTCGCCCACGTGAGAGCCCAGGATGGCGAAGTGATGGAGTATA<br>CCACAATCCTGCACCTGCGGCACGTGACCTTTGGCCACGAGGGCAGAT<br>ACCAGTGCATCATCACAAATCACTTCGGCTCTACCTATAGCCACAAGGC<br>CAGGCTGACAGTGAACGTGCTGCCTAGCTTTACCAAGATCCCACACGA<br>CATCGCCATCAGAACAGGCACCACAGCAAGGCTGGAGTGTGCAGCAA<br>CCGGACACCCAAACCCTCAGATCGCATGGCAGAAGGATGGAGGCACA<br>GACTTCCCTGCAGCCCGCGAGAGGAGAATGCACGTGATGCCAGACGA<br>TGACGTGTTCTTTATCACAGATGTGAAGATCGATGACATGGGCGTGTAC<br>TCCTGCACCGCACAGAACAGCGCCGGCAGCGTGTCCGCCAACGCCAC<br>CCTGACCGTGCTGGAGACACCATCCCTGGCCGTGCCCCTGGAGGACA<br>GGGTGGTGACCGTGGGCGAGACAGTGGCCTTTCAGTGTAAGGCCACC<br>GGCTCTCCAACACCAAGGATCACCTGGCTGAAGGGCGGCAGGCCCCT<br>GAGCCTGACAGAGCGCCACCACTTCACCCCTGGCAATCAGCTGCTGG<br>TGGTGCAGAACGTGATGATCGATGACGCCGGCAGGTATACATGCGAGA<br>TGAGCAATCCTCTGGGCACCGAGAGGGCACACTCCCAGCTGTCTATCC<br>TGCCTACCCCAGGCTGCCGGAAGGATGGCACCACA<br>Gagcctcggggccctaccatcaagccctgccccccttgcaagtgccct |

TABLE 9-continued

| SEQ ID NO | Sequence information |
|---|---|
| | gcccctaatctgctgggcggaccctccgtgttc<br>CTGTTTCCTCCAAAGCCCAAGGACACACTGATGATCTCCAGGACACCA<br>GAGGTGACCTGCGTGGTGGTGGACGTGAGCCACGAGGACCCCGAGGT<br>GAAGTTCAACTGGTACGTGGATGGCGTGGAGGTGCACAATGCCAAGA<br>CCAAGCCCAGAGAGGAGCAGTACAACTCTACCTATAGGGTGGTGAGC<br>GTGCTGACAGTGCTGCACCAGGACTGGCTGAACGGCAAGGAGTATAA<br>GTGCAAGGTGAGCAATAAGGCCCTGCCTGCCCCAATCGAGAAGACAA<br>TCTCCAAGGCCAAGGGCCAGCCAAGAGAGCCCCAGGTGTACACCCTG<br>CCCCCTAGCAGGGATGAGCTGACAAAGAACCAGGTGTCCCTGACCTG<br>TCTGGTGAAGGGCTTTTATCCCTCCGACATCGCCGTGGAGTGGGAGTC<br>TAATGGCCAGCCTGAGAATAACTACAAGACAACCCCACCCGTGCTGGA<br>TTCTGACGGCAGCTTCTTTCTGTATTCTAAGCTGACCGTGGACAAGAG<br>CAGGTGGCAGCAGGGCAACGTGTTCAGCTGCTCCGTGATGCACGAAG<br>CACTGCACAATCACTACACCCAGAAATCACTGTCACTGAGCCCTGGCA<br>AA |
| SEQ ID NO: 27 | GCTCAGGCTGGACCTAGGGCTCCTTGCGCTGCCGCCTGCACCTGTGCA<br>GGCGATTCTCTGGACTGCAGCGGCCGGGGCCTGGCCACACTGCCCAG<br>GGACCTGCCTTCCTGGACCAGATCTCTGAACCTGAGCTACAATCGGCT<br>GTCCGAGATCGATTCTGCCGCCTTTGAGGACCTGACAAATCTGCAGGA<br>GGTGTATCTGAACAGCAATGAGCTGACCGCAATCCCCTCCCTGGGAGC<br>AGCCTCTATCGGCGTGGTGAGCCTGTTCCTGCAGCACAACAAGATCCT<br>GAGCGTGGATGGCTCCCAGCTGAAGAGCTACCTGTCTCTGGAGGTGCT<br>GGACCTGAGCTCCAACAATATCACCGAGATCAGATCTAGCTGTTTTCCT<br>AATGGCCTGCGGATCAGAGAGCTGAACCTGGCCTCTAATCGGATCAGC<br>ATCCTGGAGTCCGGCGCCTTCGATGGCCTGAGCAGATCCCTGCTGACA<br>CTGCGCCTGTCCAAGAACCGGATCACCCAGCTGCCCGTGAAGGCCTTT<br>AAGCTGCCTAGGCTGACACAGCTGGACCTGAACCGGAATAGAATCAG<br>GCTGATCGAGGGCCTGACCTTCCAGGGCCTGGATAGCCTGGAGGTGCT<br>GCGCCTGCAGCGGAACAATATCTCCCGCCTGACAGACGGAGCATTTTG<br>GGGCCTGTCTAAGATGCACGTGCTGCACCTGGAGTACAATAGCCTGGT<br>GGAGGTGAACTCTGGCAGCCTGTATGGCCTGACCGCCCTGCACCAGCT<br>GCACCTGTCCAACAATAGCATCAGCAGAATCCAGAGGGATGGCTGGTC<br>CTTCTGCCAGAAGCTGCACGAGCTGATCCTGTCTTTTAACAATCTGAC<br>CAGGCTGGACGAGGAGAGCCTGGCAGAGCTGTCCTCTCTGTCCATCCT<br>GCGCCTGTCTCACAATGCCATCAGCCACATCGCCGAGGGCGCCTTTAA<br>GGGCCTGAAGAGCCTGAGGGTGCTGGATCTGGACCACAACGAGATCT<br>CTGGCACCATCGAGGATACAAGCGGCGCCTTCACAGGCCTGGACAATC<br>TGTCCAAGCTGACCCTGTTTGGCAACAAGATCAAGTCTGTGGCCAAGC<br>GGGCCTTCTCTGGCCTGGAGAGCCTGGAGCACCTGAACCTGGGCGAG<br>AATGCCATCAGATCCGTGCAGTTCGATGCCTTTGCCAAGATGAAGAAT<br>CTGAAGGAGCTGTACATCAGCTCCGAGAGCTTCCTGTGCGACTGTCAG<br>CTGAAGTGGCTGCCACCTTGGCTGATGGGAAGGATGCTGCAGGCCTTT<br>GTGACCGCCACATGCGCCCACCCAGAGAGCCTGAAGGGCCAGAGCAT<br>CTTCTCCGTGCTGCCCGATAGCTTCGTGTGCGACGATTTTCCTAAGCCA<br>CAGATCATCACCCAGCCAGAGACAACAATGGCCGTGGTGGGCAAGGA<br>CATCCGGTTTACATGTTCCGCCGCCTCTAGCTCCTCTAGCCCCATGACC<br>TTCGCCTGGAAGAAGGATAACGAGGTGCTGGCCAATGCCGACATGGA<br>GAACTTCGCCCACGTGAGAGCCCAGGATGGCGAAGTGATGGAGTATA<br>CCACAATCCTGCACCTGCGGCACGTGACCTTTGGCCACGAGGGCAGAT<br>ACCAGTGCATCATCACAAATCACTTCGGCTCTACCTATAGCCACAAGGC<br>CAGGCTGACAGTGAACGTGCTGCCTAGCTTTACCAAGATCCCACACGA<br>CATCGCCATCAGAACAGGCACCACAGCAAGGCTGGAGTGTGCAGCAA<br>CCGGACACCCAAACCCTCAGATCGCATGGCAGAAGGATGGAGGCACA<br>GACTTCCCTGCAGCCCGCGAGAGGAGAATGCACGTGATGCCAGACGA<br>TGACGTGTTCTTTATCACAGATGTGAAGATCGATGACATGGGCGTGTAC<br>TCCTGCACCGCACAGAACAGCGCCGGCAGCGTGTCCGCCAACGCCAC<br>CCTGACCGTGCTGGAGACACCATCCCTGGCCGTGCCCCTGGAGGACA<br>GGGTGGTGACCGTGGGCGAGACAGTGGCCTTTCAGTGTAAGGCCACC<br>GGCTCTCCAACACCAAGGATCACCTGGCTGAAGGGCGGCAGGCCCCT<br>GAGCCTGACAGAGCGCCACCACTTCACCCCTGGCAATCAGCTGCTGG<br>TGGTGCAGAACGTGATGATCGATGACGCCGGCAGGTATACATGCGAGA<br>TGAGCAATCCTCTGGGCACCGAGAGGGCACACTCCCAGCTGTCTATCC<br>TGCCTACCCCAGGCTGCCGGAAGGATGGCACCACA<br>cgcaacaccggccgcggcggcgaggagaagaagaaggagaaggagaaggaggagcagga<br>ggagcgcgagaccaagacccccgagtgccccagccacacccagcccctgggcgtgttc<br>CTGTTTCCTCCAAAGCCCAAGGACACACTGATGATCTCCAGGACACCA<br>GAGGTGACCTGCGTGGTGGTGGACGTGAGCCACGAGGACCCCGAGGT<br>GAAGTTCAACTGGTACGTGGATGGCGTGGAGGTGCACAATGCCAAGA<br>CCAAGCCCAGAGAGGAGCAGTACAACTCTACCTATAGGGTGGTGAGC<br>GTGCTGACAGTGCTGCACCAGGACTGGCTGAACGGCAAGGAGTATAA<br>GTGCAAGGTGAGCAATAAGGCCCTGCCTGCCCCAATCGAGAAGACAA |

TABLE 9-continued

| SEQ ID NO | Sequence information |
|---|---|
| | TCTCCAAGGCCAAGGGCCAGCCAAGAGAGCCCCAGGTGTACACCCTG<br>CCCCCTAGCAGGGATGAGCTGACAAAGAACCAGGTGTCCCTGACCTG<br>TCTGGTGAAGGGCTTTTATCCCTCCGACATCGCCGTGGAGTGGGAGTC<br>TAATGGCCAGCCTGAGAATAACTACAAGACAACCCCACCCGTGCTGGA<br>TTCTGACGGCAGCTTCTTTCTGTATTCTAAGCTGACCGTGGACAAGAG<br>CAGGTGGCAGCAGGGCAACGTGTTCAGCTGCTCCGTGATGCACGAAG<br>CACTGCACAATCACTACACCCAGAAATCACTGTCACTGAGCCCTGGCA<br>AA |
| SEQ ID NO: 28 | GCTCAGGCTGGACCTAGGGCTCCTTGCGCTGCCGCCTGCACCTGTGCA<br>GGCGATTCTCTGGACTGCAGCGGCCGGGGCCTGGCCACACTGCCCAG<br>GGACCTGCCTTCCTGGACCAGATCTCTGAACCTGAGCTACAATCGGCT<br>GTCCGAGATCGATTCTGCCGCCTTTGAGGACCTGACAAATCTGCAGGA<br>GGTGTATCTGAACAGCAATGAGCTGACCGCAATCCCCTCCCTGGGAGC<br>AGCCTCTATCGGCGTGGTGAGCCTGTTCCTGCAGCACAACAAGATCCT<br>GAGCGTGGATGGCTCCCAGCTGAAGAGCTACCTGTCTCTGGAGGTGCT<br>GGACCTGAGCTCCAACAATATCACCGAGATCAGATCTAGCTGTTTTCCT<br>AATGGCCTGCGGATCAGAGAGCTGAACCTGGCCTCTAATCGGATCAGC<br>ATCCTGGAGTCCGGCGCCTTCGATGGCCTGAGCAGATCCCTGCTGACA<br>CTGCGCCTGTCCAAGAACCGGATCACCCAGCTGCCCGTGAAGGCCTTT<br>AAGCTGCCTAGGCTGACACAGCTGGACCTGAACCGGAATAGAATCAG<br>GCTGATCGAGGGCCTGACCTTCCAGGGCCTGGATAGCCTGGAGGTGCT<br>GCGCCTGCAGCGGAACAATATCTCCCGCCTGACAGACGGAGCATTTTG<br>GGGCCTGTCTAAGATGCACGTGCTGCACCTGGAGTACAATAGCCTGGT<br>GGAGGTGAACTCTGGCAGCCTGTATGGCCTGACCGCCCTGCACCAGCT<br>GCACCTGTCCAACAATAGCATCAGCAGAATCCAGAGGGATGGCTGGTC<br>CTTCTGCCAGAAGCTGCACGAGCTGATCCTGTCTTTTAACAATCTGAC<br>CAGGCTGGACGAGGAGAGCCTGGCAGAGCTGTCCTCTCTGTCCATCCT<br>GCGCCTGTCTCACAATGCCATCAGCCACATCGCCGAGGGCGCCTTTAA<br>GGGCCTGAAGAGCCTGAGGGTGCTGGATCTGGACCACAACGAGATCT<br>CTGGCACCATCGAGGATACAAGCGGCGCCTTCACAGGCCTGGACAATC<br>TGTCCAAGCTGACCCTGTTTGGCAACAAGATCAAGTCTGTGGCCAAGC<br>GGGCCTTCTCTGGCCTGGAGAGCCTGGAGCACCTGAACCTGGGCGAG<br>AATGCCATCAGATCCGTGCAGTTCGATGCCTTTGCCAAGATGAAGAAT<br>CTGAAGGAGCTGTACATCAGCTCCGAGAGCTTCCTGTGCGACTGTCAG<br>CTGAAGTGGCTGCCACCTTGGCTGATGGGAAGGATGCTGCAGGCCTTT<br>GTGACCGCCACATGCGCCCACCCAGAGAGCCTGAAGGGCCAGAGCAT<br>CTTCTCCGTGCTGCCCGATAGCTTCGTGTGCGACGATTTTCCTAAGCCA<br>CAGATCATCACCCAGCCAGAGACAACAATGGCCGTGGTGGGCAAGGA<br>CATCCGGTTTACATGTTCCGCCGCCTCTAGCTCCTCTAGCCCCATGACC<br>TTCGCCTGGAAGAAGGATAACGAGGTGCTGGCCAATGCCGACATGGA<br>GAACTTCGCCCACGTGAGAGCCCAGGATGGCGAAGTGATGGAGTATA<br>CCACAATCCTGCACCTGCGGCACGTGACCTTTGGCCACGAGGGCAGAT<br>ACCAGTGCATCATCACAAATCACTTCGGCTCTACCTATAGCCACAAGGC<br>CAGGCTGACAGTGAACGTGCTGCCTAGCTTTACCAAGATCCCACACGA<br>CATCGCCATCAGAACAGGCACCACAGCAAGGCTGGAGTGTGCAGCAA<br>CCGGACACCCAAACCCTCAGATCGCATGGCAGAAGGATGGAGGCACA<br>GACTTCCCTGCAGCCCGCGAGAGGAGAATGCACGTGATGCCAGACGA<br>TGACGTGTTCTTTATCACAGATGTGAAGATCGATGACATGGGCGTGTAC<br>TCCTGCACCGCACAGAACAGCGCCGGCAGCGTGTCCGCCAACGCCAC<br>CCTGACCGTGCTGGAGACACCATCCCTGGCCGTGCCCCTGGAGGACA<br>GGGTGGTGACCGTGGGCGAGACAGTGGCCTTTCAGTGTAAGGCCACC<br>GGCTCTCCAACACCAAGGATCACCTGGCTGAAGGGCGGCAGGCCCCT<br>GAGCCTGACAGAGCGCCACCACTTCACCCCTGGCAATCAGCTGCTGG<br>TGGTGCAGAACGTGATGATCGATGACGCCGGCAGGTATACATGCGAGA<br>TGAGCAATCCTCTGGGCACCGAGAGGGCACACTCCCAGCTGTCTATCC<br>TGCCTACCCCAGGCTGCCGGAAGGATGGCACCACA<br>gaaccgaaatcttctgacaaaacccacacctctccgccgtctccggct<br>ccggaactgctgggtggttcttctgttttc<br>CTGTTTCCTCCAAAGCCCAAGGACACACTGATGATCTCCAGGACACCA<br>GAGGTGACCTGCGTGGTGGTGGACGTGAGCCACGAGGACCCCGAGGT<br>GAAGTTCAACTGGTACGTGGATGGCGTGGAGGTGCACAATGCCAAGA<br>CCAAGCCCAGAGAGGAGCAGTACAACTCTACCTATAGGGTGGTGAGC<br>GTGCTGACAGTGCTGCACCAGGACTGGCTGAACGGCAAGGAGTATAA<br>GTGCAAGGTGAGCAATAAGGCCCTGCCTGCCCCAATCGAGAAGACAA<br>TCTCCAAGGCCAAGGGCCAGCCAAGAGAGCCCCAGGTGTACACCCTG<br>CCCCCTAGCAGGGATGAGCTGACAAAGAACCAGGTGTCCCTGACCTG<br>TCTGGTGAAGGGCTTTTATCCCTCCGACATCGCCGTGGAGTGGGAGTC<br>TAATGGCCAGCCTGAGAATAACTACAAGACAACCCCACCCGTGCTGGA<br>TTCTGACGGCAGCTTCTTTCTGTATTCTAAGCTGACCGTGGACAAGAG<br>CAGGTGGCAGCAGGGCAACGTGTTCAGCTGCTCCGTGATGCACGAAG<br>CACTGCACAATCACTACACCCAGAAATCACTGTCACTGAGCCCTGGCA<br>AA |

As another example of the fusion protein provided in the present invention, a fusion protein, comprising the extracellular domain of the Lrig-1 protein represented by SEQ ID NO: 3; the hinge region represented by any one of SEQ ID NOs: 7 to 10; and mouse IgG2-derived heavy chain constant region 2 (CH2) and heavy chain constant region 3 (CH3) which are represented by SEQ ID NO: 6 (see Table 10 below). The fusion proteins represented by SEQ ID NOs: 29 to 32 in Table 10 below may be encoded by the nucleic acid sequences represented by SEQ ID NOs: 33 to 36 in Table 11 below (see Table 11 below).

TABLE 10

| SEQ ID NO | Sequence information |
| --- | --- |
| SEQ ID NO: 29 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT EPKSSDKTHTSPPCPAPELLGGPSVF IFPPKIKDVLMISLSPIVTCVVVDVSEDDPDVQISWFVNNVEVHTAQTQTHR EDYNSTLRVVSALPIQHQDWMSGKEFKCKVNNKDLPAPIERTISKPKGSVR APQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSR TPGK |
| SEQ ID NO: 30 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT EPRGPTIKPCPPCKCPAPNLLGGPSVF IFPPKIKDVLMISLSPIVTCVVVDVSEDDPDVQISWFVNNVEVHTAQTQTHR EDYNSTLRVVSALPIQHQDWMSGKEFKCKVNNKDLPAPIERTISKPKGSVR APQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSR TPGK |
| SEQ ID NO: 31 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL QRNNISRLTDGAFWGLSKMHVLHLEYNSLVEVNSGSLYGLTALHQLHLSN NSISRIQRDGWSFCQKLHELILSFNNLTRLDEESLAELSSLSILRLSHNAISHI AEGAFKGLKSLRVLDLDHNEISGTIEDTSGAFTGLDNLSKLTLFGNKIKSVA KRAFSGLESLEHLNLGENAIRSVQFDAFAKMKNLKELYISSESFLCDCQLK WLPPWLMGRMLQAFVTATCAHPESLKGQSIFSVLPDSFVCDDFPKPQIITQ PETTMAVVGKDIRFTCSAASSSSSPMTFAWKKDNEVLANADMENFAHVRA QDGEVMEYTTILHLRHVTFGHEGRYQCIITNHFGSTYSHKARLTVNVLPSF TKIPHDIAIRTGTTARLECAATGHPNPQIAWQKDGGTDFPAARERRMHVMP DDDVFFITDVKIDDMGVYSCTAQNSAGSVSANATLTVLETPSLAVPLEDRV VTVGETVAFQCKATGSPTPRITWLKGGRPLSLTERHHFTPGNQLLVVQNV MIDDAGRYTCEMSNPLGTERAHSQLSILPTPGCRKDGTT RNTGRGGEEKKKEKEKEEQEERETKTPECPSHTQPLGVF IFPPKIKDVLMISLSPIVTCVVVDVSEDDPDVQISWFVNNVEVHTAQTQTHR EDYNSTLRVVSALPIQHQDWMSGKEFKCKVNNKDLPAPIERTISKPKGSVR APQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSR TPGK |
| SEQ ID NO: 32 | AQAGPRAPCAAACTCAGDSLDCSGRGLATLPRDLPSWTRSLNLSYNRLSEI DSAAFEDLTNLQEVYLNSNELTAIPSLGAASIGVVSLFLQHNKILSVDGSQL KSYLSLEVLDLSSNNITEIRSSCFPNGLRIRELNLASNRISILESGAFDGLSRS LLTLRLSKNRITQLPVKAFKLPRLTQLDLNRNRIRLIEGLTFQGLDSLEVLRL |

TABLE 10-continued

| SEQ ID NO | Sequence information |
|---|---|
| | QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>EPKSSDKTHTSPPSPAPELLGGSSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |

TABLE 11

| SEQ ID NO | Sequence information |
|---|---|
| SEQ ID NO: 33 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GAGCCAAAGTCCTCTGATAAGACACACACCTCTCCACCATGCCCAGCAC<br>CAGAGCTGCTGGGAGGACCAAGCGTGTTC<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg |

TABLE 11-continued

| SEQ ID NO | Sequence information |
|---|---|
| | cgggctccccaggtgtacgtgctgcccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 34 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>Gagcctcggggccctaccatcaagccctgcccccttgcaagtgccctgcccctaatctgctgggcggaccctccgt<br>gttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgcccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 35 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC |

TABLE 11-continued

| SEQ ID NO | Sequence information |
|---|---|
| | GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>cgcaacaccggccgcggcggcgaggagaagaagaaggagaaggagaaggaggagcaggaggagcgcgaga<br>ccaagacccccgagtgccccagccacacccagcccctgggcgtgttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 36 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT |

TABLE 11-continued

| SEQ ID NO | Sequence information |
|---|---|
| | GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>gaaccgaaatcttctgacaaaacccacacctctccgccgtctccggctccggaactgctgggtggttcttctgttttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |

As yet another example of the fusion protein provided in the present invention, a fusion protein, comprising the extracellular domain of the Lrig-1 protein represented by SEQ ID NO: 1; the linker represented by SEQ ID NO: 11; the hinge region represented by any one of SEQ ID NOs: 7 to 10; and the human IgG1-derived heavy chain constant region 2 (CH2) and heavy chain constant region 3 (CH3) which are represented by SEQ ID NO: 5, may be mentioned (see Table 12 below). The fusion proteins represented by SEQ ID NOs: 37 to 40 in Table 12 below may be encoded by the nucleic acid sequences represented by SEQ ID NOs: 41 to 44 in Table 13 below (see Table 13 below).

TABLE 12

| SEQ ID NO | Sequence information |
|---|---|
| SEQ ID NO: 37 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>GS<br>EPKSSDKTHTSPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 38 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN |

TABLE 12-continued

| SEQ ID NO | Sequence information |
|---|---|
| | VVAEDAGRYTCEMSNTLGTERAHSQLSVLPAAGCRKDGTTVGIF<br>GS<br>EPRGPTIKPCPPCKCPAPNLLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 39 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>GS<br>RNTGRGGEEKKKEKEKEEQEERETKTPECPSHTQPLGVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 40 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>GS<br>EPKSSDKTHTSPPSPAPELLGGSSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |

TABLE 13

| SEQ ID NO | Sequence information |
|---|---|
| SEQ ID NO: 41 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgatcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg |

TABLE 13-continued

| SEQ ID NO | Sequence information |
|---|---|
| | ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGATCC<br>GAGCCAAAGTCCTCTGATAAGACACACACCTCTCCACCATGCCCAGCAC<br>CAGAGCTGCTGGGAGGACCAAGCGTGTTC<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 42 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGATCC<br>Gagcctcggggccctaccatcaagccctgcccccttgcaagtgccctgcccctaatctgctgggcggaccctccgt<br>gttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG |

TABLE 13-continued

| SEQ ID NO | Sequence information |
|---|---|
| | GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 43 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGATCC<br>cgcaacaccggccgcggcggcgaggagaagaagaaggagaaggagaaggaggagcaggaggagcgcgaga<br>ccaagacccccgagtgccccagccacacccagcccctgggcgtgttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 44 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca |

TABLE 13-continued

| SEQ ID NO | Sequence information |
|---|---|
| | cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGATCC<br>gaaccgaaatcttctgacaaaacccacacctctccgccgtctccggctccggaactgctgggtggttcttctgttttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |

As still yet another example of the fusion protein provided in the present invention, a fusion protein, comprising the extracellular domain of the Lrig-1 protein represented by SEQ ID NO: 3; the linker represented by SEQ ID NO: 11; the hinge region represented by any one of SEQ ID NOs: 7 to 10; and the human IgG1-derived heavy chain constant region 2 (CH2) and heavy chain constant region 3 (CH3) which are represented by SEQ ID NO: 5, may be mentioned (see Table 14 below). The fusion proteins represented by SEQ ID NOs: 45 to 48 in Table 14 below may be encoded by the nucleic acid sequences represented by SEQ ID NOs: 49 to 52 in Table 15 below (see Table 15 below).

TABLE 14

| SEQ ID NO | Sequence information |
|---|---|
| SEQ ID NO: 45 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>EPKSSDKTHTSPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 46 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>EPRGPTIKPCPPCKCPAPNLLGGPSVF |

TABLE 14-continued

| SEQ ID NO | Sequence information |
|---|---|
| | LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 47 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>RNTGRGGEEKKKEKEKEEQEERETKTPECPSHTQPLGVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 48 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>EPKSSDKTHTSPPSPAPELLGGSSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |

TABLE 15

| SEQ ID NO | Sequence information |
|---|---|
| SEQ ID NO: 49 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG |

TABLE 15-continued

| SEQ ID NO | Sequence information |
| --- | --- |
| | CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>GAGCCAAAGTCCTCTGATAAGACACACACCTCTCCACCATGCCCAGCAC<br>CAGAGCTGCTGGGAGGACCAAGCGTGTTC<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 50 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT |

TABLE 15-continued

| SEQ ID NO | Sequence information |
|---|---|
| | TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>Gagcctcggggccctaccatcaagccctgccccccttgcaagtgccctgcccctaatctgctgggcggaccctccgt<br>gttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 51 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA |

TABLE 15-continued

| SEQ ID NO | Sequence information |
|---|---|
| | GGATCC<br>cgcaacaccggccgcggcggcgaggagaagaagaaggagaaggagaaggaggagcaggaggagcgcgaga<br>ccaagacccccgagtgccccagccacacccagcccctgggcgtgttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 52 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>gaaccgaaatcttctgacaaaacccacacctctccgccgtctccggctccggaactgctgggtggttcttctgttttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT |

TABLE 15-continued

| SEQ ID NO | Sequence information |
|---|---|
| | AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |

As still yet another example of the fusion protein provided in the present invention, a fusion protein, comprising the extracellular domain of the Lrig-1 protein represented by SEQ ID NO: 3; the linker represented by SEQ ID NO: 11; the hinge region represented by any one of SEQ ID NOs: 7 to 10; and the mouse IgG2-derived heavy chain constant region 2 (CH2) and heavy chain constant region 3 (CH3) which are represented by SEQ ID NO: 6, may be mentioned (see Table 16 below). The fusion proteins represented by SEQ ID NOs: 53 to 56 in Table 16 below may be encoded by the nucleic acid sequences represented by SEQ ID NOs: 57 to 60 in Table 17 below (see Table 17 below).

TABLE 16

| SEQ ID NO | Sequence information |
|---|---|
| SEQ ID NO: 53 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>EPKSSDKTHTSPPCPAPELLGGPSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |
| SEQ ID NO: 54 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>EPRGPTIKPCPPCKCPAPNLLGGPSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |
| SEQ ID NO: 55 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA |

TABLE 16-continued

| SEQ ID NO | Sequence information |
|---|---|
| | QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>RNTGRGGEEKKKEKEKEEQEERETKTPECPSHTQPLGVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |
| SEQ ID NO: 56 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GS<br>EPKSSDKTHTSPPSPAPELLGGSSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |

TABLE 17

| SEQ ID NO | Sequence information |
|---|---|
| SEQ ID NO: 57 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT |

TABLE 17-continued

| SEQ ID NO | Sequence information |
| --- | --- |
| | ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>GAGCCAAAGTCCTCTGATAAGACACACACCTCTCCACCATGCCCAGCAC<br>CAGAGCTGCTGGGAGGACCAAGCGTGTTC<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctcccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggaccccc<br>ggcaaa |
| SEQ ID NO: 58 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>Gagcctcggggccctaccatcaagccctgccccccttgcaagtgccctgcccctaatctgctgggcggaccctccgt<br>gttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga |

TABLE 17-continued

| SEQ ID NO | Sequence information |
|---|---|
| | attcaagtgcaaagtgaacaacaaggacctgcctgcccccatcgagcggaccatctccaagcccaagggctccgtg<br>cgggctccccaggtgtacgtgctgcccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 59 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>cgcaacaccggccgcggcggcgaggagaagaagaaggagaaggagaaggaggagcaggaggagcgcgaga<br>ccaagacccccgagtgccccagccacacccagcccctgggcgtgttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgcccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 60 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA |

TABLE 17-continued

| SEQ ID NO | Sequence information |
|---|---|
| | GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGATCC<br>gaaccgaaatcttctgacaaaacccacacctctccgccgtctccggctccggaactgctgggtggttcttctgttttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggaccccc<br>ggcaaa |

As still yet another example of the fusion protein provided in the present invention, a fusion protein, comprising the extracellular domain of the Lrig-1 protein represented by SEQ ID NO: 1; the linker represented by SEQ ID NO: 12; the linker represented by SEQ ID NO: 11; the hinge region represented by any one of SEQ ID NOs: 7 to 10; and the human IgG1-derived heavy chain constant region 2 (CH2) and heavy chain constant region 3 (CH3) which are represented by SEQ ID NO: 5, may be mentioned (see Table 18 below). The fusion proteins represented by SEQ ID NOs: 61 to 64 in Table 18 below may be encoded by the nucleic acid sequences represented by SEQ ID NOs: 65 to 68 in Table 19 (see Table 19 below).

TABLE 18

| SEQ ID NO | Sequence information |
|---|---|
| SEQ ID NO: 61 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN |

TABLE 18-continued

| SEQ ID NO | Sequence information |
|---|---|
| | VVAEDAGRYTCEMSNTLGTERAHSQLSVLPAAGCRKDGTTVGIF<br>GGG<br>GS<br>EPKSSDKTHTSPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 62 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>GGG<br>GS<br>EPRGPTIKPCPPCKCPAPNLLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 63 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWF'KGDRPLSLTERHHLTPDNQLLVVQN<br>VVAEDAGRYTCEMSNTLGTERAHSQLSVLPAAGCRKDGTTVGIF<br>GGG<br>GS<br>RNTGRGGEEKKKEKEKEEQEERETKTPECPSHTQPLGVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 64 | AGPRAPCAAACTCAGDSLDCGGRGLAALPGDLPSWTRSLNLSYNKLSEID<br>PAGFEDLPNLQEVYLNNNELTAVPSLGAASSHVVSLFLQHNKIRSVEGSQL<br>KAYLSLEVLDLSLNNITEVRNTCFPHGPPIKELNLAGNRIGTLELGAFDGLS<br>RSLLTLRLSKNRITQLPVRAFKLPRLTQLDLNRNRIRLIEGLTFQGLNSLEVL<br>KLQRNNISKLTDGAFWGLSKMHVLHLEYNSLVEVNSGSLYGLTALHQLHL<br>SNNSIARIHRKGWSFCQKLHELVLSFNNLTRLDEESLAELSSLSVLRLSHNSI<br>SHIAEGAFKGLRSLRVLDLDHNEISGTIEDTSGAFSGLDSLSKLTLFGNKIKS<br>VAKRAFSGLEGLEHLNLGGNAIRSVQFDAFVKMKNLKELHISSDSFLCDCQ<br>LKWLPPWLIGRMLQAFVTATCAHPESLKGQSIFSVPPESFVCDDFLKPQIIT<br>QPETTMAMVGKDIRFTCSAASSSSSPMTFAWKKDNEVLTNADMENFVHV<br>HAQDGEVMEYTTILHLRQVTFGHEGRYQCVITNHFGSTYSHKARLTVNVL<br>PSFTKTPHDITIRTTTVARLECAATGHPNPQIAWQKDGGTDFPAARERRMH<br>VMPDDDVFFITDVKIDDAGVYSCTAQNSAGSISANATLTVLETPSLVVPLED<br>RVVSVGETVALQCKATGNPPPRITWFKGDRPLSLTERHHLTPDNQLLVVQN<br>VVAEDAGRYTCEMSNTLGTERAHSQLSVLPAAGCRKDGTTVGIF<br>GGG<br>GS<br>EPKSSDKTHTSPPSPAPELLGGSSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG |

TABLE 18-continued

| SEQ ID NO | Sequence information |
|---|---|
| | QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |

TABLE 19

| SEQ ID NO | Sequence information |
|---|---|
| SEQ ID NO: 65 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcatttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGCGGTGGC<br>GGATCC<br>GAGCCAAAGTCCTCTGATAAGACACACACCTCTCCACCATGCCCAGCAC<br>CAGAGCTGCTGGGAGGACCAAGCGTGTTC<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 66 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag |

TABLE 19-continued

| SEQ ID NO | Sequence information |
| --- | --- |
| | aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGCGGTGGC<br>GGATCC<br>Gagcctcggggccctaccatcaagccctgcccccttgcaagtgccctgcccctaatctgctgggcggaccctccgt<br>gttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 67 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGCGGTGGC<br>GGATCC<br>cgcaacaccggccgcggcggcgaggagaagaagaaggagaaggagaaggaggagcaggaggagcgcgaga<br>ccaagacccccgagtgccccagccacacccagcccctgggcgtgttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC |

TABLE 19-continued

| SEQ ID NO | Sequence information |
|---|---|
| | AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |
| SEQ ID NO: 68 | GCTGGGCCTCGGGCTCCTTGTGCTGCCGCCTGCACATGTGCAGGCGATT<br>CCCTGGACTGCGGCGGCAGAGGCCTGGCCGCCCTGCCTGGCGATCTGC<br>CATCCTGGACCCGGAGCCTGAACCTGAGCTACAACAAGCTGAGCGAGA<br>TCGATCCCGCCGGCTTTGAGGACCTGCCTAACCTGCAGGAGGTGTATCT<br>GAACAATAACGAGCTGACCGCGGTACCatccctgggcgctgcttcatcacatgtcgtctctct<br>ctttctgcagcacaacaagattcgcagcgtggaggggagccagctgaaggcctacctttccttagaagtgttagatctg<br>agtttgaacaacatcacggaagtgcggaacacctgctttccacacggaccgcctataaaggagctcaacctggcagg<br>caatcggattggcaccctggagttgggagcatttgatggtctgtcacggtcgctgctaactcttcgcctgagcaaaaac<br>aggatcacccagcttcctgtaagagcattcaagctacccaggctgacacaactggacctcaatcggaacaggattcg<br>gctgatagagggcctcaccttccaggggctcaacagcttggaggtgctgaagcttcagcgaaacaacatcagcaaac<br>tgacagatggggccttctggggactgtccaagatgcatgtgctgcacctggagtacaacagcctggtagaagtgaac<br>agcggctcgctctacggcctcacggccctgcatcagctccacctcagcaacaattccatcgctcgcattcaccgcaag<br>ggctggagcttctgccagaagctgcatgagttggtcctgtccttcaacaacctgacacggctggacgaggagagcct<br>ggccgagctgagcagcctgagtgtcctgcgtctcagccacaattccatcagccacattgcggagggtgccttcaagg<br>gactcaggagcctgcgagtcttggatctggaccataacgagatttcgggcacaatagaggacacgagcggcgccttc<br>tcagggctcgacagcctcagcaagctgactctgtttggaaacaagatcaagtctgtggctaagagagcattctcgggg<br>ctggaaggcctggagcacctgaaccttggagggaatgcgatcagatctgtccagtttgatgcctttgtgaagatgaag<br>aatcttaaagagctccatatcagcagcgacagcttcctgtgtgactgccagctgaagtggctgcccccgtggctaattg<br>gcaggatgctgcaggcctttgtgacagccacctgtgcccacccagaatcactgaagggtcagagcattttctctgtgcc<br>accagagagtttcgtgtgcgatgacttcctgaagccacagatcatcacccagccagaaaccaccatggctatggtggg<br>caaggacatccggtttacatgctcagcagccagcagcagcagctcccccatgacctttgcctggaagaaagacaatg<br>aagtcctgaccaatgcagacatggagaactttgtccacgtccacgcgcaggacggggaagtgatggagtacaccac<br>catcctgcacctccgtcaggtcactttcgggcacgagggccgctaccaatgtgtcatcaccaaccactttggctccacc<br>tattcacataaggccaggctcaccgtgaatgtgttgccatcattcaccaaaacgccccacgacataaccatccggacc<br>accaccgtggcccgcctcgaatgtgctgccacaggtcacccaaaccctcagattgcctggcagaaggatggaggca<br>cggatttccccgctgcccgtgagcgacgcatgcatgtcatgccggatgacgacgtgtttttcatcactgatgtgaaaata<br>gatgacgcaggggtttacagctgtactgctcagaactcagccggttctatttcagctaatgccaccctgactgtcctaga<br>gaccccatccttggtggtccccttggaagaccgtgtggtatctgtgggagaaacagtggccctccaatgcaaagccac<br>ggggaaccctccgccccgcatcacctggttcaaggggaccgcccgctgagcctcactgagcggcaccacctgac<br>ccctgacaaccagctcctggtggttcagaacgtggtggcagaggatgcgggccgatatacctgtgagatgtccaaca<br>ccctgggcacggagcgagctcacagccagctgagcgtcctgcccgcagcaggctgcaggaaggatgggaccacg<br>gtaggcatcttc<br>GGCGGTGGC<br>GGATCC<br>gaaccgaaatcttctgacaaaacccacacctctccgccgtctccggctccggaactgctgggtggttcttctgttttc<br>CTGTTTCCTCCAAAGCCCAAGGACACACTGATGATCTCCAGGACACCAG<br>AGGTGACCTGCGTGGTGGTGGACGTGAGCCACGAGGACCCCGAGGTG<br>AAGTTCAACTGGTACGTGGATGGCGTGGAGGTGCACAATGCCAAGACC<br>AAGCCCAGAGAGGAGCAGTACAACTCTACCTATAGGGTGGTGAGCGTG<br>CTGACAGTGCTGCACCAGGACTGGCTGAACGGCAAGGAGTATAAGTGC<br>AAGGTGAGCAATAAGGCCCTGCCTGCCCCAATCGAGAAGACAATCTCC<br>AAGGCCAAGGGCCAGCCAAGAGAGCCCCAGGTGTACACCCTGCCCCCT<br>AGCAGGGATGAGCTGACAAAGAACCAGGTGTCCCTGACCTGTCTGGTG<br>AAGGGCTTTTATCCCTCCGACATCGCCGTGGAGTGGGAGTCTAATGGCC<br>AGCCTGAGAATAACTACAAGACAACCCCACCCGTGCTGGATTCTGACG<br>GCAGCTTCTTTCTGTATTCTAAGCTGACCGTGGACAAGAGCAGGTGGCA<br>GCAGGGCAACGTGTTCAGCTGCTCCGTGATGCACGAAGCACTGCACAA<br>TCACTACACCCAGAAATCACTGTCACTGAGCCCTGGCAAA |

As still yet another example of the fusion protein provided in the present invention, a fusion protein, comprising the extracellular domain of the Lrig-1 protein represented by SEQ ID NO: 3; the linker represented by SEQ ID NO: 12; the linker represented by SEQ ID NO: 11; the hinge region represented by any one of SEQ ID NOs: 7 to 10; and the human IgG1-derived heavy chain constant region 2 (CH2) and heavy chain constant region 3 (CH3) which are represented by SEQ ID NO: 5, may be mentioned (see Table 20 below). The fusion proteins represented by SEQ ID NOs: 69 to 72 in Table 20 below may be encoded by the nucleic acid sequences represented by SEQ ID NOs: 73 to 76 in Table 21 below (see Table 21 below).

TABLE 20

| SEQ ID NO | Sequence information |
|---|---|
| SEQ ID NO: 69 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK |

TABLE 20-continued

| SEQ ID NO | Sequence information |
| --- | --- |
| | WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>EPKSSDKTHTSPPCPAPELLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 70 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>EPRGPTIKPCPPCKCPAPNLLGGPSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 71 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>RNTGRGGEEKKKEKEKEEQEERETKTPECPSHTQPLGVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |
| SEQ ID NO: 72 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV |

TABLE 20-continued

| SEQ ID NO | Sequence information |
|---|---|
| | MIDDAGRYTCEMSNPLGTERAHSQLSILPTPGCRKDGTT<br>GGG<br>GS<br>EPKSSDKTHTSPPSPAPELLGGSSVF<br>LFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKG<br>QPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLS<br>LSPGK |

TABLE 21

| SEQ ID NO | Sequence information |
|---|---|
| SEQ ID NO: 73 | GCTCAGGCTGGACCTAGGGCTCCTTGCGCTGCCGCCTGCACCTG<br>TGCAGGCGATTCTCTGGACTGCAGCGGCCGGGGCCTGGCCACAC<br>TGCCCAGGGACCTGCCTTCCTGGACCAGATCTCTGAACCTGAGC<br>TACAATCGGCTGTCCGAGATCGATTCTGCCGCCTTTGAGGACCTG<br>ACAAATCTGCAGGAGGTGTATCTGAACAGCAATGAGCTGACCGC<br>AATCCCCTCCCTGGGAGCAGCCTCTATCGGCGTGGTGAGCCTGTT<br>CCTGCAGCACAACAAGATCCTGAGCGTGGATGGCTCCCAGCTGA<br>AGAGCTACCTGTCTCTGGAGGTGCTGGACCTGAGCTCCAACAAT<br>ATCACCGAGATCAGATCTAGCTGTTTTCCTAATGGCCTGCGGATC<br>AGAGAGCTGAACCTGGCCTCTAATCGGATCAGCATCCTGGAGTC<br>CGGCGCCTTCGATGGCCTGAGCAGATCCCTGCTGACACTGCGCC<br>TGTCCAAGAACCGGATCACCCAGCTGCCCGTGAAGGCCTTTAAG<br>CTGCCTAGGCTGACACAGCTGGACCTGAACCGGAATAGAATCAG<br>GCTGATCGAGGGCCTGACCTTCCAGGGCCTGGATAGCCTGGAGG<br>TGCTGCGCCTGCAGCGGAACAATATCTCCCGCCTGACAGACGGA<br>GCATTTTGGGGCCTGTCTAAGATGCACGTGCTGCACCTGGAGTAC<br>AATAGCCTGGTGGAGGTGAACTCTGGCAGCCTGTATGGCCTGAC<br>CGCCCTGCACCAGCTGCACCTGTCCAACAATAGCATCAGCAGAA<br>TCCAGAGGGATGGCTGGTCCTTCTGCCAGAAGCTGCACGAGCTG<br>ATCCTGTCTTTTAACAATCTGACCAGGCTGGACGAGGAGAGCCT<br>GGCAGAGCTGTCCTCTCTGTCCATCCTGCGCCTGTCTCACAATGC<br>CATCAGCCACATCGCCGAGGGCGCCTTTAAGGGCCTGAAGAGCC<br>TGAGGGTGCTGGATCTGGACCACAACGAGATCTCTGGCACCATC<br>GAGGATACAAGCGGCGCCTTCACAGGCCTGGACAATCTGTCCAA<br>GCTGACCCTGTTTGGCAACAAGATCAAGTCTGTGGCCAAGCGGG<br>CCTTCTCTGGCCTGGAGAGCCTGGAGCACCTGAACCTGGGCGAG<br>AATGCCATCAGATCCGTGCAGTTCGATGCCTTTGCCAAGATGAAG<br>AATCTGAAGGAGCTGTACATCAGCTCCGAGAGCTTCCTGTGCGA<br>CTGTCAGCTGAAGTGGCTGCCACCTTGGCTGATGGGAAGGATGC<br>TGCAGGCCTTTGTGACCGCCACATGCGCCCACCCAGAGAGCCTG<br>AAGGGCCAGAGCATCTTCTCCGTGCTGCCCGATAGCTTCGTGTGC<br>GACGATTTTCCTAAGCCACAGATCATCACCCAGCCAGAGACAAC<br>AATGGCCGTGGTGGGCAAGGACATCCGGTTTACATGTTCCGCCG<br>CCTCTAGCTCCTCTAGCCCCATGACCTTCGCCTGGAAGAAGGATA<br>ACGAGGTGCTGGCCAATGCCGACATGGAGAACTTCGCCCACGTG<br>AGAGCCCAGGATGGCGAAGTGATGGAGTATACCACAATCCTGCA<br>CCTGCGGCACGTGACCTTTGGCCACGAGGGCAGATACCAGTGCA<br>TCATCACAAATCACTTCGGCTCTACCTATAGCCACAAGGCCAGGC<br>TGACAGTGAACGTGCTGCCTAGCTTTACCAAGATCCCACACGAC<br>ATCGCCATCAGAACAGGCACCACAGCAAGGCTGGAGTGTGCAG<br>CAACCGGACACCCAAACCCTCAGATCGCATGGCAGAAGGATGGA<br>GGCACAGACTTCCCTGCAGCCCGCGAGAGGAGAATGCACGTGAT<br>GCCAGACGATGACGTGTTCTTTATCACAGATGTGAAGATCGATGA<br>CATGGGCGTGTACTCCTGCACCGCACAGAACAGCGCCGGCAGCG<br>TGTCCGCCAACGCCACCCTGACCGTGCTGGAGACACCATCCCTG<br>GCCGTGCCCCTGGAGGACAGGGTGGTGACCGTGGGCGAGACAG<br>TGGCCTTTCAGTGTAAGGCCACCGGCTCTCCAACACCAAGGATC<br>ACCTGGCTGAAGGGCGGCAGGCCCCTGAGCCTGACAGAGCGCC<br>ACCACTTCACCCCTGGCAATCAGCTGCTGGTGGTGCAGAACGTG<br>ATGATCGATGACGCCGGCAGGTATACATGCGAGATGAGCAATCCT<br>CTGGGCACCGAGAGGGCACACTCCCAGCTGTCTATCCTGCCTAC<br>CCCAGGCTGCCGGAAGGATGGCACCACA<br>GGCGGTGGC<br>GGATCC<br>GAGCCAAAGTCCTCTGATAAGACACACACCTCTCCACCATGCCC<br>AGCACCAGAGCTGCTGGGAGGACCAAGCGTGTTC<br>CTGTTTCCTCCAAAGCCCAAGGACACACTGATGATCTCCAGGAC<br>ACCAGAGGTGACCTGCGTGGTGGTGGACGTGAGCCACGAGGAC<br>CCCGAGGTGAAGTTCAACTGGTACGTGGATGGCGTGGAGGTGCA<br>CAATGCCAAGACCAAGCCCAGAGAGGAGCAGTACAACTCTACCT<br>ATAGGGTGGTGAGCGTGCTGACAGTGCTGCACCAGGACTGGCTG |

TABLE 21-continued

| SEQ ID NO | Sequence information |
|---|---|
| | AACGGCAAGGAGTATAAGTGCAAGGTGAGCAATAAGGCCCTGCC<br>TGCCCCAATCGAGAAGACAATCTCCAAGGCCAAGGGCCAGCCA<br>AGAGAGCCCCAGGTGTACACCCTGCCCCCTAGCAGGGATGAGCT<br>GACAAAGAACCAGGTGTCCCTGACCTGTCTGGTGAAGGGCTTTT<br>ATCCCTCCGACATCGCCGTGGAGTGGGAGTCTAATGGCCAGCCT<br>GAGAATAACTACAAGACAACCCCACCCGTGCTGGATTCTGACGG<br>CAGCTTCTTTCTGTATTCTAAGCTGACCGTGGACAAGAGCAGGTG<br>GCAGCAGGGCAACGTGTTCAGCTGCTCCGTGATGCACGAAGCAC<br>TGCACAATCACTACACCCAGAAATCACTGTCACTGAGCCCTGGC<br>AAA |
| SEQ ID NO: 74 | GCTCAGGCTGGACCTAGGGCTCCTTGCGCTGCCGCCTGCACCTG<br>TGCAGGCGATTCTCTGGACTGCAGCGGCCGGGGCCTGGCCACAC<br>TGCCCAGGGACCTGCCTTCCTGGACCAGATCTCTGAACCTGAGC<br>TACAATCGGCTGTCCGAGATCGATTCTGCCGCCTTTGAGGACCTG<br>ACAAATCTGCAGGAGGTGTATCTGAACAGCAATGAGCTGACCGC<br>AATCCCCTCCCTGGGAGCAGCCTCTATCGGCGTGGTGAGCCTGTT<br>CCTGCAGCACAACAAGATCCTGAGCGTGGATGGCTCCCAGCTGA<br>AGAGCTACCTGTCTCTGGAGGTGCTGGACCTGAGCTCCAACAAT<br>ATCACCGAGATCAGATCTAGCTGTTTTCCTAATGGCCTGCGGATC<br>AGAGAGCTGAACCTGGCCTCTAATCGGATCAGCATCCTGGAGTC<br>CGGCGCCTTCGATGGCCTGAGCAGATCCCTGCTGACACTGCGCC<br>TGTCCAAGAACCGGATCACCCAGCTGCCCGTGAAGGCCTTTAAG<br>CTGCCTAGGCTGACACAGCTGGACCTGAACCGGAATAGAATCAG<br>GCTGATCGAGGGCCTGACCTTCCAGGGCCTGGATAGCCTGGAGG<br>TGCTGCGCCTGCAGCGGAACAATATCTCCCGCCTGACAGACGGA<br>GCATTTTGGGGCCTGTCTAAGATGCACGTGCTGCACCTGGAGTAC<br>AATAGCCTGGTGGAGGTGAACTCTGGCAGCCTGTATGGCCTGAC<br>CGCCCTGCACCAGCTGCACCTGTCCAACAATAGCATCAGCAGAA<br>TCCAGAGGGATGGCTGGTCCTTCTGCCAGAAGCTGCACGAGCTG<br>ATCCTGTCTTTTAACAATCTGACCAGGCTGGACGAGGAGAGCCT<br>GGCAGAGCTGTCCTCTCTGTCCATCCTGCGCCTGTCTCACAATGC<br>CATCAGCCACATCGCCGAGGGCGCCTTTAAGGGCCTGAAGAGCC<br>TGAGGGTGCTGGATCTGGACCACAACGAGATCTCTGGCACCATC<br>GAGGATACAAGCGGCGCCTTCACAGGCCTGGACAATCTGTCCAA<br>GCTGACCCTGTTTGGCAACAAGATCAAGTCTGTGGCCAAGCGGG<br>CCTTCTCTGGCCTGGAGAGCCTGGAGCACCTGAACCTGGGCGAG<br>AATGCCATCAGATCCGTGCAGTTCGATGCCTTTGCCAAGATGAAG<br>AATCTGAAGGAGCTGTACATCAGCTCCGAGAGCTTCCTGTGCGA<br>CTGTCAGCTGAAGTGGCTGCCACCTTGGCTGATGGGAAGGATGC<br>TGCAGGCCTTTGTGACCGCCACATGCGCCCACCCAGAGAGCCTG<br>AAGGGCCAGAGCATCTTCTCCGTGCTGCCCGATAGCTTCGTGTGC<br>GACGATTTTCCTAAGCCACAGATCATCACCCAGCCAGAGACAAC<br>AATGGCCGTGGTGGGCAAGGACATCCGGTTTACATGTTCCGCCG<br>CCTCTAGCTCCTCTAGCCCCATGACCTTCGCCTGGAAGAAGGATA<br>ACGAGGTGCTGGCCAATGCCGACATGGAGAACTTCGCCCACGTG<br>AGAGCCCAGGATGGCGAAGTGATGGAGTATACCACAATCCTGCA<br>CCTGCGGCACGTGACCTTTGGCCACGAGGGCAGATACCAGTGCA<br>TCATCACAAATCACTTCGGCTCTACCTATAGCCACAAGGCCAGGC<br>TGACAGTGAACGTGCTGCCTAGCTTTACCAAGATCCCACACGAC<br>ATCGCCATCAGAACAGGCACCACAGCAAGGCTGGAGTGTGCAG<br>CAACCGGACACCCAAACCCTCAGATCGCATGGCAGAAGGATGGA<br>GGCACAGACTTCCCTGCAGCCCGCGAGAGGAGAATGCACGTGAT<br>GCCAGACGATGACGTGTTCTTTATCACAGATGTGAAGATCGATGA<br>CATGGGCGTGTACTCCTGCACCGCACAGAACAGCGCCGGCAGCG<br>TGTCCGCCAACGCCACCCTGACCGTGCTGGAGACACCATCCCTG<br>GCCGTGCCCCTGGAGGACAGGGTGGTGACCGTGGGCGAGACAG<br>TGGCCTTTCAGTGTAAGGCCACCGGCTCTCCAACACCAAGGATC<br>ACCTGGCTGAAGGGCGGCAGGCCCCTGAGCCTGACAGAGCGCC<br>ACCACTTCACCCCTGGCAATCAGCTGCTGGTGGTGCAGAACGTG<br>ATGATCGATGACGCCGGCAGGTATACATGCGAGATGAGCAATCCT<br>CTGGGCACCGAGAGGGCACACTCCCAGCTGTCTATCCTGCCTAC<br>CCCAGGCTGCCGGAAGGATGGCACCACA<br>GGCGGTGGC<br>GGATCC<br>Gagcctcggggccctaccatcaagccctgcccccctt gcaagtgccctgcccctaatctgctgggc<br>ggaccctccgtgttc<br>CTGTTTCCTCCAAAGCCCAAGGACACACTGATGATCTCCAGGAC<br>ACCAGAGGTGACCTGCGTGGTGGTGGACGTGAGCCACGAGGAC<br>CCCGAGGTGAAGTTCAACTGGTACGTGGATGGCGTGGAGGTGCA<br>CAATGCCAAGACCAAGCCCAGAGAGGAGCAGTACAACTCTACCT<br>ATAGGGTGGTGAGCGTGCTGACAGTGCTGCACCAGGACTGGCTG<br>AACGGCAAGGAGTATAAGTGCAAGGTGAGCAATAAGGCCCTGCC<br>TGCCCCAATCGAGAAGACAATCTCCAAGGCCAAGGGCCAGCCA<br>AGAGAGCCCCAGGTGTACACCCTGCCCCCTAGCAGGGATGAGCT<br>GACAAAGAACCAGGTGTCCCTGACCTGTCTGGTGAAGGGCTTTT<br>ATCCCTCCGACATCGCCGTGGAGTGGGAGTCTAATGGCCAGCCT<br>GAGAATAACTACAAGACAACCCCACCCGTGCTGGATTCTGACGG |

TABLE 21-continued

| SEQ ID NO | Sequence information |
|---|---|
| | CAGCTTCTTTCTGTATTCTAAGCTGACCGTGGACAAGAGCAGGTG<br>GCAGCAGGGCAACGTGTTCAGCTGCTCCGTGATGCACGAAGCAC<br>TGCACAATCACTACACCCAGAAATCACTGTCACTGAGCCCTGGC<br>AAA |
| SEQ ID NO: 75 | GCTCAGGCTGGACCTAGGGCTCCTTGCGCTGCCGCCTGCACCTG<br>TGCAGGCGATTCTCTGGACTGCAGCGGCCGGGGCCTGGCCACAC<br>TGCCCAGGGACCTGCCTTCCTGGACCAGATCTCTGAACCTGAGC<br>TACAATCGGCTGTCCGAGATCGATTCTGCCGCCTTTGAGGACCTG<br>ACAAATCTGCAGGAGGTGTATCTGAACAGCAATGAGCTGACCGC<br>AATCCCCTCCCTGGGAGCAGCCTCTATCGGCGTGGTGAGCCTGTT<br>CCTGCAGCACAACAAGATCCTGAGCGTGGATGGCTCCCAGCTGA<br>AGAGCTACCTGTCTCTGGAGGTGCTGGACCTGAGCTCCAACAAT<br>ATCACCGAGATCAGATCTAGCTGTTTTCCTAATGGCCTGCGGATC<br>AGAGAGCTGAACCTGGCCTCTAATCGGATCAGCATCCTGGAGTC<br>CGGCGCCTTCGATGGCCTGAGCAGATCCCTGCTGACACTGCGCC<br>TGTCCAAGAACCGGATCACCCAGCTGCCCGTGAAGGCCTTTAAG<br>CTGCCTAGGCTGACACAGCTGGACCTGAACCGGAATAGAATCAG<br>GCTGATCGAGGGCCTGACCTTCCAGGGCCTGGATAGCCTGGAGG<br>TGCTGCGCCTGCAGCGGAACAATATCTCCCGCCTGACAGACGGA<br>GCATTTTGGGGCCTGTCTAAGATGCACGTGCTGCACCTGGAGTAC<br>AATAGCCTGGTGGAGGTGAACTCTGGCAGCCTGTATGGCCTGAC<br>CGCCCTGCACCAGCTGCACCTGTCCAACAATAGCATCAGCAGAA<br>TCCAGAGGGATGGCTGGTCCTTCTGCCAGAAGCTGCACGAGCTG<br>ATCCTGTCTTTTAACAATCTGACCAGGCTGGACGAGGAGAGCCT<br>GGCAGAGCTGTCCTCTCTGTCCATCCTGCGCCTGTCTCACAATGC<br>CATCAGCCACATCGCCGAGGGCGCCTTTAAGGGCCTGAAGAGCC<br>TGAGGGTGCTGGATCTGGACCACAACGAGATCTCTGGCACCATC<br>GAGGATACAAGCGGCGCCTTCACAGGCCTGGACAATCTGTCCAA<br>GCTGACCCTGTTTGGCAACAAGATCAAGTCTGTGGCCAAGCGGG<br>CCTTCTCTGGCCTGGAGAGCCTGGAGCACCTGAACCTGGGCGAG<br>AATGCCATCAGATCCGTGCAGTTCGATGCCTTTGCCAAGATGAAG<br>AATCTGAAGGAGCTGTACATCAGCTCCGAGAGCTTCCTGTGCGA<br>CTGTCAGCTGAAGTGGCTGCCACCTTGGCTGATGGGAAGGATGC<br>TGCAGGCCTTTGTGACCGCCACATGCGCCCACCCAGAGAGCCTG<br>AAGGGCCAGAGCATCTTCTCCGTGCTGCCCGATAGCTTCGTGTGC<br>GACGATTTTCCTAAGCCACAGATCATCACCCAGCCAGAGACAAC<br>AATGGCCGTGGTGGGCAAGGACATCCGGTTTACATGTTCCGCCG<br>CCTCTAGCTCCTCTAGCCCCATGACCTTCGCCTGGAAGAAGGATA<br>ACGAGGTGCTGGCCAATGCCGACATGGAGAACTTCGCCCACGTG<br>AGAGCCCAGGATGGCGAAGTGATGGAGTATACCACAATCCTGCA<br>CCTGCGGCACGTGACCTTTGGCCACGAGGGCAGATACCAGTGCA<br>TCATCACAAATCACTTCGGCTCTACCTATAGCCACAAGGCCAGGC<br>TGACAGTGAACGTGCTGCCTAGCTTTACCAAGATCCCACACGAC<br>ATCGCCATCAGAACAGGCACCACAGCAAGGCTGGAGTGTGCAG<br>CAACCGGACACCCAAACCCTCAGATCGCATGGCAGAAGGATGGA<br>GGCACAGACTTCCCTGCAGCCCGCGAGAGGAGAATGCACGTGAT<br>GCCAGACGATGACGTGTTCTTTATCACAGATGTGAAGATCGATGA<br>CATGGGCGTGTACTCCTGCACCGCACAGAACAGCGCCGGCAGCG<br>TGTCCGCCAACGCCACCCTGACCGTGCTGGAGACACCATCCCTG<br>GCCGTGCCCCTGGAGGACAGGGTGGTGACCGTGGGCGAGACAG<br>TGGCCTTTCAGTGTAAGGCCACCGGCTCTCCAACACCAAGGATC<br>ACCTGGCTGAAGGGCGGCAGGCCCCTGAGCCTGACAGAGCGCC<br>ACCACTTCACCCCTGGCAATCAGCTGCTGGTGGTGCAGAACGTG<br>ATGATCGATGACGCCGGCAGGTATACATGCGAGATGAGCAATCCT<br>CTGGGCACCGAGAGGGCACACTCCCAGCTGTCTATCCTGCCTAC<br>CCCAGGCTGCCGGAAGGATGGCACCACA<br>GGCGGTGGC<br>GGATCC<br>cgcaacaccggccgcggcggcgaggagaagaagaaggagaaggagaaggaggagcaggaggagc<br>gcgagaccaagacccccgagtgccccagccacacccagcccctgggcgtgttc<br>CTGTTTCCTCCAAAGCCCAAGGACACACTGATGATCTCCAGGAC<br>ACCAGAGGTGACCTGCGTGGTGGTGGACGTGAGCCACGAGGAC<br>CCCGAGGTGAAGTTCAACTGGTACGTGGATGGCGTGGAGGTGCA<br>CAATGCCAAGACCAAGCCCAGAGAGGAGCAGTACAACTCTACCT<br>ATAGGGTGGTGAGCGTGCTGACAGTGCTGCACCAGGACTGGCTG<br>AACGGCAAGGAGTATAAGTGCAAGGTGAGCAATAAGGCCCTGCC<br>TGCCCCAATCGAGAAGACAATCTCCAAGGCCAAGGGCCAGCCA<br>AGAGAGCCCCAGGTGTACACCCTGCCCCCTAGCAGGGATGAGCT<br>GACAAAGAACCAGGTGTCCCTGACCTGTCTGGTGAAGGGCTTTT<br>ATCCCTCCGACATCGCCGTGGAGTGGGAGTCTAATGGCCAGCCT<br>GAGAATAACTACAAGACAACCCCACCCGTGCTGGATTCTGACGG<br>CAGCTTCTTTCTGTATTCTAAGCTGACCGTGGACAAGAGCAGGTG<br>GCAGCAGGGCAACGTGTTCAGCTGCTCCGTGATGCACGAAGCAC<br>TGCACAATCACTACACCCAGAAATCACTGTCACTGAGCCCTGGC<br>AAA |

TABLE 21-continued

| SEQ ID NO | Sequence information |
|---|---|
| SEQ ID NO: 76 | GCTCAGGCTGGACCTAGGGCTCCTTGCGCTGCCGCCTGCACCTG TGCAGGCGATTCTCTGGACTGCAGCGGCCGGGGCCTGGCCACAC TGCCCAGGGACCTGCCTTCCTGGACCAGATCTCTGAACCTGAGC TACAATCGGCTGTCCGAGATCGATTCTGCCGCCTTTGAGGACCTG ACAAATCTGCAGGAGGTGTATCTGAACAGCAATGAGCTGACCGC AATCCCCTCCCTGGGAGCAGCCTCTATCGGCGTGGTGAGCCTGTT CCTGCAGCACAACAAGATCCTGAGCGTGGATGGCTCCCAGCTGA AGAGCTACCTGTCTCTGGAGGTGCTGGACCTGAGCTCCAACAAT ATCACCGAGATCAGATCTAGCTGTTTTCCTAATGGCCTGCGGATC AGAGAGCTGAACCTGGCCTCTAATCGGATCAGCATCCTGGAGTC CGGCGCCTTCGATGGCCTGAGCAGATCCCTGCTGACACTGCGCC TGTCCAAGAACCGGATCACCCAGCTGCCCGTGAAGGCCTTTAAG CTGCCTAGGCTGACACAGCTGGACCTGAACCGGAATAGAATCAG GCTGATCGAGGGCCTGACCTTCCAGGGCCTGGATAGCCTGGAGG TGCTGCGCCTGCAGCGGAACAATATCTCCCGCCTGACAGACGGA GCATTTTGGGGCCTGTCTAAGATGCACGTGCTGCACCTGGAGTAC AATAGCCTGGTGGAGGTGAACTCTGGCAGCCTGTATGGCCTGAC CGCCCTGCACCAGCTGCACCTGTCCAACAATAGCATCAGCAGAA TCCAGAGGGATGGCTGGTCCTTCTGCCAGAAGCTGCACGAGCTG ATCCTGTCTTTTAACAATCTGACCAGGCTGGACGAGGAGAGCCT GGCAGAGCTGTCCTCTCTGTCCATCCTGCGCCTGTCTCACAATGC CATCAGCCACATCGCCGAGGGCGCCTTTAAGGGCCTGAAGAGCC TGAGGGTGCTGGATCTGGACCACAACGAGATCTCTGGCACCATC GAGGATACAAGCGGCGCCTTCACAGGCCTGGACAATCTGTCCAA GCTGACCCTGTTTGGCAACAAGATCAAGTCTGTGGCCAAGCGGG CCTTCTCTGGCCTGGAGAGCCTGGAGCACCTGAACCTGGGCGAG AATGCCATCAGATCCGTGCAGTTCGATGCCTTTGCCAAGATGAAG AATCTGAAGGAGCTGTACATCAGCTCCGAGAGCTTCCTGTGCGA CTGTCAGCTGAAGTGGCTGCCACCTTGGCTGATGGGAAGGATGC TGCAGGCCTTTGTGACCGCCACATGCGCCCACCCAGAGAGCCTG AAGGGCCAGAGCATCTTCTCCGTGCTGCCCGATAGCTTCGTGTGC GACGATTTTCCTAAGCCACAGATCATCACCCAGCCAGAGACAAC AATGGCCGTGGTGGGCAAGGACATCCGGTTTACATGTTCCGCCG CCTCTAGCTCCTCTAGCCCCATGACCTTCGCCTGGAAGAAGGATA ACGAGGTGCTGGCCAATGCCGACATGGAGAACTTCGCCCACGTG AGAGCCCAGGATGGCGAAGTGATGGAGTATACCACAATCCTGCA CCTGCGGCACGTGACCTTTGGCCACGAGGGCAGATACCAGTGCA TCATCACAAATCACTTCGGCTCTACCTATAGCCACAAGGCCAGGC TGACAGTGAACGTGCTGCCTAGCTTTACCAAGATCCCACACGAC ATCGCCATCAGAACAGGCACCACAGCAAGGCTGGAGTGTGCAG CAACCGGACACCCAAACCCTCAGATCGCATGGCAGAAGGATGGA GGCACAGACTTCCCTGCAGCCCGCGAGAGGAGAATGCACGTGAT GCCAGACGATGACGTGTTCTTTATCACAGATGTGAAGATCGATGA CATGGGCGTGTACTCCTGCACCGCACAGAACAGCGCCGGCAGCG TGTCCGCCAACGCCACCCTGACCGTGCTGGAGACACCATCCCTG GCCGTGCCCCTGGAGGACAGGGTGGTGACCGTGGGCGAGACAG TGGCCTTTCAGTGTAAGGCCACCGGCTCTCCAACACCAAGGATC ACCTGGCTGAAGGGCGGCAGGCCCCTGAGCCTGACAGAGCGCC ACCACTTCACCCCTGGCAATCAGCTGCTGGTGGTGCAGAACGTG ATGATCGATGACGCCGGCAGGTATACATGCGAGATGAGCAATCCT CTGGGCACCGAGAGGGCACACTCCCAGCTGTCTATCCTGCCTAC CCCAGGCTGCCGGAAGGATGGCACCACA GGCGGTGGC GGATCC gaaccgaaatcttctgacaaaacccacacctctccgccgtctccggctccggaactgctgggtgg ttcttctgttttc CTGTTTCCTCCAAAGCCCAAGGACACACTGATGATCTCCAGGAC ACCAGAGGTGACCTGCGTGGTGGTGGACGTGAGCCACGAGGAC CCCGAGGTGAAGTTCAACTGGTACGTGGATGGCGTGGAGGTGCA CAATGCCAAGACCAAGCCCAGAGAGGAGCAGTACAACTCTACCT ATAGGGTGGTGAGCGTGCTGACAGTGCTGCACCAGGACTGGCTG AACGGCAAGGAGTATAAGTGCAAGGTGAGCAATAAGGCCCTGCC TGCCCCAATCGAGAAGACAATCTCCAAGGCCAAGGGCCAGCCA AGAGAGCCCCAGGTGTACACCCTGCCCCCTAGCAGGGATGAGCT GACAAAGAACCAGGTGTCCCTGACCTGTCTGGTGAAGGGCTTTT ATCCCTCCGACATCGCCGTGGAGTGGGAGTCTAATGGCCAGCCT GAGAATAACTACAAGACAACCCCACCCGTGCTGGATTCTGACGG CAGCTTCTTTCTGTATTCTAAGCTGACCGTGGACAAGAGCAGGTG GCAGCAGGGCAACGTGTTCAGCTGCTCCGTGATGCACGAAGCAC TGCACAATCACTACACCCAGAAATCACTGTCACTGAGCCCTGGC AAA |

As still yet another example of the fusion protein provided in the present invention, a fusion protein, comprising the extracellular domain of the Lrig-1 protein represented by SEQ ID NO: 3; the linker represented by SEQ ID NO: 12; the linker represented by SEQ ID NO: 11; the hinge region represented by any one of SEQ ID NOs: 7 to 10; and the mouse IgG2-derived heavy chain constant region 2 (CH2) and heavy chain constant region 3 (CH3) which are represented by SEQ ID NO: 6, may be mentioned (see Table 22 below). The fusion proteins represented by SEQ ID NOs: 77 to 80 in Table 22 below may be encoded by the nucleic acid sequences represented by SEQ ID NOs: 81 to 84 in Table 23 below (see Table 23 below).

TABLE 22

| SEQ ID NO | Sequence information |
|---|---|
| SEQ ID NO: 77 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>EPKSSDKTHTSPPCPAPELLGGPSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |
| SEQ ID NO: 78 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>EPRGPTIKPCPPCKCPAPNLLGGPSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |
| SEQ ID NO: 79 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>RNTGRGGEEKKKEKEKEEQEERETKTPECPSHTQPLGVF<br>IFPPKIKDVLMISLSPIVTCVVVDVSEDDPDVQISWFVNNVEVHTAQTQTHR |

TABLE 22-continued

| SEQ ID NO | Sequence information |
|---|---|
| | EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |
| SEQ ID NO: 80 | AQAGPRAPCAAACTCAGDSLDCSGRGLATLPRDLPSWTRSLNLSYNRLSEI<br>DSAAFEDLTNLQEVYLNSNELTAIPSLGAASIGVVSLFLQHNKILSVDGSQL<br>KSYLSLEVLDLSSNNITEIRSSCFPNGLRIRELNLASNRISILESGAFDGLSRS<br>LLTLRLSKNRITQLPVKAFKLPRLTQLDLNRNRIRLIEGLTFQGLDSLEVLRL<br>QRNNISRLTDGAFWGLSKMHVLHLEYNSLVEVNSGSLYGLTALHQLHLSN<br>NSISRIQRDGWSFCQKLHELILSFNNLTRLDEESLAELSSLSILRLSHNAISHI<br>AEGAFKGLKSLRVLDLDHNEISGTIEDTSGAFTGLDNLSKLTLFGNKIKSVA<br>KRAFSGLESLEHLNLGENAIRSVQFDAFAKMKNLKELYISSESFLCDCQLK<br>WLPPWLMGRMLQAFVTATCAHPESLKGQSIFSVLPDSFVCDDFPKPQIITQ<br>PETTMAVVGKDIRFTCSAASSSSSPMTFAWKKDNEVLANADMENFAHVRA<br>QDGEVMEYTTILHLRHVTFGHEGRYQCIITNHFGSTYSHKARLTVNVLPSF<br>TKIPHDIAIRTGTTARLECAATGHPNPQIAWQKDGGTDFPAARERRMHVMP<br>DDDVFFITDVKIDDMGVYSCTAQNSAGSVSANATLTVLETPSLAVPLEDRV<br>VTVGETVAFQCKATGSPTPRITWLKGGRPLSLTERHHFTPGNQLLVVQNV<br>MIDDAGRYTCEMSNPLGTERAHSQLSILPTPGCRKDGTT<br>GGG<br>GS<br>EPKSSDKTHTSPPSPAPELLGGSSVF<br>IFPPKIKDVLMISLSPIVTCVVVDVSEDDPDVQISWFVNNVEVHTAQTQTHR<br>EDYNSTLRVVSALPIQHQDWMSGKEFKCKVNNKDLPAPIERTISKPKGSVR<br>APQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSR<br>TPGK |

TABLE 23

| SEQ ID NO | Sequence information |
|---|---|
| SEQ ID NO: 81 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT |

TABLE 23-continued

| SEQ ID NO | Sequence information |
| --- | --- |
| | GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGCGGTGGC<br>GGATCC<br>GAGCCAAAGTCCTCTGATAAGACACACACCTCTCCACCATGCCCAGCAC<br>CAGAGCTGCTGGGAGGACCAAGCGTGTTC<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggaccccc<br>ggcaaa |
| SEQ ID NO: 82 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGCGGTGGC<br>GGATCC<br>Gagcctcggggccctaccatcaagccctgcccccttgcaagtgccctgcccctaatctgctgggcggaccctccgt<br>gttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg |

TABLE 23-continued

| SEQ ID NO | Sequence information |
|---|---|
| | tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 83 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG<br>GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGCGGTGGC<br>GGATCC<br>cgcaacaccggccgcggcggcgaggagaagaagaaggagaaggagaaggaggagcaggaggagcgcgaga<br>ccaagacccccgagtgccccagccacacccagcccctgggcgtgttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggacccccc<br>ggcaaa |
| SEQ ID NO: 84 | GCTCAGGCTGGACCTAGGGCTCCTTGCGCTGCCGCCTGCACCTGTGCAG<br>GCGATTCTCTGGACTGCAGCGGCCGGGGCCTGGCCACACTGCCCAGGG<br>ACCTGCCTTCCTGGACCAGATCTCTGAACCTGAGCTACAATCGGCTGTC<br>CGAGATCGATTCTGCCGCCTTTGAGGACCTGACAAATCTGCAGGAGGTG<br>TATCTGAACAGCAATGAGCTGACCGCAATCCCCTCCCTGGGAGCAGCCT<br>CTATCGGCGTGGTGAGCCTGTTCCTGCAGCACAACAAGATCCTGAGCGT<br>GGATGGCTCCCAGCTGAAGAGCTACCTGTCTCTGGAGGTGCTGGACCTG<br>AGCTCCAACAATATCACCGAGATCAGATCTAGCTGTTTTCCTAATGGCCT<br>GCGGATCAGAGAGCTGAACCTGGCCTCTAATCGGATCAGCATCCTGGAG<br>TCCGGCGCCTTCGATGGCCTGAGCAGATCCCTGCTGACACTGCGCCTGT<br>CCAAGAACCGGATCACCCAGCTGCCCGTGAAGGCCTTTAAGCTGCCTA<br>GGCTGACACAGCTGGACCTGAACCGGAATAGAATCAGGCTGATCGAGG |

TABLE 23-continued

| SEQ ID NO | Sequence information |
|---|---|
| | GCCTGACCTTCCAGGGCCTGGATAGCCTGGAGGTGCTGCGCCTGCAGC<br>GGAACAATATCTCCCGCCTGACAGACGGAGCATTTTGGGGCCTGTCTAA<br>GATGCACGTGCTGCACCTGGAGTACAATAGCCTGGTGGAGGTGAACTCT<br>GGCAGCCTGTATGGCCTGACCGCCCTGCACCAGCTGCACCTGTCCAACA<br>ATAGCATCAGCAGAATCCAGAGGGATGGCTGGTCCTTCTGCCAGAAGCT<br>GCACGAGCTGATCCTGTCTTTTAACAATCTGACCAGGCTGGACGAGGAG<br>AGCCTGGCAGAGCTGTCCTCTCTGTCCATCCTGCGCCTGTCTCACAATG<br>CCATCAGCCACATCGCCGAGGGCGCCTTTAAGGGCCTGAAGAGCCTGA<br>GGGTGCTGGATCTGGACCACAACGAGATCTCTGGCACCATCGAGGATAC<br>AAGCGGCGCCTTCACAGGCCTGGACAATCTGTCCAAGCTGACCCTGTTT<br>GGCAACAAGATCAAGTCTGTGGCCAAGCGGGCCTTCTCTGGCCTGGAG<br>AGCCTGGAGCACCTGAACCTGGGCGAGAATGCCATCAGATCCGTGCAG<br>TTCGATGCCTTTGCCAAGATGAAGAATCTGAAGGAGCTGTACATCAGCT<br>CCGAGAGCTTCCTGTGCGACTGTCAGCTGAAGTGGCTGCCACCTTGGCT<br>GATGGGAAGGATGCTGCAGGCCTTTGTGACCGCCACATGCGCCCACCC<br>AGAGAGCCTGAAGGGCCAGAGCATCTTCTCCGTGCTGCCCGATAGCTTC<br>GTGTGCGACGATTTTCCTAAGCCACAGATCATCACCCAGCCAGAGACAA<br>CAATGGCCGTGGTGGGCAAGGACATCCGGTTTACATGTTCCGCCGCCTC<br>TAGCTCCTCTAGCCCCATGACCTTCGCCTGGAAGAAGGATAACGAGGTG<br>CTGGCCAATGCCGACATGGAGAACTTCGCCCACGTGAGAGCCCAGGAT<br>GGCGAAGTGATGGAGTATACCACAATCCTGCACCTGCGGCACGTGACCT<br>TTGGCCACGAGGGCAGATACCAGTGCATCATCACAAATCACTTCGGCTC<br>TACCTATAGCCACAAGGCCAGGCTGACAGTGAACGTGCTGCCTAGCTTT<br>ACCAAGATCCCACACGACATCGCCATCAGAACAGGCACCACAGCAAGG<br>CTGGAGTGTGCAGCAACCGGACACCCAAACCCTCAGATCGCATGGCAG<br>AAGGATGGAGGCACAGACTTCCCTGCAGCCCGCGAGAGGAGAATGCAC<br>GTGATGCCAGACGATGACGTGTTCTTTATCACAGATGTGAAGATCGATG<br>ACATGGGCGTGTACTCCTGCACCGCACAGAACAGCGCCGGCAGCGTGT<br>CCGCCAACGCCACCCTGACCGTGCTGGAGACACCATCCCTGGCCGTGC<br>CCCTGGAGGACAGGGTGGTGACCGTGGGCGAGACAGTGGCCTTTCAGT<br>GTAAGGCCACCGGCTCTCCAACACCAAGGATCACCTGGCTGAAGGGCG<br>GCAGGCCCCTGAGCCTGACAGAGCGCCACCACTTCACCCCTGGCAATC<br>AGCTGCTGGTGGTGCAGAACGTGATGATCGATGACGCCGGCAGGTATAC<br>ATGCGAGATGAGCAATCCTCTGGGCACCGAGAGGGCACACTCCCAGCT<br>GTCTATCCTGCCTACCCCAGGCTGCCGGAAGGATGGCACCACA<br>GGCGGTGGC<br>GGATCC<br>gaaccgaaatcttctgacaaaacccacacctctccgccgtctccggctccggaactgctgggtggttcttctgttttc<br>atcttcccacccaagatcaaggacgtgctgatgatctccctgtcccccatcgtgacctgcgtggtggtggacgtgtccg<br>aggacgaccccgacgtgcagatcagttggttcgtgaacaacgtggaagtgcacaccgcccagacccagacccaca<br>gagaggactacaactccaccctgcgggtggtgtccgccctgcccatccagcaccaggactggatgtccggcaaaga<br>attcaagtgcaaagtgaacaacaaggacctgcctgcccccatcgagcggaccatctccaagcccaagggctccgtg<br>cgggctccccaggtgtacgtgctgccccctccagaggaagagatgaccaagaagcaggtcacactgacctgcatgg<br>tcaccgacttcatgcccgaggacatctacgtggaatggaccaacaatggcaagaccgagctgaactacaagaacac<br>cgagcctgtgctggactccgacggctcctacttcatgtactccaagctgcgggtggaaaagaagaactgggtcgagc<br>ggaactcctactcctgctccgtggtgcacgagggcctgcacaaccaccacaccaccaagtccttctcccggaccccc<br>ggcaaa |

The fusion protein provided in the present invention can interact with a ligand for Lrig-1 protein, which is present on effector T cells, to inhibit the interaction between the effector T cells and regulatory T cells (Treg cells) having the Lrig-1 protein on their surface, so that activity of the regulatory T cells is inhibited and activity of the effector T cells is maintained or elevated, thereby effectively inhibiting growth of cancer cells, in particular, solid cancer cells.

According to another embodiment of the present invention, there is provided a nucleic acid molecule, which encodes the fusion protein provided in the present invention.

The nucleic acid molecule of the present invention includes any nucleic acid molecule obtained by causing the amino acid sequence of the fusion protein provided in the present invention to be translated into a polynucleotide sequence as is known to those skilled in the art. Therefore, various polynucleotide sequences can be prepared due to open reading frame (ORF), all of which are also included in the nucleic acid molecule of the present invention.

As a preferred example of the present invention, the nucleic acid molecule may be represented by, but is not limited to, any one of SEQ ID NOs: 17 to 20, 25 to 28, 33 to 36, 41 to 44, 49 to 52, 57 to 60, 65 to 68, 73 to 76, and 81 to 84.

According to yet another embodiment of the present invention, there is provided an expression vector, into which the isolated nucleic acid molecule provided in the present invention is inserted.

In the present invention, the "vector" is a nucleic acid molecule that is capable of transporting another nucleic acid linked thereto. One type of vector is a "plasmid," which refers to circular double-stranded DNA into which additional DNA segments can be ligated. Another type of vector is a phage vector. Yet another type of vector is a viral vector, in which additional DNA segments can be ligated into the viral genome. Certain vectors are capable of autonomous replication in a host cell into which they are introduced (for example, bacterial vectors having a bacterial origin of replication are episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form of vector.

Specific examples of the expression vector in the present invention may be selected from, but are not limited to, the group consisting of commercially widely used pCDNA vectors, F, R1, RP1, Col, pBR322, ToL, Ti vectors; cosmids; phages such as lambda, lambdoid, M13, Mu, p1 P22, Qμ, T-even, T2, T3, T7; plant viruses. Any expression vector known, to those skilled in the art, as an expression vector can be used in the present invention, and the expression vector is selected depending on the nature of the target host cell. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. The vector may preferably contain at least one selection marker. However, the present invention is not limited thereto, and selection can be made using the vector that contains no selection marker, depending on whether or not a product is produced. The selection marker is selected depending on the target host cell, which is done using methods already known to those skilled in the art, and thus the present invention has no limitation thereon.

In order to facilitate purification of the nucleic acid molecule of the present invention, a tag sequence may be inserted into and fused to an expression vector. The tag includes, but is not limited to, hexa-histidine tag, hemagglutinin tag, myc tag, or flag tag, and any tag known to those skilled in the art which facilitates purification can be used in the present invention.

According to still yet another embodiment of the present invention, there is provided a host cell line, transfected with the expression vector provided in the present invention.

In the present invention, the "host cell" includes individual cells or cell cultures which may be or have been recipients of the vector(s) for incorporation of a polypeptide insert. The host cell includes progeny of a single host cell, and the progeny may not necessarily be completely identical (in morphology or in genomic DNA complement) to the original parent cell due to natural, accidental, or intentional mutation. The host cell includes cells transfected in vivo with the polynucleotide(s) herein.

In the present invention, the host cell may include cells of mammalian, plant, insect, fungal, or cellular origin, and may be, for example, bacterial cells such as *E. coli, Streptomyces, Salmonella typhimurium*; fungal cells such as yeast cells and *Pichia pastoris*; insect cells such as *Drosophila* and *Spodoptera* Sf9 cells; animal cells such as CHO(Chinese hamster ovary) cells, SP2/0 (mouse myeloma), human lymphoblastoid, COS, NSO (mouse myeloma), 293T, Bowes melanoma cells, HT-1080, baby hamster kidney (BHK) cells, human embryonic kidney (HEK) cells, or PERC.6 (human retinal cells); or plant cells. However, the host cell is not limited thereto, and any cell known to those skilled in the art which can be used as a host cell line is available.

According to still yet another embodiment of the present invention, there is provided a pharmaceutical composition for preventing or treating cancer, comprising, as an active ingredient, the fusion protein provided in the present invention.

As used herein, the term "cancer" refers to or indicates a physiological condition characterized by cell growth in mammals which is not regulated in a typical manner. The cancer to be prevented, ameliorated, or treated in the present invention may be solid tumor formed of agglomerates caused by abnormal growth of cells in a solid organ, and may be, but is not limited to, gastric cancer, liver cancer, gliocytoma, ovarian cancer, colorectal cancer, head and neck cancer, bladder cancer, renal cell cancer, breast cancer, metastatic cancer, prostate cancer, pancreatic cancer, melanoma, lung cancer, or the like, depending on location of the solid organ, with melanoma or colorectal cancer being preferred.

Meanwhile, in the present invention, the "prevention" may include, without limitation, any act of blocking symptoms of a disease, or suppressing or delaying the symptoms, using the pharmaceutical composition of the present invention.

In addition, in the present invention, the "treatment" may include, without limitation, any act of ameliorating or beneficially altering symptoms of a disease, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

In the present invention, the pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

In the present invention, the route of administration of the pharmaceutical composition includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

In the present invention, the "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary widely depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the invention in any way. The pharmaceutical composition according to the present invention may be formulated in the form of pills, sugar-coated tablets, capsules, liquids, gels, syrups, slurries, or suspensions.

According to still yet another embodiment of the present invention, there is provided a method for preventing or treating cancer, comprising a step of administering, to an individual, the fusion protein according to the present invention or a composition comprising the same.

The fusion protein of the present invention can interact with a ligand for Lrig-1 protein, which is present on effector T cells, to inhibit the interaction between the effector T cells and regulatory T cells (Treg cells) having the Lrig-1 protein on their surface, so that activity of the regulatory T cells is inhibited and activity of the effector T cells is maintained or elevated, thereby effectively inhibiting growth of cancer cells, in particular, solid cancer cells.

In the present invention, the "individual" is an individual suspected of developing cancer, and the individual suspected of developing cancer means a mammal, such as humans, mice, and domestic animals, who has developed or is likely to develop the disease in question. However, any individual, who is treatable with the fusion protein of the present invention or the composition comprising the same, is included therein without limitation.

The method of the present invention may comprise administering a fusion protein or a composition comprising the same in a pharmaceutically effective amount. An appropriate total daily amount used may be determined by an attending physician or veterinarian within the scope of sound medical judgment, and administration may be made once or several times. However, for the purposes of the present invention, a specific therapeutically effective amount for a particular patient is preferably applied differently depending on various factors, including type and degree of reaction to be achieved, the specific composition including whether other agents are used therewith as the case may be, the patient's age, body weight, general health status, sex, and diet, time of administration, route of administration, secretion rate of the composition, duration of treatment, and drugs used simultaneously or in combination with the specific composition, and similar factors well known in the medical field.

Meanwhile, the method for preventing or treating cancer may be, but is not limited to, a combination therapy that further comprises administering a compound or substance having therapeutic activity against one or more cancer diseases.

In the present invention, the "combination" should be understood to represent simultaneous, individual, or sequential administration. In a case where the administration is made in a sequential or individual manner, the second component should be administered at intervals such that beneficial effects of the combination are not lost.

In the present invention, the dosage of the fusion protein may be, but is not limited to, about 0.0001 μg to 500 mg per kg of patient's body weight.

Advantageous Effects of Invention

The fusion protein provided in the present invention can interact with a ligand for Lrig-1 protein, which is present on effector T cells, to inhibit the interaction between the effector T cells and regulatory T cells (Treg cells) having the Lrig-1 protein on their surface, so that activity of the regulatory T cells is inhibited and activity of the effector T cells is maintained or elevated, thereby effectively inhibiting growth of cancer cells, in particular, solid cancer cells.

BRIEF DESCRIPTION OF DRAWINGS

FIG. 3 illustrates prediction results for epitopes of the Lrig-1 protein according to an embodiment of the present invention (top to bottom, SEQ ID NOS: 96-117, respectively).

FIG. 4 illustrates prediction results for epitopes of the Lrig-1 protein according to an embodiment of the present invention.

DETAILED DESCRIPTION OF INVENTION

Figure 1:
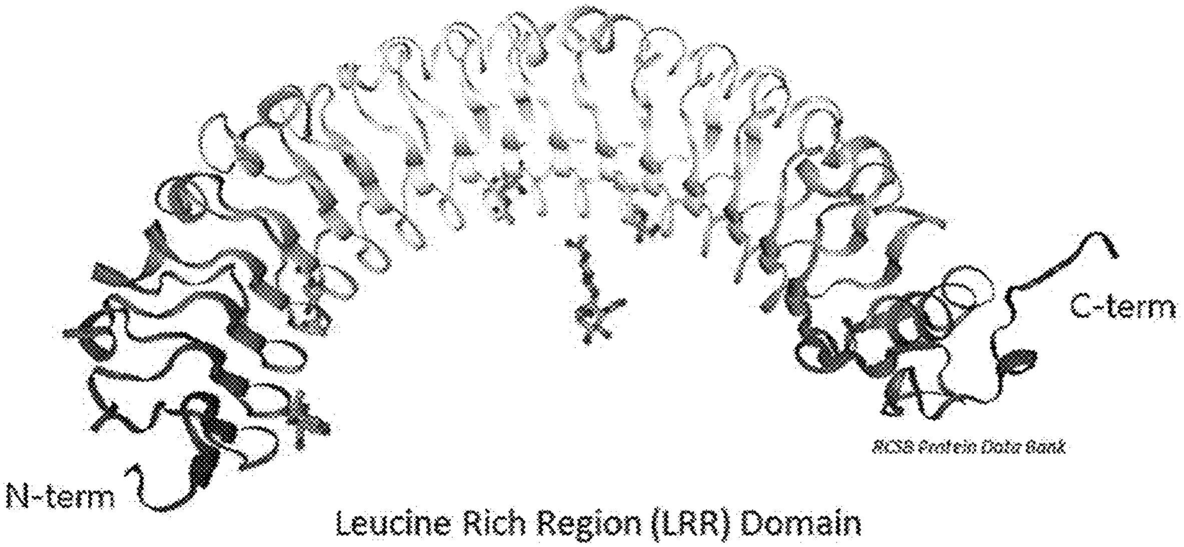
FIG. 1 illustrates a structure of the Lrig-1 protein according to an embodiment of the present invention.

According to an embodiment of the present invention, there is provided a fusion protein, comprising an extracellular domain of leucine-rich and immunoglobulin-like domains 1 (Lrig-1) protein and an immunoglobulin Fc region.

As an example of the present invention, the immunoglobulin Fc region may be an IgG-, IgA-, IgM-, IgD-, or IgE-derived Fc region, or may include an IgG-, IgA-, IgM-, IgD-, or IgE-derived heavy chain constant region 2 (CH2) and heavy chain constant region 3 (CH3). However, the present invention is not limited thereto.

As an example of the present invention, the immunoglobulin Fc region may include an IgG-, IgA-, IgM-, IgD-, IgE-, or Abatacept-derived hinge region. However, the present invention is not limited thereto.

In the present invention, the extracellular domain of the Lrig-1 protein may be connected, via a linker, to the N-terminus or C-terminus of the immunoglobulin Fc region. However, the present invention is not limited thereto.

According to another embodiment of the present invention, there is provided a pharmaceutical composition for preventing or treating cancer, comprising, as an active ingredient, the fusion protein of the present invention.

The fusion protein provided in the present invention can interact with a ligand for Lrig-1 protein, which is present on effector T cells, to inhibit the interaction between the effector T cells and regulatory T cells (Treg cells) having the Lrig-1 protein on their surface, so that activity of the regulatory T cells is inhibited and activity of the effector T cells is maintained or elevated, thereby effectively inhibiting growth of cancer cells, in particular, solid cancer cells.

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

[Preparation Example 1] T Cell Subtype Cell Culture

In order to identify whether the Lrig-1 protein is expressed only in regulatory T cells (Treg), the subsets of T cells, Th0, Th1, Th2, Th17, and iTreg, were prepared. The iTreg refers to cells whose differentiation has been artificially induced in a medium having the following composition, unlike nTreg which has been naturally isolated.

The subsets of the T cells were induced to differentiate into respective cells by first isolating naive T cells obtained from the spleen of mice, causing RPMI1640 (Invitrogen Gibco, Grand Island, N.Y.) nutrient medium that contains 10% fetal bovine serum (FBS; HyClone, Logan, Utah) to further contain the respective ingredients of Table 24 below, and performing 72-hour incubation in an incubator at 37° C., 5% $CO_2$.

TABLE 24

| Differentiated cell | Composition |
|---|---|
| Th0 | anti-CD3, anti-CD28 |
| Th1 | IL-12, anti-IL-4 antibody |
| Th2 | IL-4, anti-IFNβ |
| Th17 | IL-6, TGFβ, anti-IFNβ, anti-IL-4 |
| iTreg | IL-2, TGFβ |

[Example 1] Structural Analysis of Lrig-1

A three-dimensional steric structure of the extracellular domain of the Lrig-1 protein was predicted to produce a fusion protein comprising the extracellular domain of Lrig-1 protein, a surface protein of regulatory T cells.

First, in order to predict base sequences of epitopes, tools of Uniprot and RCSB Protein Data Bank were used to predict a three-dimensional steric structure of the extracellular domain (ECD) of the Lrig-1 protein so that the structure of ECD is identified. Then, the results are illustrated in FIGS. 1 and 2.

As illustrated in FIG. 1, a total of 15 leucine-rich regions of LRR1 to LRR15 exist in the Lrig-LRR domain (amino acid sequence at positions 41 to 494) in the extracellular domain of the Lrig-1 protein. Each of the LRR domains is composed of 23 to 27 amino acids, with 3 to 5 leucine being present.

Figure 2:
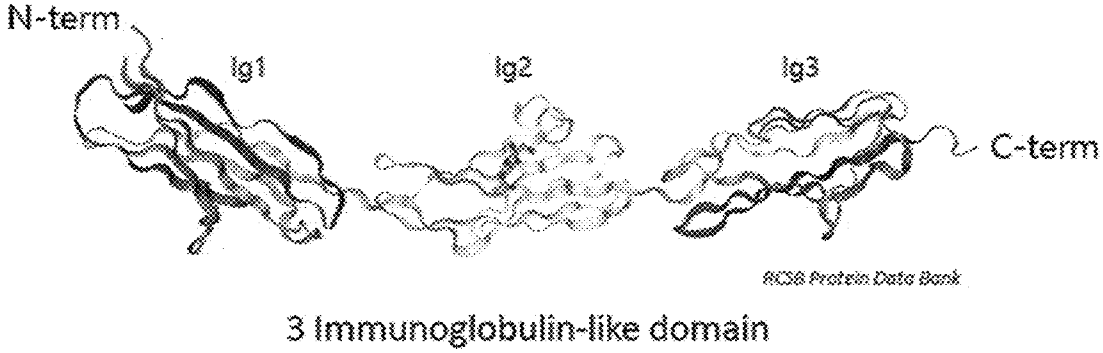
FIG. 2 illustrates a structure of the Lrig-1 protein according to an embodiment of the present invention.

In addition, as illustrated in FIG. 2, three immunoglobulin-like domains exist in amino acid sequences at positions 494 to 781 of the Lrig-1 protein in the extracellular domain of the Lrig-1 protein.

[Example 2] Prediction of Lrig-1 Epitope Amino Acid Sequence

Prediction of the above base sequence was performed using Ellipro server (http://tools.iedb.org/ellipro/) which is an epitope prediction software based on a structure of the Lrig-1 protein. The Ellipro search engine was used because it corresponds to a search engine known to be the most reliable among the existing algorithms for predicting an epitope.

The extracellular domain analyzed in Example 1 was entered into the epitope prediction software, and then predicted contiguous or discontiguous amino acid sequences of the predicted epitopes are illustrated in FIGS. 3 and 4.

As illustrated in FIGS. 3 and 4, a total of 22 contiguous epitope amino acid sequences were predicted, and a total of 8 discontiguous epitope amino acid sequences were predicted.

[Example 3] Identification of Specific Expression of Lrig-1 mRNA in Regulatory T Cells Verification was made of whether the Lrig-1 protein can act as a biomarker specific for regulatory T cells.

For the verification, $CD4^+$ T cells were isolated using magnet-activated cell sorting (MACS), through CD4 beads, from the spleen of mice. Subsequently, regulatory T ($CD4^+CD25^+$ T) cells and non-regulatory T ($CD4^+CD25^-$ T) cells were isolated with a fluorescence-activated cell sorter (FACS) using a CD25 antibody. For the respective cells and the cells differentiated in Preparation Example 1, mRNA was extracted using Trizol, and then gDNA was removed from genomic RNA using gDNA extraction kit (Qiagen) according to the protocol provided by the manufacturer. The gDNA-removed mRNA was synthesized into cDNA through the BDsprint cDNA Synthesis Kit (Clonetech).

Real-time polymerase chain reaction (RT PCR) was performed to quantitatively identify an expression level of Lrig-1 mRNA in the cDNA.

The real-time polymerase chain reaction was performed with primers shown in Table 25 below using SYBR Green (Molecular Probes) according to the protocol provided by the manufacturer under conditions of 40 cycles consisting of 95° C. for 3 minutes, 61° C. for 15 seconds, 72° C. for 30 seconds, a relative gene expression level was calculated using the ΔCT method, and normalized using HPRT. The results are illustrated in FIGS. 5 to 8.

TABLE 25

| Primer | Sequence |
|---|---|
| Mouse Lrig-1 | Forward 5'-GAC GGA ATT CAG TGA GGA GAA CCT-3'<br>Reverse 5'-CAA CTG GTA GTG GCA GCT TGT AGG-3' |
| Mouse Lrig-2 | forward 5'-TCA CAA GGA ACA TTG TCT GAA CCA-3'<br>reverse 5'-GCC TGA TCT AAC ACA TCC TCC TCA-3' |
| Mouse Lrig-3 | forward 5'-CAG CAC CTT GAG CTG AAC AGA AAC-3'<br>reverse 5'-CCA GCC TTT GGT AAT CTC GGT TAG-3' |
| Mouse FOXP3 | forward 5'-CTT TCA CCT ATC CCA CCC TTA TCC-3'<br>reverse 5'-ATT CAT CTA CGG TCC ACA CTG CTC-3' |
| ACTG1 | forward 5'-GGC GTC ATG GTG GGC ATG GG-3'<br>reverse 5'-ATG GCG TGG GGA AGG GCG TA-3' |

Figure 5:
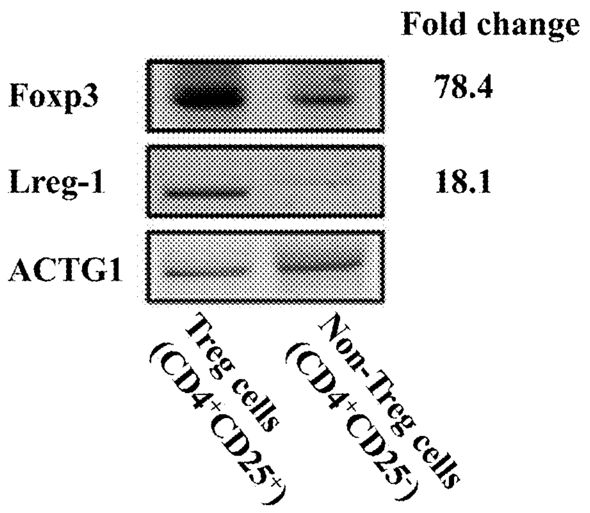
FIG. 5 illustrates an expression level of Lrig-1 mRNA according to an embodiment of the present invention.

As illustrated in FIG. 5, it can be seen that the expression of Lrig-1 in regulatory T ($CD4^+CD25^+$ T) cells is 18.1 times higher than non-regulatory T ($CD4^+CD25^-$ T) cells. This was about 10 times higher expression level than Lag3 and Ikzf4, which are previously known markers for regulatory T cells.

Figure 6:
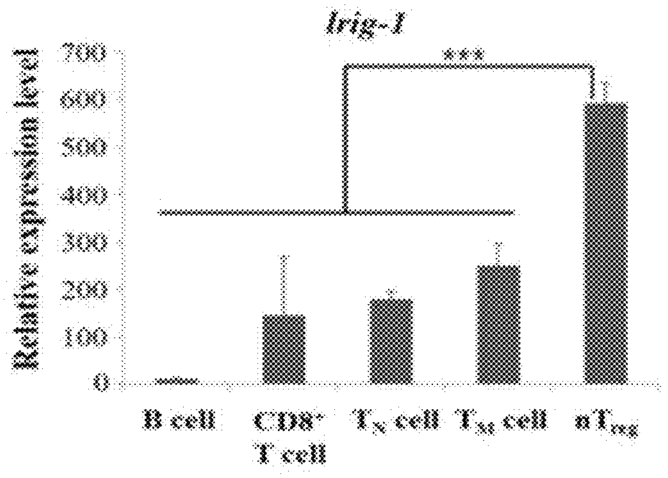
FIG. 6 illustrates an expression level of Lrig-1 mRNA according to an embodiment of the present invention.
Figure 7:
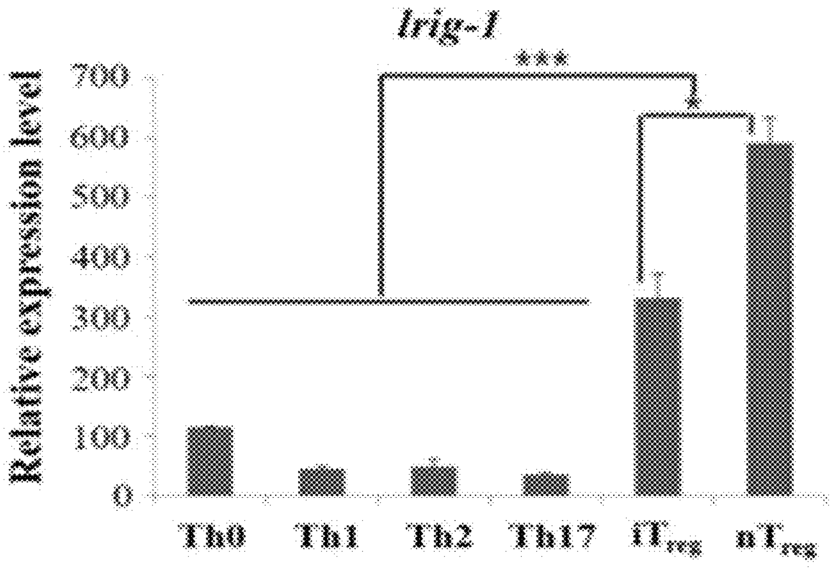
FIG. 7 illustrates an expression level of Lrig-1 mRNA according to an embodiment of the present invention.

In addition, as illustrated in FIGS. 6 and 7, the expression of Lrig-1 mRNA was remarkably high in regulatory T cells as compared with other types of immune cells, and in particular, was remarkably high in naturally isolated regulatory T cells (nTreg) as compared with induced regulatory T cells (iTreg).

Figure 8:
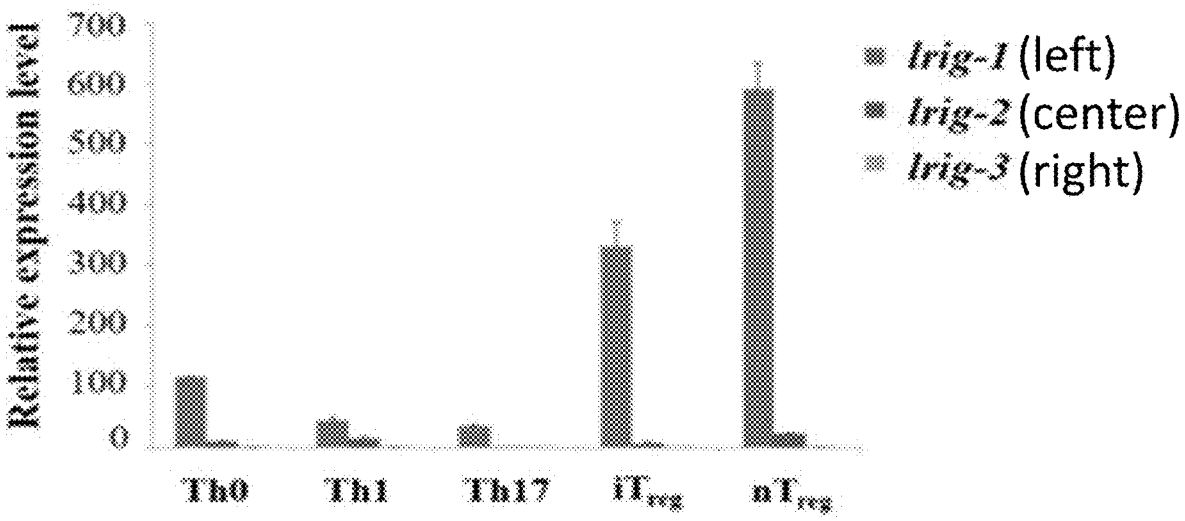
FIG. 8 illustrates expression levels of Lrig-1, Lrig-2, and Lrig-3 mRNAs according to an embodiment of the present invention.

In addition, as illustrated in FIG. 8, the expression of Lrig-1 was the highest among Lrig-1, Lrig-2, and Lrig-3 which correspond to the Lrig family.

From the above results, it can be seen that the Lrig-1 protein according to the present invention is specifically expressed in regulatory T cells, in particular, naturally-occurring regulatory T cells.

[Example 4] Identification of Specific Expression of Lrig-1 Protein in Regulatory T Cells It was identified whether the Lrig-1 protein expressed from Lrig-1 mRNA is specifically expressed only in regulatory T cells.

Using FOXP3-RFP-knocked-in mice, the FOXP3-RFP obtained by coupling red fluorescence protein (RFP) to FOXP3 promoter, which is a transcription factor specific for regulatory T cells, $CD4^+$ T cells were isolated using magnet-activated cell sorting (MACS), through CD4 beads, from the spleen of the mice. Subsequently, using RFP protein, regulatory T ($CD4^+RFP^+$ T) cells and non-regulatory T ($CD4^+RFP^-$ T) cells were obtained by performing isolation through a fluorescence-activated cell sorter (FACS). The respective cells were stained with the purchased Lrig-1 antibody and a negative control was stained with an isotype-matched control antibody, to measure an expression level of Lrig-1 with the fluorescence-activated cell sorter. The results are illustrated in FIG. 9.

Figure 9:
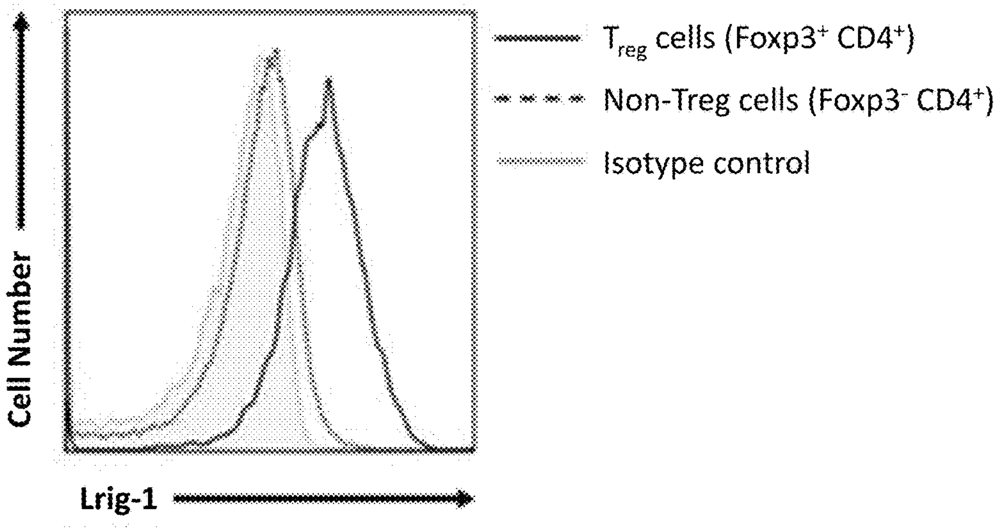
FIG. 9 illustrates results obtained by comparing expression levels of Lrig-1 protein in regulatory T cells and non-regulated T cells according to an embodiment of the present invention.

As illustrated in FIG. 9, the non-regulatory T cells indicated by a dotted line showed almost the same expression level of Lrig-1 as the negative control, whereas there were a large number of cells with high expression level of Lrig-1 in the regulatory T cells.

From the above results, it can be seen that the Lrig-1 protein according to the present invention is specifically expressed in regulatory T cells.

[Example 5] Identification of Specific Expression of Lrig-1 Protein on Surface of Regulatory T Cells From the viewpoint that in order to be a target of cell therapy, the Lrig-1 protein must be expressed on the surface of regulatory T cells, which in turn allows a more effective target therapy, it was identified whether the Lrig-1 protein is expressed on the surface of the regulatory T cells.

The respective differentiated T cell subsets of Preparation Example 1 were stained with anti-CD4-APC and anti-Lrig-1-PE antibodies, and expression levels of Lrig-1 were measured at the respective cell surfaces using a fluorescence-activated cell sorter (FACS). The results are illustrated in FIG. 10.

Figure 10:
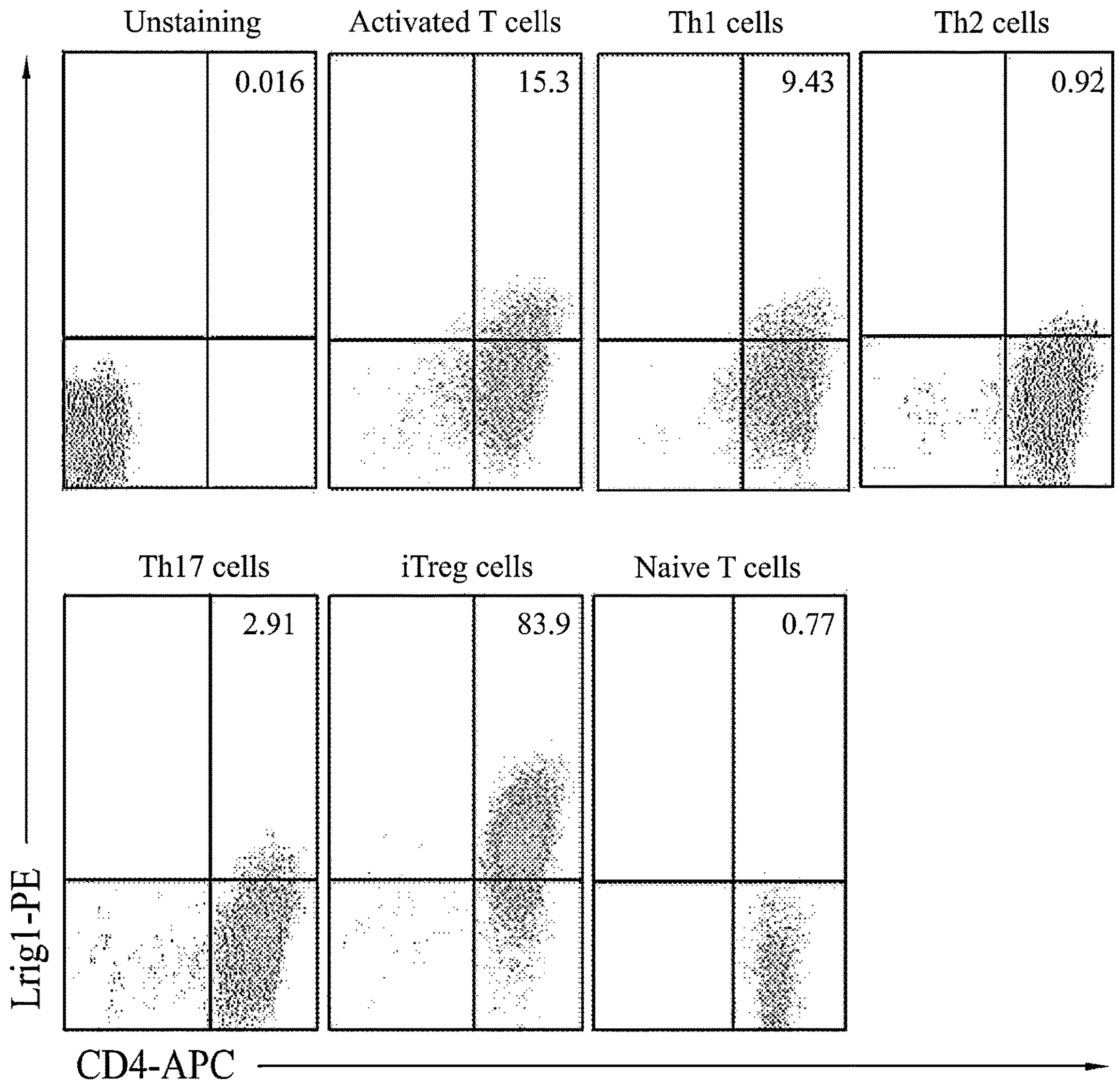
FIG. 10 illustrates expression of the Lrig-1 protein on the surface of regulatory T cells according to an embodiment of the present invention.

As illustrated in FIG. 10, Lrig-1 was expressed in an amount of 0.77 to 15.3 in activated T cells, Th1 cells, Th2 cells, Th17 cells, and naive T cells, whereas Lrig-1 was expressed as high as 83.9 in differentiation-induced T cells (iTreg cells).

From the above results, it can be seen that the Lrig-1 protein according to the present invention is not only specifically expressed in regulatory T (Treg) cells, but also is, in particular, expressed at a higher level on the surface of the Treg cells.

[Preparation Example] Production of Fusion Protein

1. Construction of Expression Vector

In order to produce the fusion protein according to the present invention, respective nucleic acid sequences encoding respective fusion proteins as shown in Table 26 were synthesized. NheI and EcoRI restriction enzyme sequences were added to the 5' and 3' ends of the nucleic acid sequence, respectively, and the following sequences were inserted after the restriction enzyme sequence at the 5' end: the Kozak's sequence (GCCACC), a start codon for protein translation, and the mouse IgG kappa light chain signal peptide (ATG-GAAACCGATACTCTGCTGCTGTGGG TGCTGCTGCTGTGGGTGCCAGGCTCTA CCGGG; SEQ ID NO:95) that allows an expressed protein to secrete outside the cell. Subsequently, a stop codon was inserted after the nucleic acid sequence encoding each of the fusion proteins as shown in Table 26, in which the each fusion protein includes the extracellular domain of human-derived Lrig-1 protein; optionally a linker; a hinge region; human IgG1-derived heavy chain constant region 2 (CH2) and heavy chain constant region 3 (CH3). The nucleic acid sequence encoding the fusion protein of the present invention was cloned into pcDNA3.1(+) expression vector using the two restriction enzyme sequences, NheI and EcoRI.

TABLE 26

| No. | Amino acid sequence of fusion protein | Nucleic acid sequence of fusion protein |
|---|---|---|
| Preparation Example 1 | SEQ ID NO: 13 | SEQ ID NO: 17 |
| Preparation Example 2 | SEQ ID NO: 14 | SEQ ID NO: 18 |
| Preparation Example 3 | SEQ ID NO: 15 | SEQ ID NO: 19 |
| Preparation Example 4 | SEQ ID NO: 16 | SEQ ID NO: 20 |
| Preparation Example 5 | SEQ ID NO: 21 | SEQ ID NO: 25 |
| Preparation Example 6 | SEQ ID NO: 22 | SEQ ID NO: 26 |
| Preparation Example 7 | SEQ ID NO: 23 | SEQ ID NO: 27 |
| Preparation Example 8 | SEQ ID NO: 24 | SEQ ID NO: 28 |
| Preparation Example 9 | SEQ ID NO: 29 | SEQ ID NO: 33 |
| Preparation Example 10 | SEQ ID NO: 30 | SEQ ID NO: 34 |
| Preparation Example 11 | SEQ ID NO: 31 | SEQ ID NO: 35 |
| Preparation Example 12 | SEQ ID NO: 32 | SEQ ID NO: 36 |
| Preparation Example 13 | SEQ ID NO: 37 | SEQ ID NO: 41 |
| Preparation Example 14 | SEQ ID NO: 38 | SEQ ID NO: 42 |
| Preparation Example 15 | SEQ ID NO: 39 | SEQ ID NO: 43 |
| Preparation Example 16 | SEQ ID NO: 40 | SEQ ID NO: 44 |
| Preparation Example 17 | SEQ ID NO: 45 | SEQ ID NO: 49 |
| Preparation Example 18 | SEQ ID NO: 46 | SEQ ID NO: 50 |
| Preparation Example 19 | SEQ ID NO: 47 | SEQ ID NO: 51 |
| Preparation Example 20 | SEQ ID NO: 48 | SEQ ID NO: 52 |
| Preparation Example 21 | SEQ ID NO: 53 | SEQ ID NO: 57 |
| Preparation Example 22 | SEQ ID NO: 54 | SEQ ID NO: 58 |
| Preparation Example 23 | SEQ ID NO: 55 | SEQ ID NO: 59 |
| Preparation Example 24 | SEQ ID NO: 56 | SEQ ID NO: 60 |

TABLE 26-continued

| No. | Amino acid sequence of fusion protein | Nucleic acid sequence of fusion protein |
|---|---|---|
| Preparation Example 25 | SEQ ID NO: 61 | SEQ ID NO: 65 |
| Preparation Example 26 | SEQ ID NO: 62 | SEQ ID NO: 66 |
| Preparation Example 27 | SEQ ID NO: 63 | SEQ ID NO: 67 |
| Preparation Example 28 | SEQ ID NO: 64 | SEQ ID NO: 68 |
| Preparation Example 29 | SEQ ID NO: 69 | SEQ ID NO: 73 |
| Preparation Example 30 | SEQ ID NO: 70 | SEQ ID NO: 74 |
| Preparation Example 31 | SEQ ID NO: 71 | SEQ ID NO: 75 |
| Preparation Example 32 | SEQ ID NO: 72 | SEQ ID NO: 76 |
| Preparation Example 33 | SEQ ID NO: 77 | SEQ ID NO: 81 |
| Preparation Example 34 | SEQ ID NO: 78 | SEQ ID NO: 82 |
| Preparation Example 35 | SEQ ID NO: 79 | SEQ ID NO: 83 |
| Preparation Example 36 | SEQ ID NO: 80 | SEQ ID NO: 84 |

2. Purification of Fusion Protein 293F cells were transformed with the expression vector as constructed in item no. 1. above using polyethyleneimine, and then cultured for 6 days under conditions of 37° C. and 8% $CO_2$. The culture supernatant was filtered, passed through Protein A resin, and washed with 1×PBS. Elution was performed with a 0.1 M glycine solution at pH 3.5. Then, to the obtained solution was added a 1 M TRIS solution at pH 9.0 to neutralize the pH. Subsequently, the solution was dialyzed against a PBS solution, and then concentrated and used.

[Example 6] Effects of Inhibiting Suppression Activity of Regulatory T Cells on Effector T Cells, Exhibited by Fusion Protein According to Present Invention The following experiment was conducted to identify whether the fusion protein according to the present invention represented by SEQ ID NO: 21, which has been produced in Preparation Example 5 (produced using the nucleic acid sequence represented by SEQ ID NO: 25), binds to a ligand for the Lrig-1 protein, so that the interaction between the ligand and regulatory T cells is inhibited, thereby ultimately decreasing suppression activity of the regulatory T cells on proliferation of effector T cells. Specifically, the fusion protein of Preparation Example 5 was added under a condition in which the regulatory T cells and the effector T cells are co-cultured, to identify changes in suppression activity of the regulatory T cells on proliferation of the effector T cells. The results are illustrated in FIG. 11.

Figure 11:
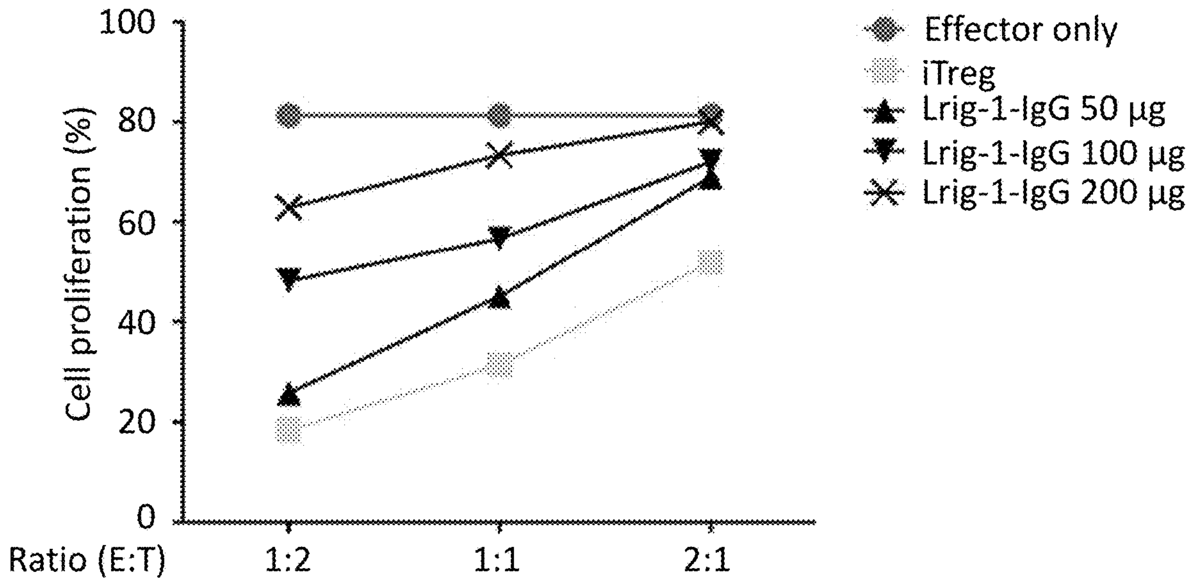
FIG. 11 illustrates effects of inhibiting suppression activity of regulatory T cells on effector T cells, exhibited by the fusion protein according to an embodiment of the present invention.

As illustrated in FIG. 11, it was found that treatment with the fusion protein according to the present invention results in decreased suppression activity of the regulatory T cells on proliferation of the effector T cells.

From these results, it can be seen that the fusion protein according to the present invention interacts with a ligand for Lrig-1 protein to inhibit the interaction between the ligand and regulatory T cells having the Lrig-1 protein on their surface, so that activity of the regulatory T cells is inhibited and activity of effector T cells is maintained or elevated.

[Example 7] Identification of Distribution of Lrig-1 Ligand Recognized by Fusion Protein According to Present Invention As shown in Example 6, it can be seen that the fusion protein according to the present invention represented by SEQ ID NO: 21, which has been produced in Preparation Example 5 (produced using the nucleic acid sequence represented by SEQ ID NO: 25), can recognize the Lrig-1 ligand. Thus, in order to discover immune cells in which the Lrig-1 ligand is present, naive T cells, thought to be targets of regulatory T cells, were induced to differentiate into activated T cells, Th1 cells, Th2 cells, or Th17 cells, and then these differentiated cells were stained with the fusion protein (primary antibody) of Preparation Example 5 and anti-human-PE antibody (secondary antibody). Expression levels of the fusion protein were measured at the respective cell surfaces using a fluorescence-activated cell sorter (FACS). The results are illustrated in FIG. 12.

Figure 12:
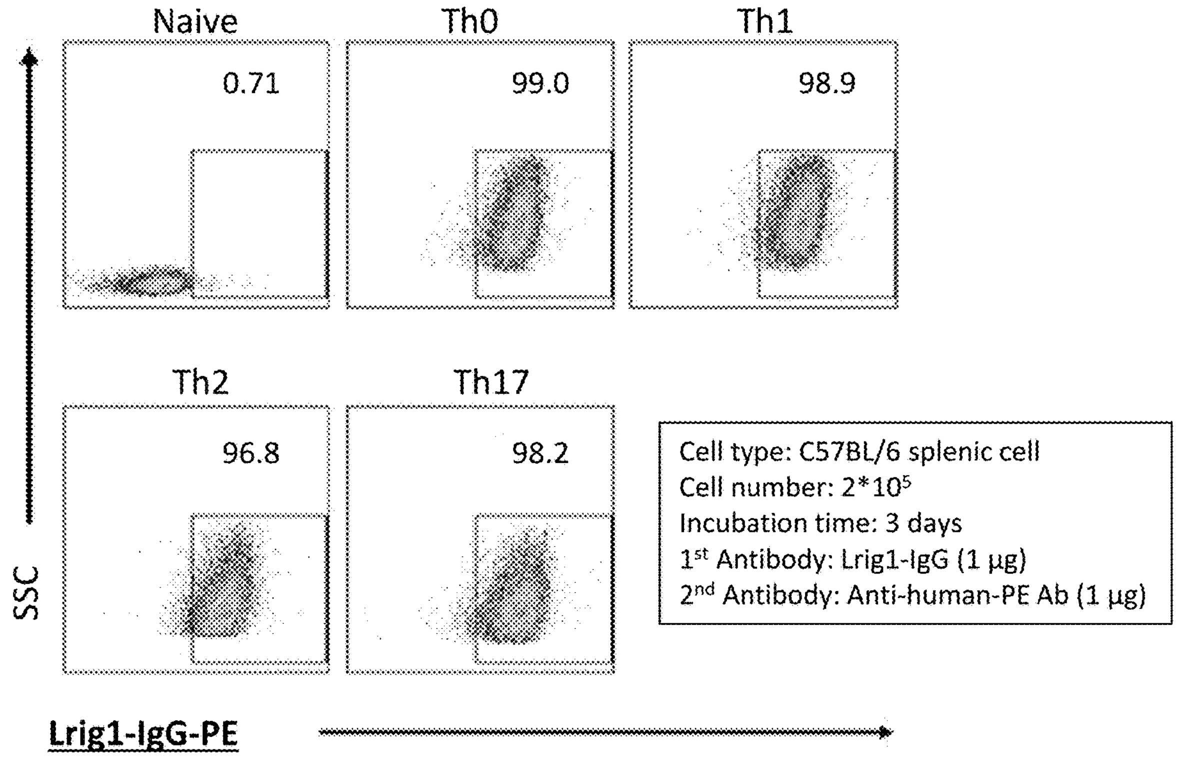
FIG. 12 illustrates subsets of T cells in which a ligand recognized by the fusion protein according to an embodiment of the present invention is present.

As illustrated in FIG. 12, the fusion protein according to the present invention hardly stained the antigens on the surface of the naive T cells (0.71%), while staining 96% or more of the antigens on the surface of the activated T cells, the Th1 cells, the Th2 cells, and the Th17 cells.

From these results, it was found that the Lrig-1 ligand is a surface protein induced by stimulation with a T cell receptor.

Figure 13:
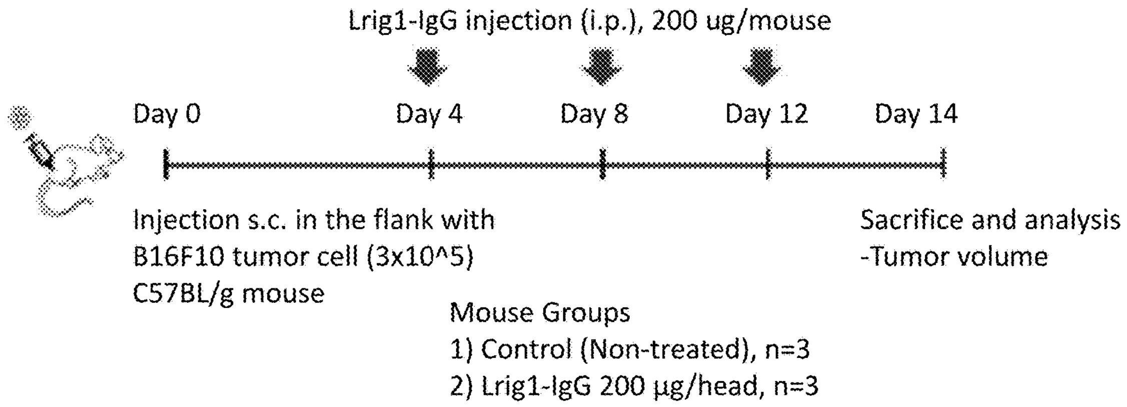
FIG. 13 illustrates an experimental design diagram for a cancer treatment experiment using the fusion protein according to an embodiment of the present invention.

[Example 8] Cancer Therapeutic Effects of Fusion Protein According to Present Invention In order to identify therapeutic effects, on solid cancer, of the fusion protein according to the present invention represented by SEQ ID NO: 21, which has been produced in Preparation Example 5 (produced using the nucleic acid sequence represented by SEQ ID NO: 25), as illustrated in FIG. 13, B16F10 melanoma cells were subcutaneously injected into the dorsal area of mice in an amount of $3\times10^5$ cells, and then the fusion protein of Preparation Example 5 was intraperitoneally injected into the mice in an amount of 200 ug on days 4, 8, and 12. After transplantation of the melanoma cells, changes in tumor volume over time were measured and the results are illustrated in FIG. 14.

Figure 14:
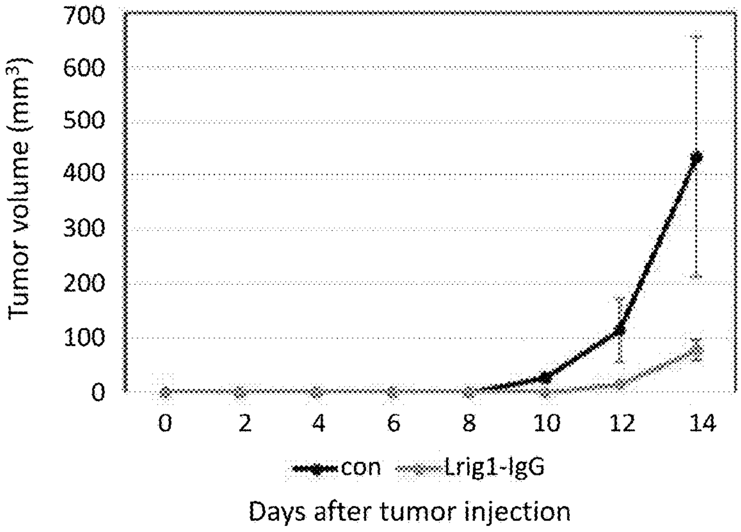
FIG. 14 illustrates results obtained by analyzing cancer therapeutic effects achieved by the fusion protein according to an embodiment of the present invention.

As illustrated in FIG. 14, it was found that remarkably decreased melanoma tumor sizes are observed in a case of being treated with the fusion protein of the present invention, as compared with a negative control for which no treatment has been made.

[Example 9] Cancer Therapeutic Effects of Fusion Protein According to Present Invention In order to identify therapeutic effects, on solid cancer, of the fusion protein according to the present invention represented by SEQ ID NO: 78, which has been produced in Preparation Example 34 (produced using the nucleic acid sequence represented by SEQ ID NO: 82), CT-26 colorectal cancer cells were subcutaneously injected into the dorsal area of mice in an amount of $3\times10^5$ cells, and then the fusion protein of Preparation Example 34 was intraperitoneally injected into the mice in an amount of 200 ug on days 4, 8, and 12. After transplantation of the colorectal cancer cells, changes in tumor volume over time were measured and the results are illustrated in FIG. 15.

Figure 15:
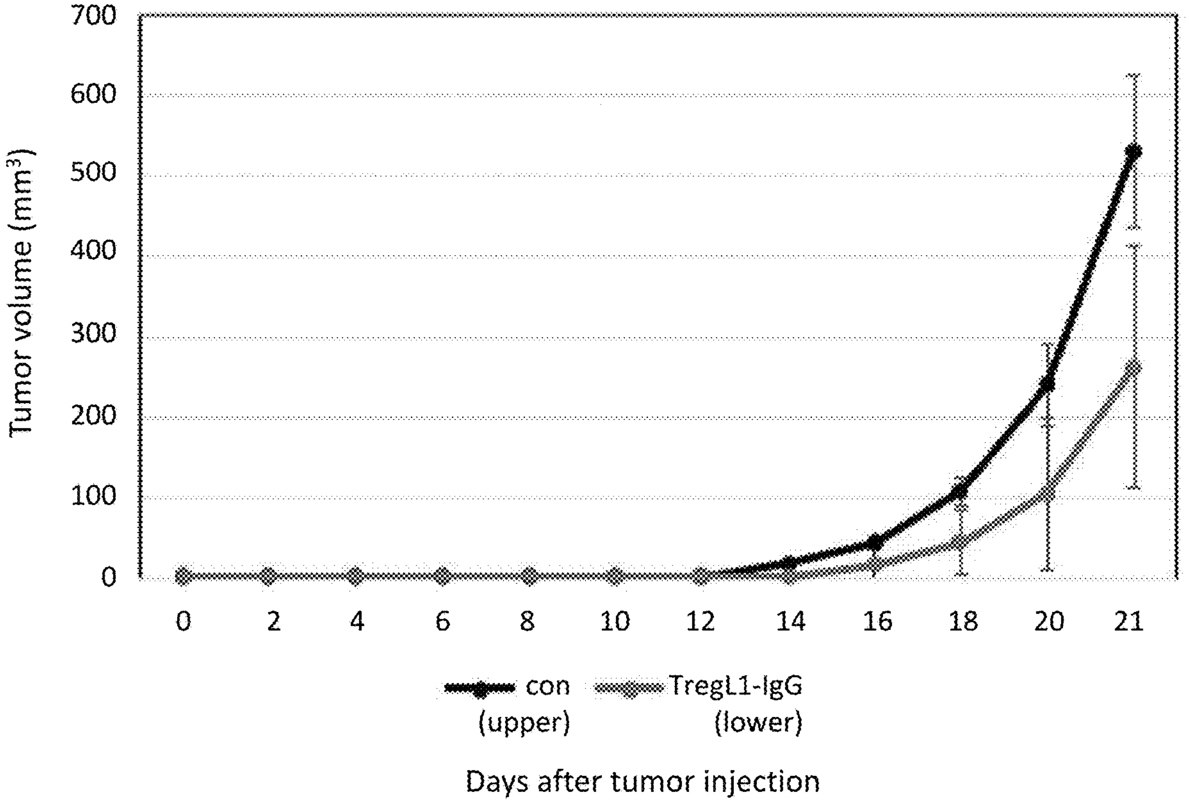
FIG. 15 illustrates results obtained by analyzing cancer therapeutic effects achieved by the fusion protein according to an embodiment of the present invention.

As illustrated in FIG. 15, it was found that remarkably decreased colorectal cancer tumor sizes are observed in a case of being treated with the fusion protein of the present invention, as compared with a negative control for which no treatment has been made.

From these results, it can be seen that the fusion protein comprising the extracellular domain of the Lrig-1 protein and the immunoglobulin Fc region, according to the present invention, is capable of inhibiting the interaction between regulatory T cells and effector T cells so that activity of the regulatory T cells is inhibited and activity of the effector T cells is maintained or elevated, thereby effectively inhibiting growth of cancer cells, in particular, solid cancer cells.

Although the present invention has been described in detail above, the scope of the present invention is not limited thereto. It will be obvious to those skilled in the art that various modifications and changes can be made without departing from the technical spirit of the present invention described in the claims.

INDUSTRIAL AVAILABILITY

The present invention relates to a novel fusion protein comprising an extracellular domain of Lrig-1 protein and an immunoglobulin Fc region, and to a use thereof for the prevention or treatment of cancer.

The invention claimed is:

1. A fusion protein, comprising:

an extracellular domain of leucine-rich and immunoglobulin-like domains 1 (Lrig-1) protein; and an immunoglobulin Fc region, the immunoglobulin Fc region including the sequence of SEQ ID NO: 5 or SEQ ID NO: 6.

2. The fusion protein according to claim 1, wherein the extracellular domain of the Lrig-1 protein has the sequence of SEQ ID NO: 1 or 3.

3. The fusion protein according to claim 1, wherein the immunoglobulin Fc region includes a total of 1 to 4 domains selected from the group consisting of CH1, CH2, CH3, and CH4 domains.

4. The fusion protein according to claim 1, wherein the immunoglobulin Fc region further includes an Fc region of IgG, IgA, IgD, IgE or IgM, a hinge, a fragment thereof, or a combination thereof.

5. The fusion protein according to claim 1, wherein the immunoglobulin Fc region includes a hinge region.

6. The fusion protein according to claim 5, wherein the hinge region is a hinge region of IgG, IgA, IgM, IgD, IgE or Abatacept.

7. The fusion protein according to claim 5, wherein the hinge region is a hinge region of IgG1, IgG2, IgG3, IgG4, IgD, or Abatacept.

8. The fusion protein according to claim 1, wherein the immunoglobulin Fc region includes a hinge region having the sequence of any one of SEQ ID NOs: 7 to 10.

9. The fusion protein according to claim 1, wherein the extracellular domain of the Lrig-1 protein is directly connected to the N-terminus or C-terminus of the immunoglobulin Fc region.

10. The fusion protein according to claim 1, wherein the extracellular domain of the Lrig-1 protein is connected via a linker to the N-terminus or C-terminus of the immunoglobulin Fc region.

11. The fusion protein according to claim 10, wherein the linker is at least one of a peptide linker having the sequence of SEQ ID NO: 11 and a peptide linker having the sequence of SEQ ID NO: 12.

12. A pharmaceutical composition for treating cancer, comprising as an active ingredient:

the fusion protein according to claim 1; and a pharmaceutically-acceptable carrier.

13. A method for treating cancer, comprising administering, to an individual, the fusion protein of claim 1.

14. The method according to claim 13, wherein the cancer is a solid cancer.

15. The method according to claim 13, wherein the cancer is gastric cancer, liver cancer, gliocytoma, ovarian cancer, colorectal cancer, head and neck cancer, bladder cancer, renal cell cancer, breast cancer, metastatic cancer, prostate cancer, pancreatic cancer, melanoma, or lung cancer.

16. The fusion protein according to claim 1, wherein the immunoglobulin Fc region includes the sequence of SEQ ID NO: 5.

17. The fusion protein according to claim 1, wherein the immunoglobulin Fc region includes the sequence of SEQ ID NO: 6.

* * * * *